US009882150B2

(12) United States Patent
Li et al.

(10) Patent No.: US 9,882,150 B2
(45) Date of Patent: Jan. 30, 2018

(54) METAL COMPOUNDS, METHODS, AND USES THEREOF

(71) Applicant: ARIZONA BOARD OF REGENTS FOR AND ON BEHALF OF ARIZONA STATE UNIVERSITY, Scottsdale, AZ (US)

(72) Inventors: Jian Li, Phoenix, AZ (US); Guijie Li, Mesa, AZ (US)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 374 days.

(21) Appl. No.: 14/430,454

(22) PCT Filed: Sep. 24, 2013

(86) PCT No.: PCT/US2013/061353
§ 371 (c)(1),
(2) Date: Mar. 23, 2015

(87) PCT Pub. No.: WO2014/047616
PCT Pub. Date: Mar. 27, 2014

(65) Prior Publication Data
US 2015/0228914 A1 Aug. 13, 2015

Related U.S. Application Data

(60) Provisional application No. 61/704,880, filed on Sep. 24, 2012.

(51) Int. Cl.
| | | |
|---|---|---|
| *H01L 51/00* | (2006.01) | |
| *C09K 11/06* | (2006.01) | |
| *C07F 15/00* | (2006.01) | |
| *H01L 51/42* | (2006.01) | |
| *H01L 51/50* | (2006.01) | |

(52) U.S. Cl.
CPC ...... *H01L 51/0087* (2013.01); *C07F 15/0086* (2013.01); *C09K 11/06* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/185* (2013.01); *H01L 51/42* (2013.01); *H01L 51/5012* (2013.01); *H01L 51/5016* (2013.01); *H01L 51/5036* (2013.01); *Y02E 10/549* (2013.01)

(58) Field of Classification Search
CPC .. C07D 213/06; C07D 213/30; C07D 213/53; C07D 213/64; C07D 213/74; C07D 277/28; C07D 401/14; C07D 409/14; C07F 15/0086; C09K 11/06; C09K 2211/1037; C09K 2211/1033; C09K 2211/1029; C09K 2211/1007; C09K 2211/1059; C09K 2211/185; C09K 2211/1044; H01L 51/0087; H01L 51/5036; H01L 51/5012; H01L 51/5016; H01L 51/42; H05B 33/14; Y02E 10/549

See application file for complete search history.

(56) References Cited

U.S. PATENT DOCUMENTS

| | | | |
|---|---|---|---|
| 4,769,292 A | 9/1988 | Tang et al. | |
| 5,707,745 A | 1/1998 | Forrest et al. | |
| 5,844,363 A | 12/1998 | Gu et al. | |
| 6,200,695 B1 * | 3/2001 | Arai | H01L 51/5088 313/504 |
| 6,303,238 B1 | 10/2001 | Thompson et al. | |
| 6,780,528 B2 | 8/2004 | Tsuboyama et al. | |
| 7,002,013 B1 | 2/2006 | Chi et al. | |
| 7,037,599 B2 | 5/2006 | Culligan et al. | |
| 7,279,704 B2 | 10/2007 | Walters et al. | |
| 7,332,232 B2 | 2/2008 | Ma et al. | |
| 7,442,797 B2 | 10/2008 | Itoh et al. | |
| 7,501,190 B2 | 3/2009 | Ise | |
| 7,655,322 B2 | 2/2010 | Forrest et al. | |
| 7,947,383 B2 | 5/2011 | Ise et al. | |
| 8,389,725 B2 | 3/2013 | Li et al. | |
| 8,617,723 B2 | 12/2013 | Stoessel | |
| 8,816,080 B2 | 8/2014 | Li et al. | |
| 8,871,361 B2 | 10/2014 | Xia et al. | |
| 8,927,713 B2 | 1/2015 | Li et al. | |
| 8,946,417 B2 | 2/2015 | Li et al. | |
| 9,059,412 B2 | 6/2015 | Zeng et al. | |
| 9,224,963 B2 | 12/2015 | Li et al. | |
| 9,238,668 B2 | 1/2016 | Li et al. | |
| 9,312,505 B2 | 4/2016 | Brooks | |
| 9,324,957 B2 | 4/2016 | Li et al. | |
| 9,382,273 B2 | 7/2016 | Li et al. | |
| 9,385,329 B2 | 7/2016 | Li et al. | |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Murakami; JP 2007258550, English machine translation from EPO, Oct. 4, 2007. 80 pages.
Murakami; JP 2007324309, English machine translation from EPO, Dec. 13, 2007, 89 pages.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
Wong; Challenges in organometallic research—Great opportunity for solar cells and OLEDs, Journal of Organometallic Chemistry, 2009, 694, 2644-2647.

(Continued)

*Primary Examiner* — Alexander Kollias
(74) *Attorney, Agent, or Firm* — Fish & Richardson P.C.

(57) ABSTRACT

Disclosed herein are metal compounds useful in devices, such as, for example, OLEDs.

16 Claims, 1 Drawing Sheet

(56) References Cited

U.S. PATENT DOCUMENTS

| | | | |
|---|---|---|---|
| 9,425,415 | B2 | 8/2016 | Li et al. |
| 9,461,254 | B2 | 10/2016 | Tsai |
| 9,550,801 | B2 | 1/2017 | Li |
| 9,617,291 | B2 | 4/2017 | Li |
| 9,673,409 | B2 | 6/2017 | Li |
| 9,755,163 | B2 | 9/2017 | Li |
| 2002/0068190 | A1 | 6/2002 | Tsuboyama et al. |
| 2003/0062519 | A1 | 4/2003 | Yamazaki et al. |
| 2003/0186077 | A1* | 10/2003 | Chen .............. C07D 209/80 428/690 |
| 2005/0170207 | A1 | 8/2005 | Ma et al. |
| 2005/0260446 | A1 | 11/2005 | Mackenzie et al. |
| 2006/0073359 | A1 | 4/2006 | Ise et al. |
| 2006/0094875 | A1 | 5/2006 | Itoh et al. |
| 2006/0202197 | A1 | 9/2006 | Nakayama et al. |
| 2006/0210831 | A1 | 9/2006 | Sano et al. |
| 2006/0263635 | A1 | 11/2006 | Ise |
| 2006/0286406 | A1 | 12/2006 | Igarashi et al. |
| 2007/0057630 | A1 | 3/2007 | Nishita et al. |
| 2007/0059551 | A1 | 3/2007 | Yamazaki |
| 2007/0082284 | A1 | 4/2007 | Stoessel et al. |
| 2007/0103060 | A1* | 5/2007 | Itoh .............. C07D 213/06 313/504 |
| 2008/0001530 | A1 | 1/2008 | Ise et al. |
| 2008/0036373 | A1 | 2/2008 | Itoh et al. |
| 2008/0054799 | A1 | 3/2008 | Satou |
| 2008/0079358 | A1 | 4/2008 | Satou |
| 2008/0241518 | A1 | 10/2008 | Satou et al. |
| 2008/0241589 | A1 | 10/2008 | Fukunaga et al. |
| 2009/0026936 | A1 | 1/2009 | Satou et al. |
| 2009/0026939 | A1 | 1/2009 | Kinoshita et al. |
| 2009/0032989 | A1 | 2/2009 | Karim et al. |
| 2009/0039768 | A1 | 2/2009 | Igarashi et al. |
| 2009/0079340 | A1 | 3/2009 | Kinoshita et al. |
| 2009/0128008 | A1 | 5/2009 | Ise et al. |
| 2009/0218561 | A1 | 9/2009 | Kitamura et al. |
| 2009/0261721 | A1 | 10/2009 | Murakami et al. |
| 2009/0267500 | A1 | 10/2009 | Kinoshita et al. |
| 2010/0000606 | A1 | 1/2010 | Thompson et al. |
| 2010/0013386 | A1 | 1/2010 | Thompson et al. |
| 2010/0171111 | A1 | 7/2010 | Takada et al. |
| 2012/0095232 | A1 | 4/2012 | Li et al. |
| 2012/0181528 | A1 | 7/2012 | Takada et al. |
| 2012/0215001 | A1 | 8/2012 | Li et al. |
| 2012/0223634 | A1 | 9/2012 | Xia et al. |
| 2012/0302753 | A1 | 11/2012 | Li |
| 2013/0048963 | A1 | 2/2013 | Beers et al. |
| 2013/0168656 | A1 | 7/2013 | Tsai et al. |
| 2013/0203996 | A1 | 8/2013 | Li et al. |
| 2013/0237706 | A1 | 9/2013 | Li |
| 2013/0341600 | A1 | 12/2013 | Lin et al. |
| 2014/0014922 | A1 | 1/2014 | Lin et al. |
| 2014/0027733 | A1 | 1/2014 | Zeng et al. |
| 2014/0084261 | A1 | 3/2014 | Brooks et al. |
| 2014/0114072 | A1 | 4/2014 | Li et al. |
| 2014/0203248 | A1 | 7/2014 | Zhou et al. |
| 2014/0330019 | A1 | 11/2014 | Li et al. |
| 2014/0364605 | A1 | 12/2014 | Li et al. |
| 2015/0008419 | A1 | 1/2015 | Li |
| 2015/0028323 | A1 | 1/2015 | Xia et al. |
| 2015/0069334 | A1 | 3/2015 | Xia et al. |
| 2015/0105556 | A1 | 4/2015 | Li et al. |
| 2015/0162552 | A1 | 6/2015 | Li et al. |
| 2015/0194616 | A1 | 7/2015 | Li et al. |
| 2015/0287938 | A1 | 10/2015 | Li et al. |
| 2015/0318500 | A1 | 11/2015 | Li et al. |
| 2015/0349279 | A1 | 12/2015 | Li et al. |
| 2016/0028028 | A1 | 1/2016 | Li et al. |
| 2016/0043331 | A1 | 2/2016 | Li et al. |
| 2016/0133862 | A1 | 5/2016 | Li et al. |
| 2016/0197291 | A1 | 7/2016 | Li et al. |
| 2016/0285015 | A1 | 9/2016 | Li et al. |
| 2016/0359120 | A1 | 12/2016 | Li |
| 2016/0359125 | A1 | 12/2016 | Li |
| 2017/0005278 | A1 | 1/2017 | Li |
| 2017/0012224 | A1 | 1/2017 | Li |
| 2017/0047533 | A1 | 2/2017 | Li |
| 2017/0066792 | A1 | 3/2017 | Li |
| 2017/0069855 | A1 | 3/2017 | Li |

FOREIGN PATENT DOCUMENTS

| | | |
|---|---|---|
| CN | 101142223 A | 3/2008 |
| CN | 101667626 A | 3/2010 |
| CN | 102449108 A | 5/2012 |
| CN | 102892860 A | 1/2013 |
| CN | 102971396 A | 3/2013 |
| CN | 104232076 A | 12/2014 |
| CN | 104693243 A | 6/2015 |
| CN | 105367605 A1 | 3/2016 |
| CN | 105418591 A1 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 A | 9/2005 |
| JP | 2005310733 A | 11/2005 |
| JP | 2006047240 A | 2/2006 |
| JP | 2006232784 A | 9/2006 |
| JP | 2006242080 A | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007042875 A | 2/2007 |
| JP | 2007053132 | 3/2007 |
| JP | 2007066581 A | 3/2007 |
| JP | 2007073620 A | 3/2007 |
| JP | 2007073845 A | 3/2007 |
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 | 4/2007 |
| JP | 2007096259 A | 4/2007 |
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009266943 A | 11/2009 |
| JP | 2009267171 | 11/2009 |
| JP | 2009267244 | 11/2009 |
| JP | 2009272339 A | 11/2009 |
| JP | 2009283891 | 12/2009 |
| JP | 2010135689 | 6/2010 |
| JP | 2012222255 A | 11/2012 |
| JP | 2013525436 | 6/2013 |
| JP | 5604505 | 10/2014 |
| JP | 2014221807 | 11/2014 |
| JP | 2015081257 | 4/2015 |

(56) References Cited

FOREIGN PATENT DOCUMENTS

| | | |
|---|---|---|
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| TW | 201710277 A1 | 3/2017 |
| WO | WO 2000070655 | 11/2000 |
| WO | WO2004003108 A1 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 A1 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 A2 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 A1 | 1/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 A1 | 9/2015 |
| WO | WO2016025921 A1 | 2/2016 |
| WO | WO2016029186 A1 | 2/2016 |

OTHER PUBLICATIONS

JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
International Search Report mailed by the International Searching Authority dated Jan. 28, 2014 for PCT/US2013/061353 filed Sep. 24, 2013 and published as WO/2014/047616 on Mar. 27, 2014 (Applicant—Arizona Board of Regents for and on behalf of Arizona State University / Inventors—Jian Li, et al.) (pp. 1-4).
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6 Aug. 25, 2013.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)$_3$ and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
International Preliminary Report on Patentability issued by the International Searching Authority dated Apr. 2, 2015 for PCT/US2013/061353 filed Sep. 24, 2013, 10 pages.
Vanessa Wood et al., "Colloidal quantum dot light-emitting devices," Nano Reviews , vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater. , vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O^N^C^N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O^N^C^N ligands: high efficiency OLEDs with excellent efficiency stability," Chem. Commun., 2013, vol. 49, pp. 1497-1499.

(56) References Cited

OTHER PUBLICATIONS

Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.

* cited by examiner

METAL COMPOUNDS, METHODS, AND USES THEREOF

CROSS-REFERENCE TO RELATED APPLICATIONS

This application is a U.S. National Phase Application of International Patent Application No. PCT/US2013/061353 filed Sep. 24, 2013, which claims U.S. Provisional Application Ser. No. 61/704,880 entitled "TETRADENTATE CYCLOMETALATED METAL COMPLEXES" and filed on Sep. 24, 2012, the contents of both of which are incorporated herein by reference in their entirety.

BACKGROUND

Technical Field

The present disclosure relates to metal compounds that are useful in devices, such as, for example, organic light emitting diodes (OLEDs).

Technical Background

Compounds capable of absorbing and/or emitting light can be ideally suited for use in a wide variety of optical and electro-optical devices, including, for example, photo-absorbing devices such as solar- and photo-sensitive devices, photo-emitting devices, OLEDs, or devices capable of both photo-absorption and emission. Much research has been devoted to the discovery and optimization of organic and organometallic materials for using in optical and electro-optical devices. Generally, research in this area aims to accomplish a number of goals, including improvements in absorption and emission efficiency, as well as improvements in processing ability.

Despite significant advances in research devoted to optical and electro-optical materials, many currently available materials exhibit a number of disadvantages, including poor processing ability, inefficient emission or absorption, and less than ideal stability, among others. Thus, a need exists for new materials which exhibit improved performance in optical and electro-optical devices. This need and other needs are satisfied by the present invention.

SUMMARY

Disclosed herein are metal compounds that are useful in devices, such as, for example, organic light emitting diodes (OLEDs).

Disclosed herein is a compound having the formula

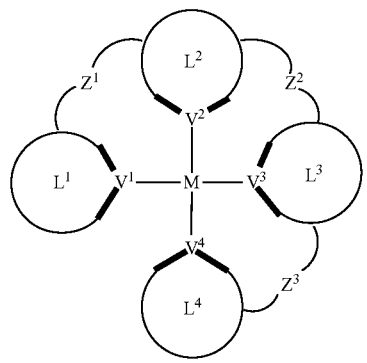

wherein each of $L^1$, $L^2$, $L^3$, and $L^4$ independently is a substituted or unsubstituted aryl, cycloalkyl, cycloalkenyl, heterocyclyl, heteroaryl, carbene, or N-heterocyclic carbene,
wherein each of $Z^1$, $Z^2$, and $Z^3$ independently is present or absent, and if present each of $Z^1$, $Z^2$, and $Z^3$ independently is A, $A^1$, or $A^2$,
wherein each of A, $A^1$, or $A^2$ independently is O, S, S=O, $SO_2$, Se, $NR^3$, $PR^3$, RP=O, $CR^1R^2$, C=O, $SiR^1R^2$, $GeR^1R^2$, BH, P(O)H, PH, NH, $CR^1H$, $CH_2$, $SiH_2$, $SiHR^1$, BH, or $BR^3$,
wherein M is Pt, Pd, Au, Ir, Rh, Ru, Fe, Co, Ni, Cu, Zn, Ag, Hg, Cd, or Zr,
wherein at least one of $L^1$, $L^2$, $L^3$, and $L^4$ comprises

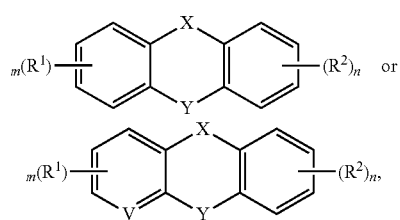

wherein m and n independently is an integer from 0 to 4,
wherein each of V, X, and Y independently is $V^1$, $V^2$, $V^3$, $V^4$, O, S, S=O, $SO_2$, Se, $NR^3$, $PR^3$, $R^1P$=O, $CR^1R^2$, C=O, $SiR^1R^2$, $GeR^1R^2$, BH, P(O)H, PH, NH, $CR^1H$, $CH_2$, $SiH_2$, $SiHR^1$, BH, or $BR^3$, or any one of

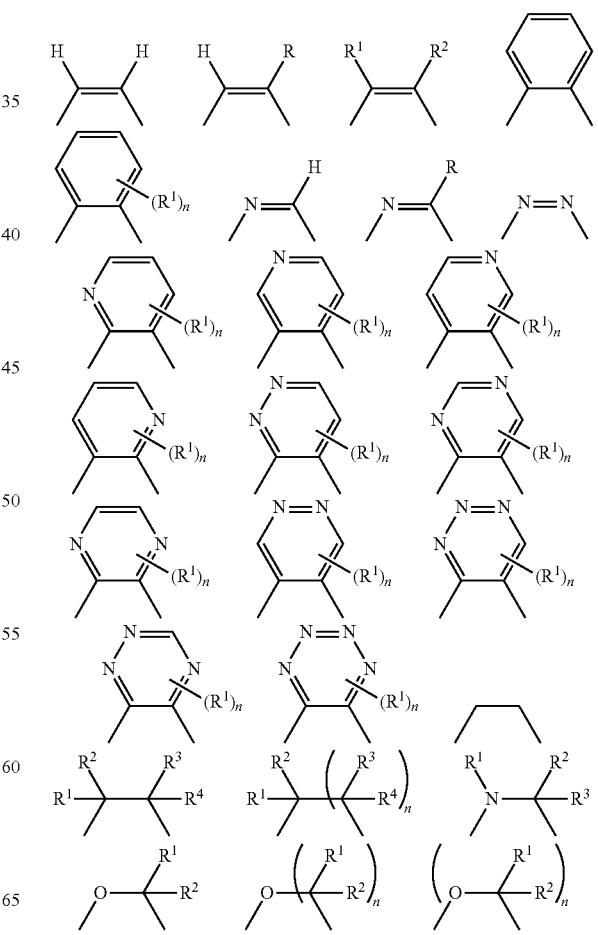

-continued

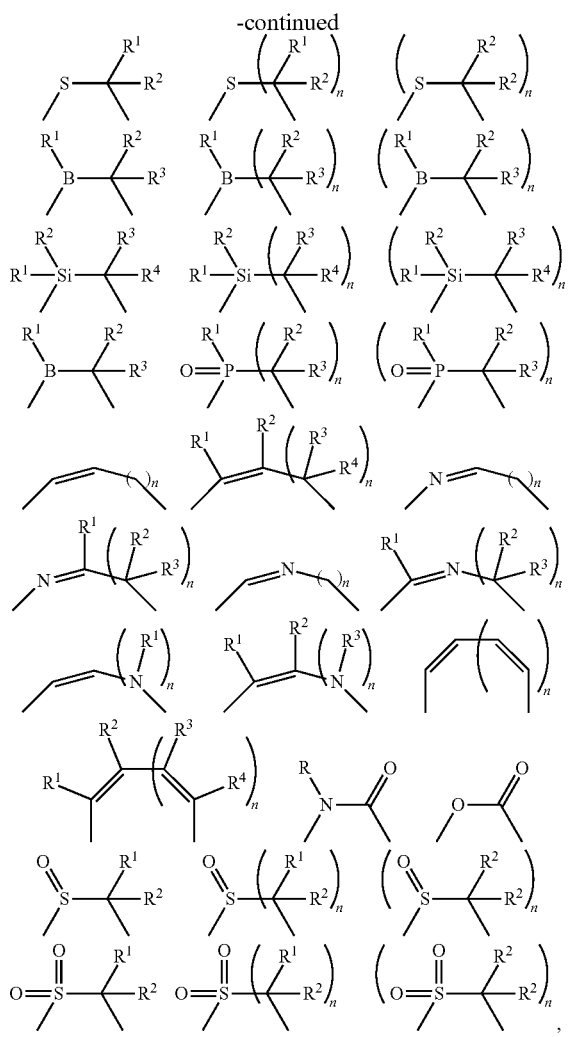

wherein at least one of V, X, and Y is $V^1$, $V^2$, $V^3$, or $V^4$, wherein m and n independently is an integer from 0 to 4, wherein each of $V^1$, $V^2$, $V^3$ and $V^4$ independently is coordinated to M, and wherein each of $V^1$, $V^2$, $V^3$ and $V^4$ independently is N, C, CH, P, B, SiH, or Si, wherein each of R, $R^1$, $R^2$, $R^3$, and $R^4$, independently is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof,
wherein each of $V^1$, $V^2$, $V^3$ and $V^4$ independently optionally is substituted for any one of $V^1$, $V^2$, $V^3$ and $V^4$.

Also disclosed herein are devices, such as, for example, OLEDs, comprising one or more of the disclosed compounds.

BRIEF DESCRIPTION OF THE FIGURES

The accompanying figures, which are incorporated in and constitute a part of this specification, illustrate several aspects and together with the description serve to explain the principles of the invention.

Figure 1:
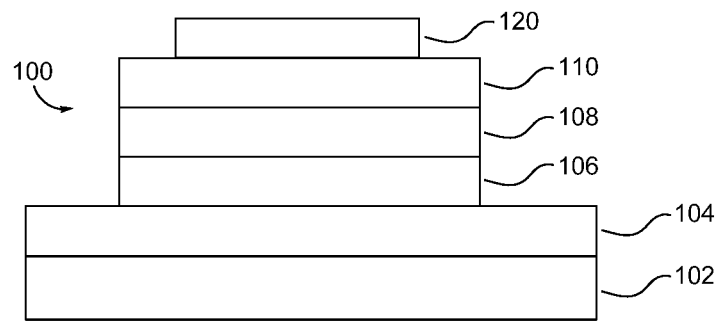
FIG. 1 shows a drawing of a cross-section of an exemplary organic light-emitting diode (OLED).
Figure 2:
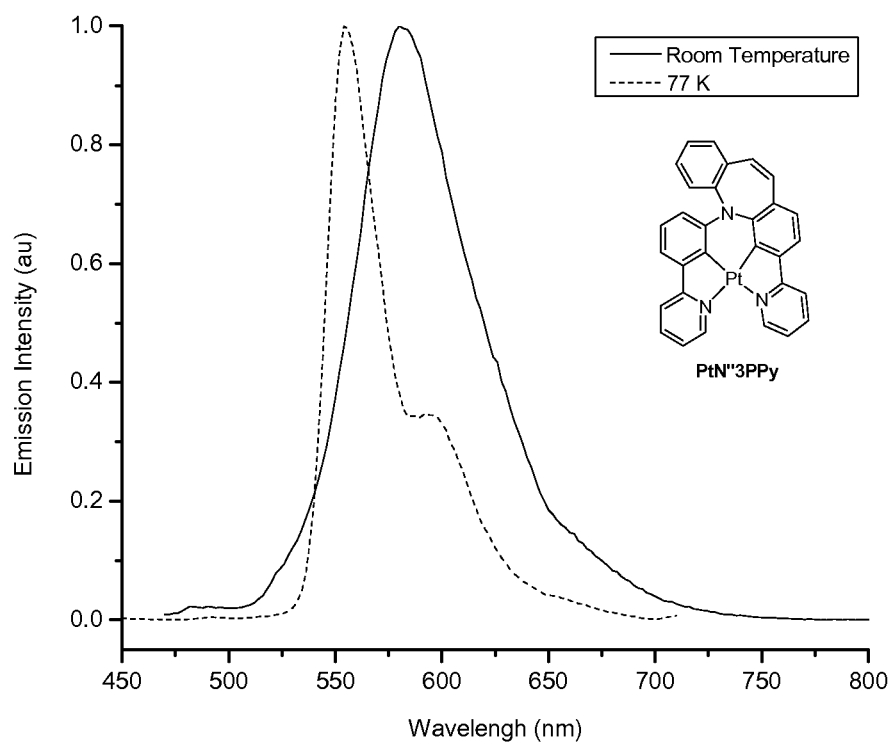
FIG. 2 is a emission spectra of PtN"3PPy in $CH_2Cl_2$ at room temperature and in 2-MeTHF at 77K.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

1. Definitions

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As referred to herein, a linking atom connect two groups such as, for example, a N and C group. The linking atom can, if valency permits, have other chemical moieties attached. For example, an oxygen would not have any other chemical groups attached as the valency is satisfied once it is bonded to the two groups (N and/or C groups). In another example, when carbon is the linking atom, two additional chemical moieties would be attached to the carbon as valency would require such. Suitable chemical moieties includes, but are not limited to, hydrogen, hydroxyl, alkyl, alkoxy, =O, halogen, nitro, amine, amide, thiol, aryl, heteroaryl, cycloalkyl, and heterocyclyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "nitrile" as used herein is represented by the formula —CN.

The term "thiol" as used herein is represented by the formula —SH.

The term "heterocyclyl" or the like terms refer to cyclic structures including a heteroatom. Thus, "heterocyclyl" includes both aromatic and non-aromatic ring structures with one or more heteroatoms. Non-limiting examples of heterocyclic includes, pyridine, isoquinoline, methylpyrrole and thiophene etc. "Heteroaryl" specifically denotes an aromoatic cyclic structure including a heteroatom.

As briefly described above, the present invention is directed to multidentate, for example, tetradentate cyclometalated metal complexes. In one aspect, such complexes can be incorporated with heptacyclic or higher order materials. In another aspect, such complexes can be useful, for example, in displays and lighting applications.

In various aspects, the compounds of the present disclosure can comprise one or more of platinum (Pt) complexes, palladium (Pd) complexes, gold (Au) complexes, iridium (Ir) complexes, rhodium (Rh) complexes, ruthenium (Ru) complexes, iron (Fe) complexes, cobalt (Co) complexes, nickel (Ni) complexes, copper (Cu) complexes, zinc (Zn) complexes, silver (Ag) complexes, mercury (Hg) complexes, cadmium (Cd) complexes, zirconium (Zr) complexes, or other metal complexes not specifically recited herein which are capable of emitting light and are thus useful as an emissive materials in devices.

The term "each of $V^1$, $V^2$, $V^3$ and $V^4$ independently optionally is substituted for any one of $V^1$, $V^2$, $V^3$ and $V^4$" as used herein means that any one of $V^1$, $V^2$, $V^3$, and $V^4$ can be substituted for another of $V^1$, $V^2$, $V^3$, and $V^4$. For example, $V^1$ can be substituted for $V^2$, $V^3$, or $V^4$. In another example, $V^3$ can be substituted for $V^1$, $V^2$, or $V^4$. In one example, $V^2$ can be substituted for $V^1$. In another example, $V^3$ can be substituted for $V^1$. In another example, $V^4$ can be substituted for $V^2$. In another example, $V^3$ can be substituted for $V^2$. In one aspect, V, as described herein, can be $V^1$, $V^2$, $V^3$, or $V^4$ as described herein. For example, V can be $V^1$. In another example, V can be $V^2$. In another example, V can be $V^3$. In another example, V can be $V^4$.

As used herein, the terms "compound" and "complex" are used interchangeably.

2. Compounds

In one aspect, disclosed herein are compounds comprising a metal, such as platinum (Pt), palladium (Pd), gold (Au), iridium (Ir), rhodium (Rh), ruthenium (Ru), iron (Fe), cobalt (Co), nickel (Ni), copper (Cu), zinc (Zn), silver (Ag), mercury (Hg), cadmium (Cd), or zirconium (Zr). The disclosed compounds can emit electromagnetic radiation. In another aspect, the emission of the disclosed compounds can be tuned, for example, from the ultraviolet to near-infrared, by, for example, modifying the ligand structure. In another aspect, the disclosed compounds can provide emission over a majority of the visible spectrum. In a specific example, the disclosed compounds can emit light over a range of from about 400 nm to about 700 nm. In another aspect, the disclosed compounds have improved stability and efficiency over traditional emission complexes. In yet another aspect, the disclosed compounds can be useful as luminescent labels in, for example, bio-applications, anti-cancer agents, emitters in organic light emitting diodes (OLED), or a combination thereof. In another aspect, the disclosed compounds can be useful in light emitting devices, such as, for example, compact fluorescent lamps (CFL), light emitting diodes (LED), incandescent lamps, and combinations thereof.

The disclosed compounds can be, for example, multidentate compounds.

Disclosed herein are compounds having the formula

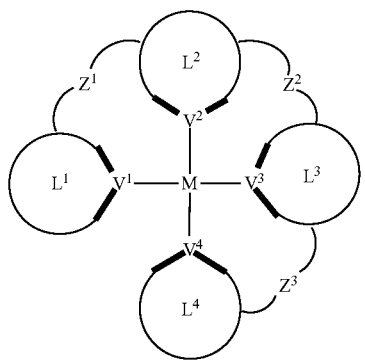

wherein each of $L^1$, $L^2$, $L^3$, and $L^4$ independently is a substituted or unsubstituted aryl, cycloalkyl, cycloalkenyl, heterocyclyl, heteroaryl, carbene, or N-heterocyclic carbene, wherein each of $Z^1$, $Z^2$, and $Z^3$ independently is present or absent, and if present each of $Z^1$, $Z^2$, and $Z^3$ independently is A, $A^1$, or $A^2$, wherein each of A, $A^1$, or $A^2$ independently is O, S, S=O, $SO_2$, Se, $NR^3$, $PR^3$, RP=O, $CR^1R^2$, C=O, $SiR^1R^2$, $GeR^1R^2$, BH, P(O)H, PH, NH, $CR^1H$, $CH_2$, $SiH_2$, $SiHR^1$, BH, or $BR^3$, wherein M is Pt, Pd, Au, Ir, Rh, Ru, Fe, Co, Ni, Cu, Zn, Ag, Hg, Cd, or Zr, wherein at least one of $L^1$, $L^2$, $L^3$, and $L^4$ comprises

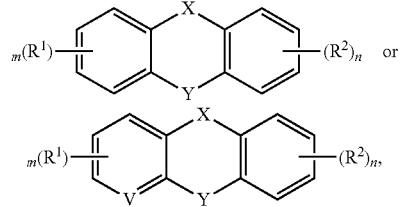

wherein m and n independently is an integer from 0 to 4, wherein each of V, X, and Y independently is $V^1$, $V^2$, $V^3$, $V^4$, O, S, S=O, $SO_2$, Se, $NR^3$, $PR^3$, $R^1P=O$, $CR^1R^2$, C=O, $SiR^1R^2$, $GeR^1R^2$, BH, P(O)H, PH, NH, $CR^1H$, $CH_2$, $SiH_2$, $SiHR^1$, BH, or $BR^3$, or any one of

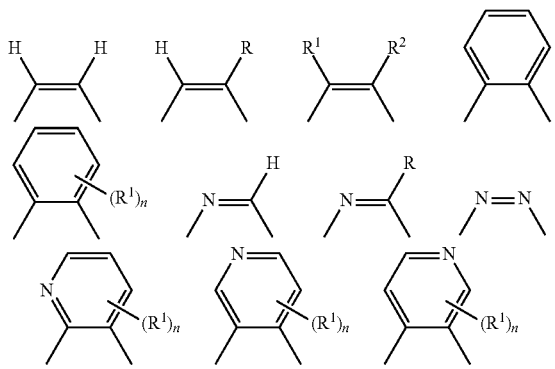

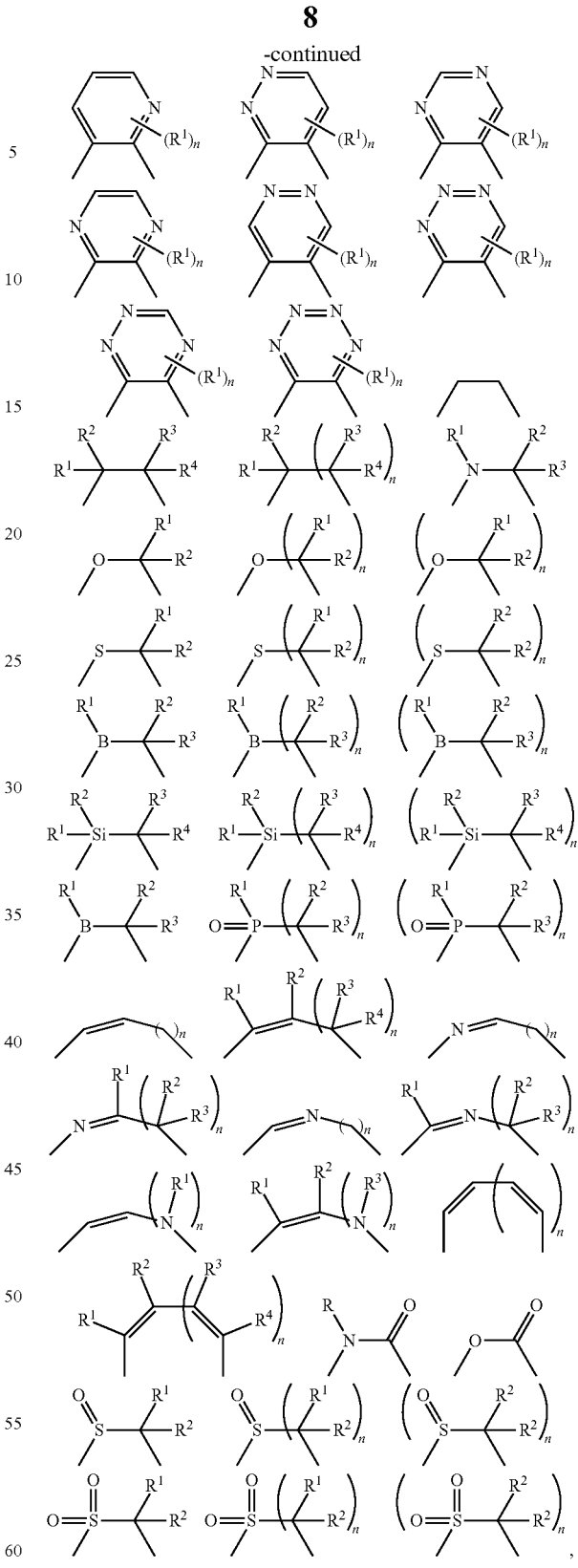

wherein at least one of V, X, and Y is $V^1$, $V^2$, $V^3$, or $V^4$, wherein m and n independently is an integer from 0 to 4, wherein each of $V^1$, $V^2$, $V^3$ and $V^4$ independently is coordinated to M, and wherein each of $V^1$, $V^2$, $V^3$ and $V^4$ independently is N, C, CH, P, B, SiH, or Si, wherein each of R, $R^1$, $R^2$, $R^3$, and $R^4$, independently is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof, wherein each of $V^1$, $V^2$, $V^3$ and $V^4$ independently optionally is substituted for any one of $V^1$, $V^2$, $V^3$ and $V^4$.

In one aspect each of $Z^1$, $Z^2$, and $Z^3$ independently is present. In another aspect, $Z^1$ and $Z^2$ are present and $Z^3$ is absent. In yet another aspect, $Z^2$ and $Z^3$ are present and $Z^1$ is absent. In yet another aspect, $Z^1$ and $Z^3$ are present and $Z^2$ is absent. In yet another aspect, each of $Z^1$, $Z^2$, and $Z^3$ independently is absent. In another aspect, $Z^1$ and $Z^2$ are absent and $Z^3$ is present. In yet another aspect, $Z^2$ and $Z^3$ are absent and $Z^1$ is present. In yet another aspect, $Z^1$ and $Z^3$ are absent and $Z^2$ is present.

In one aspect, the compound can have the structure

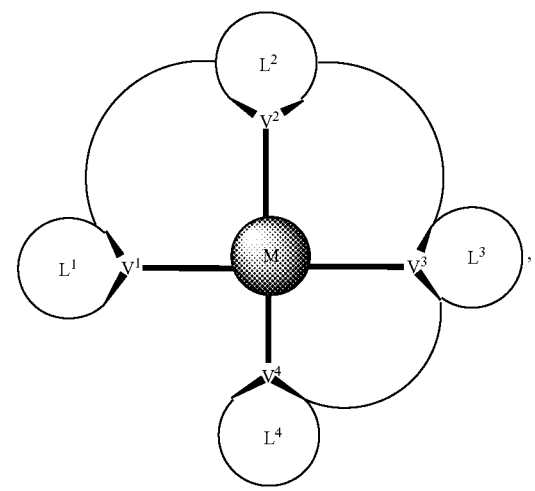

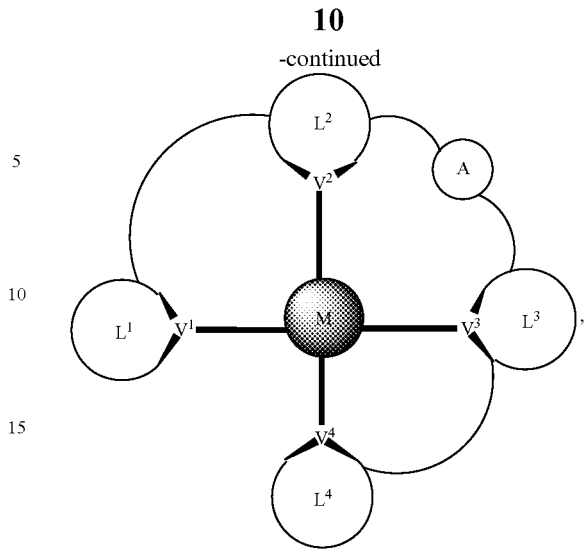

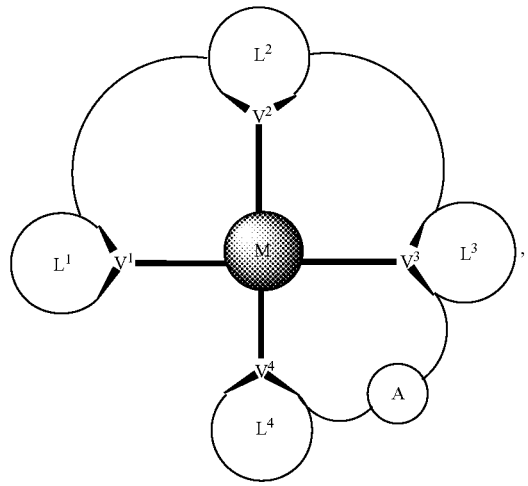

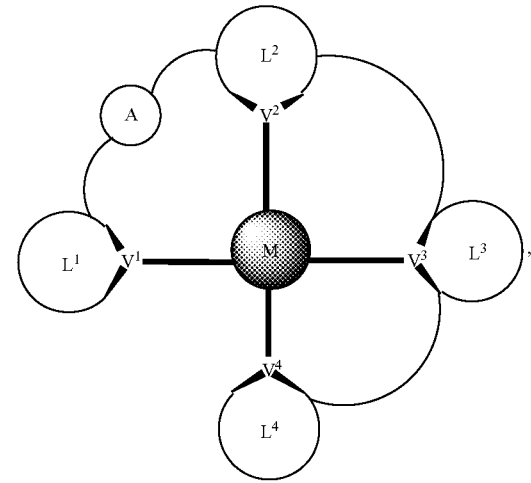

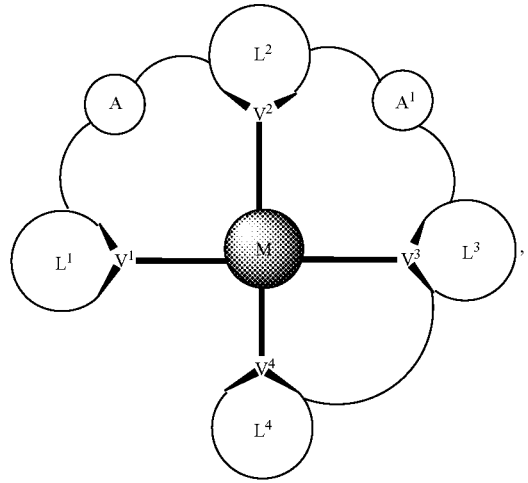

-continued
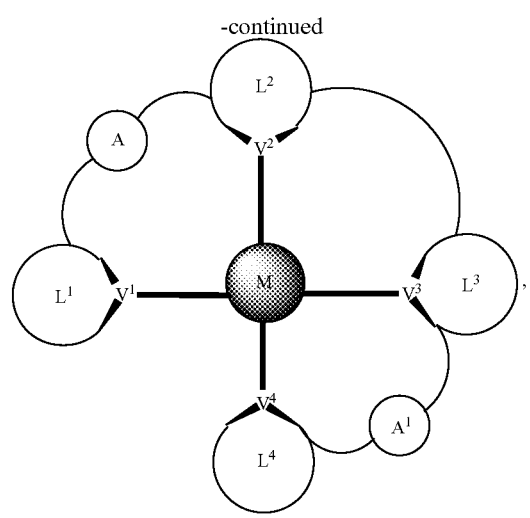
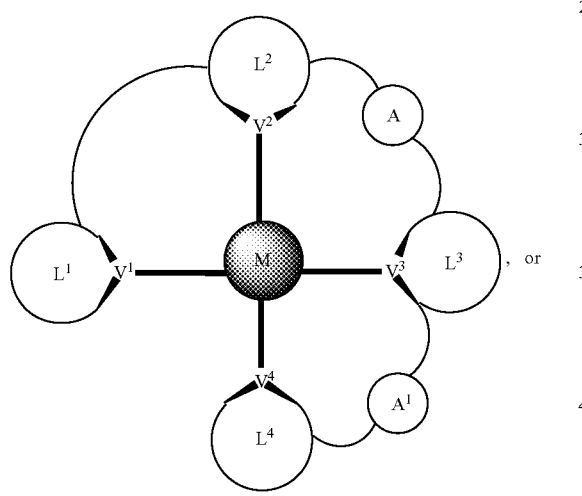
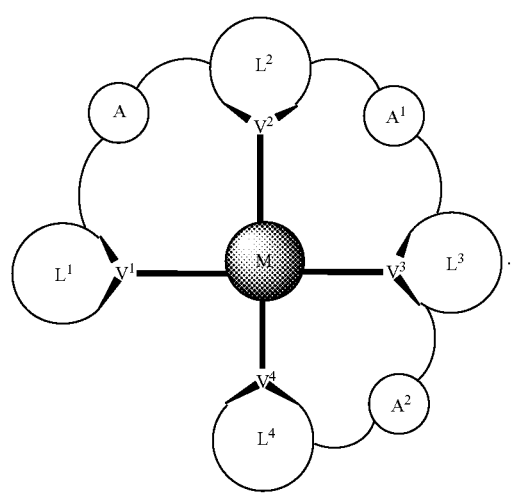
In another aspect, the compound can have the structure:
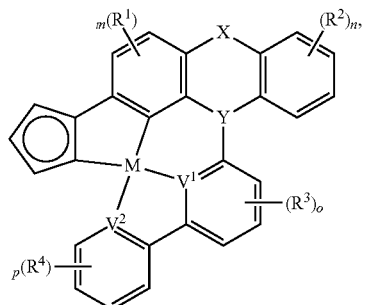
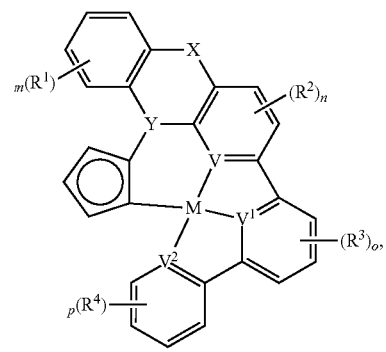
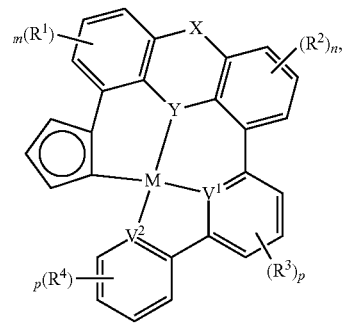
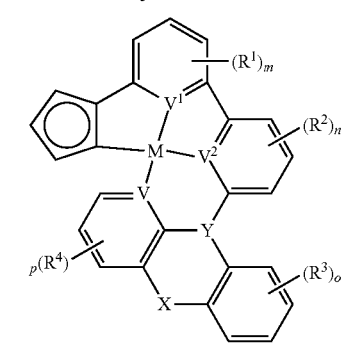
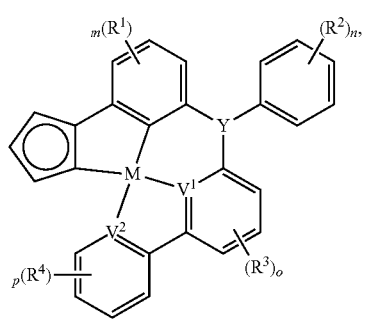

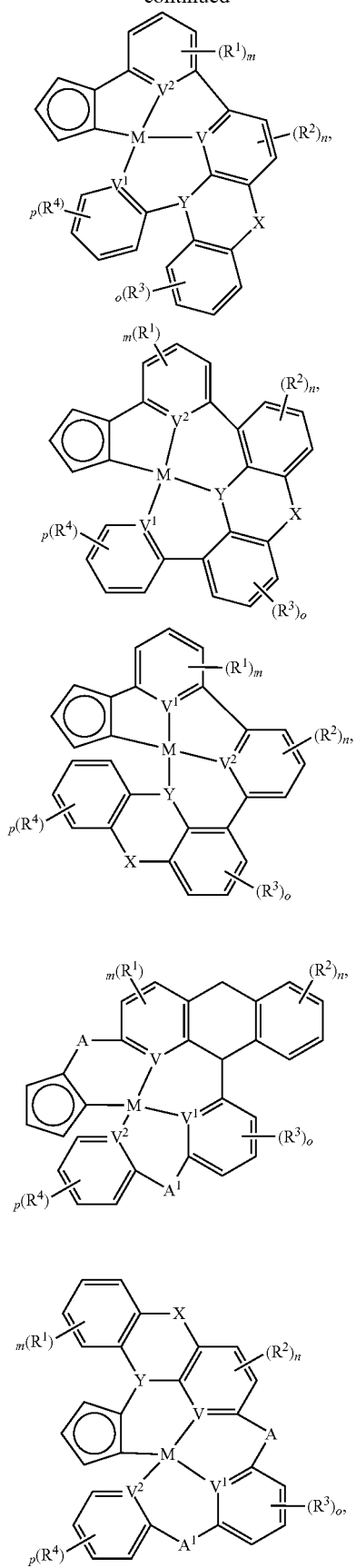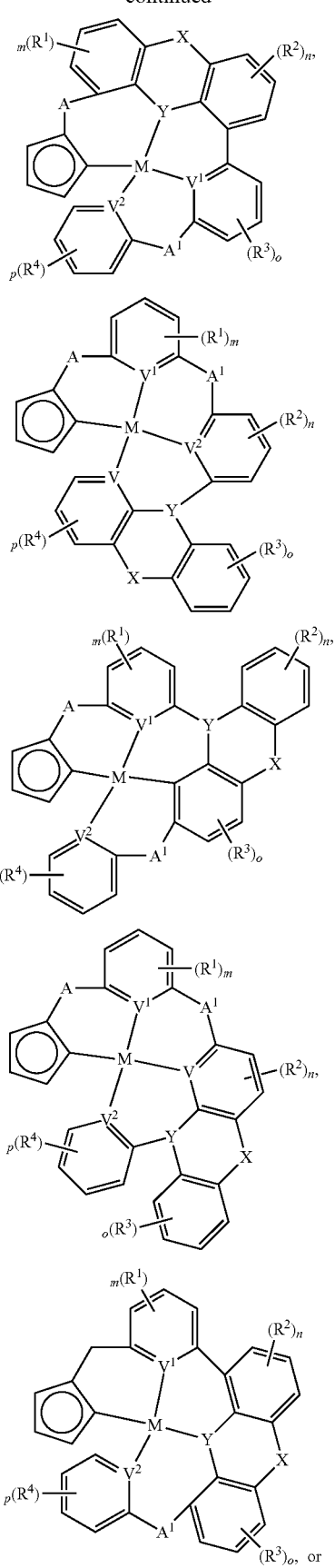

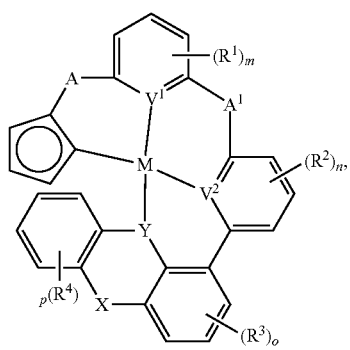
wherein each of o and p independently is an integer of 0 to 4.
In another aspect, the compound can have the structure:
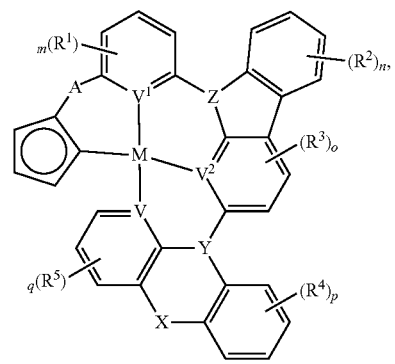
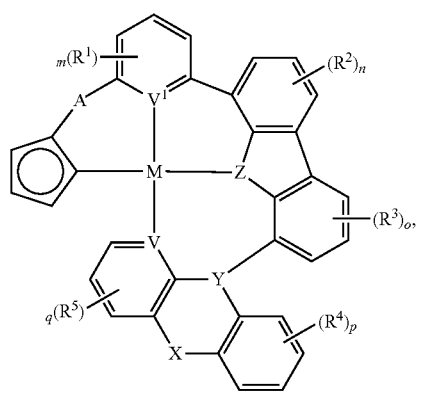
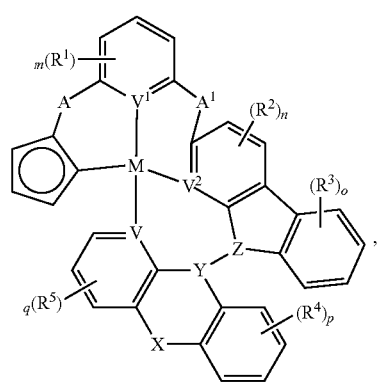
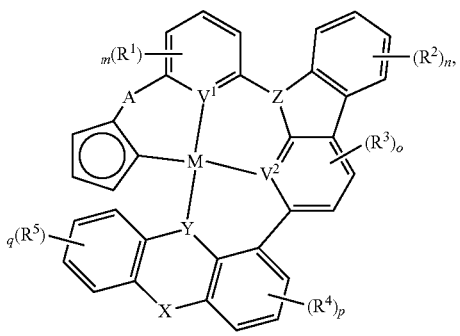
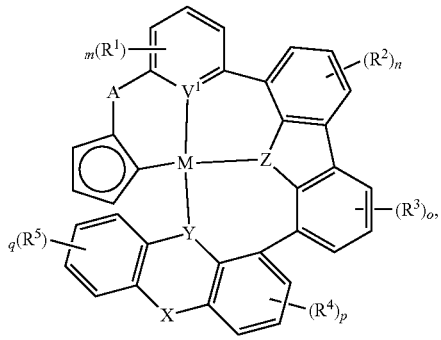
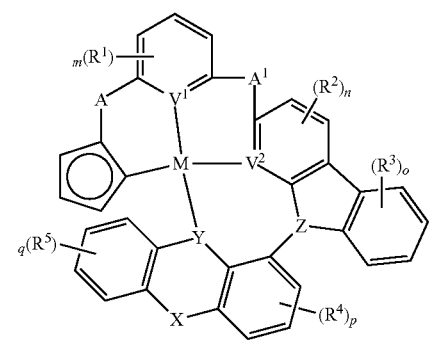
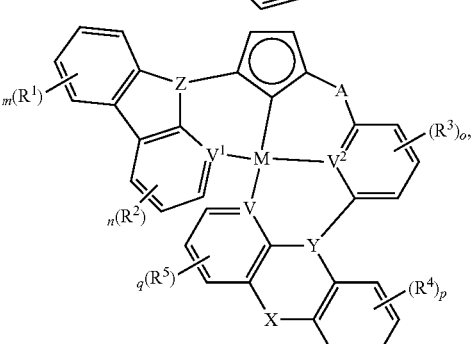
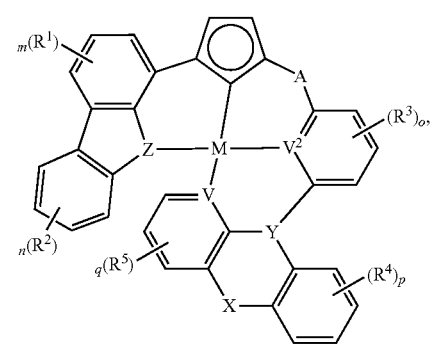

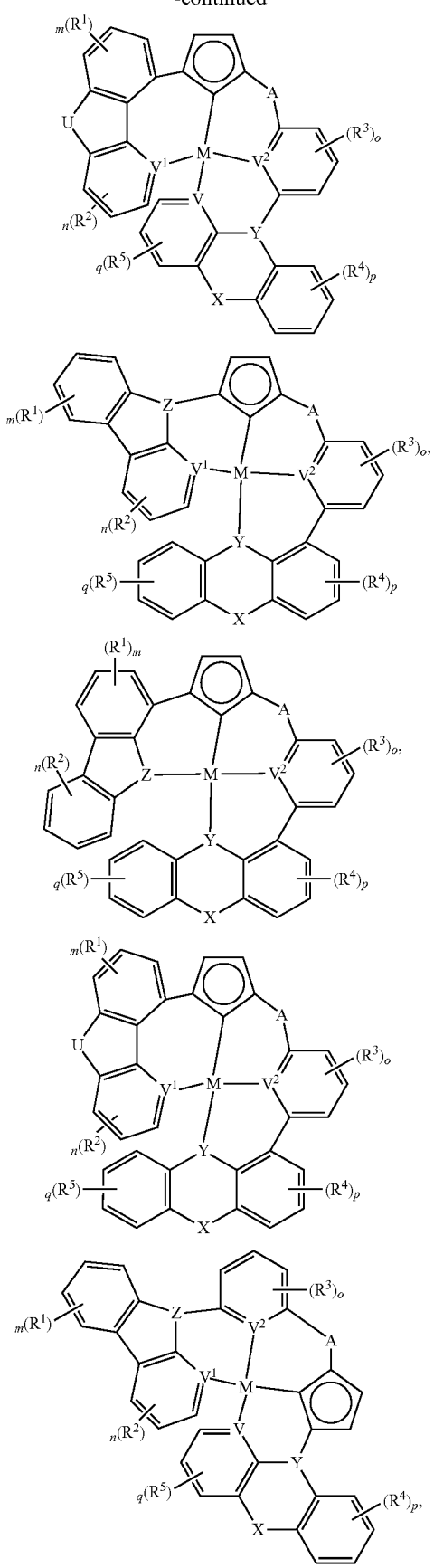
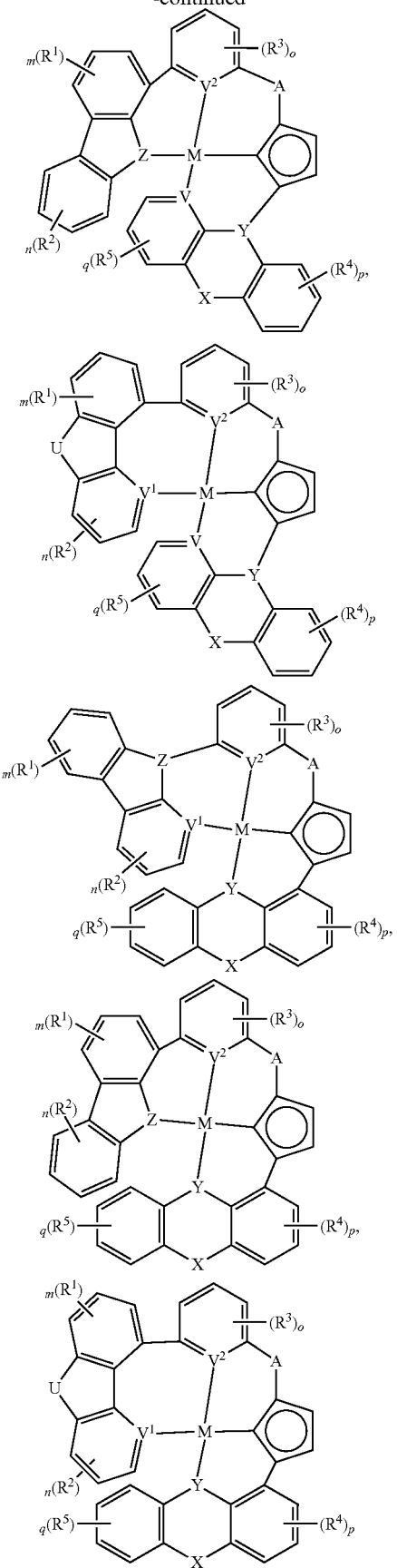

-continued
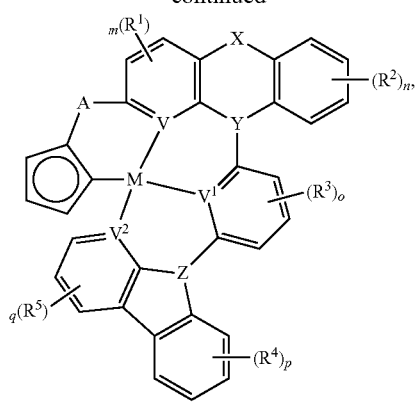
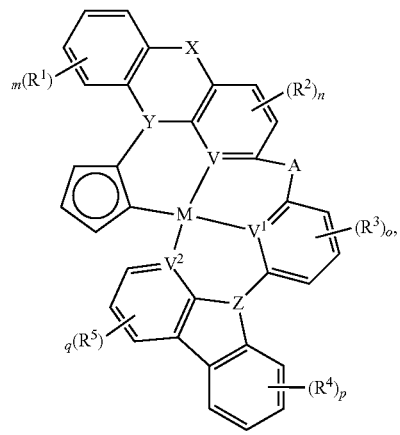
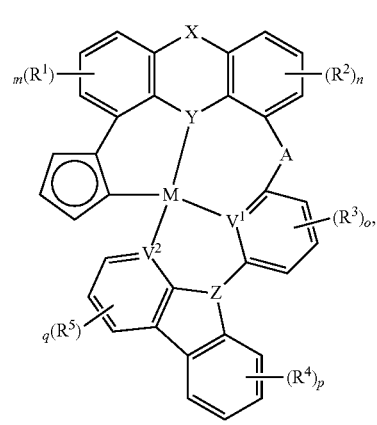
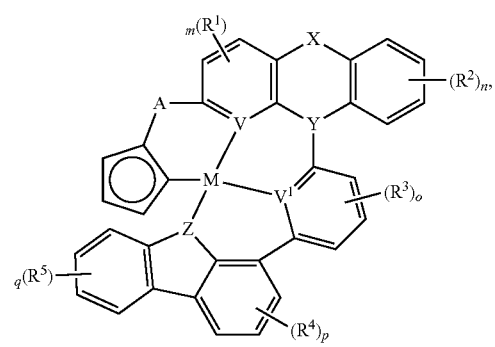
-continued
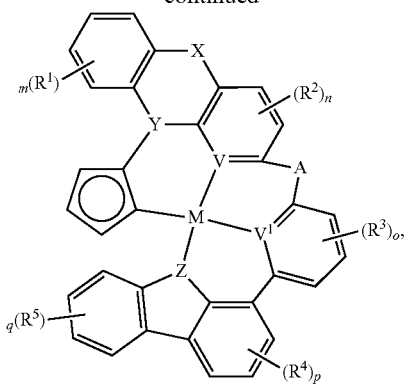
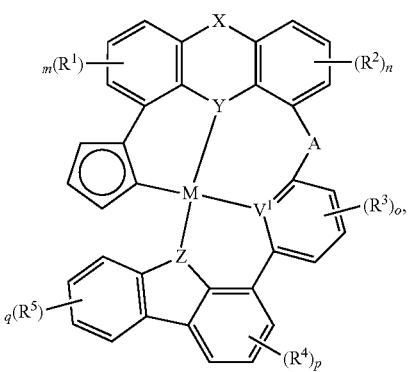
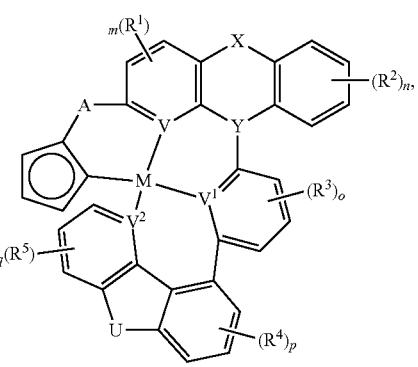
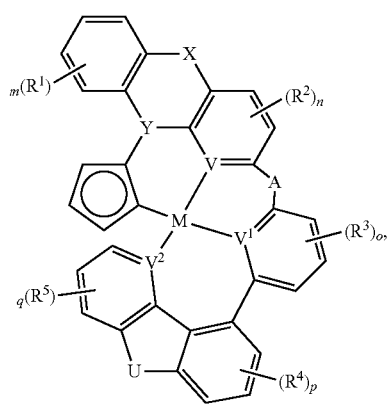

-continued
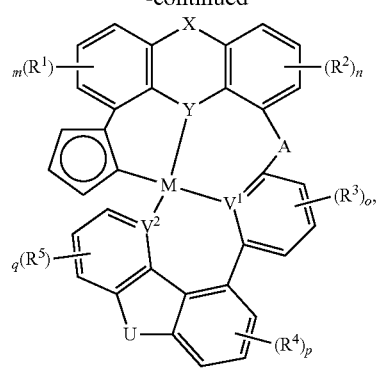
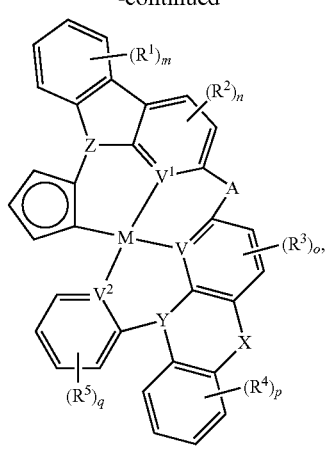
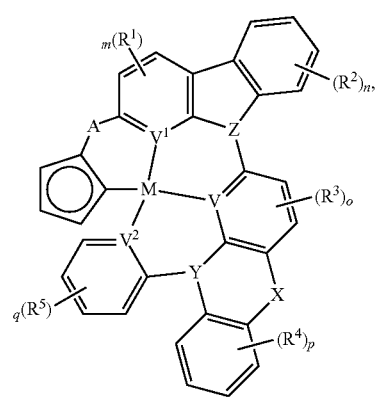
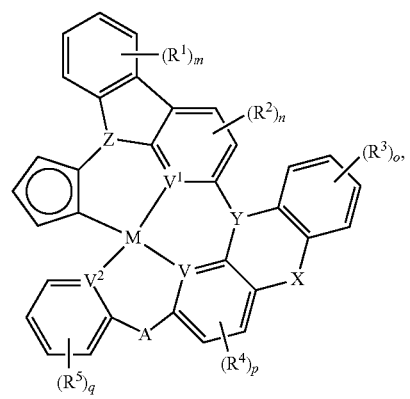
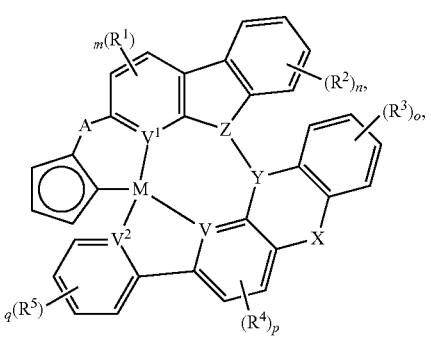
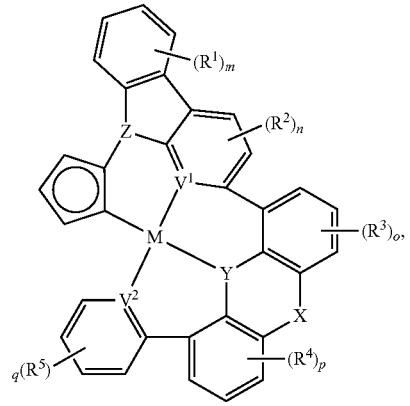
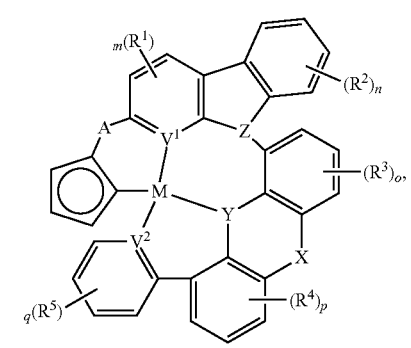
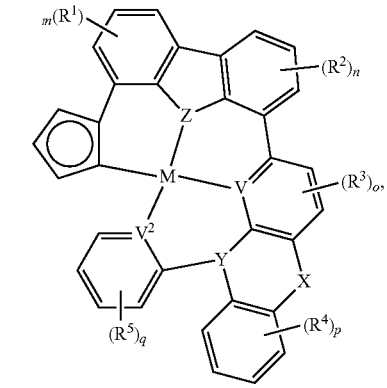

-continued
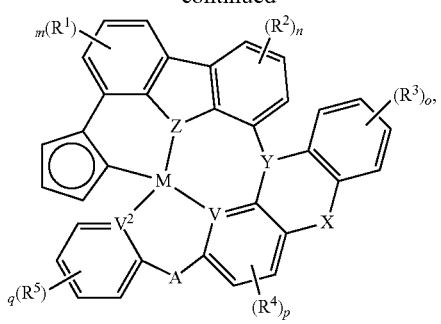
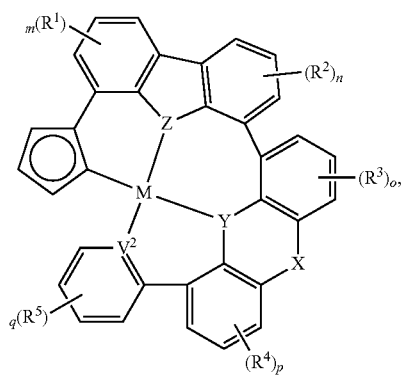
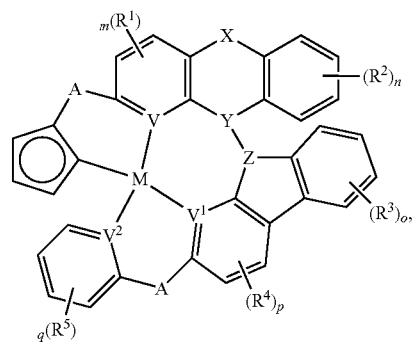
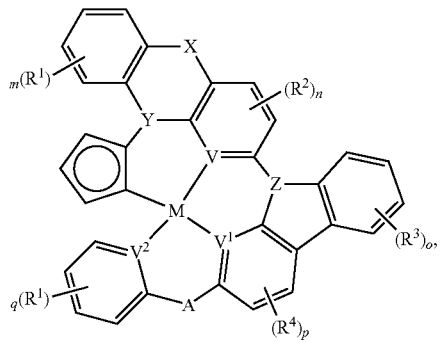
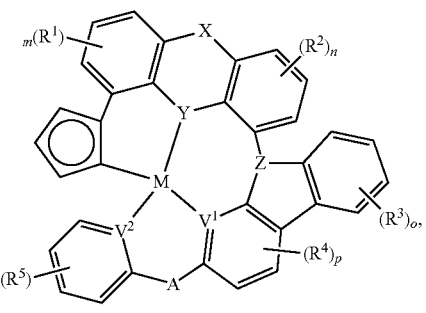
-continued
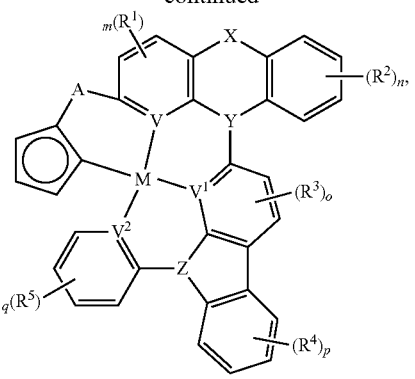
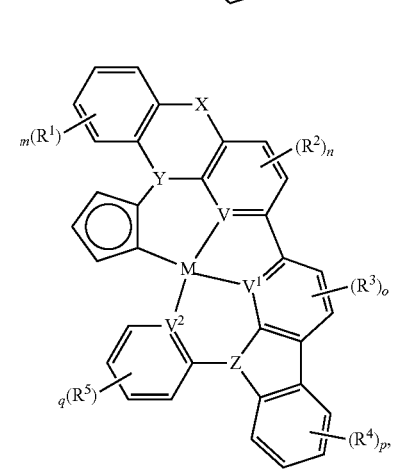
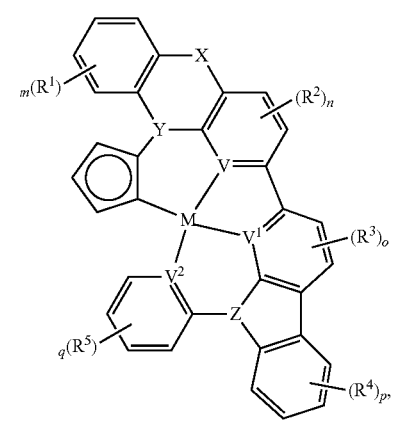
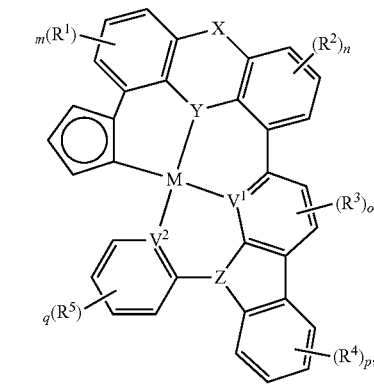
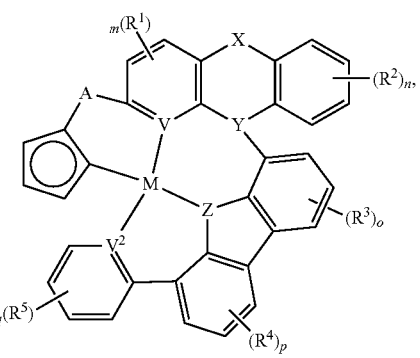

-continued
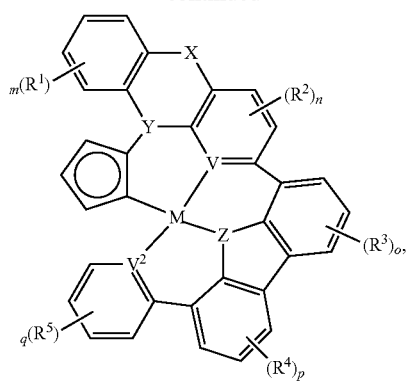
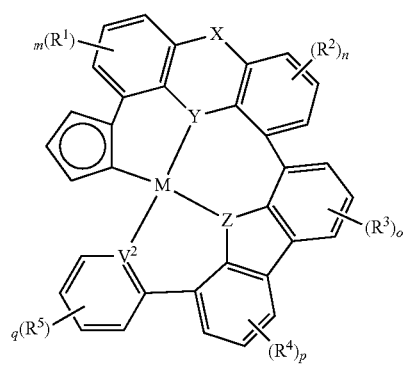
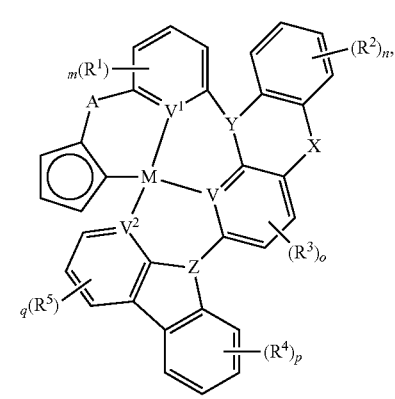
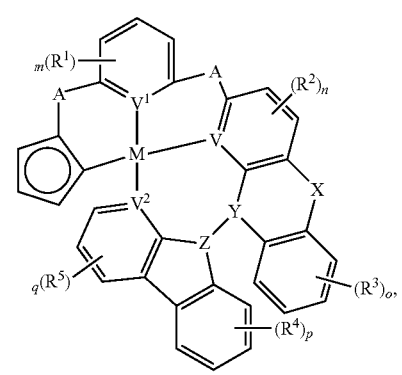
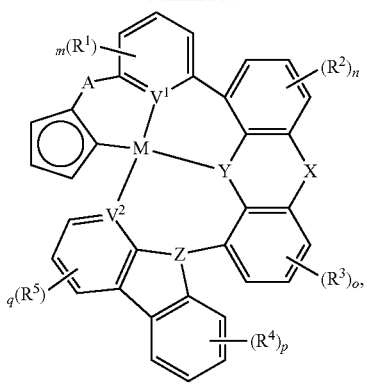
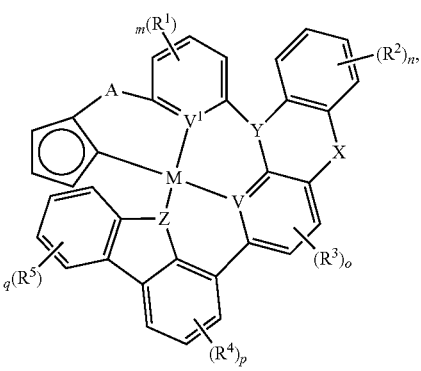
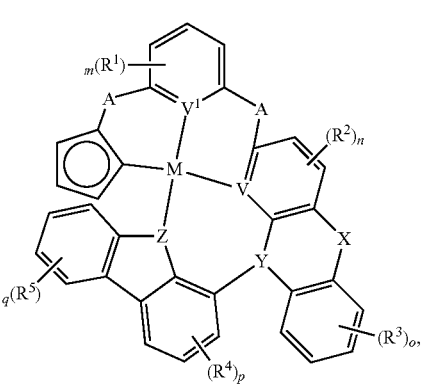
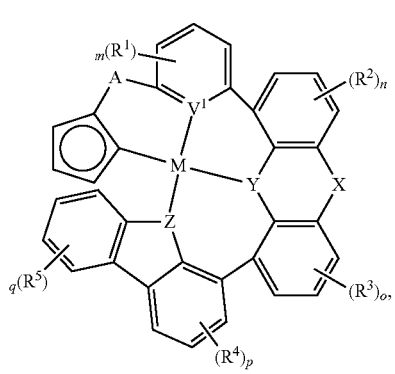

-continued
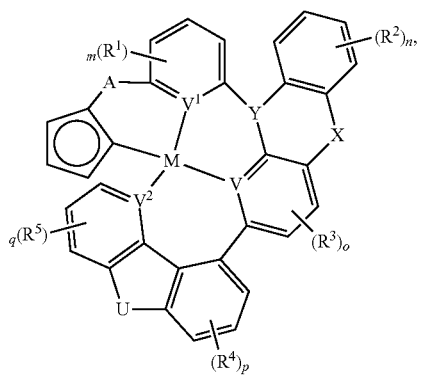
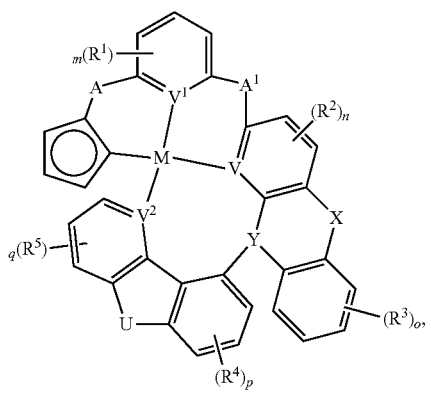
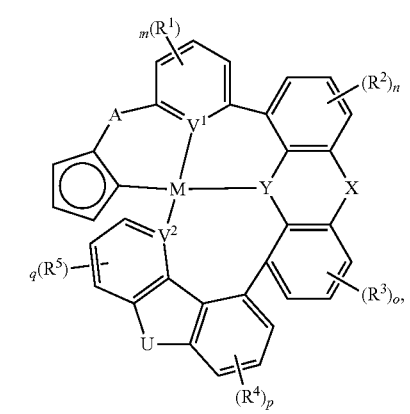
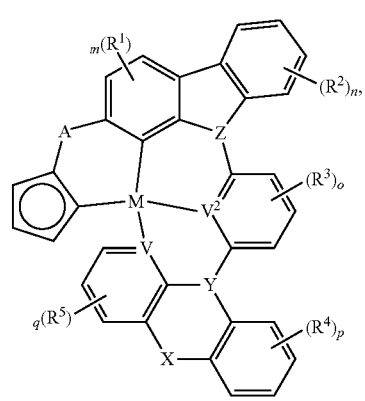
-continued
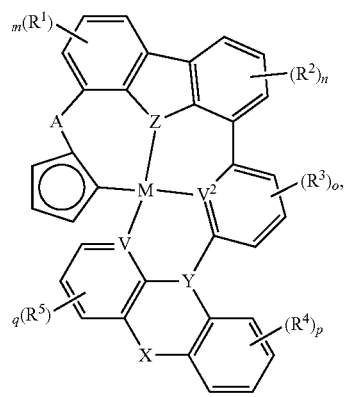
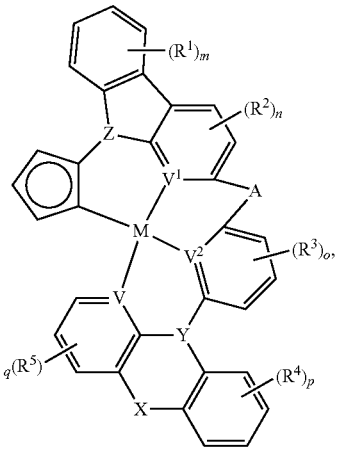
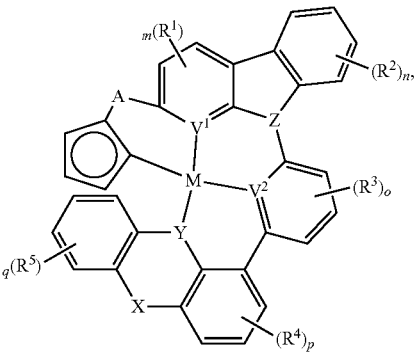
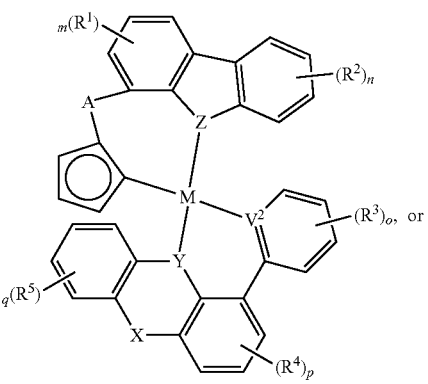

-continued

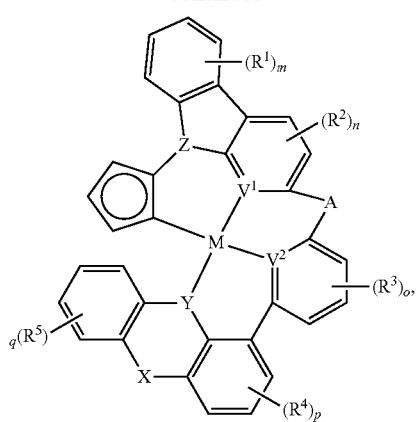

wherein each of o, p, and q independently is an integer of 0 to 4, wherein each of Z and U independently is $V^1$, $V^2$, $V^3$, $V^4$, O, S, S=O, SO$_2$, Se, NR$^3$, PR$^3$, R$^1$P=O, CR$^1$R$^2$, C=O, SiR$^1$R$^2$, GeR$^1$R$^2$, BH, P(O)H, PH, NH, CR$^1$H, CH$_2$, SiH$_2$, SiHR$^1$, BH, or BR$^3$, or any one of

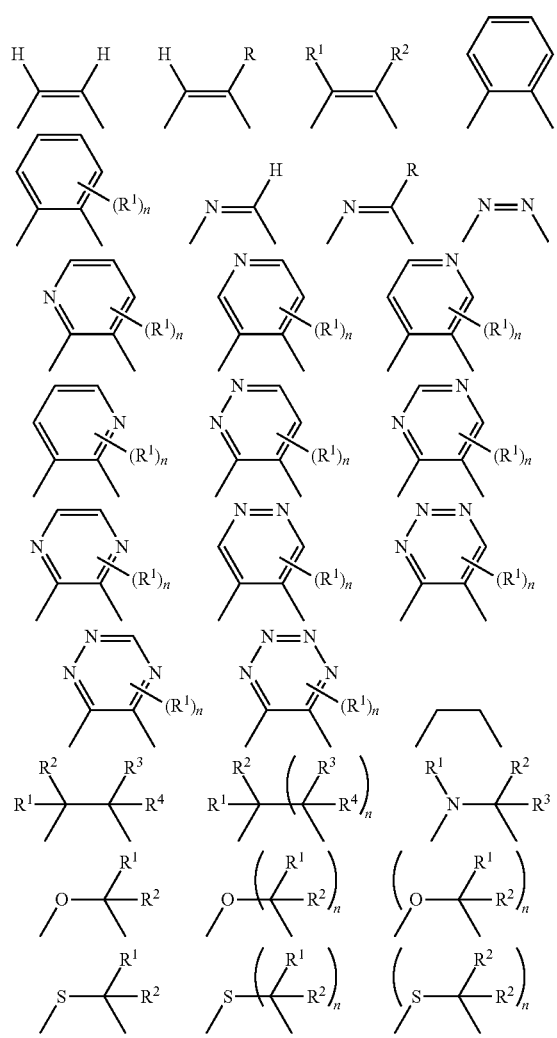

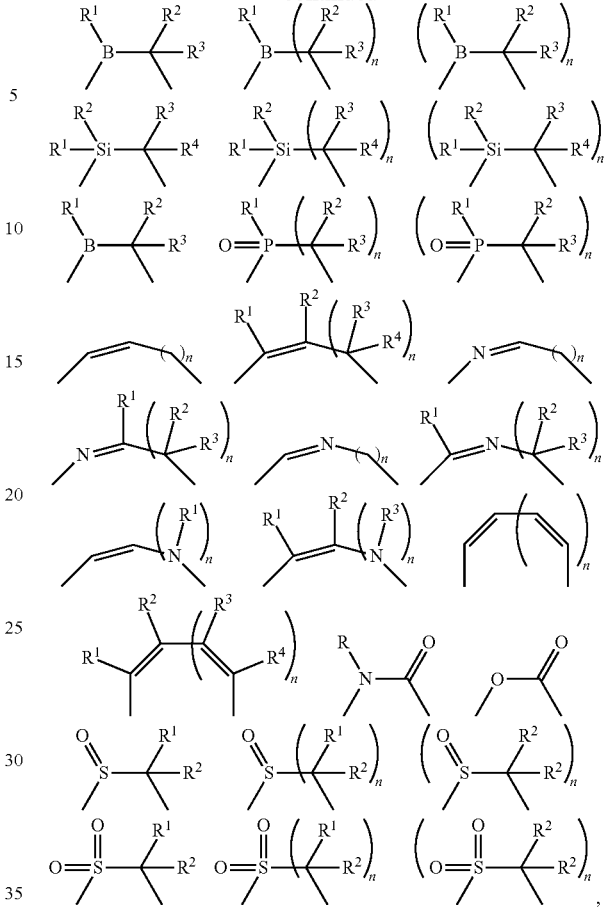

wherein at least one of U, V, X, Y, and Z is $V^1$, $V^2$, $V^3$, or $V^4$.

wherein each $R^5$ independently is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof In one aspect, the compound can have the structure:

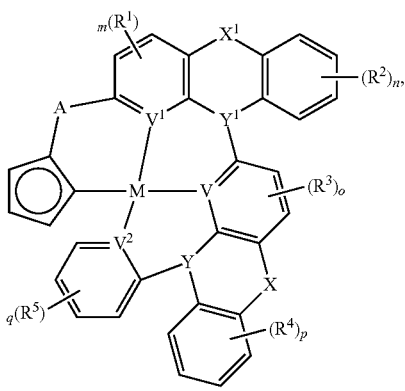

-continued
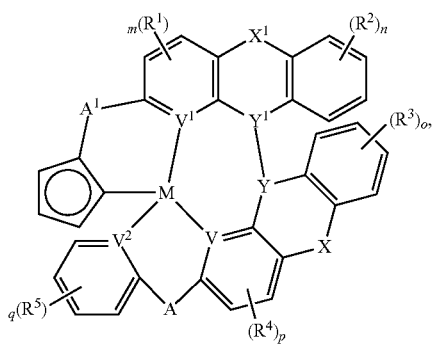
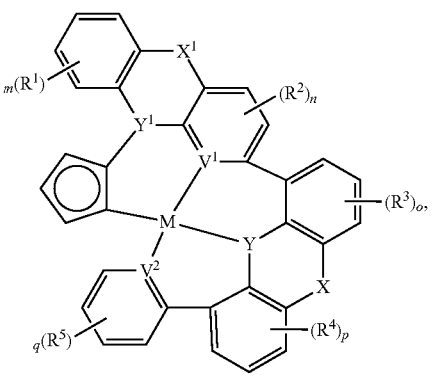
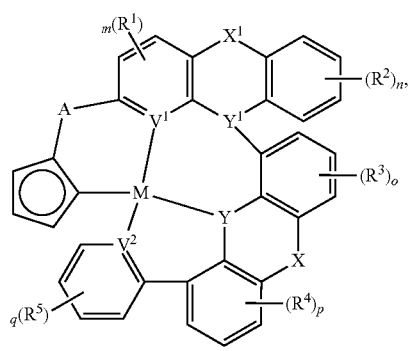
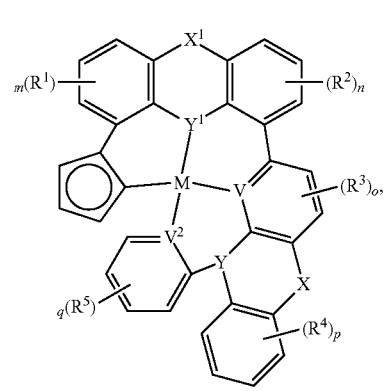
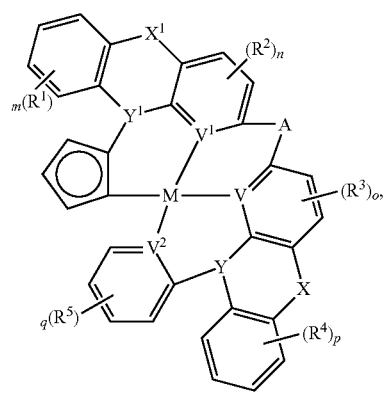
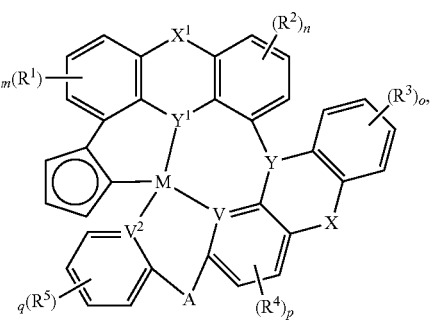
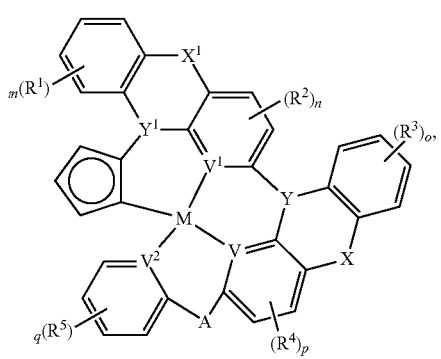
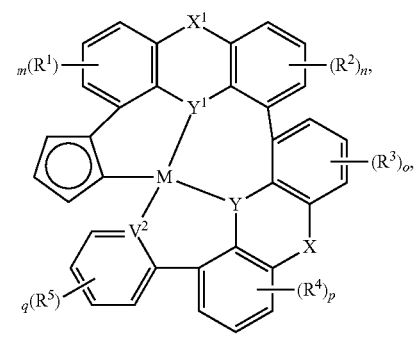

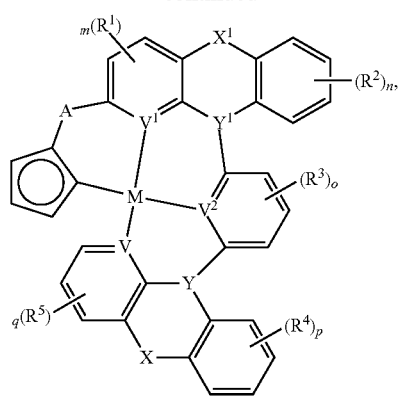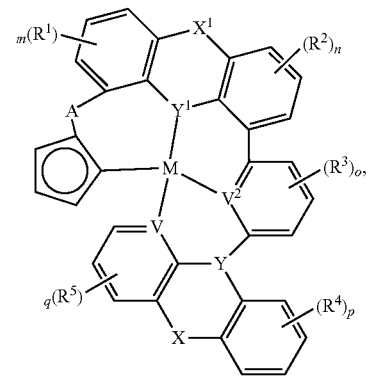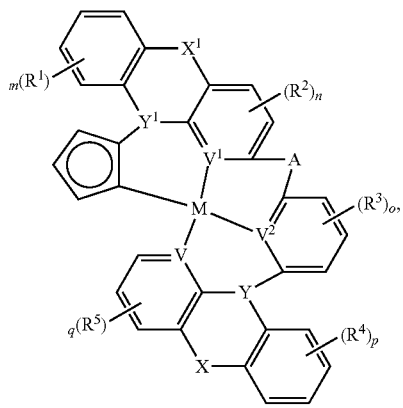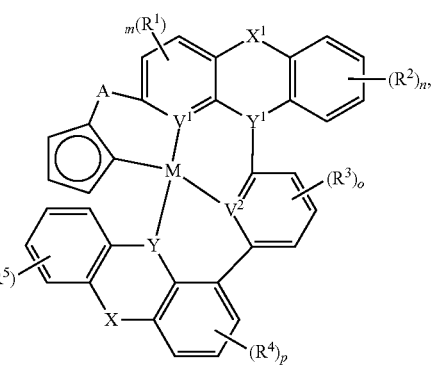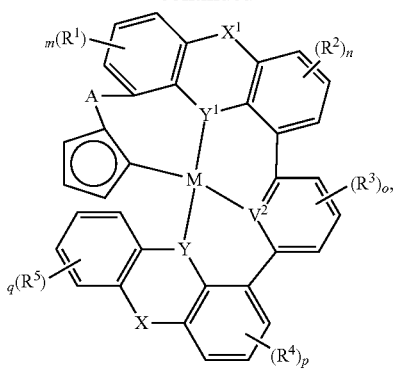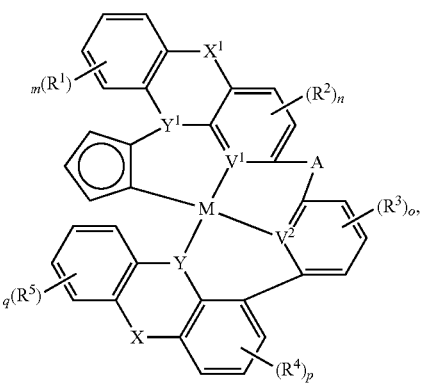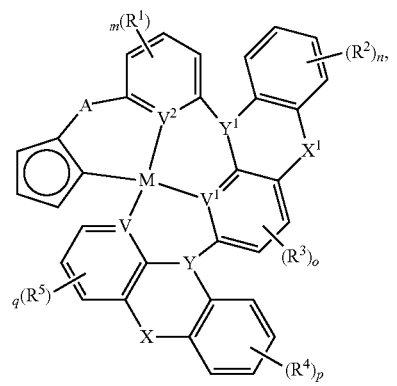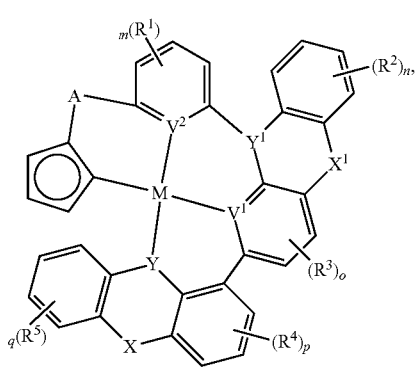

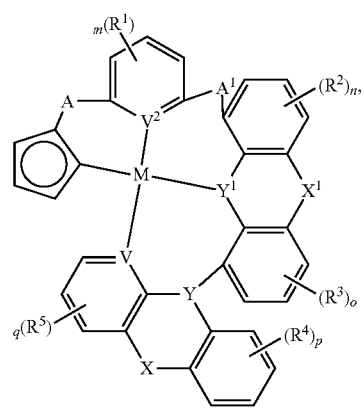
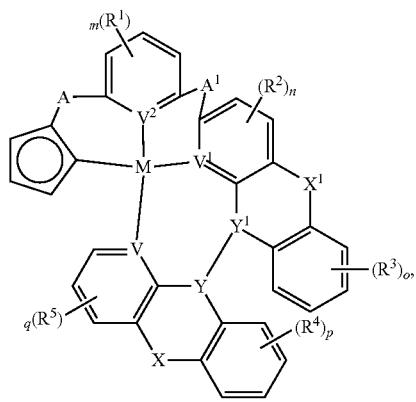
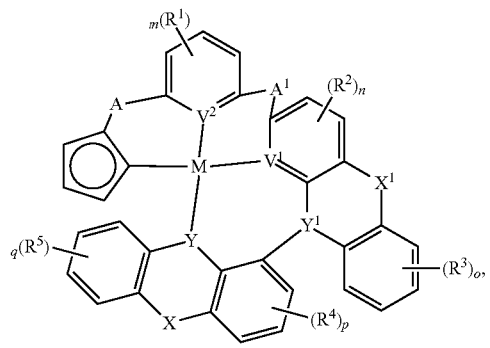
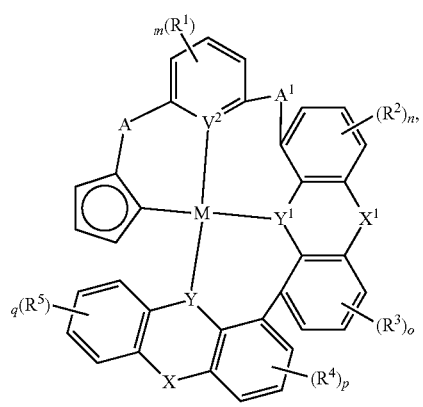
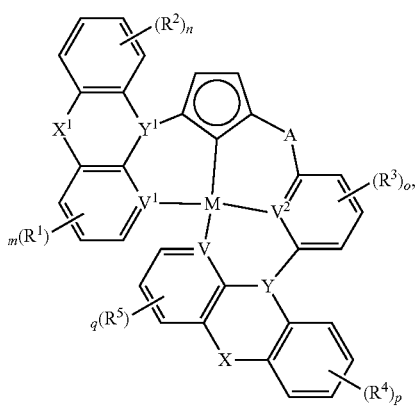
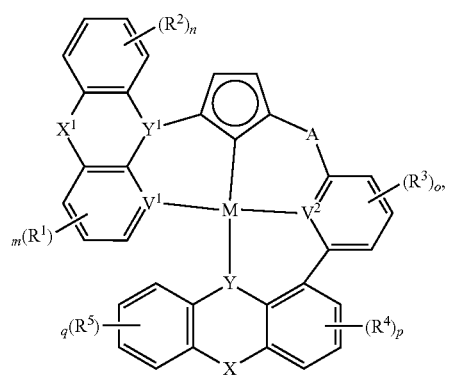
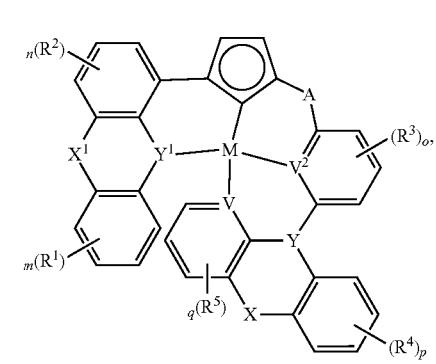
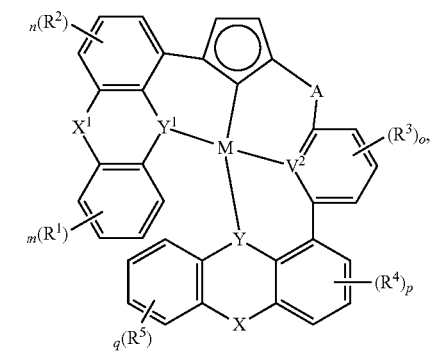

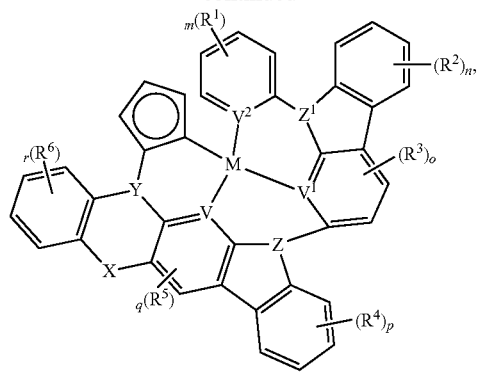
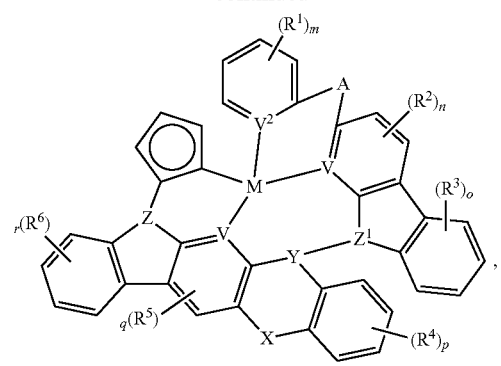
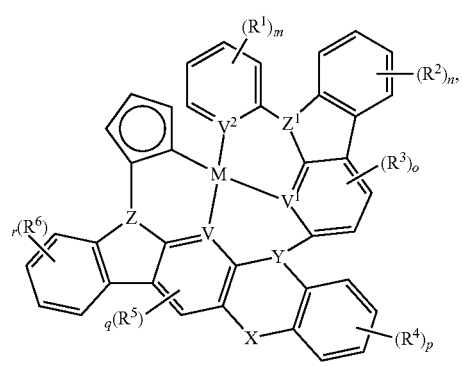
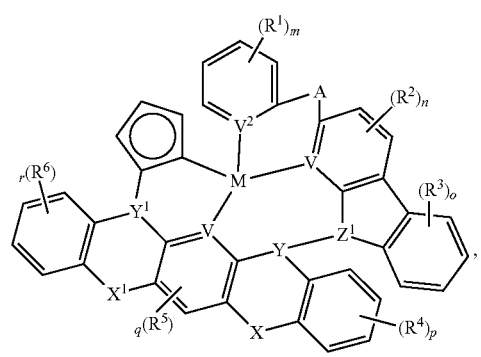
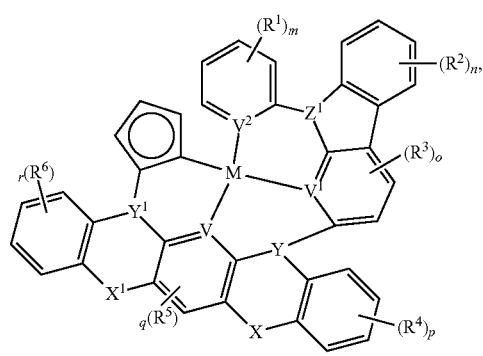
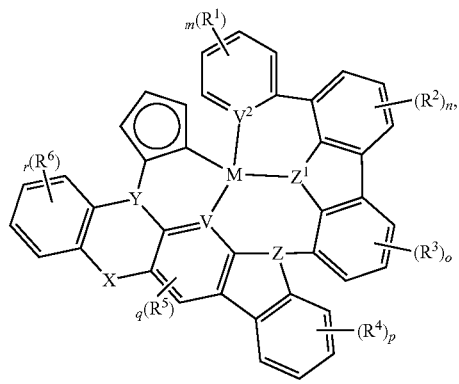
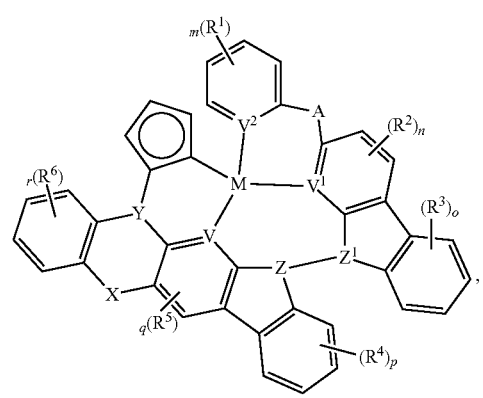
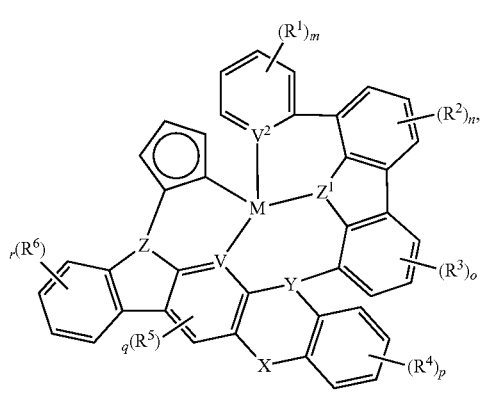

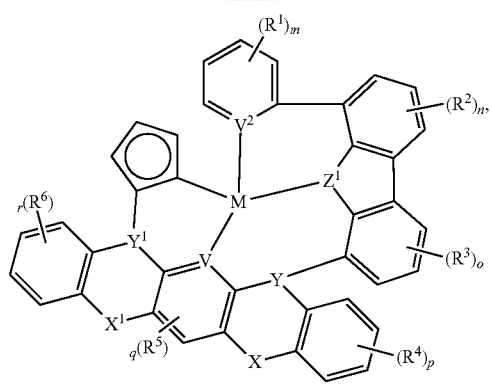
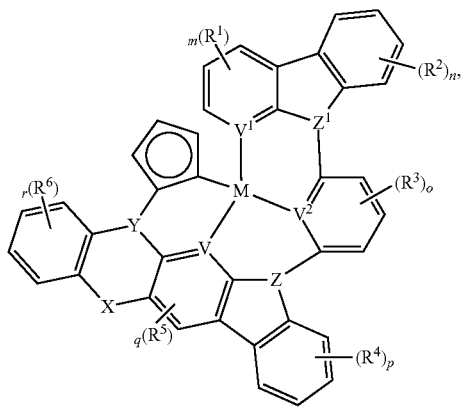
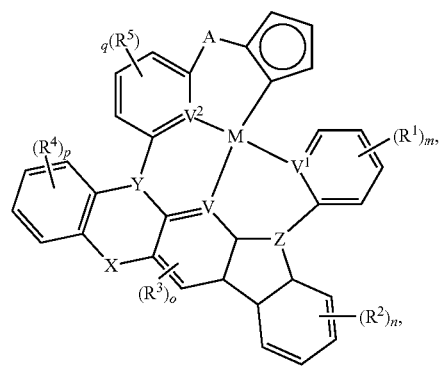
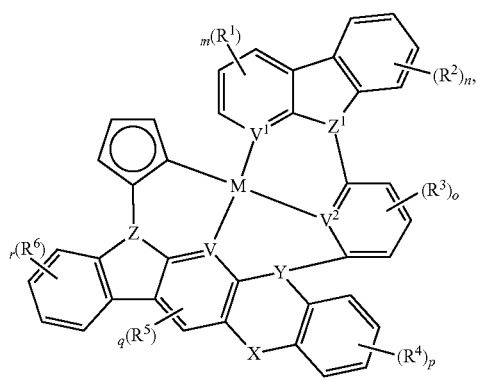
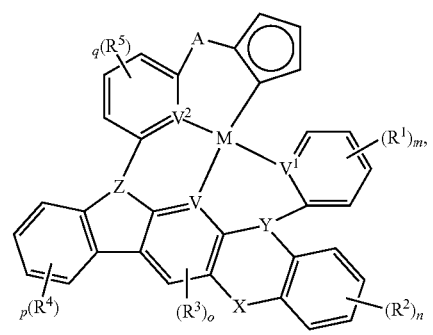
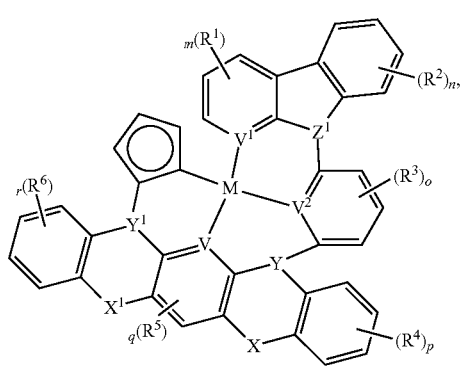
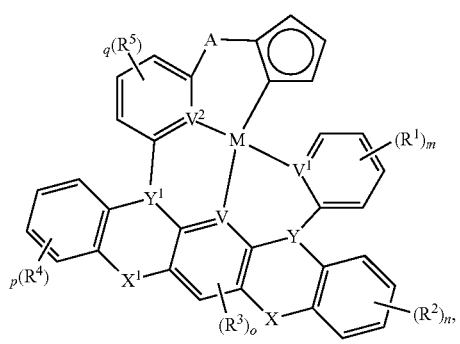
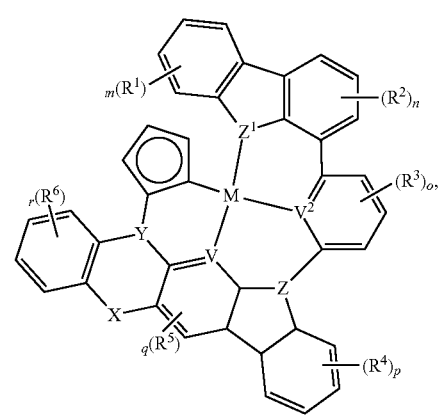

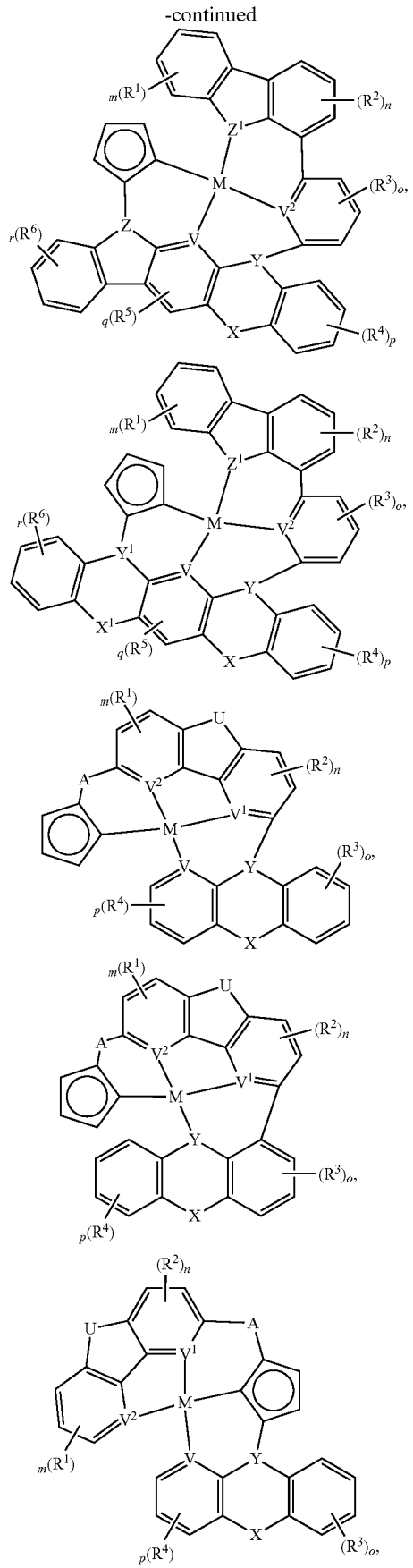
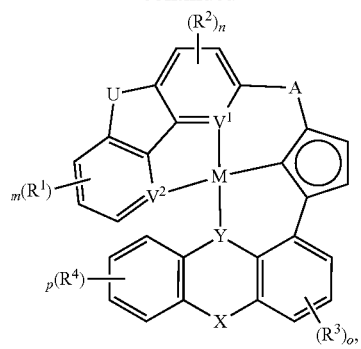
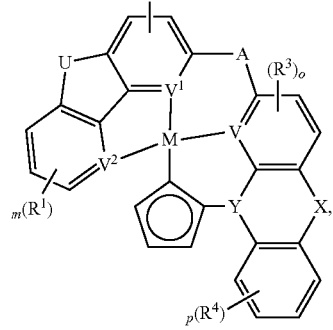
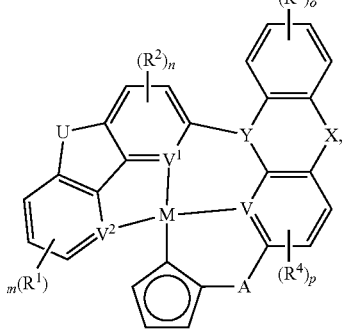
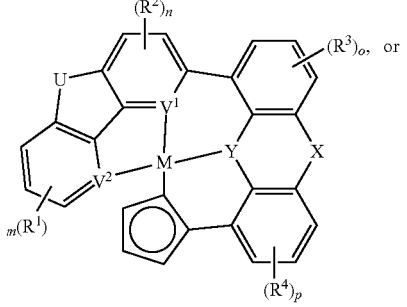, or
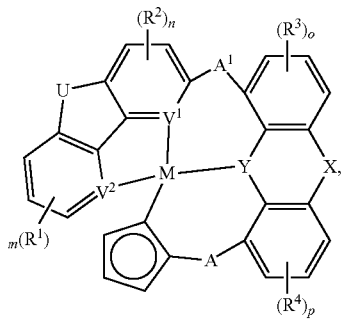

wherein each of o, p, q, and r independently is an integer of 0 to 4, wherein each of U, Y$^1$, X$^1$, Z, and Z$^1$, independently is V$^1$, V$^2$, V$^3$, V$^4$, O, S, S=O, SO$_2$, Se, NR$^3$, PR$^3$, R$^1$P=O, CR$^1$R$^2$, C=O, SiR$^1$R$^2$, GeR$^1$R$^2$, BH, P(O)H, PH, NH, CR$^1$H, CH$_2$, SiH$_2$, SiHR$^1$, BH, or BR$^3$, or any one of

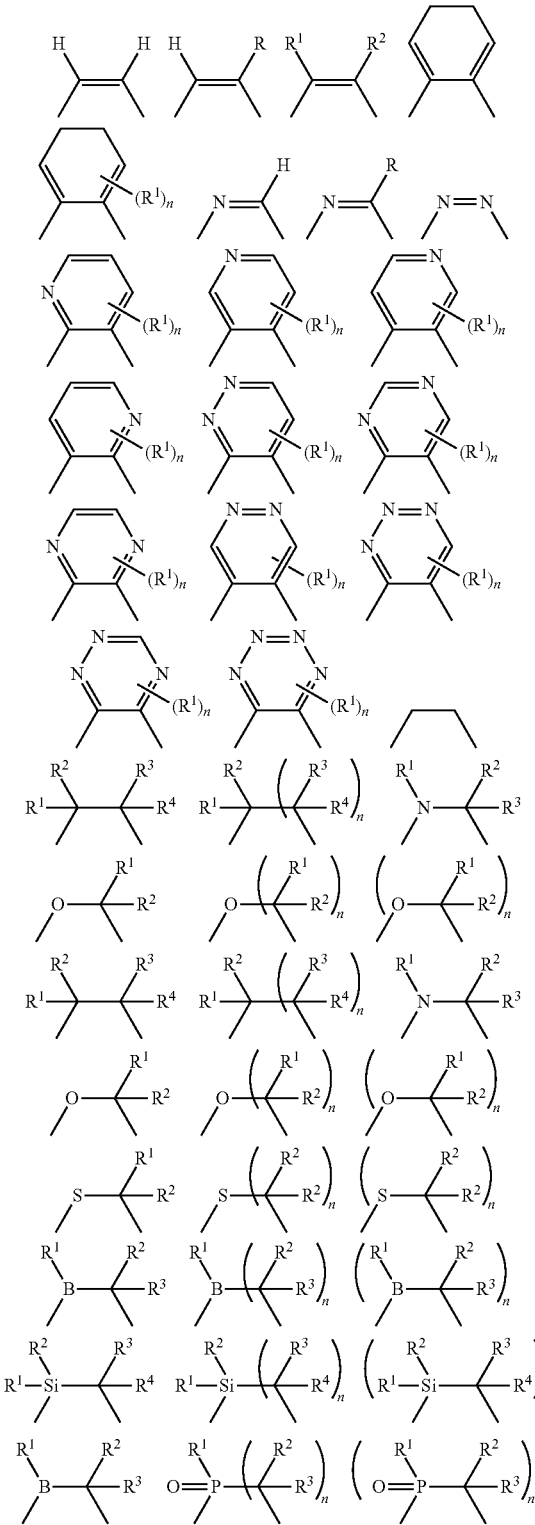

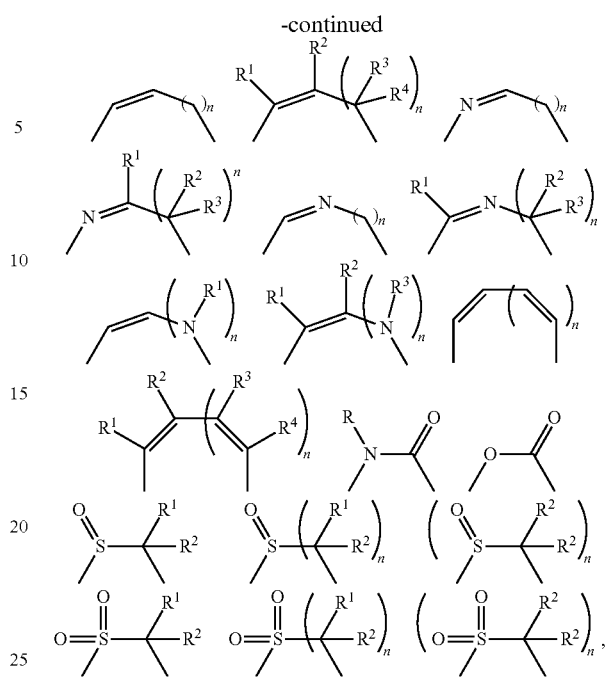

wherein at least one of U, V, X, Y, and Z is V$^1$, V$^2$, V$^3$, or V$^4$, wherein each R$^5$ independently is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, in the disclosed compounds,

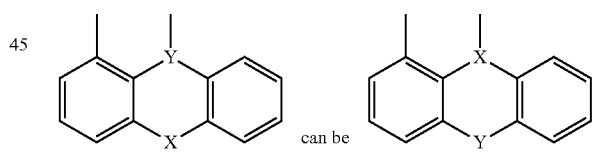

In one aspect, in the disclosed compounds.

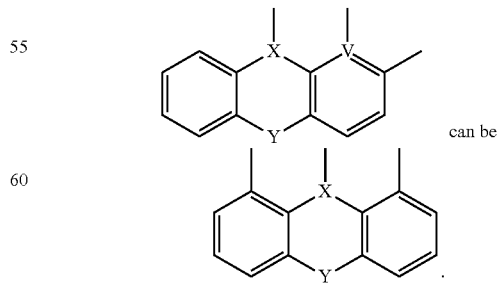

In one aspect, at least two of L$^1$, L$^2$, L$^3$, and L$^4$ is substituted or un substituted aryl or heteroaryl.

In one aspect, at least one of $V^1$, $V^2$, $V^3$, and $V^4$ is N. In another aspect, at least one of $V^1$, $V^2$, $V^3$, and $V^4$ is C. In yet another aspect, at least one of $V^1$, $V^2$, $V^3$, and $V^4$ is N and at least one of $V^1$, $V^2$, $V^3$, and $V^4$ is C. In yet another aspect, at least two of $V^1$, $V^2$, $V^3$, and $V^4$ is N and at least one of $V^1$, $V^2$, $V^3$, and $V^4$ is C. In yet another aspect, at least one of $V^1$, $V^2$, $V^3$, and $V^4$ is N and at least two of $V^1$, $V^2$, $V^3$, and $V^4$ is C.

In one aspect, at least one of $L^1$, $L^2$, $L^3$, and $L^4$ together with $V^1$, $V^2$, $V^3$, and $V^4$ respectively can comprise one or more of the following structures:

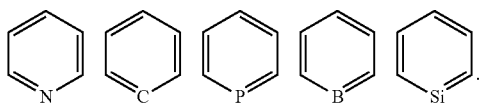

In another aspect, at least one of $L^1$, $L^2$, $L^3$, and $L^4$ together with $V^1$, $V^2$, $V^3$, and $V^4$ respectively or

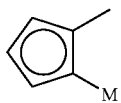

can comprise one or more of the following structures:

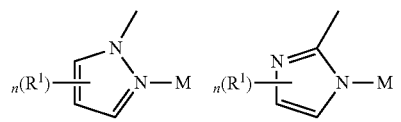
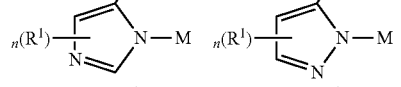
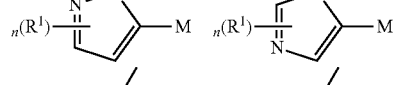

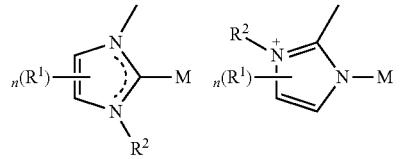

-continued

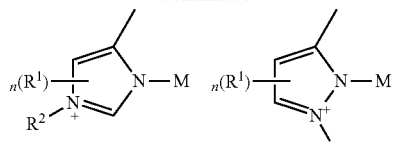
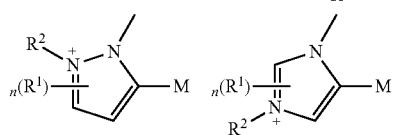
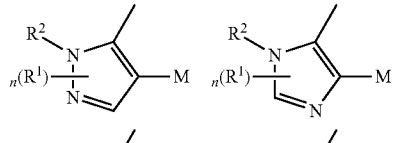
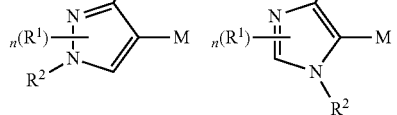
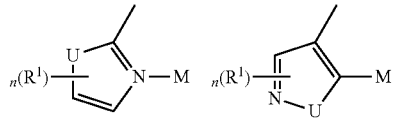
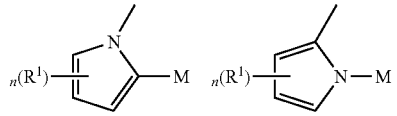
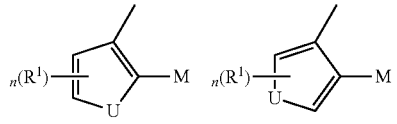
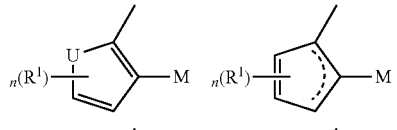
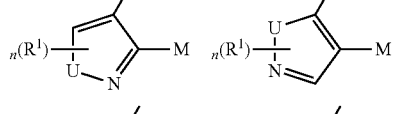
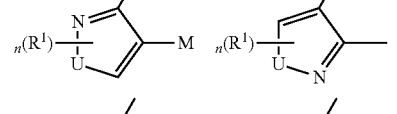
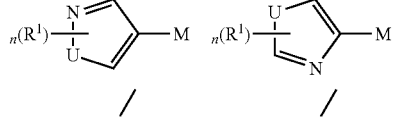
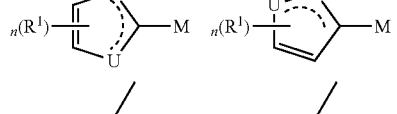
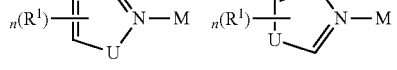

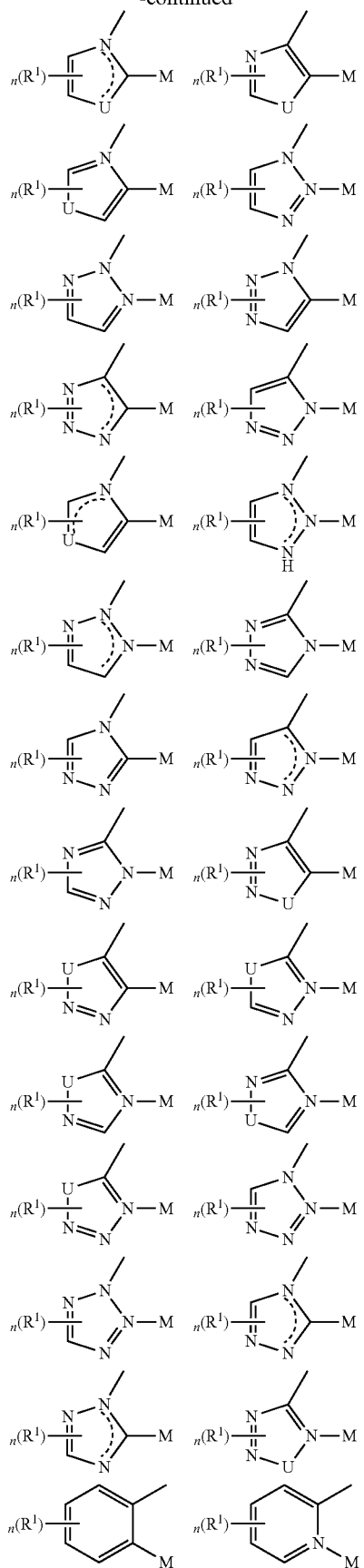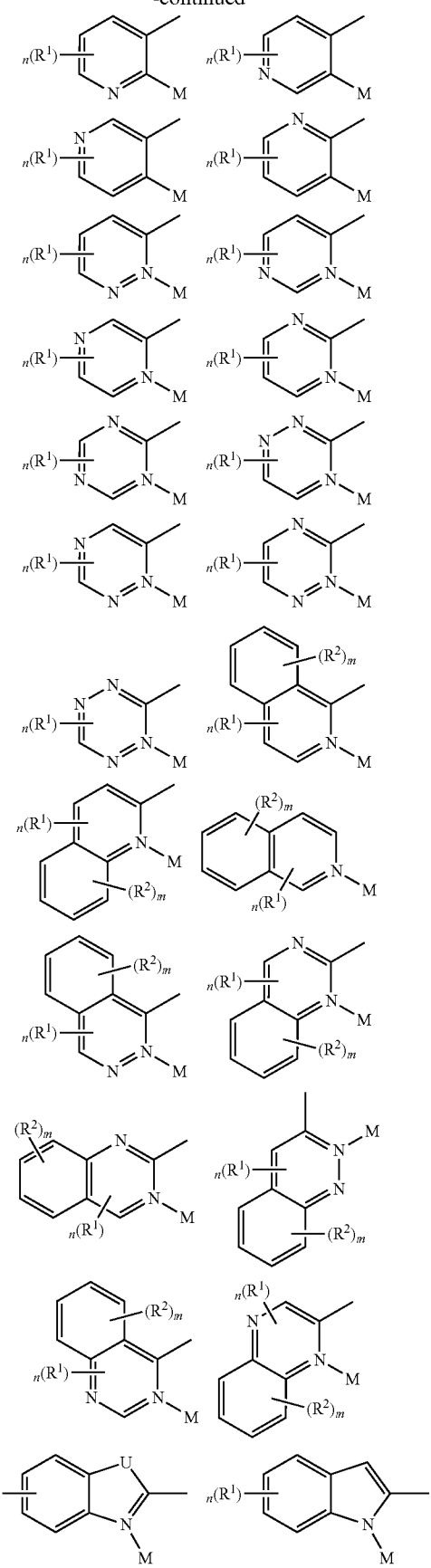

-continued
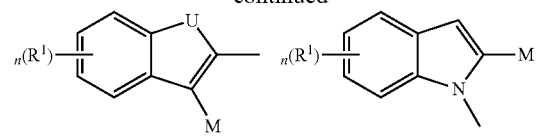
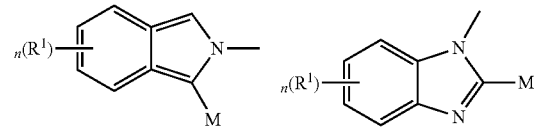
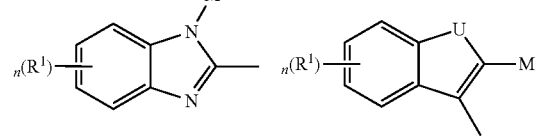
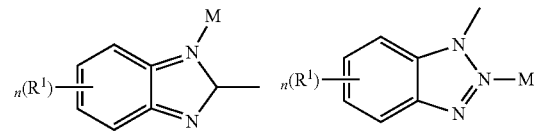
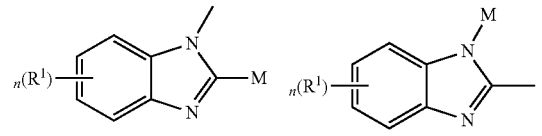
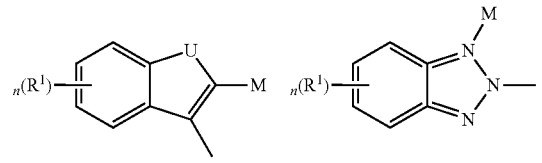
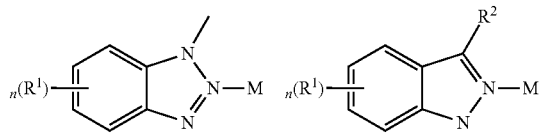
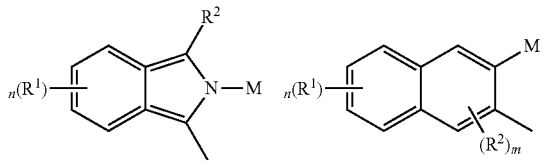
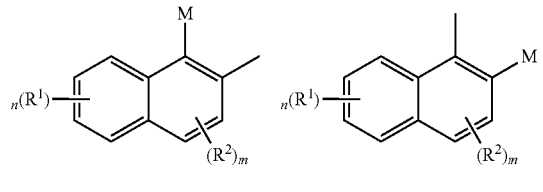
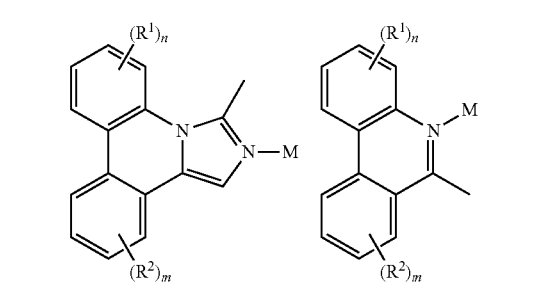
-continued
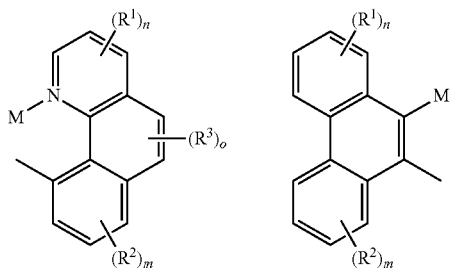
In one aspect,
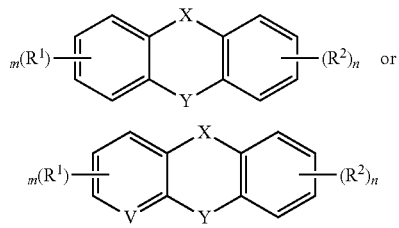
can have the structure
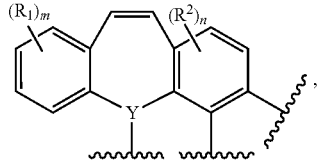
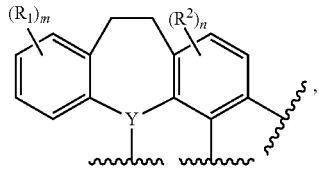
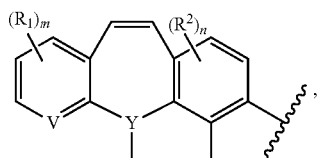
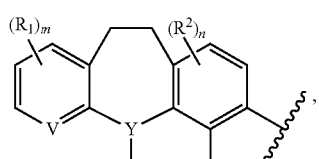
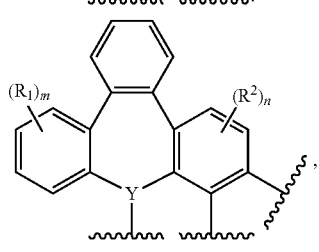

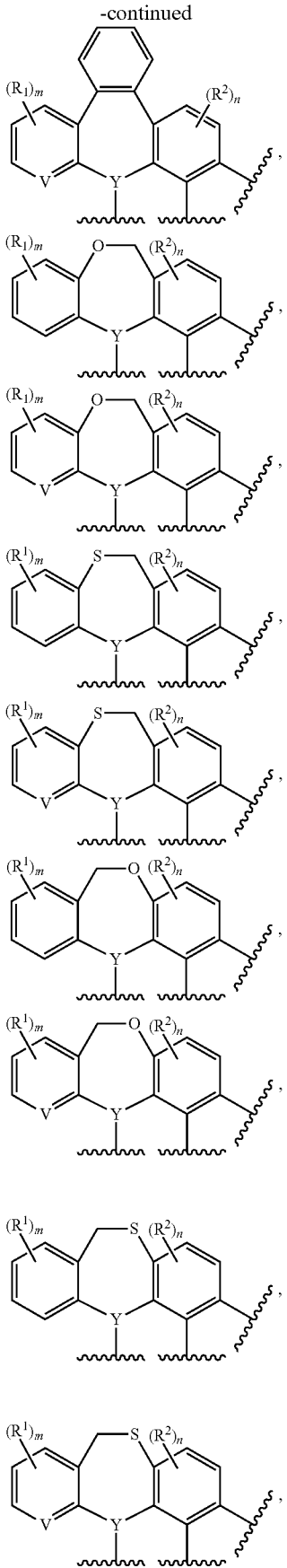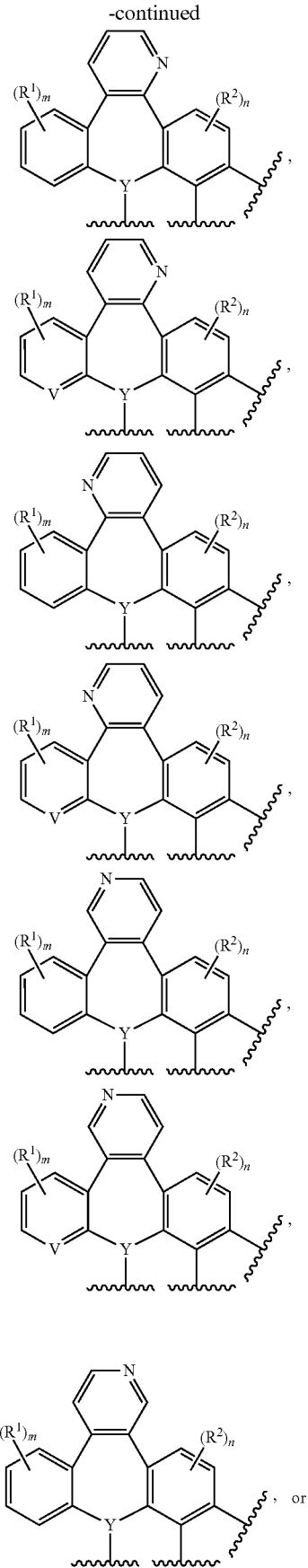

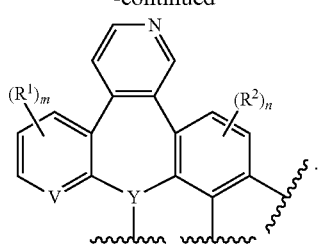
Such as for example,
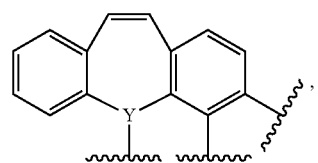
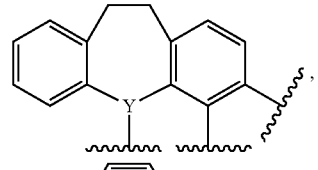

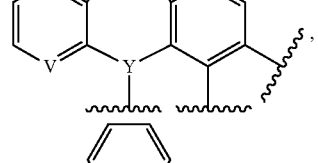
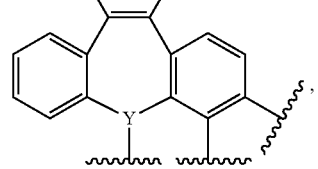
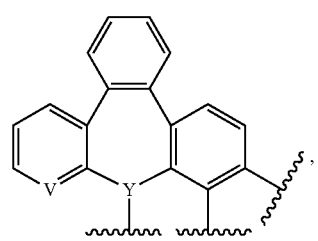
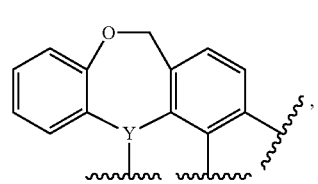
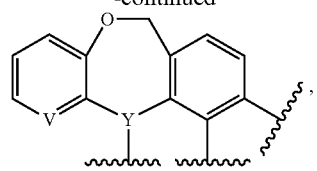
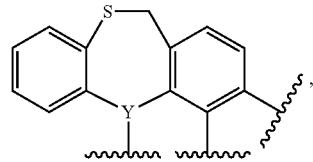
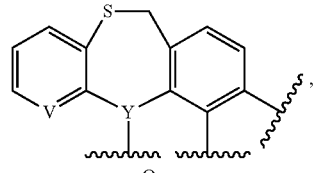

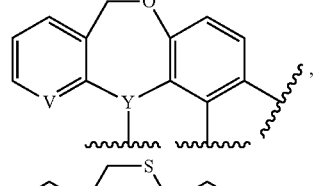

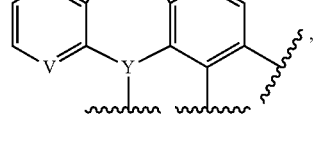
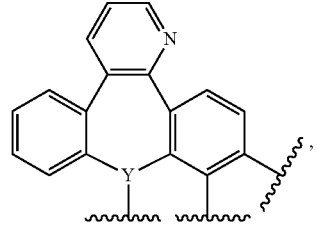
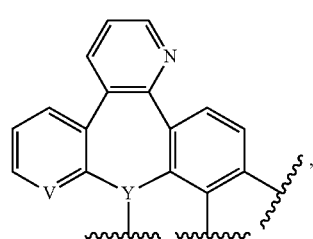

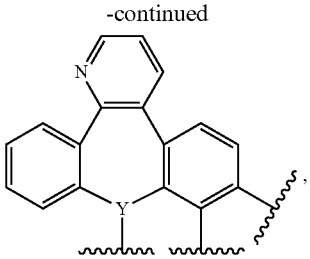,

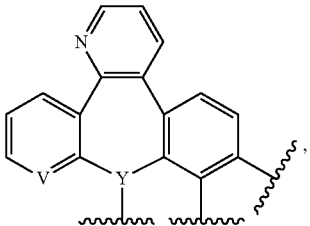,

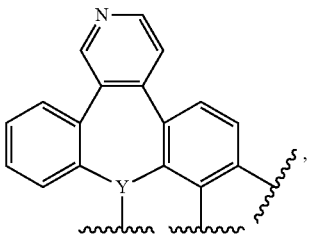,

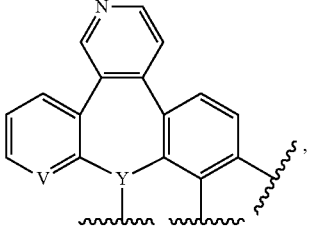,

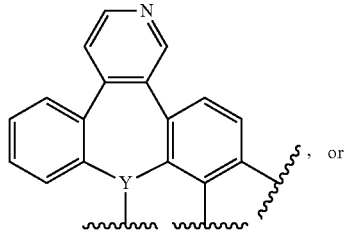, or

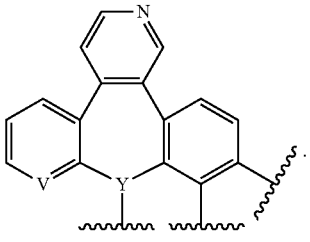.

In one aspect, each of m, n, o, p, q, or r can independently be 0. In another aspect, each of m, n, o, p, q, or r can independently be 0 or 1. In another aspect, each of m, n, o, p, q, or r can independently be 1.

The compound of any one claims 1-10, wherein the compound comprises at least one phenyl and at least one pyridine.

In one aspect, for any of the formulas illustrated in this disclosure,

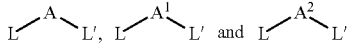

are intended to mean that L and L' are either linked directly or that L and L' are linked by a linkage group, wherein each of the linkage groups can independently be an oxygen (O), sulfur (S), nitrogen (N), phosphor (P), carbon (C), silicon (Si) or boron (B). In another aspect,

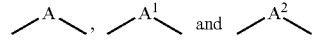

can each independently represent one or more of the following structures:

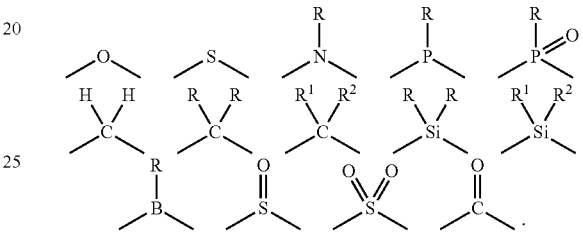

In another aspect, for any of the formulas illustrated in this disclosure,

can represent one or more of the following structures:

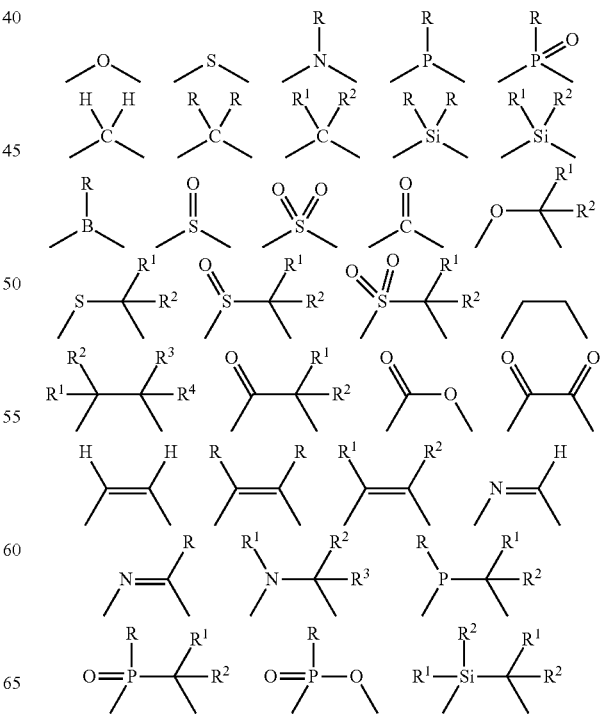

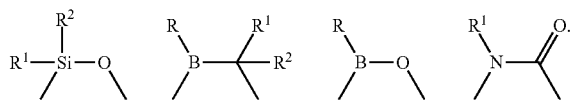

In yet another aspect, for any of the formulas illustrated in this disclosure,

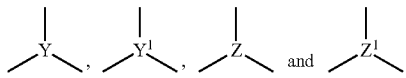

can each independently represent one or more of the following structures:

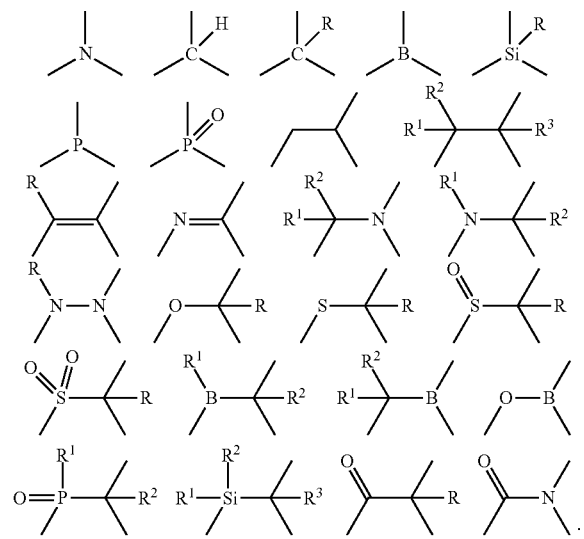

In still another aspect,

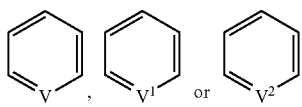

as shown in the disclosed compounds can be one of the following structures:

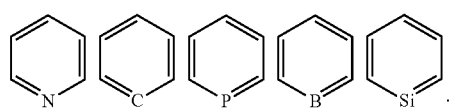

In still another aspect, for any of the formulas illustrated in this disclosure,

can represent one or more of the following structures:

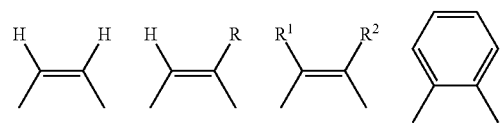
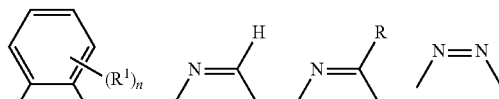
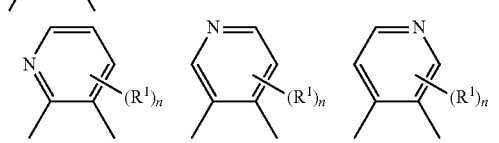
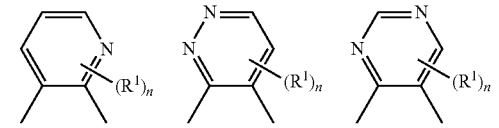
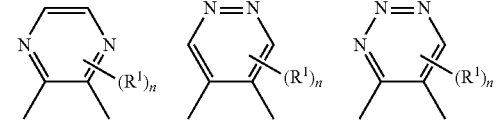
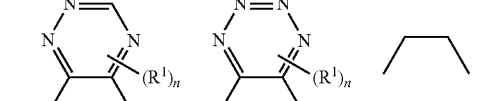
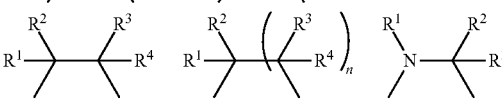
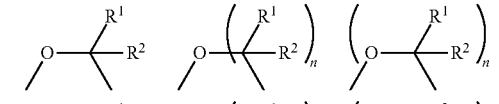
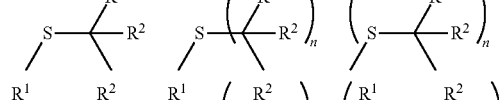
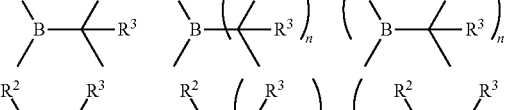
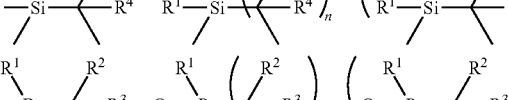
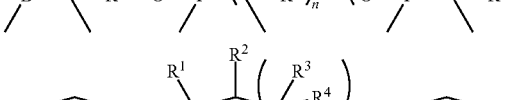
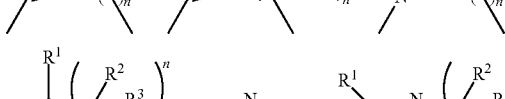
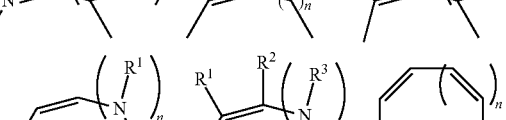

-continued

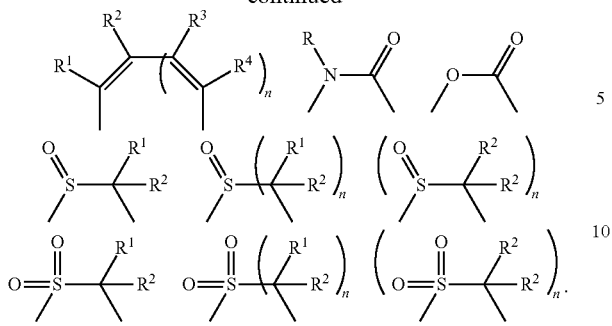

In one aspect, each of $R^1$, $R^2$, $R^3$, $R^4$, and $R^5$ can independently be hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof. In another aspect, each of $R^1$, $R^2$, $R^3$, $R^4$, and $R^5$ can independently be aryl, cycloalkyl, cycloalkenyl, heterocyclyl, heteroaryl, alkyl, alkenyl, alkynyl, halogen, hydroxyl, thiol, nitro, amino, haloalkyl, or any conjugate or a combination thereof. In yet another aspect, each of $R^1$, $R^2$, $R^3$, $R^4$, and $R^5$ can independently be aryl, cycloalkyl, cycloalkenyl, heterocyclyl, heteroaryl, alkyl, alkenyl, halogen, or hydroxyl, or a combination thereof.

In one aspect, for any of the metal complexes illustrated in this disclosure, can comprise one or more of the following structures. In another aspect, they can also comprise other structures or portions thereof not specifically recited herein, and the present invention is not intended to be limited to those structures or portions thereof specifically recited.

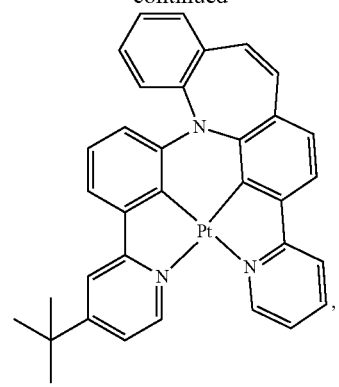

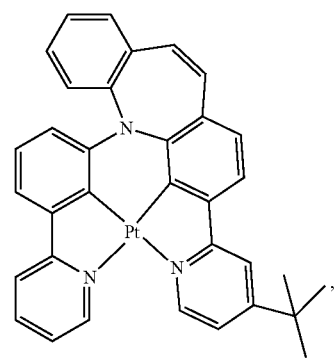

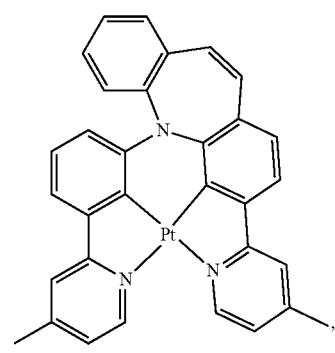

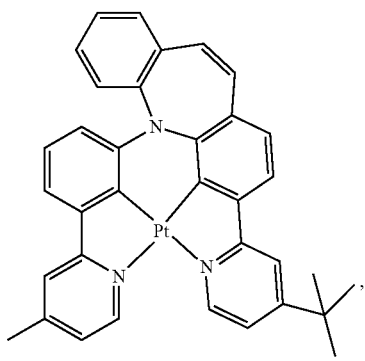

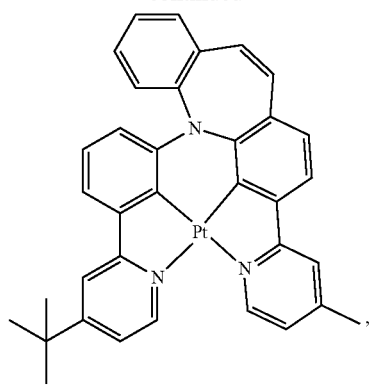
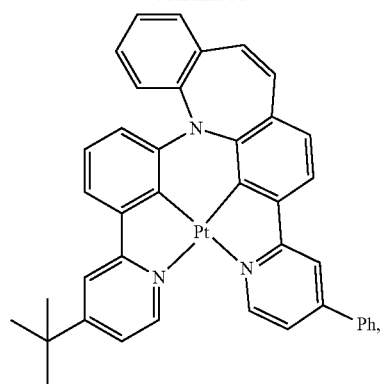
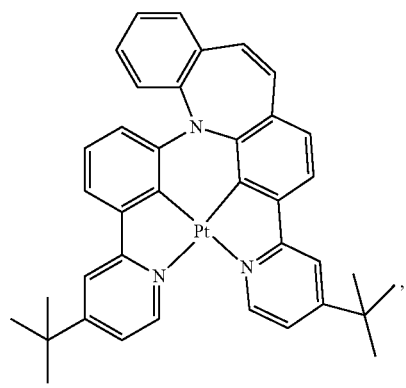
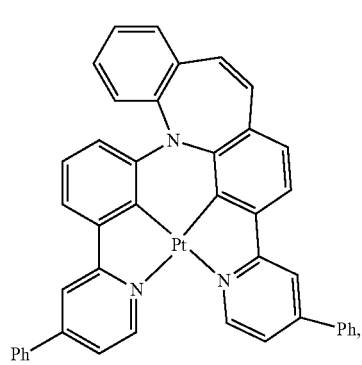
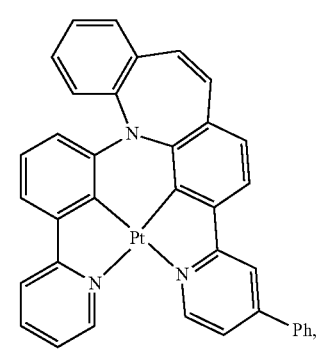
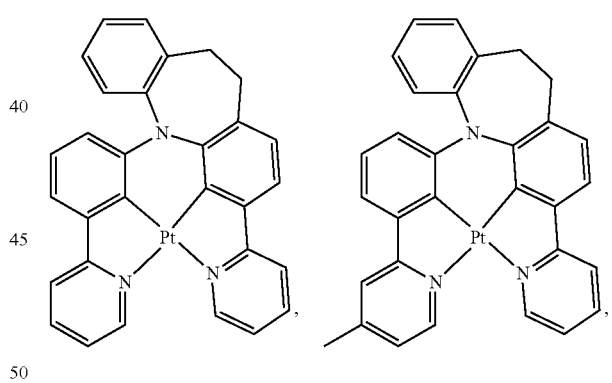
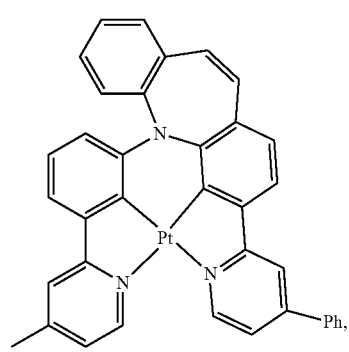
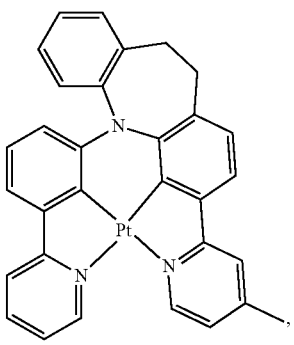

63
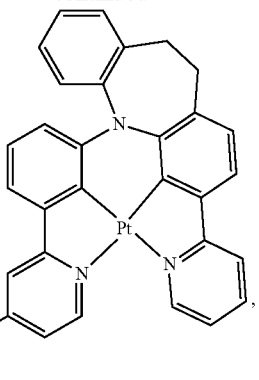
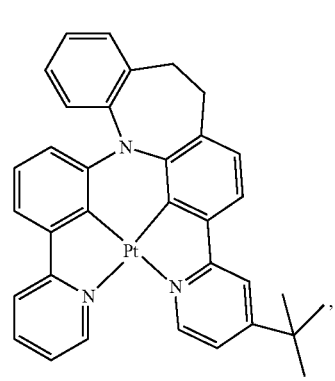
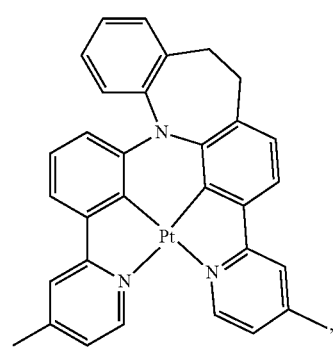
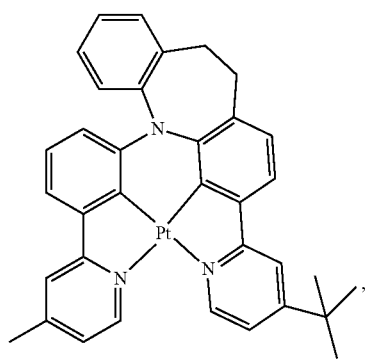
64
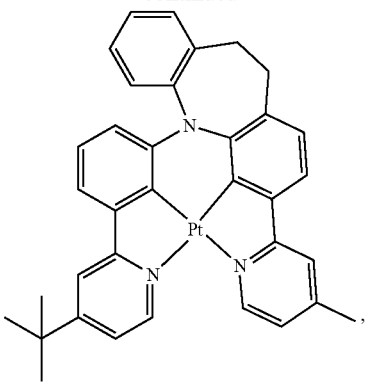
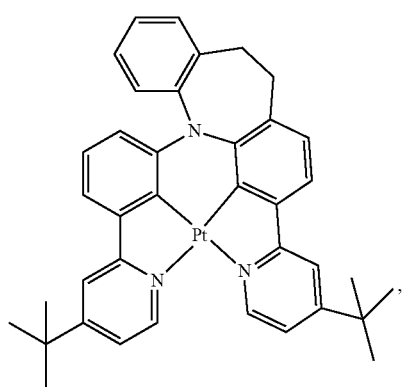
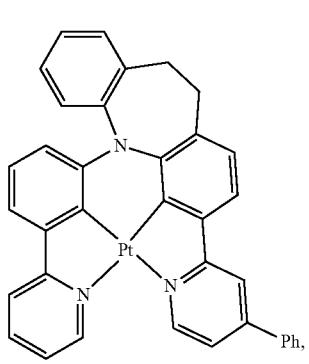
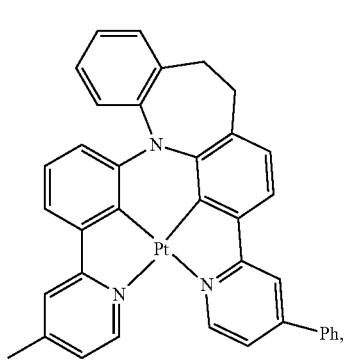

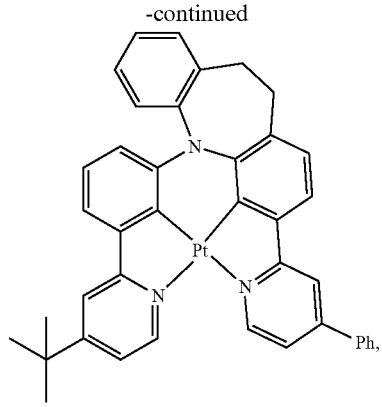
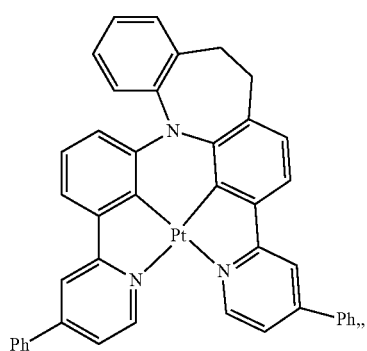
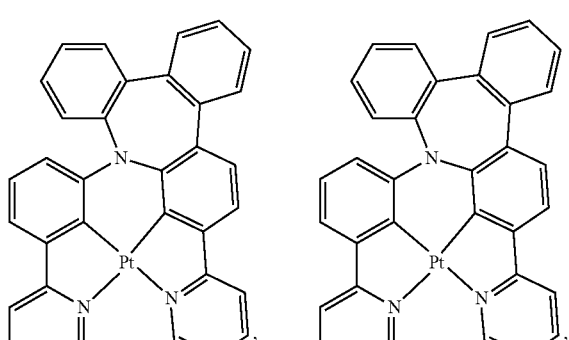
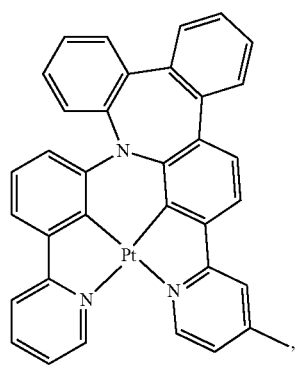
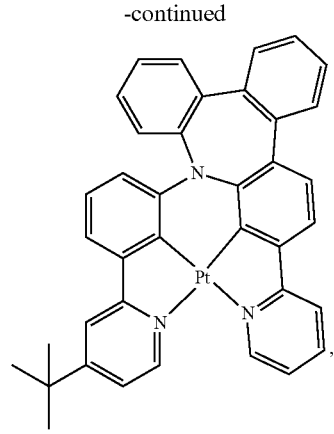
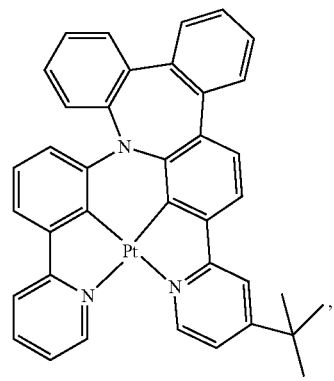
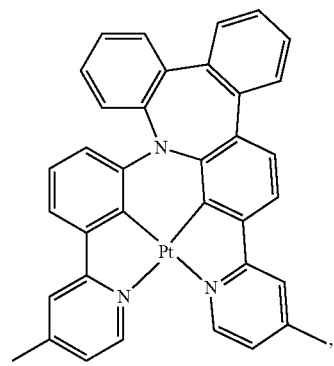
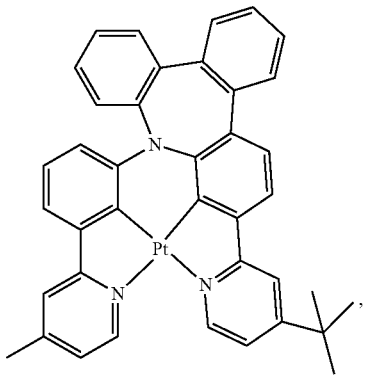

67
-continued
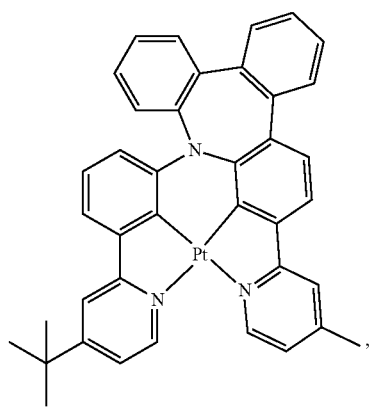
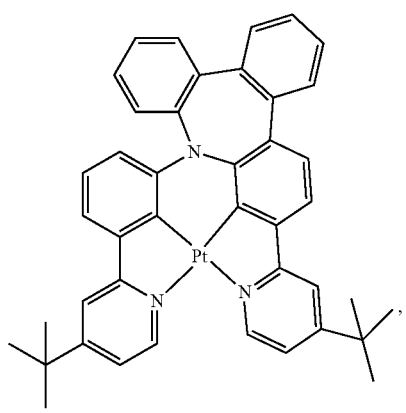
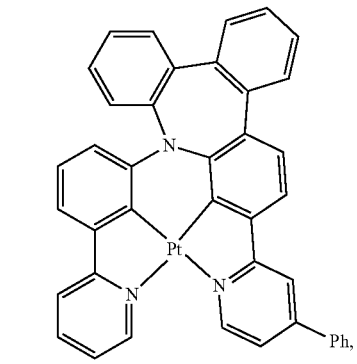
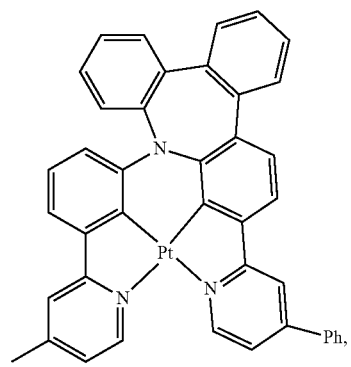
68
-continued
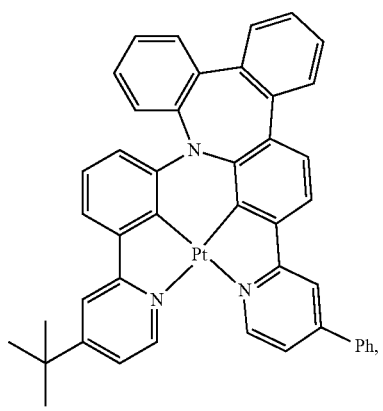
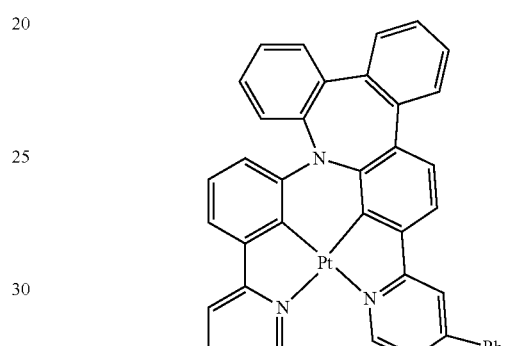
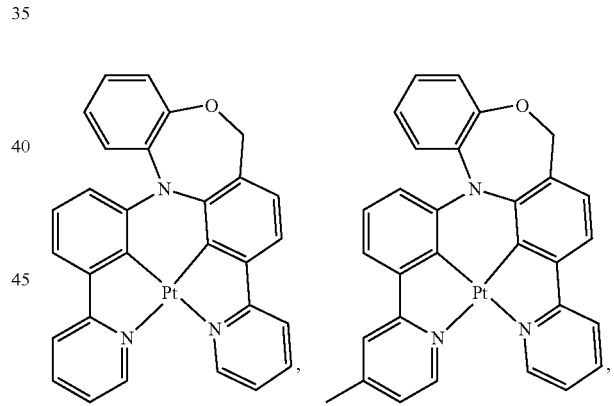
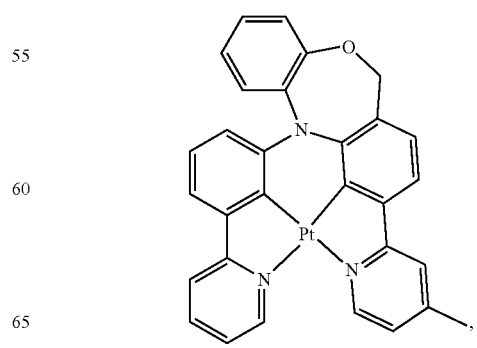

69
-continued
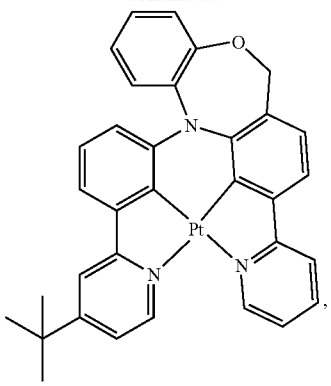
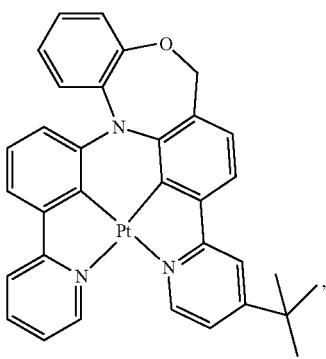
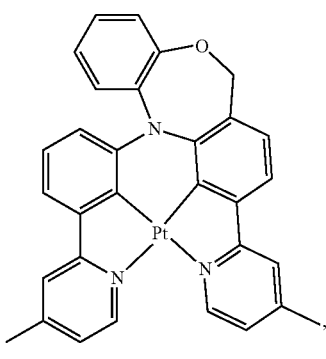
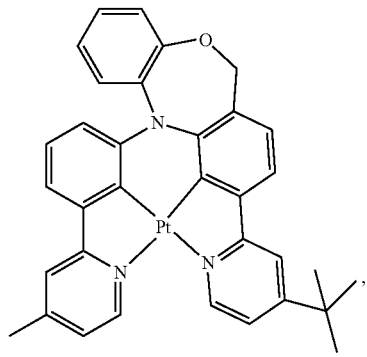
70
-continued
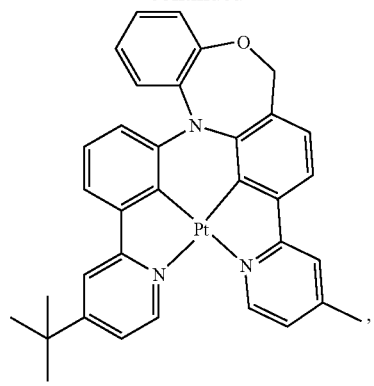
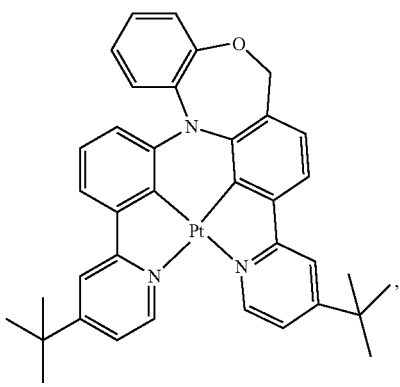
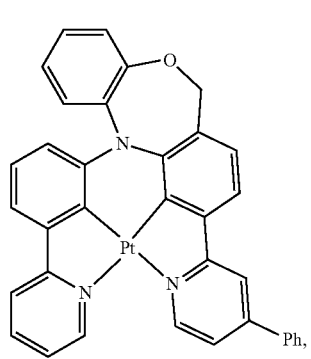
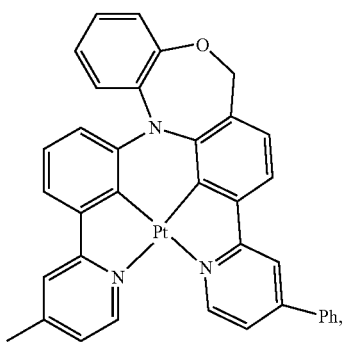

71
-continued
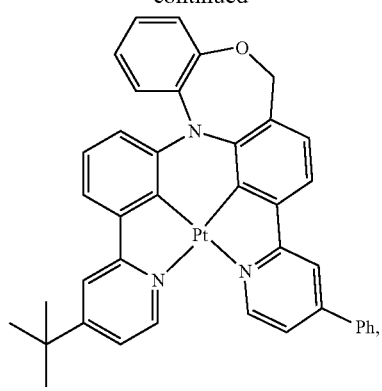
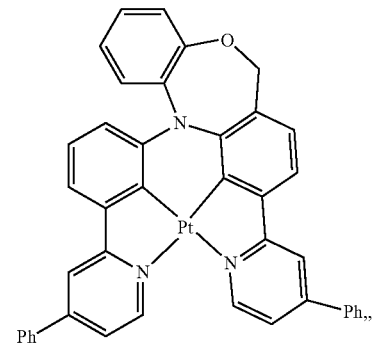
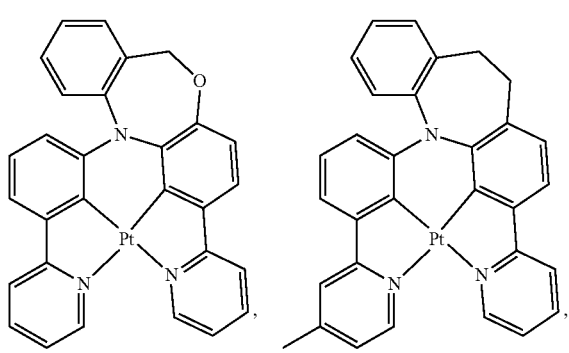
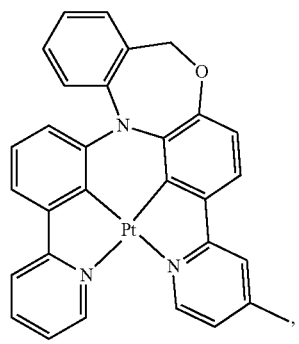
72
-continued
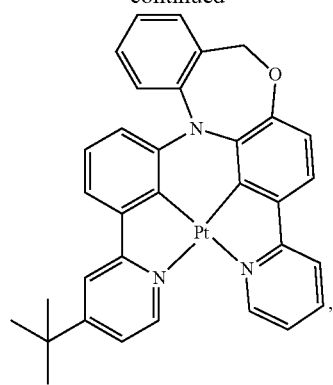
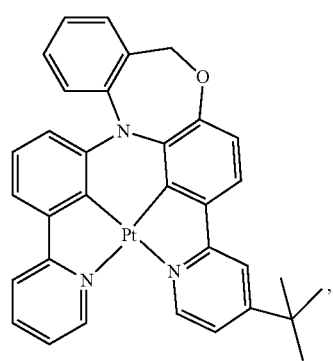
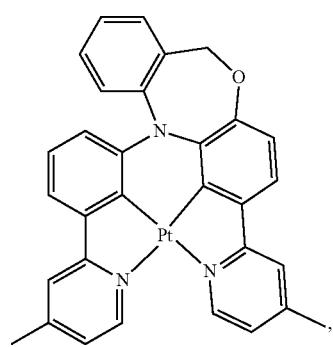
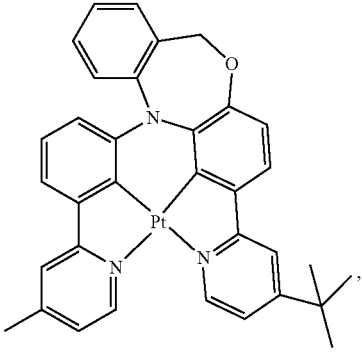

-continued
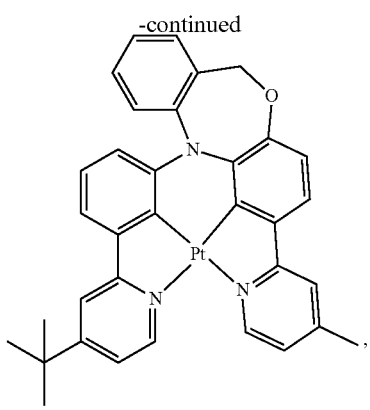
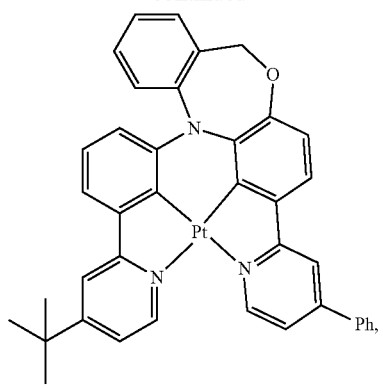
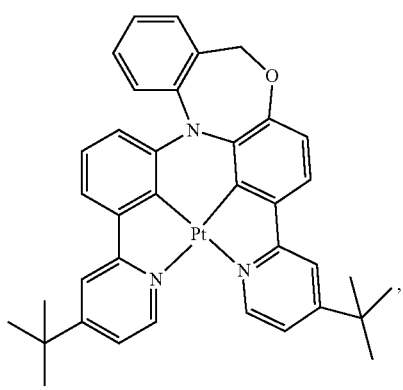
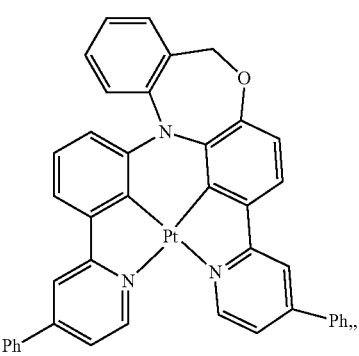
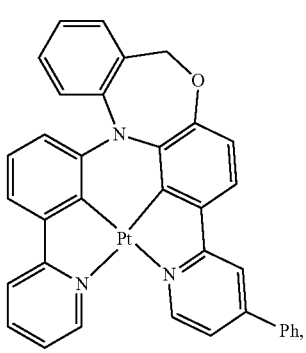
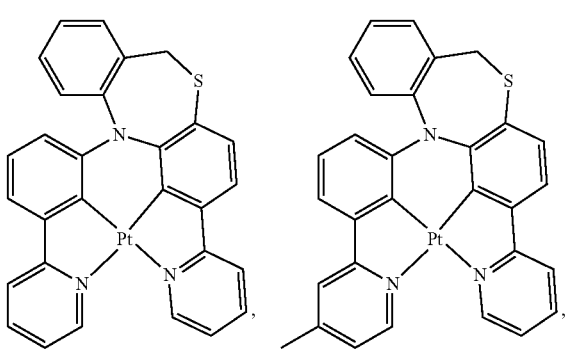
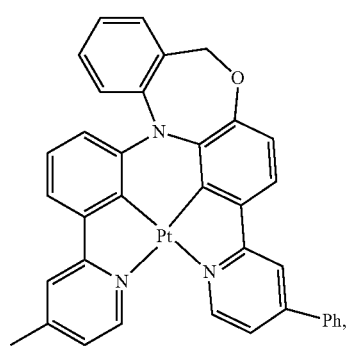
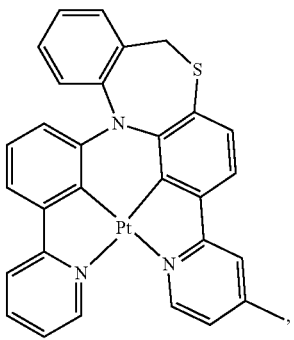

75
-continued
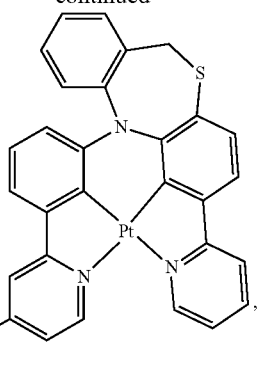
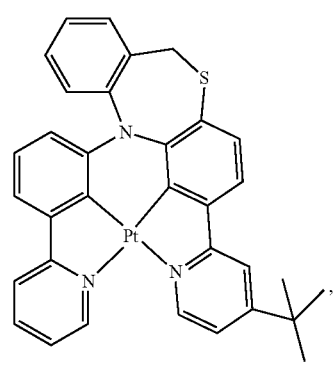
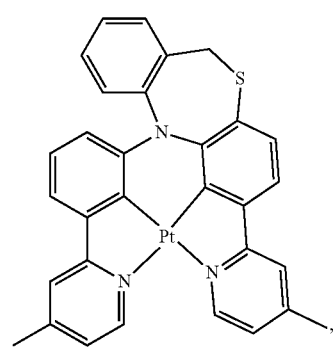
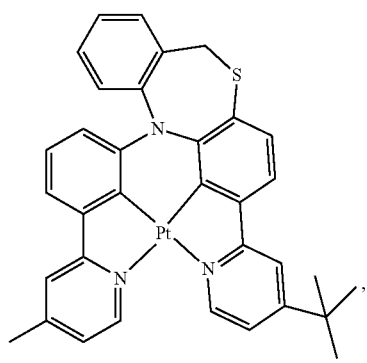
76
-continued
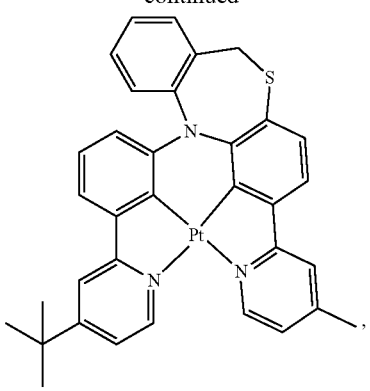
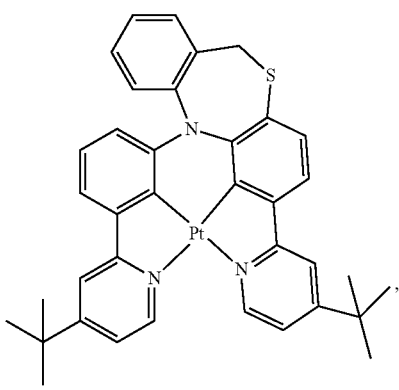
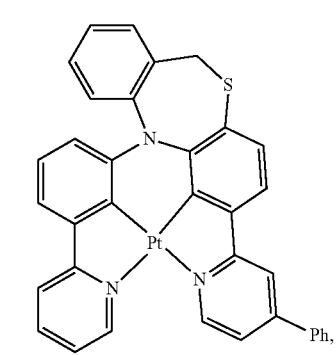
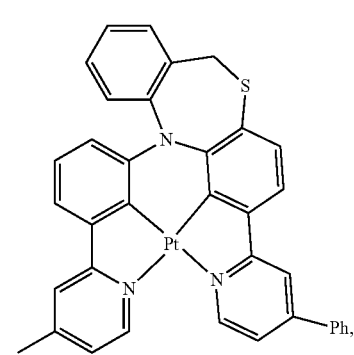

-continued
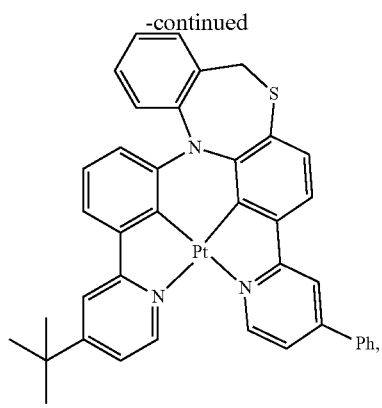
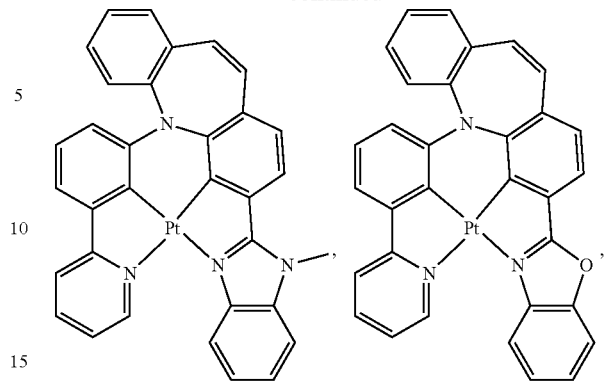
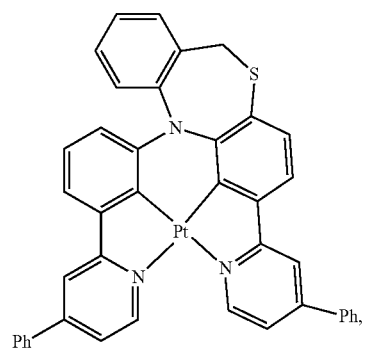
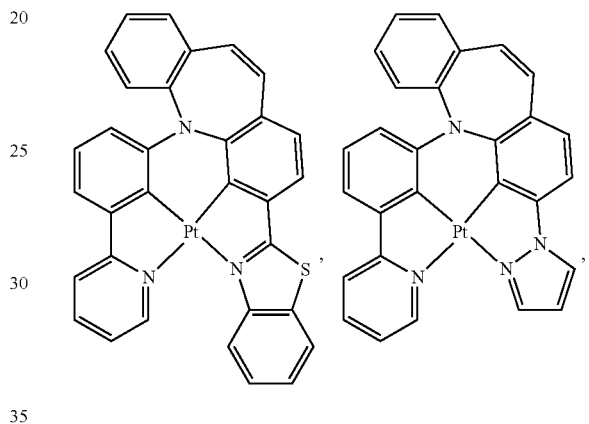
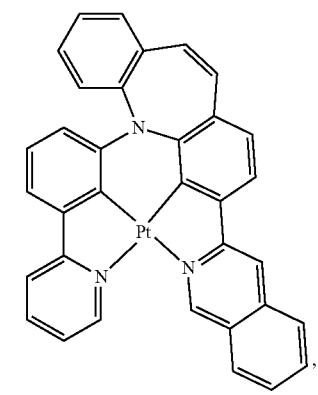
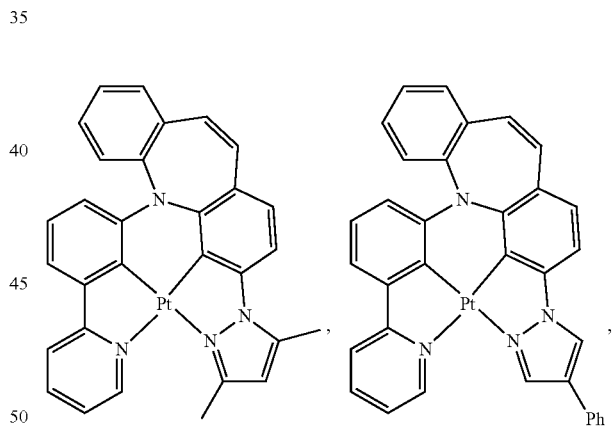
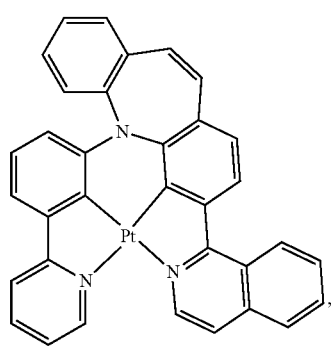
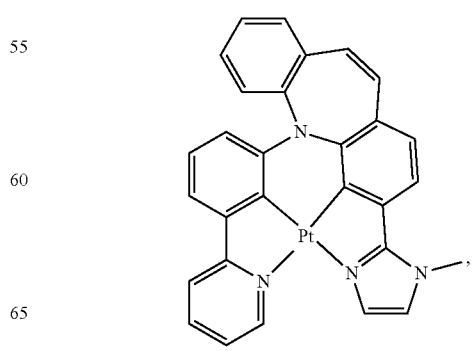

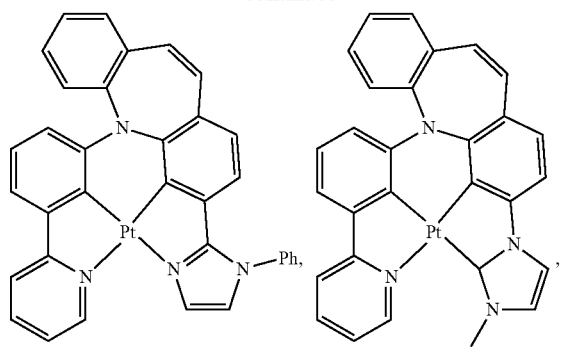
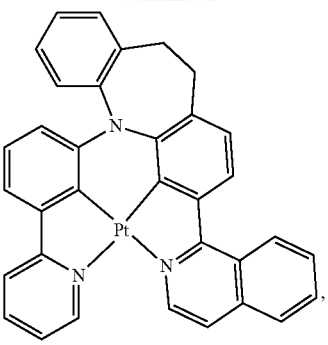
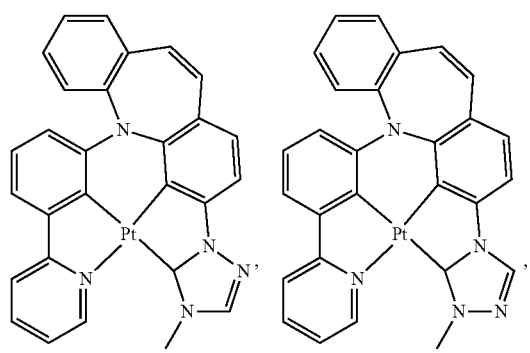
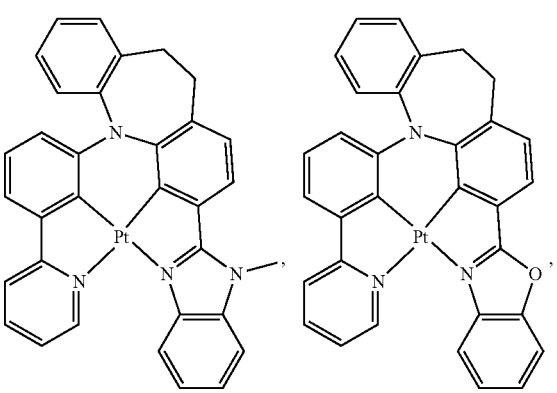
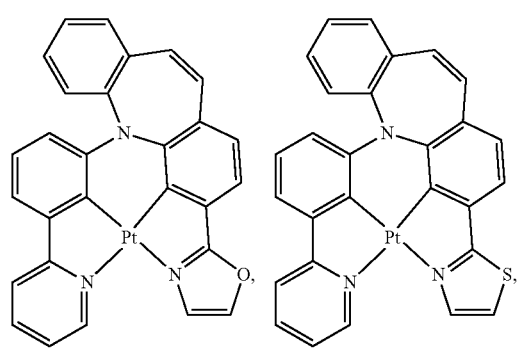
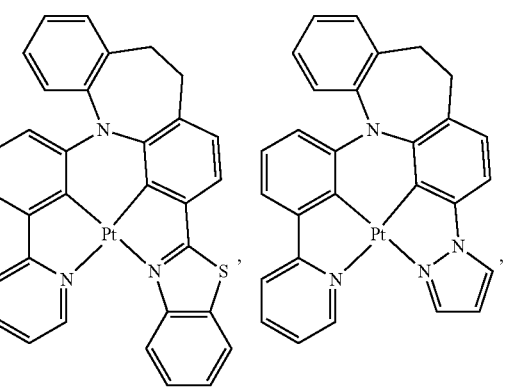
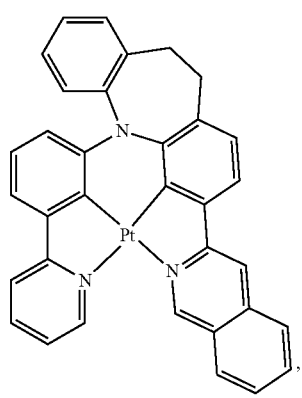
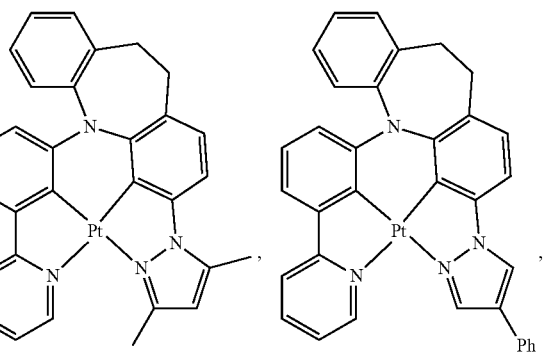

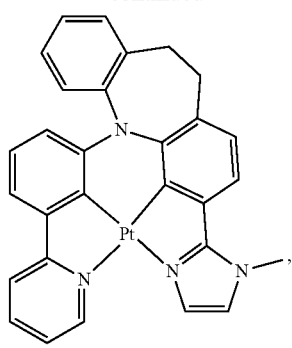
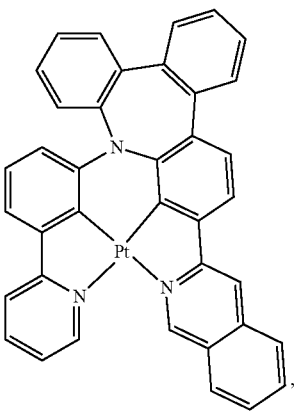
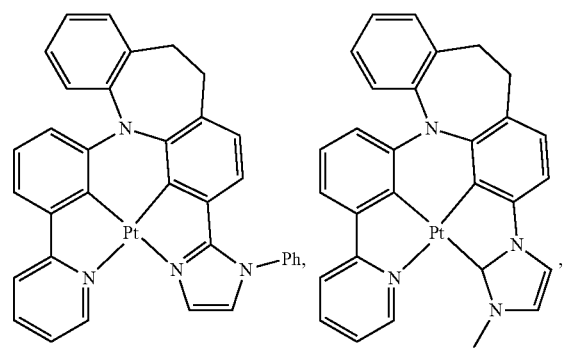
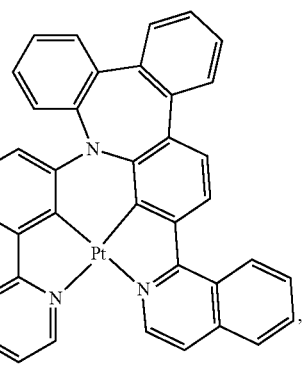
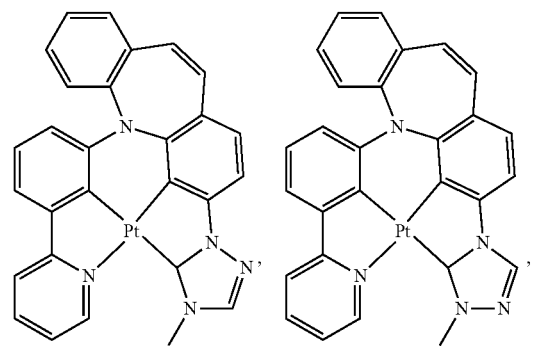
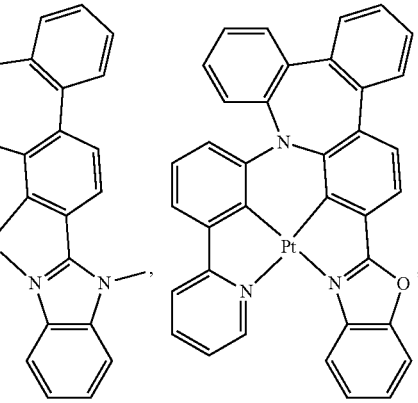
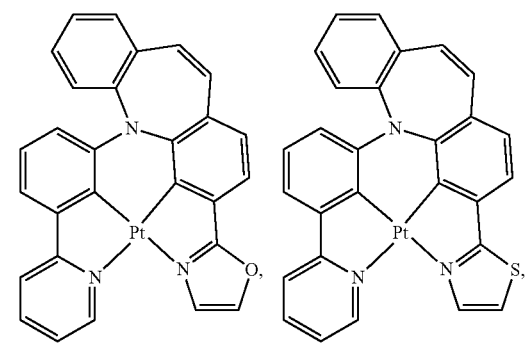
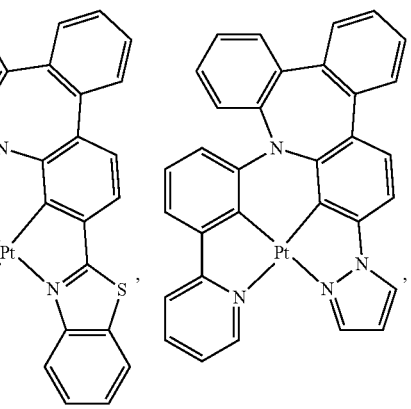

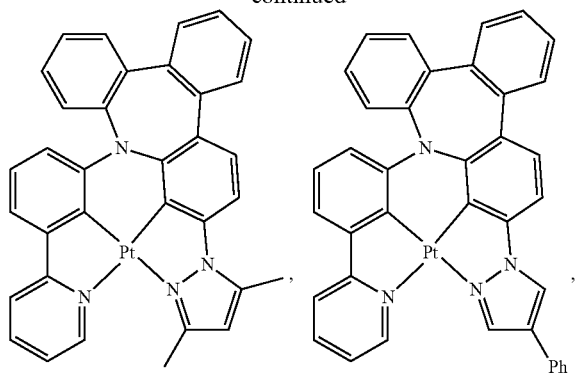
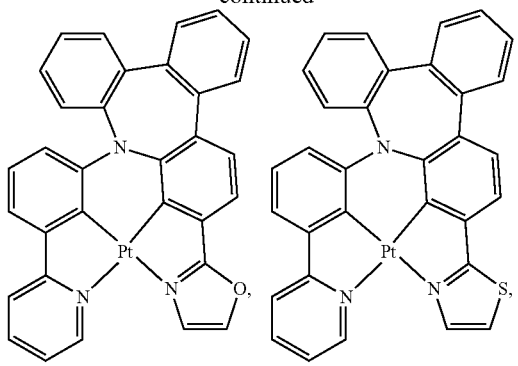
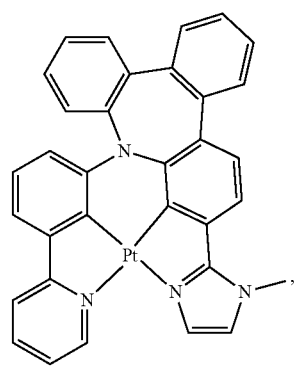
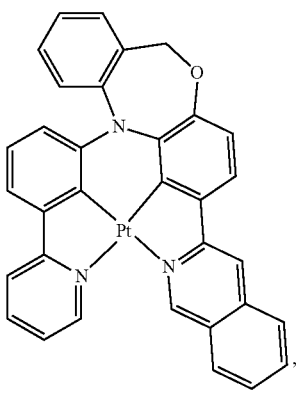
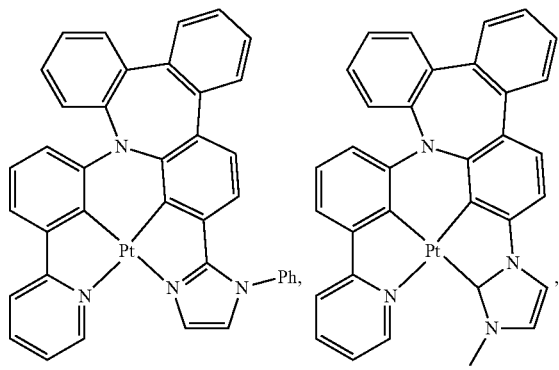
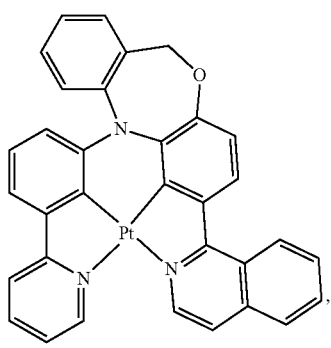
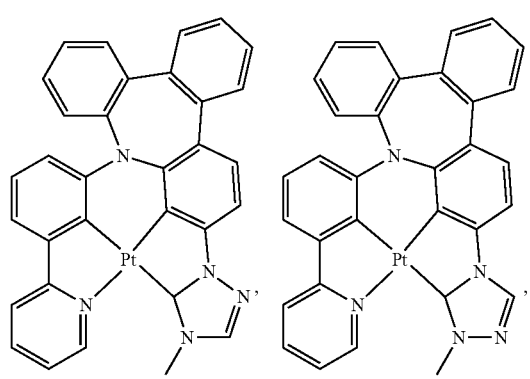
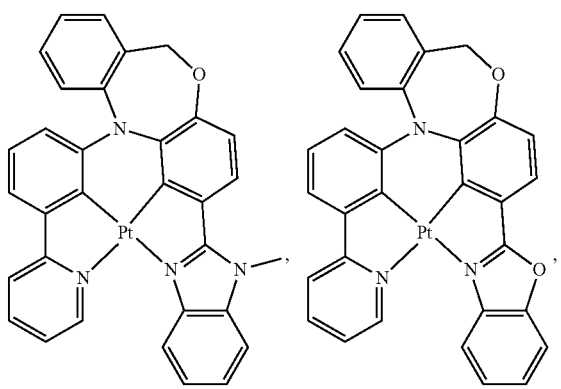

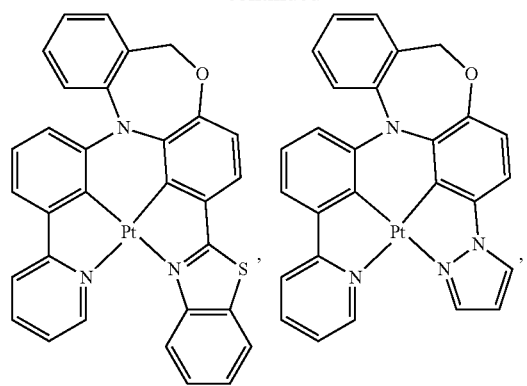
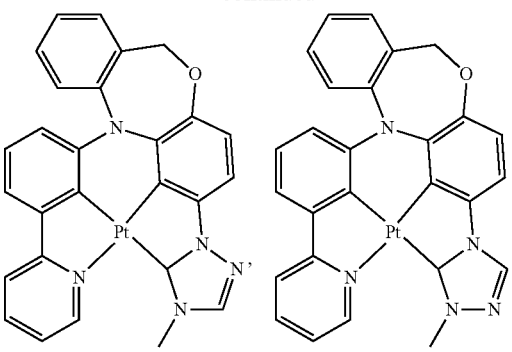
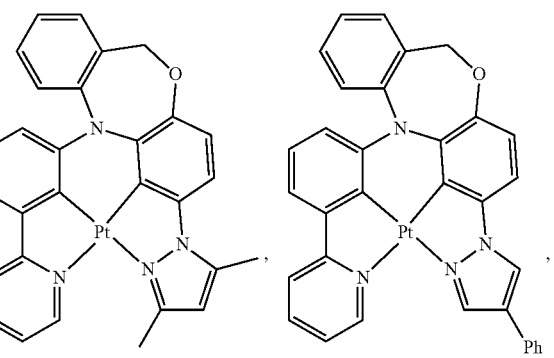
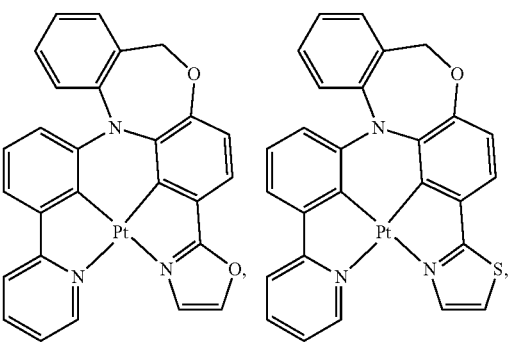
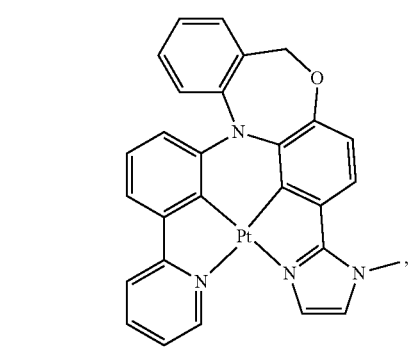
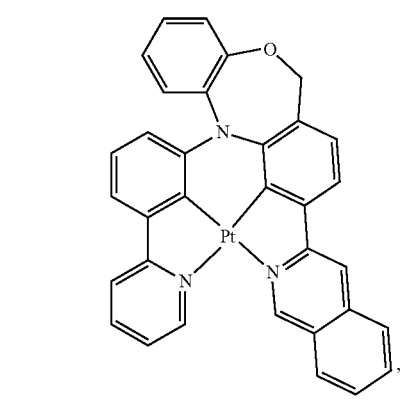

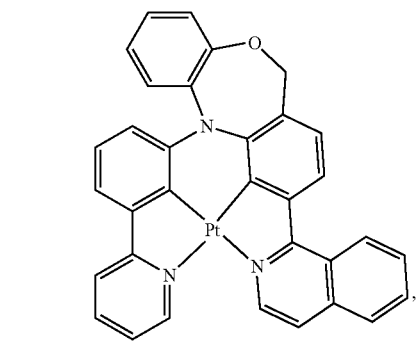

87
-continued
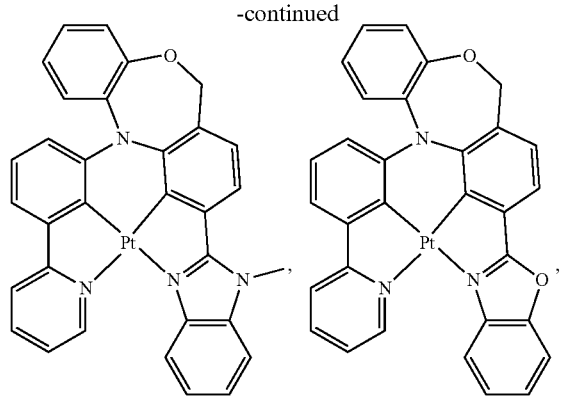
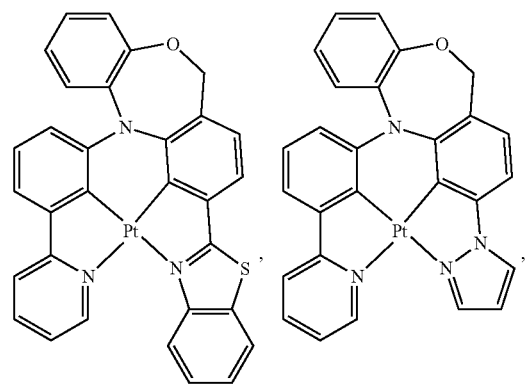
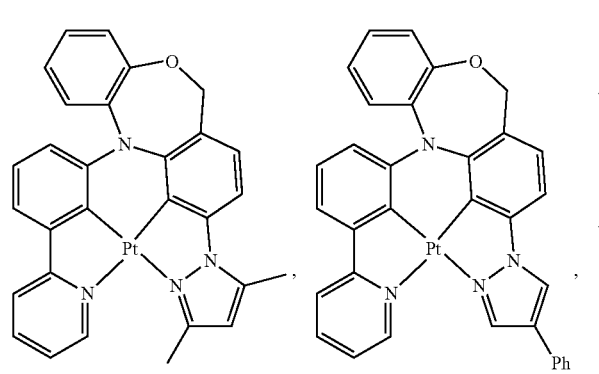
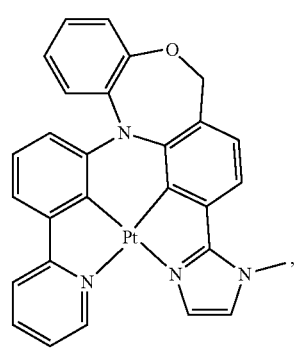
88
-continued
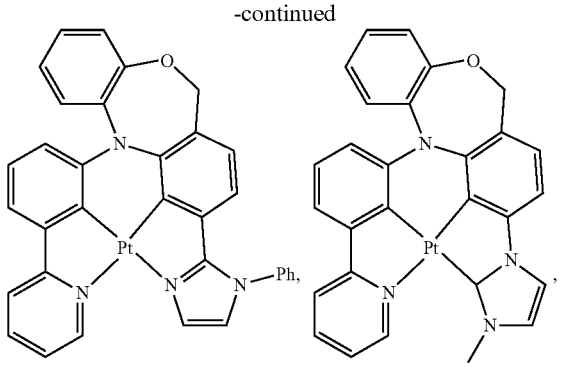
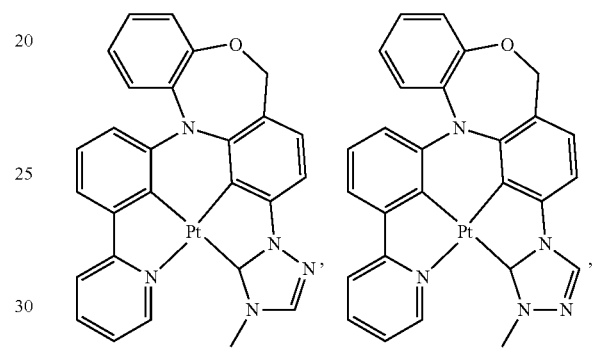
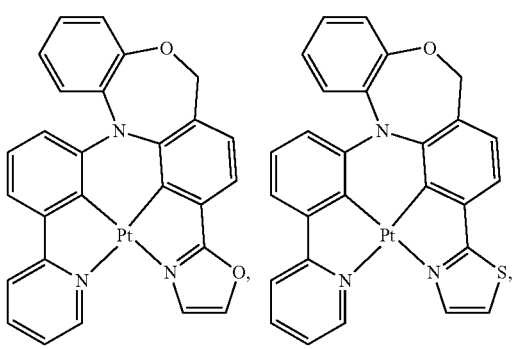
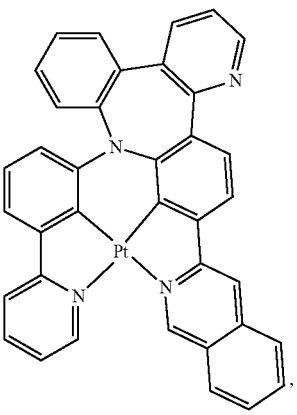

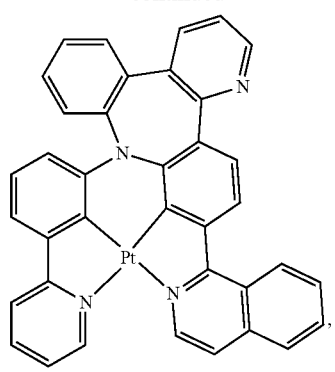
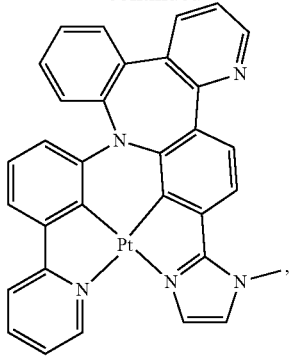
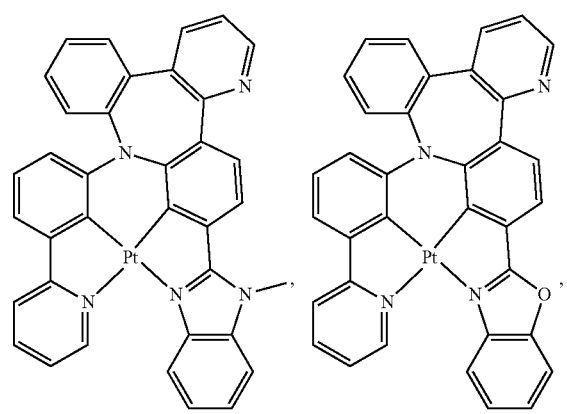
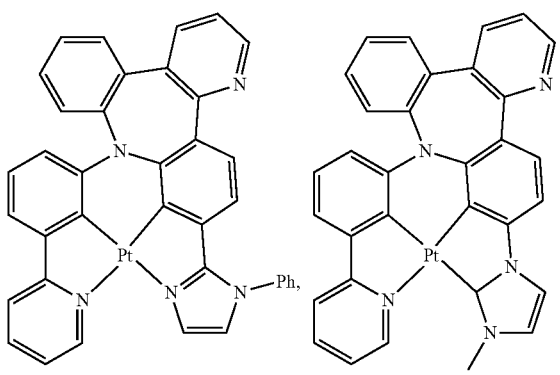
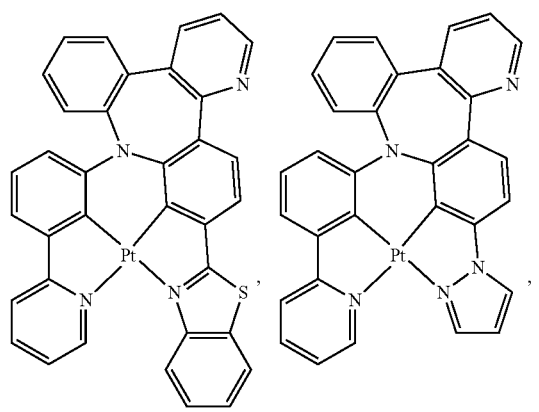
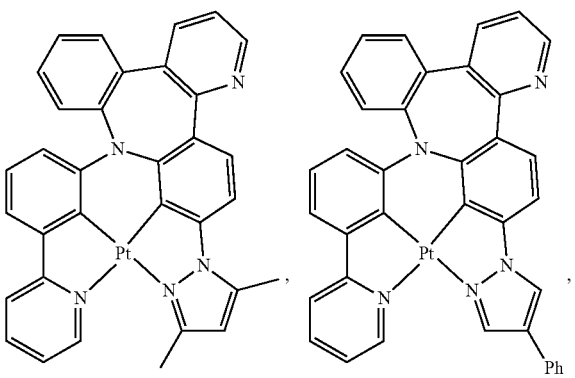
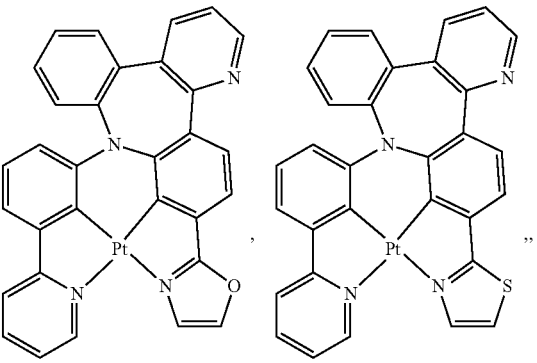

-continued
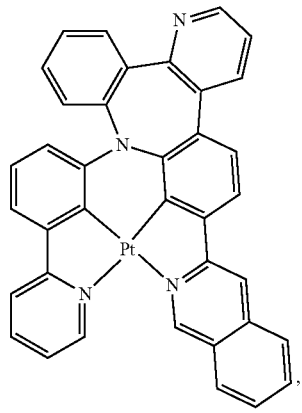
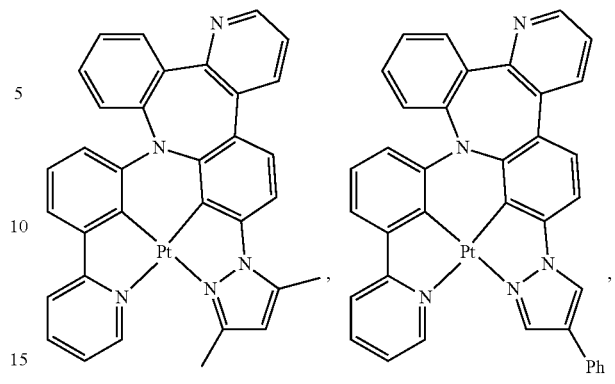
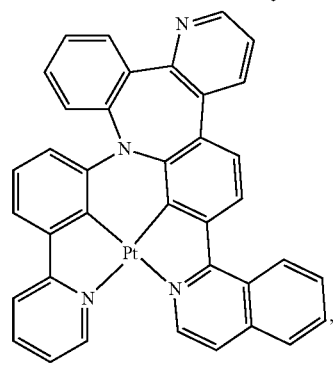
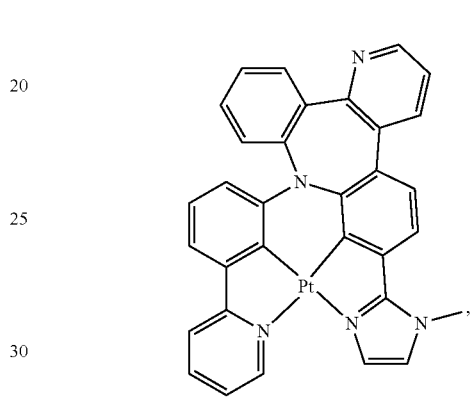
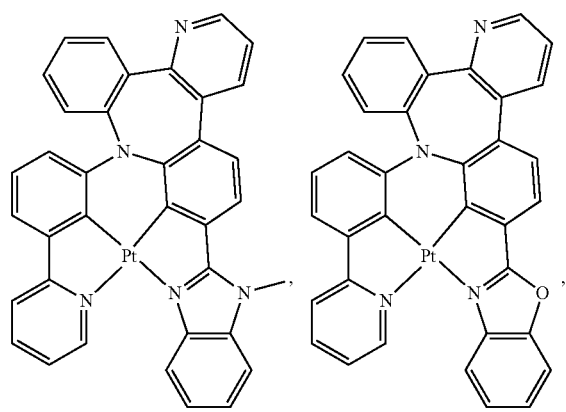
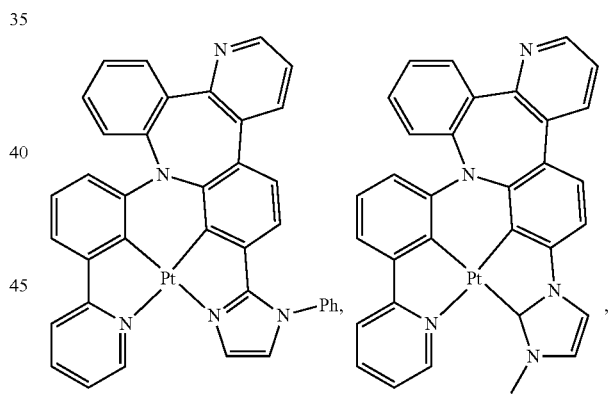
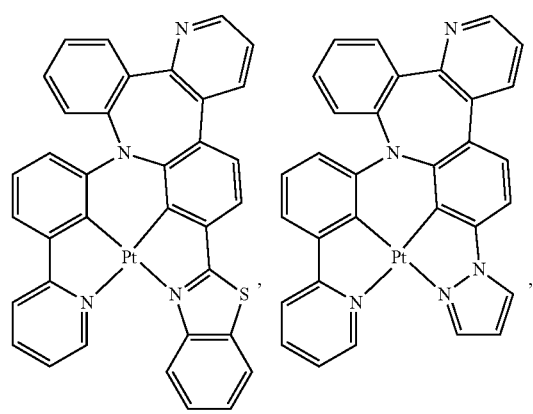
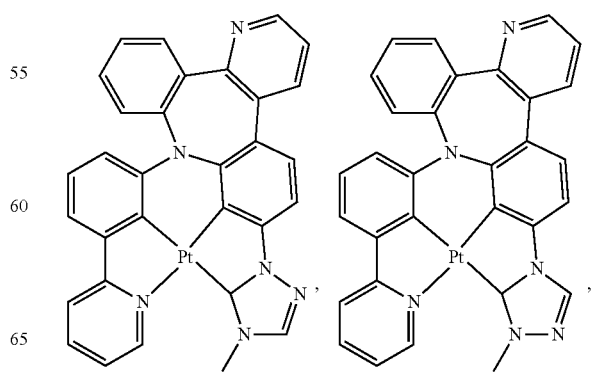

-continued
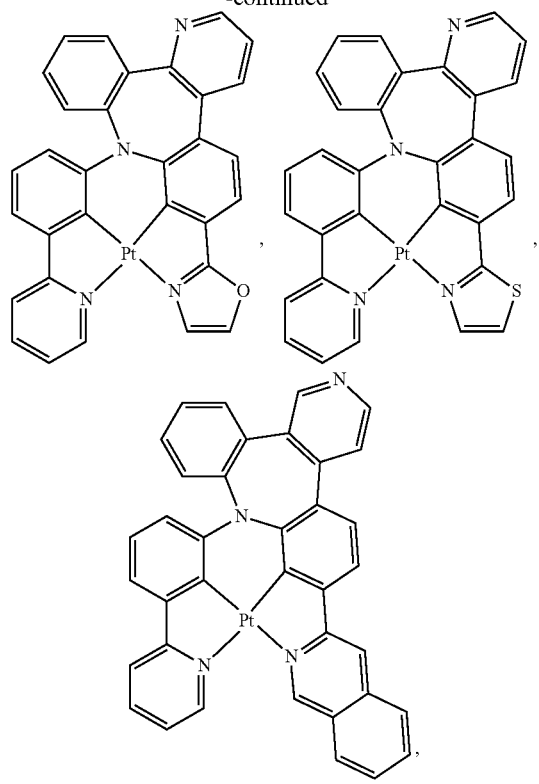
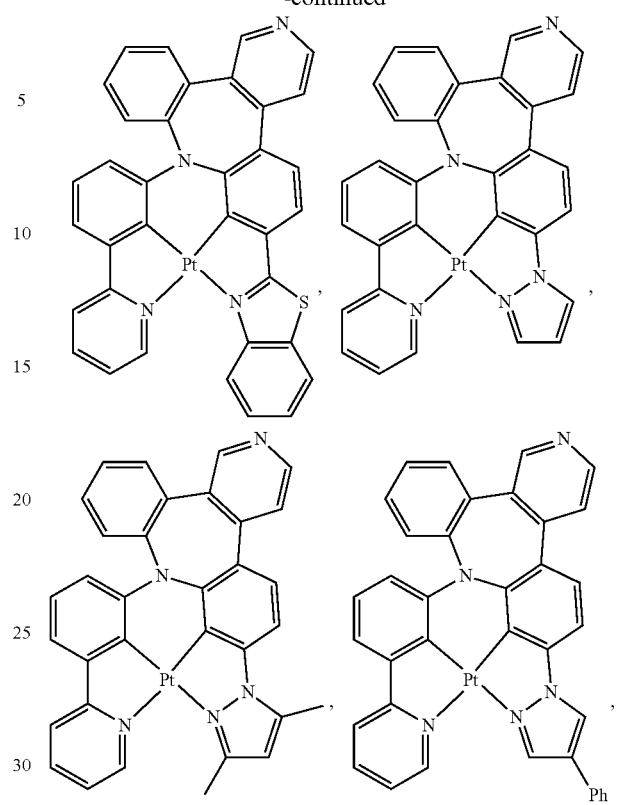
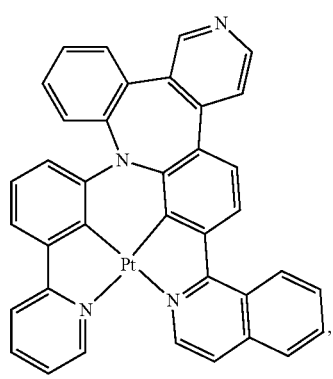
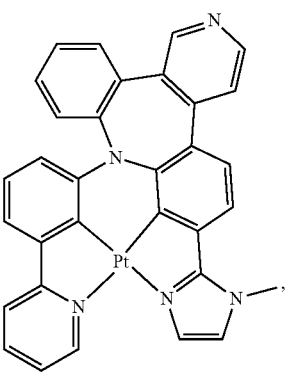
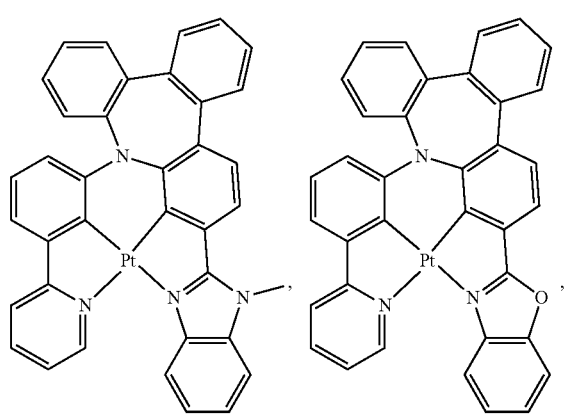
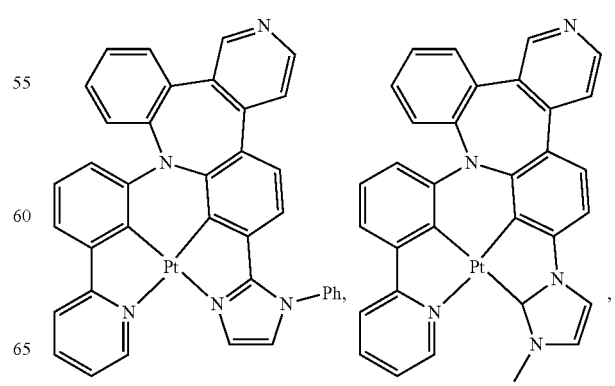

95
-continued
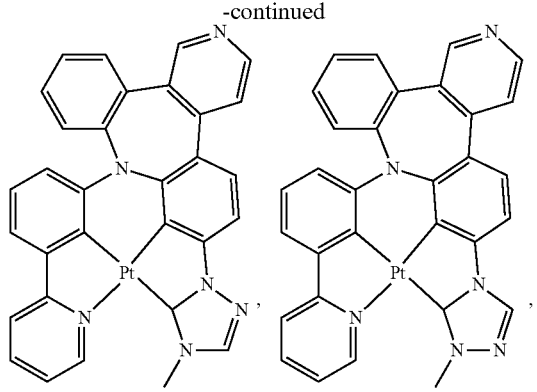
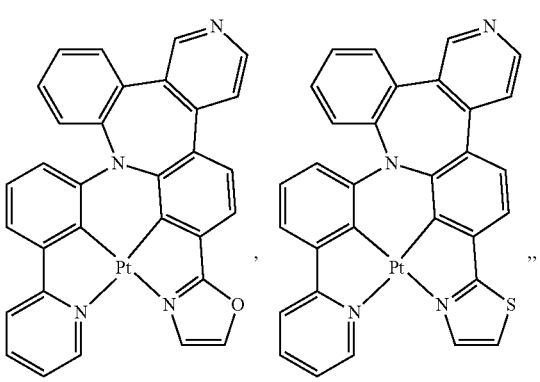
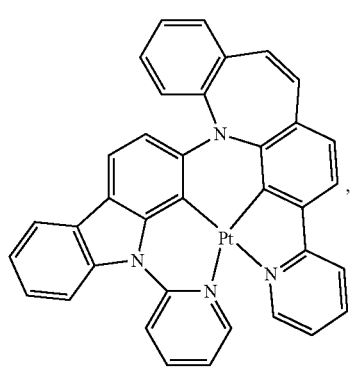
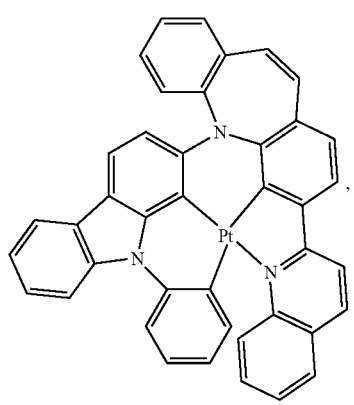
96
-continued
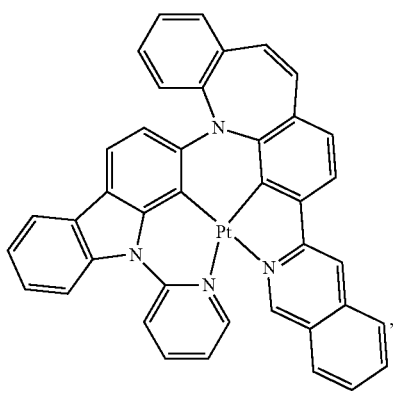
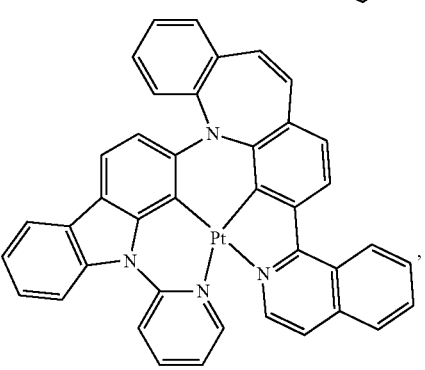
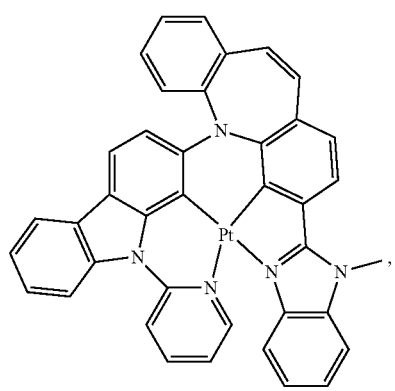
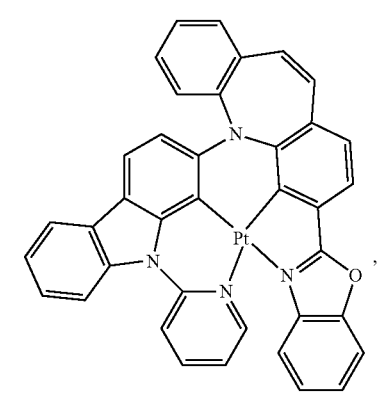

97
-continued
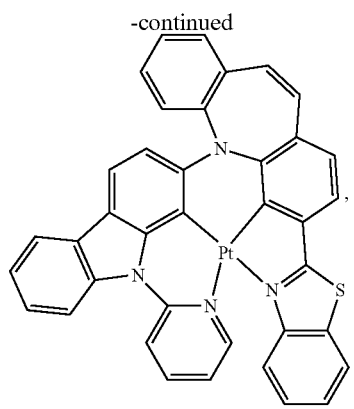
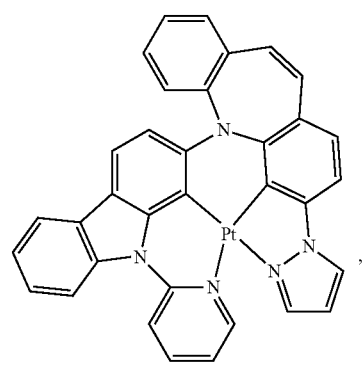
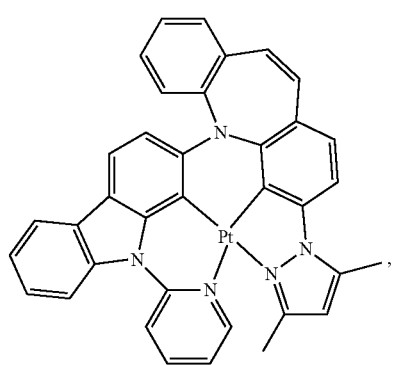
98
-continued
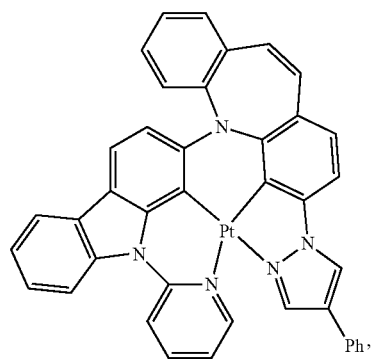
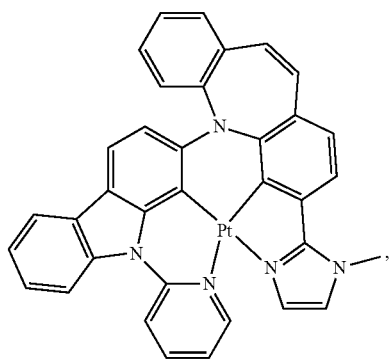
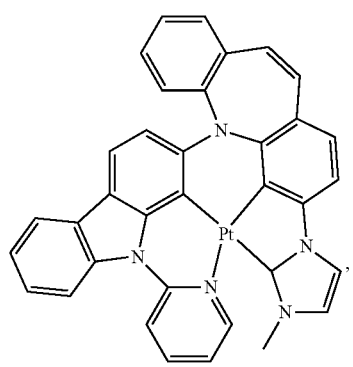
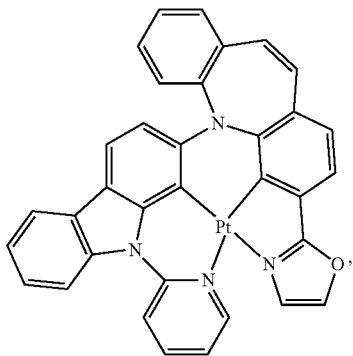

99
-continued
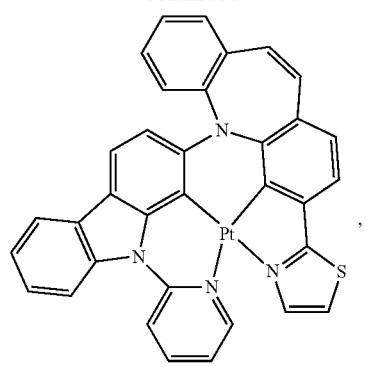
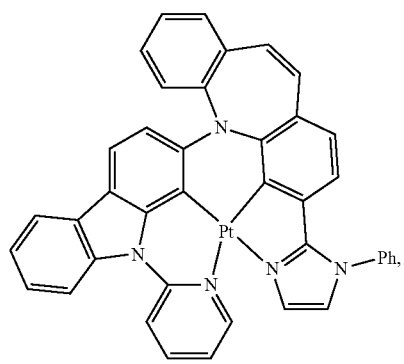
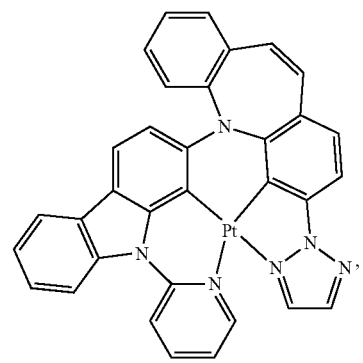
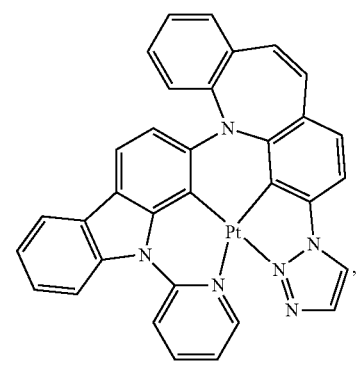
100
-continued
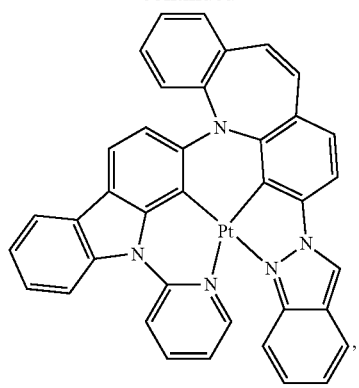
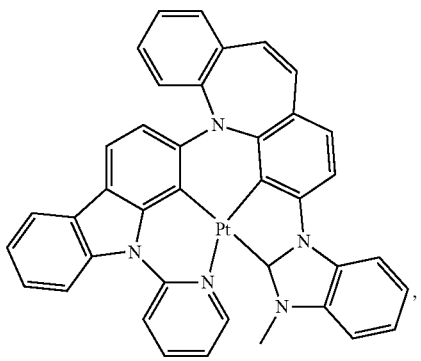
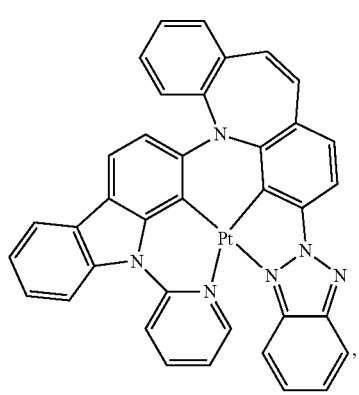
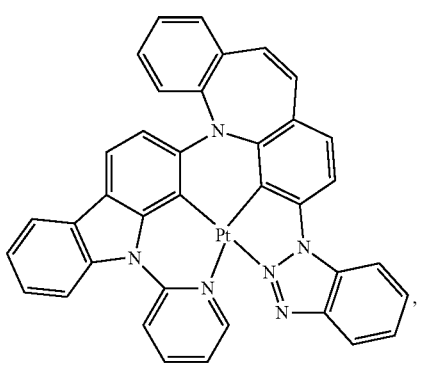

101
-continued
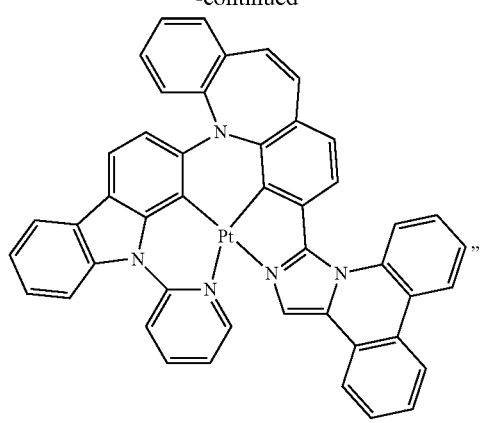
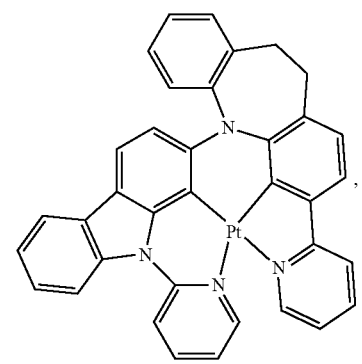
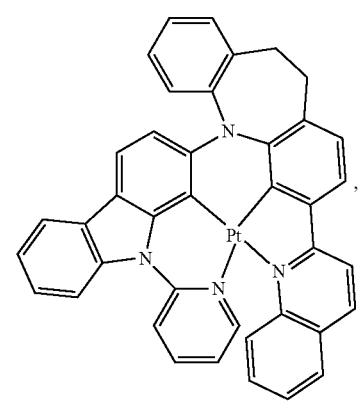
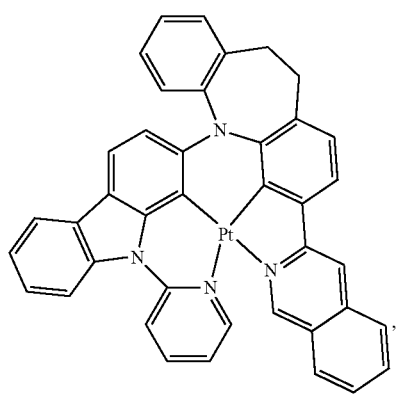
102
-continued
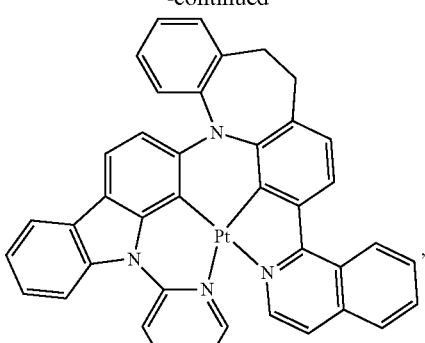
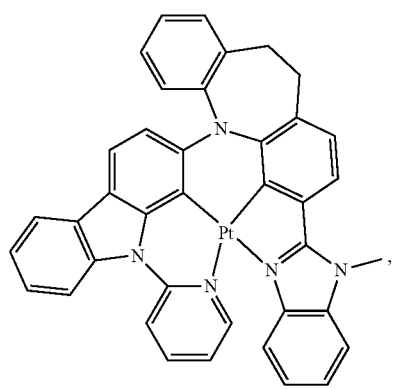
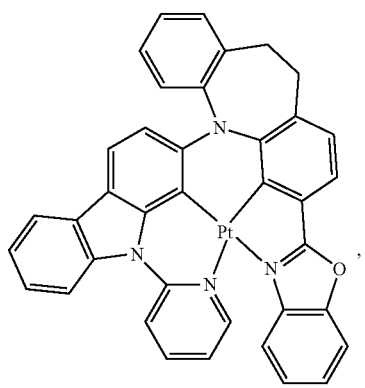
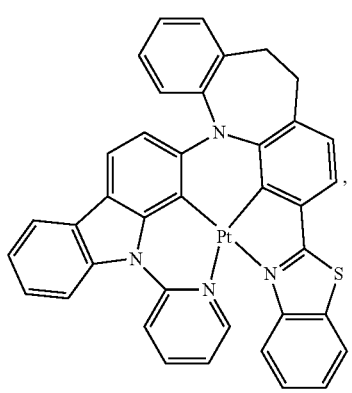

103
-continued
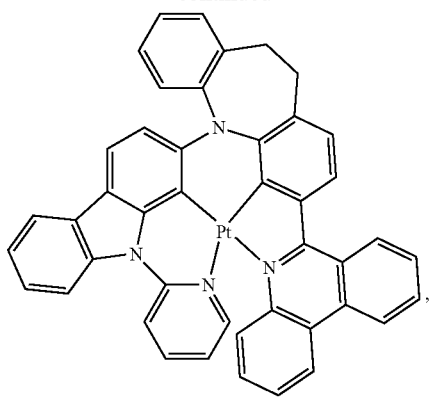
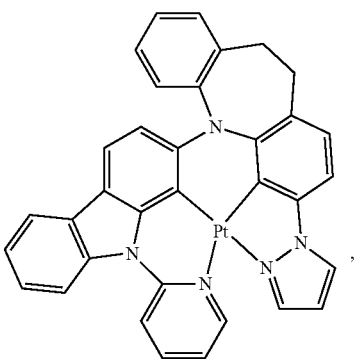
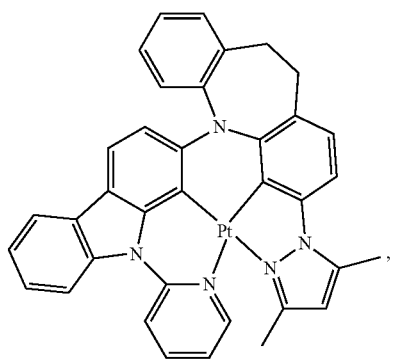
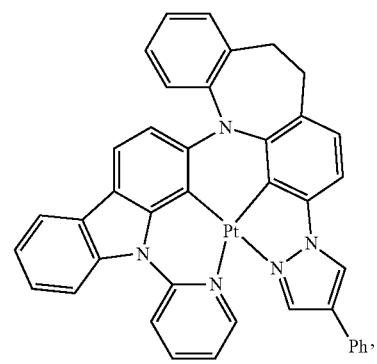
104
-continued
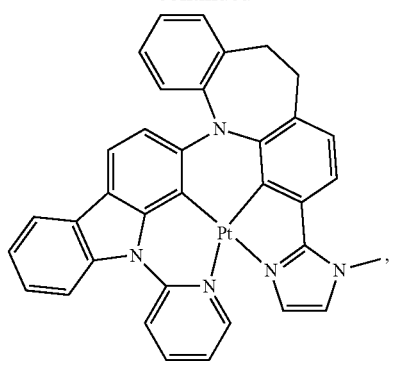
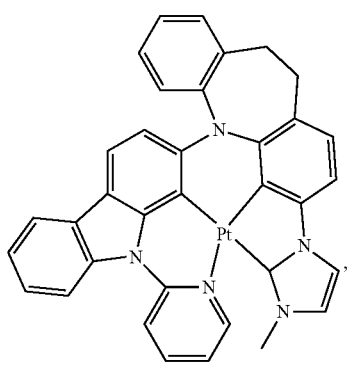
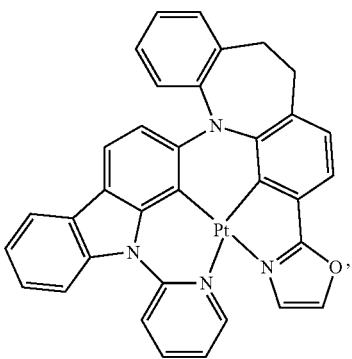
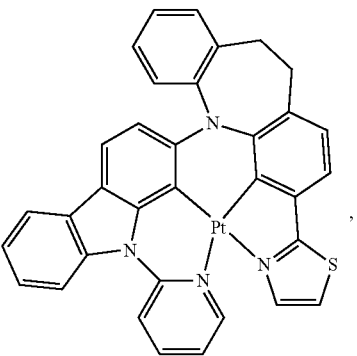

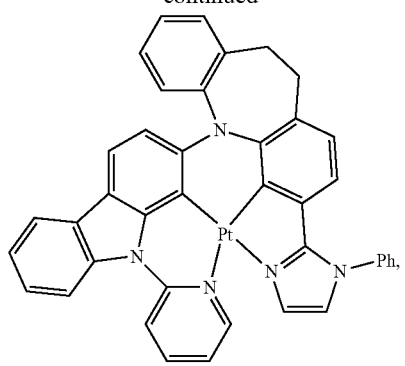
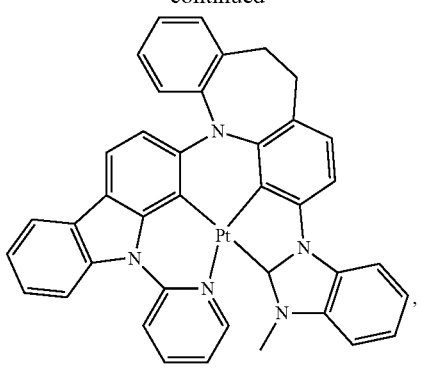
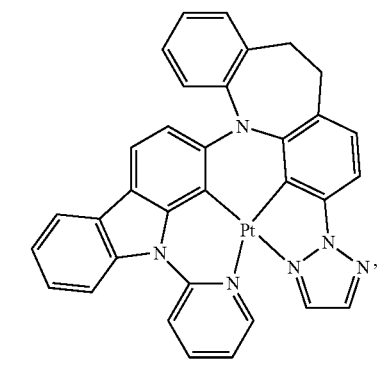
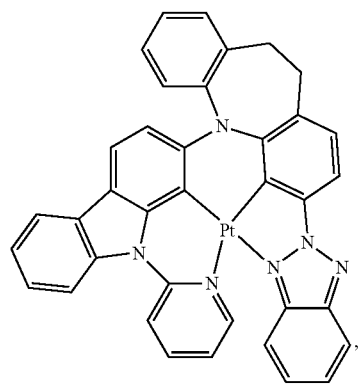
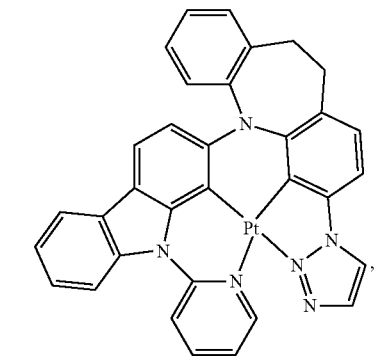
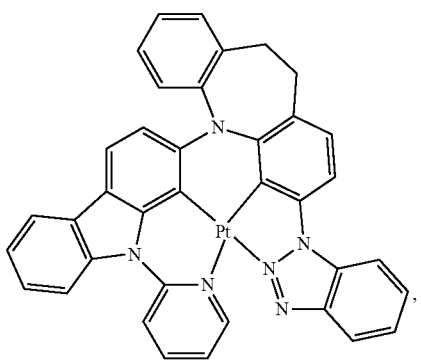
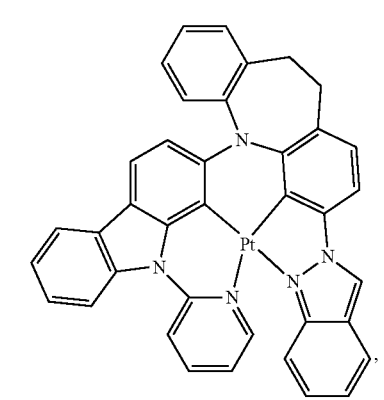
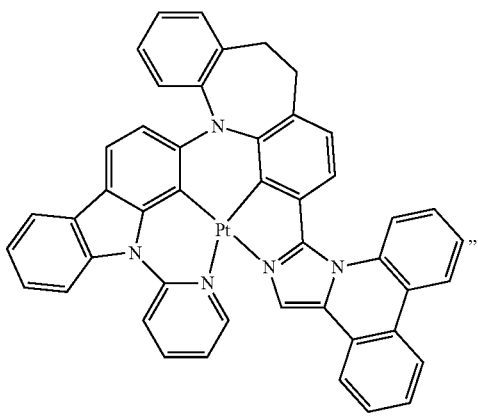

107
-continued
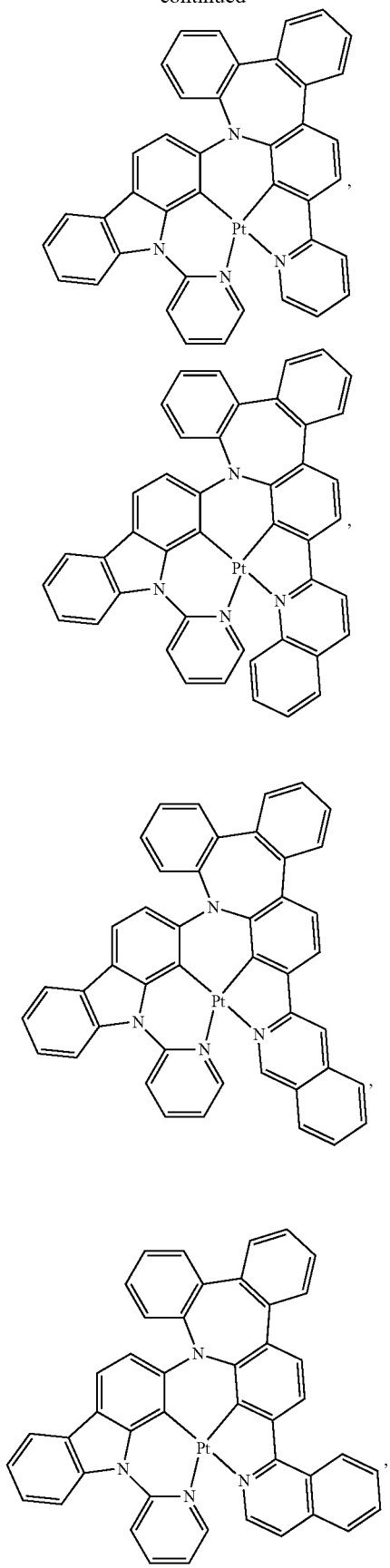
108
-continued
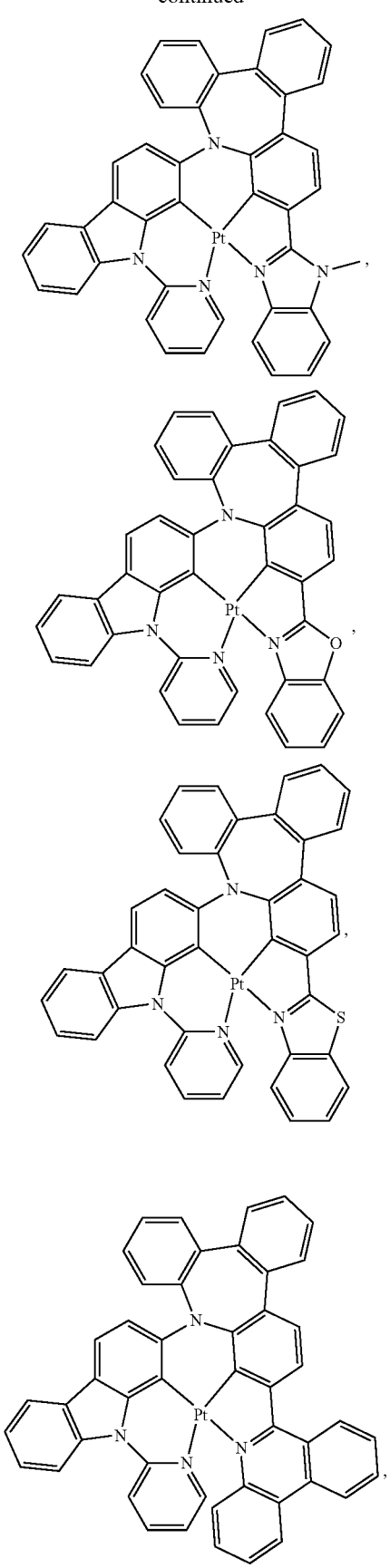

109
-continued
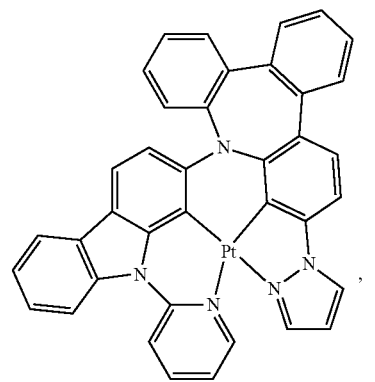
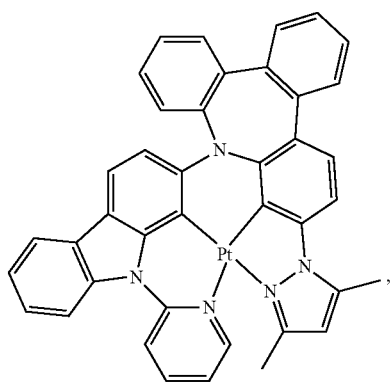
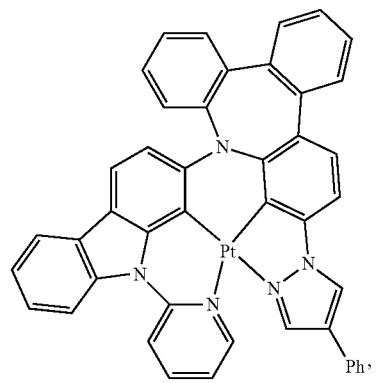
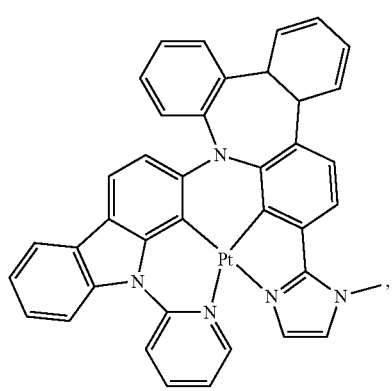
110
-continued
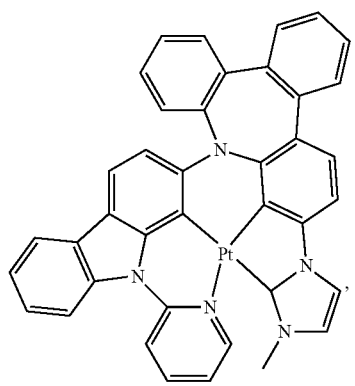
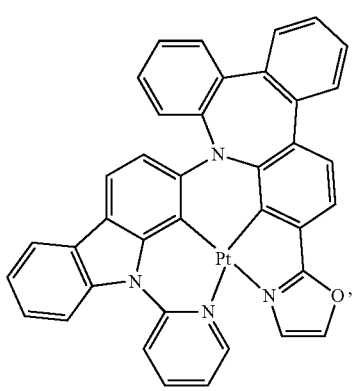
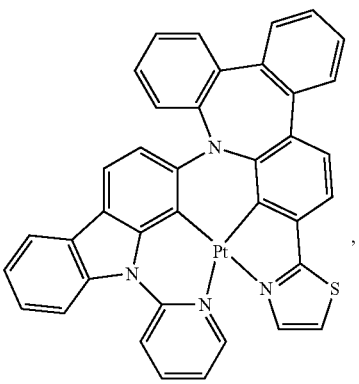
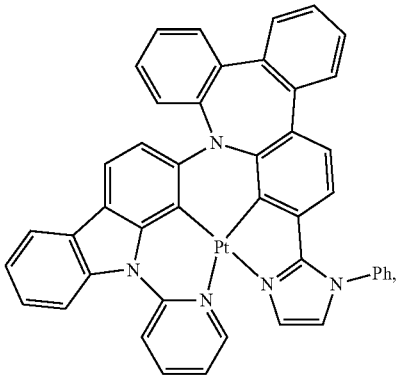

111
-continued
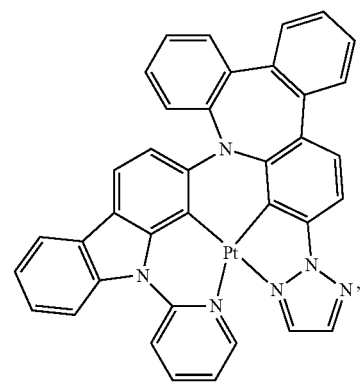
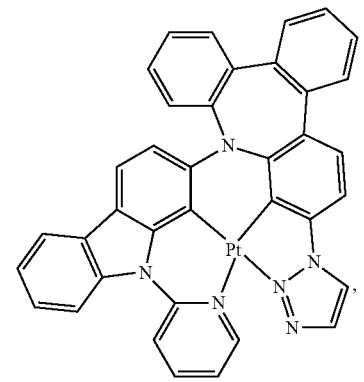
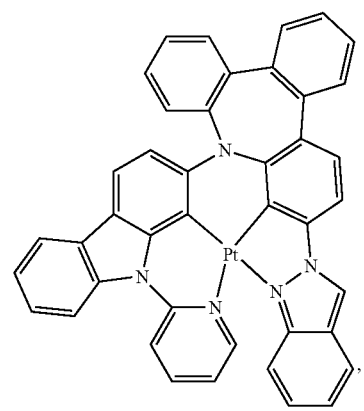
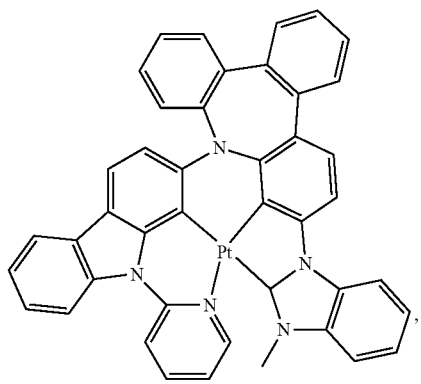
112
-continued
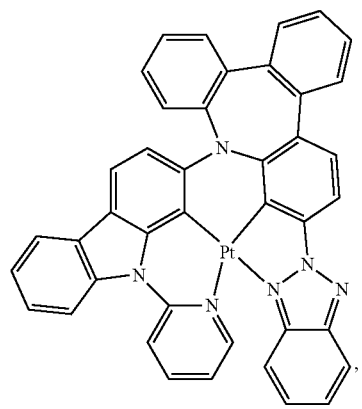
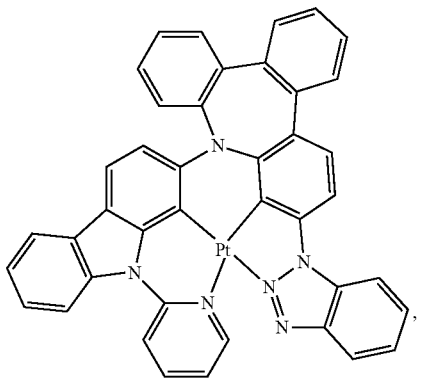
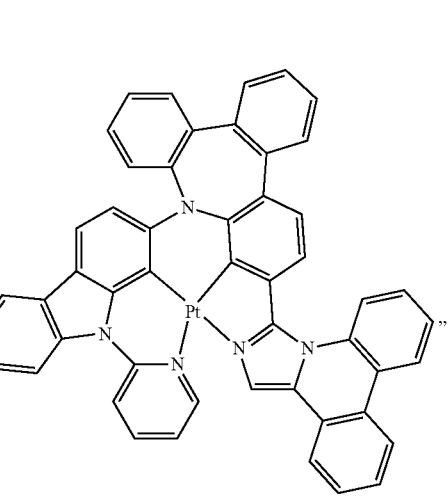
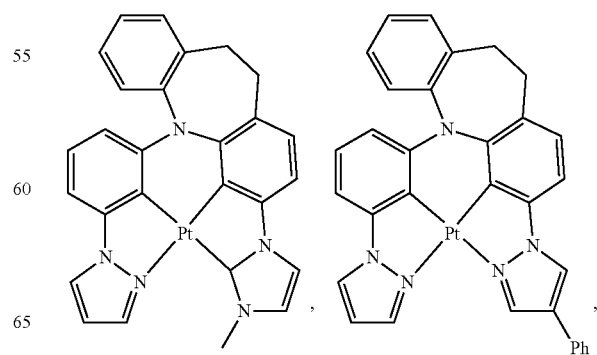

113
-continued
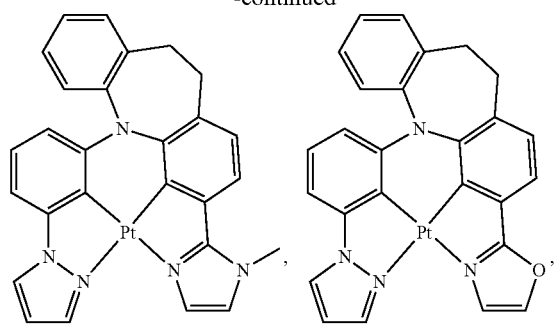
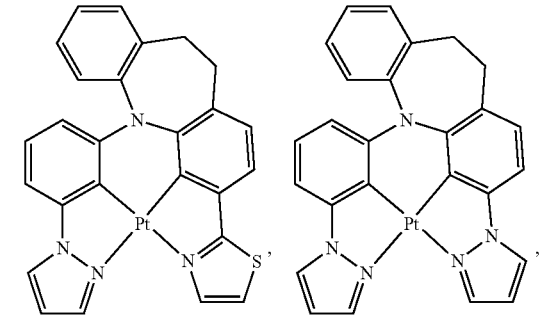
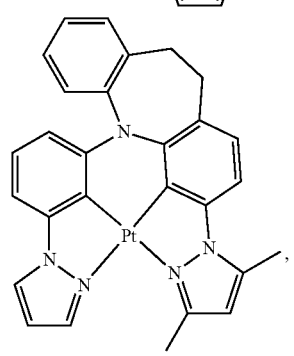
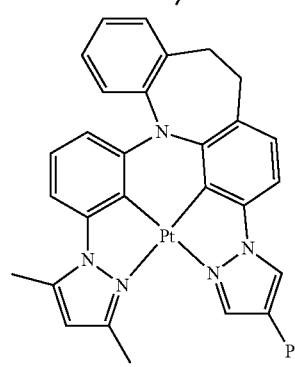
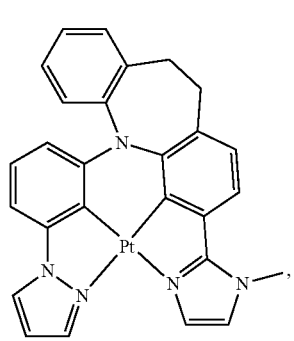
114
-continued
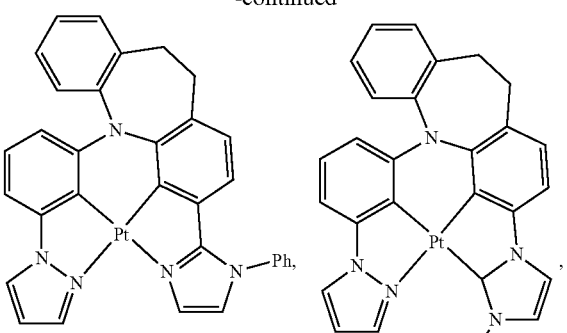
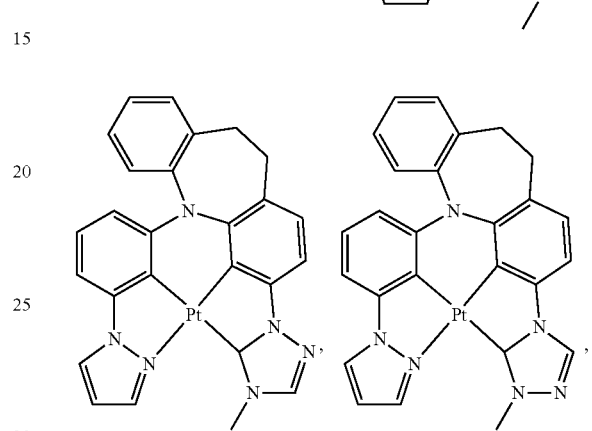
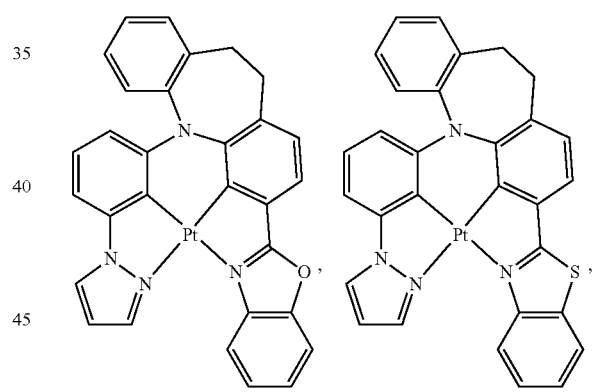
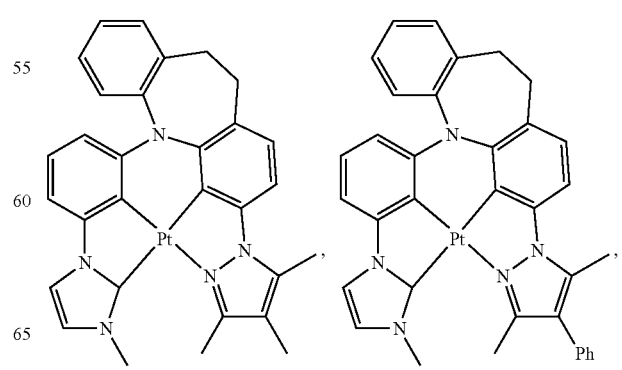

115
-continued
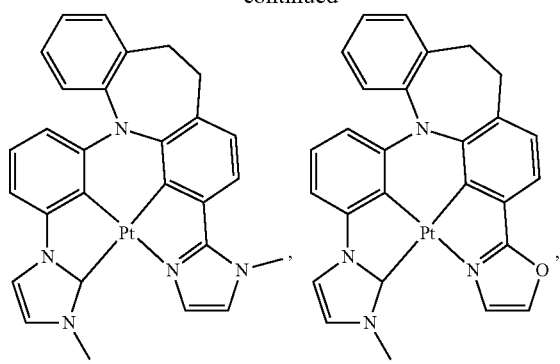
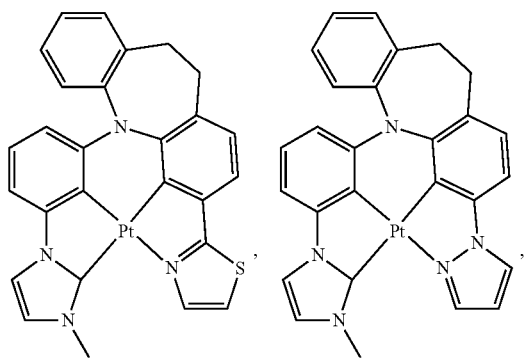
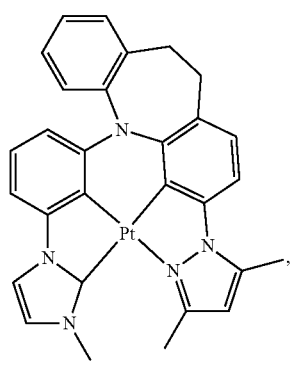
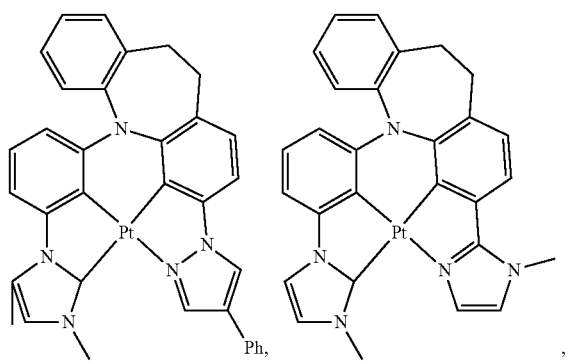
116
-continued
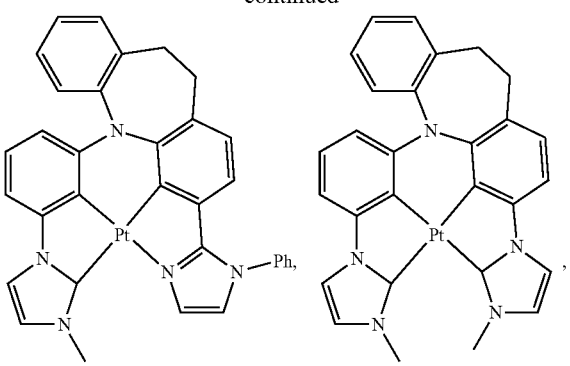
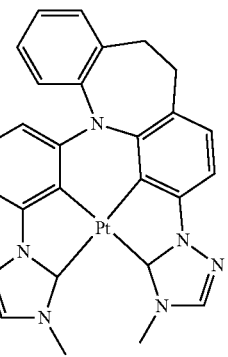
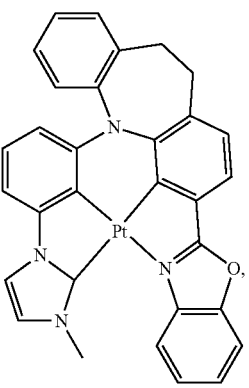
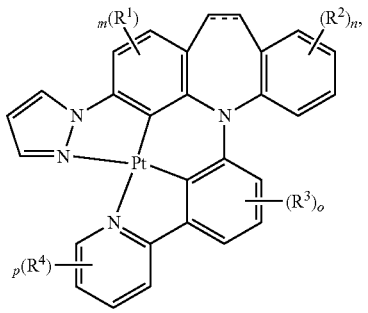

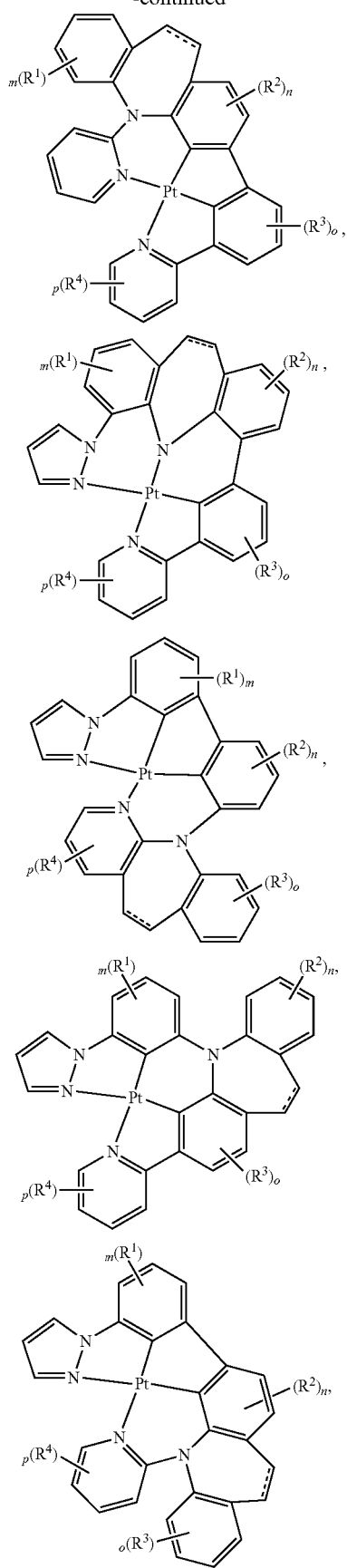
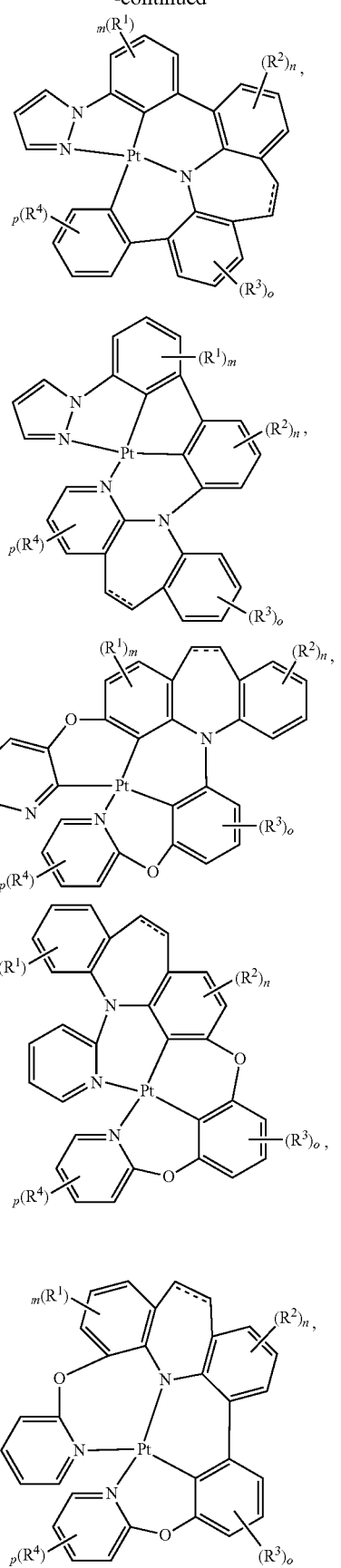

119
-continued
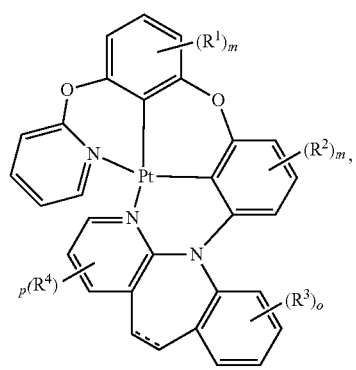
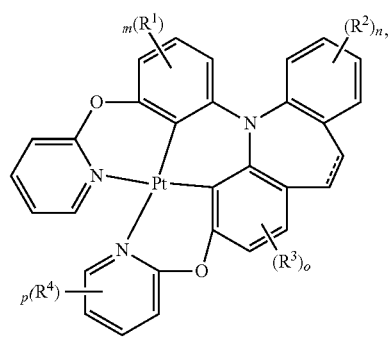
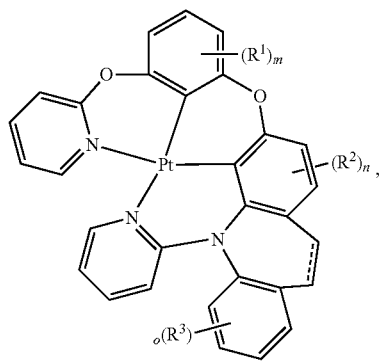
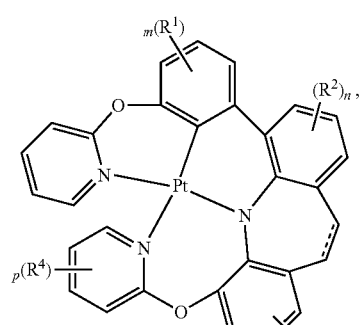
120
-continued
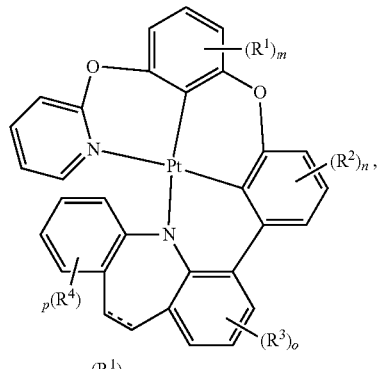
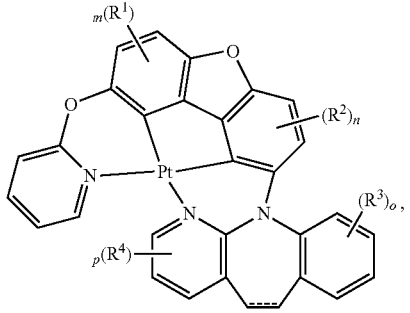
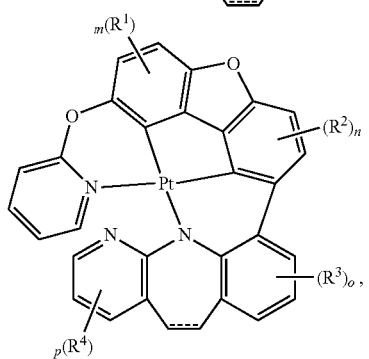
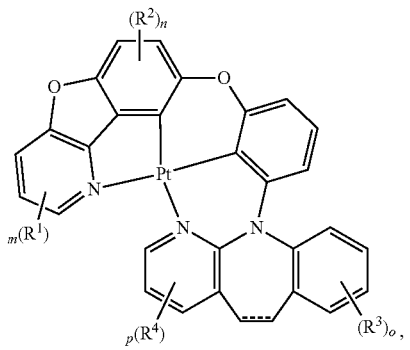
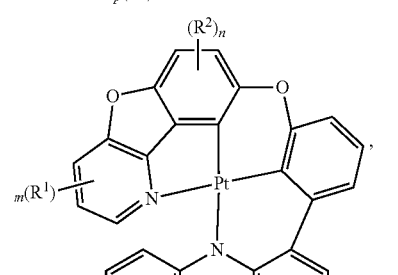

121
-continued
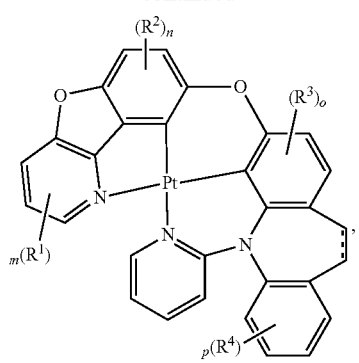
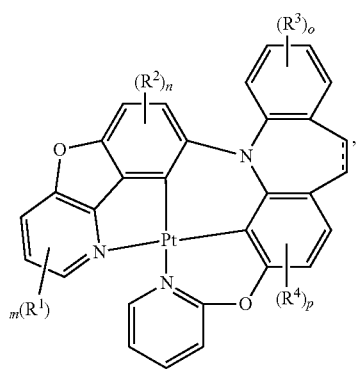
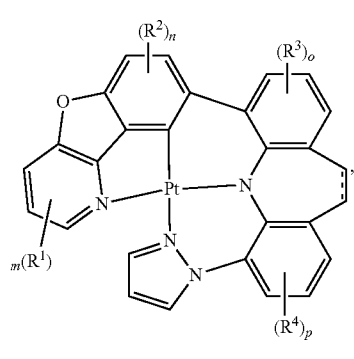
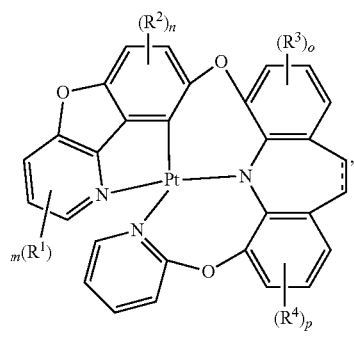
122
-continued
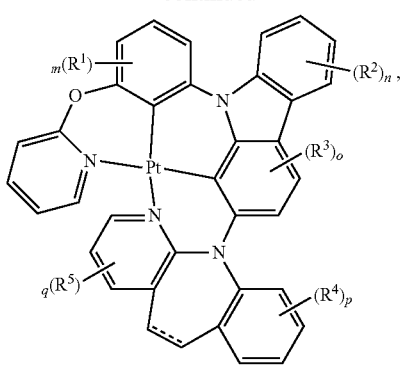
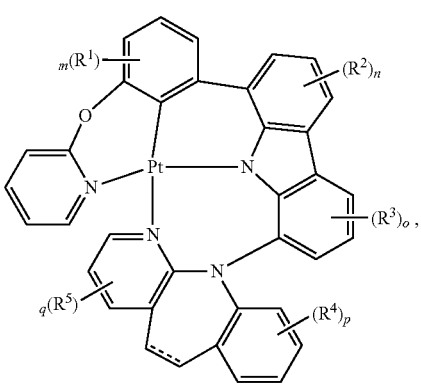
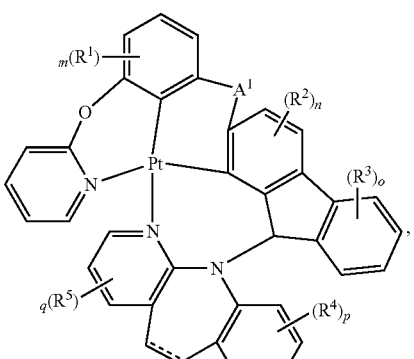
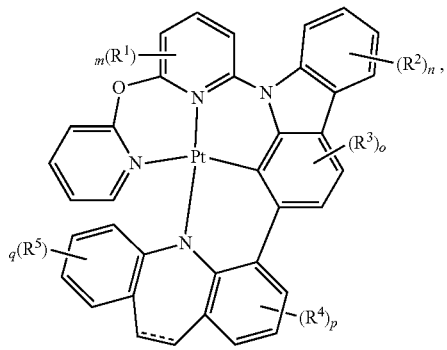

123
-continued
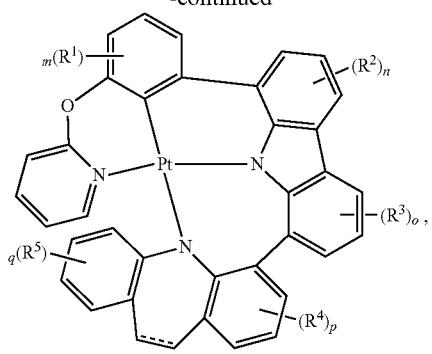
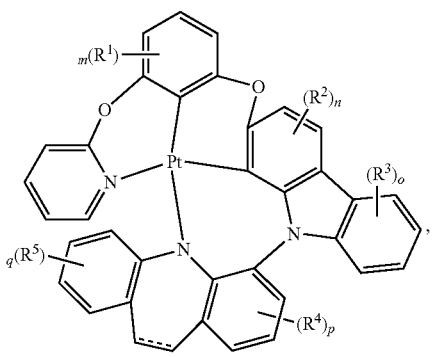
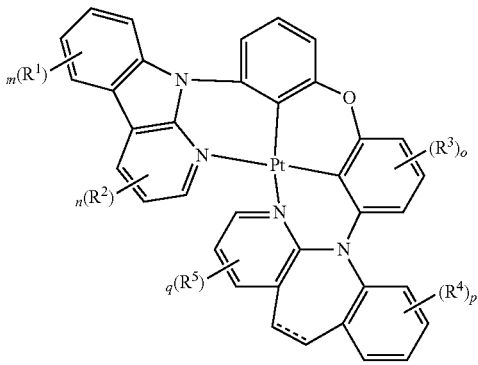
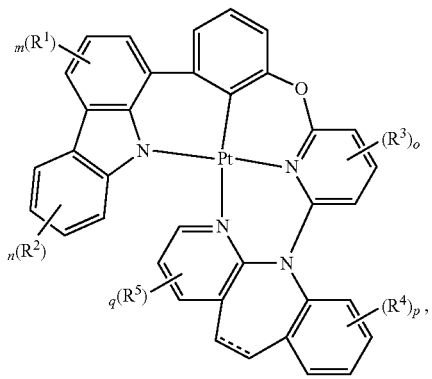
124
-continued
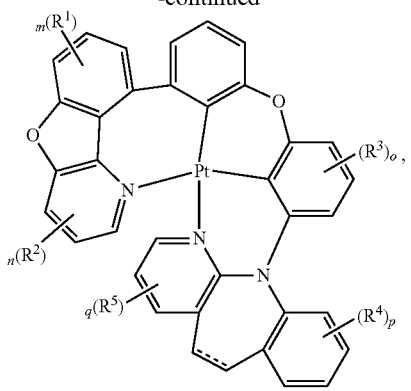
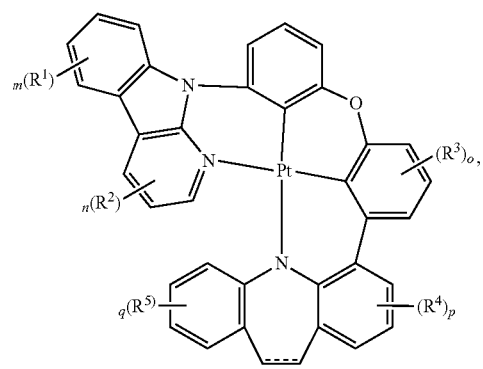
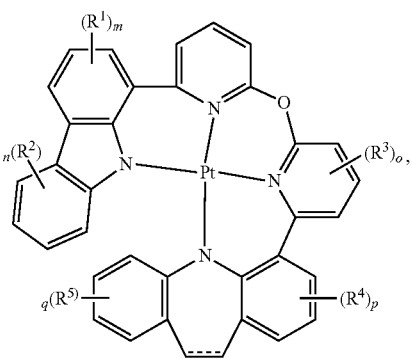
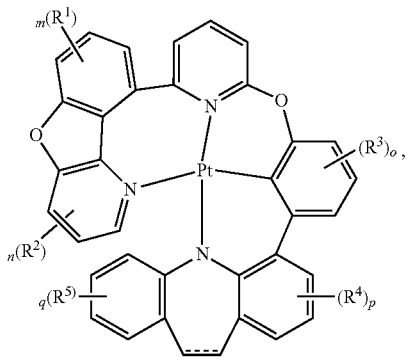

125
-continued
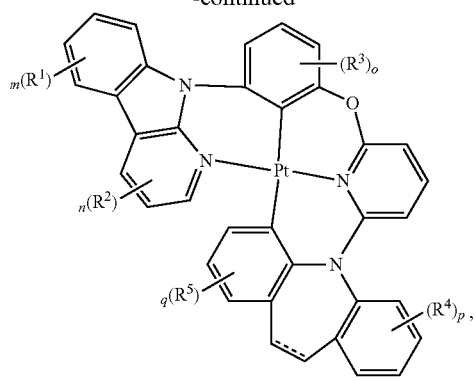
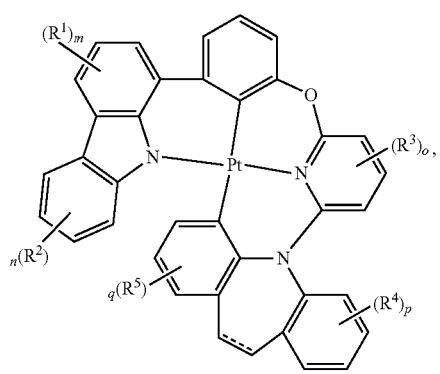
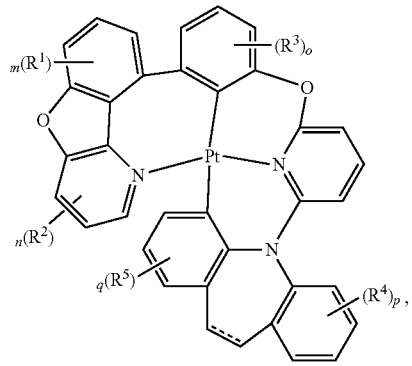
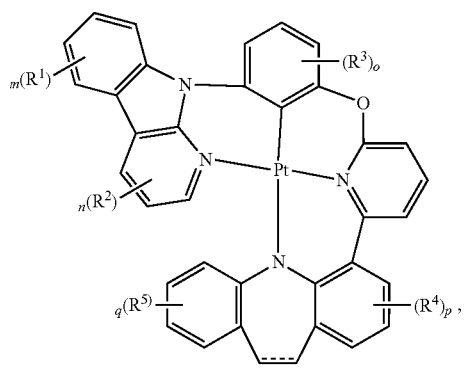
126
-continued
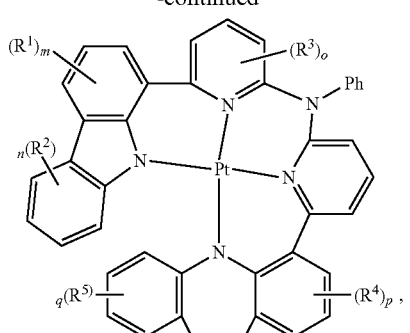
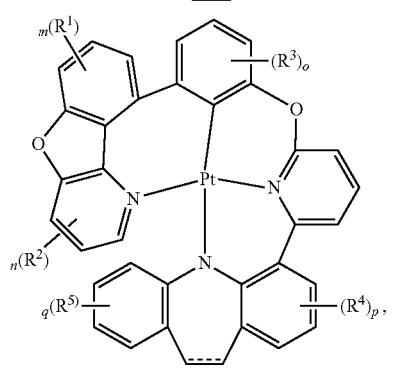
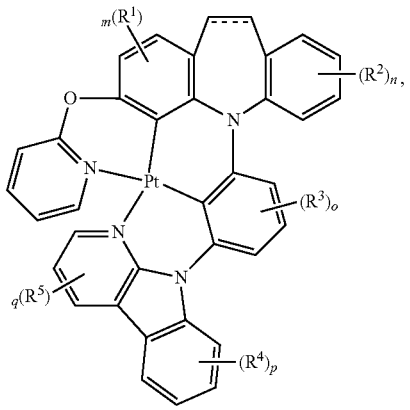
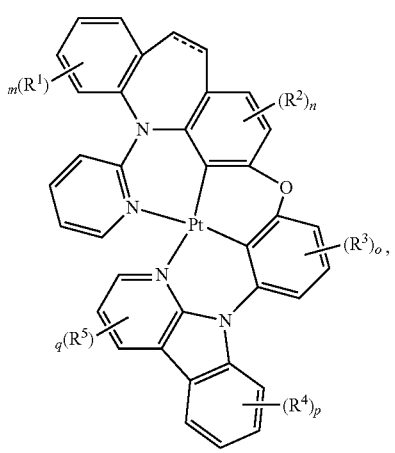

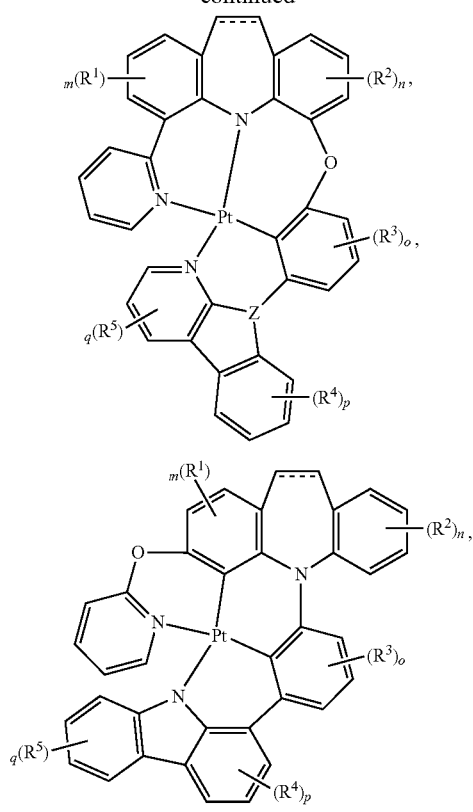
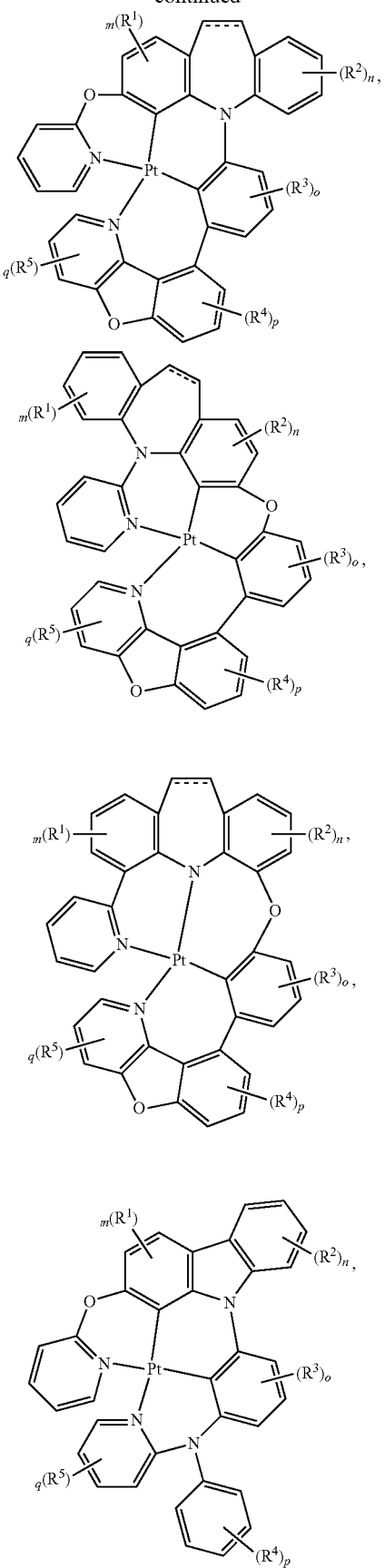

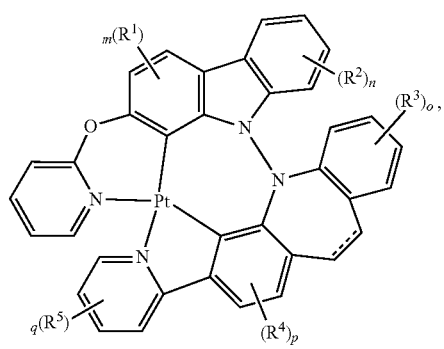
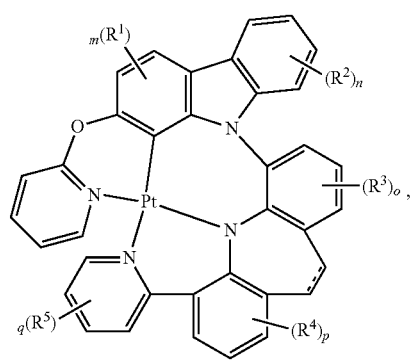
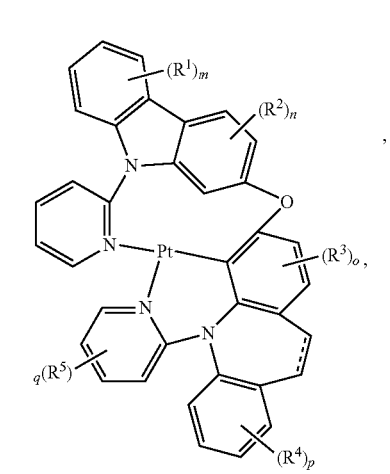
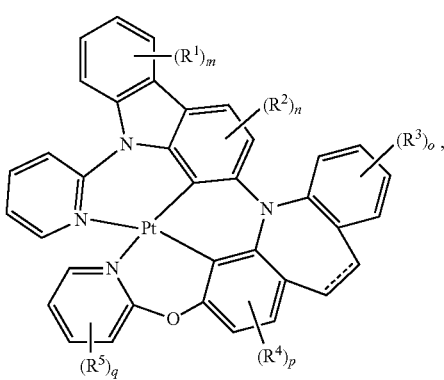
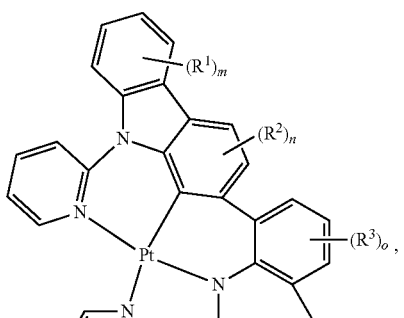
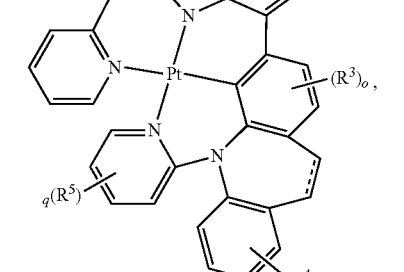
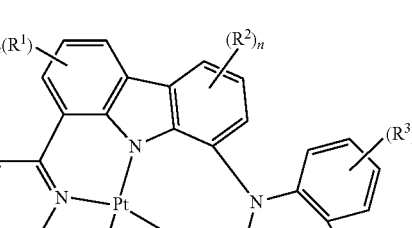
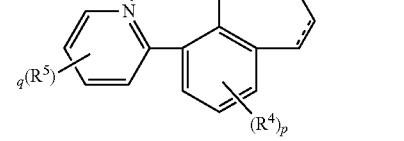

131
-continued
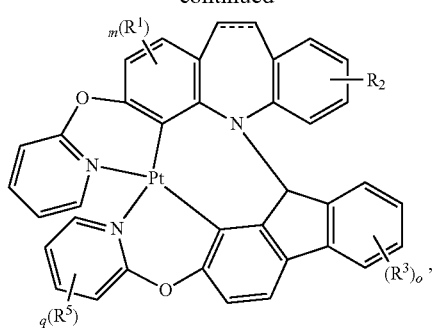
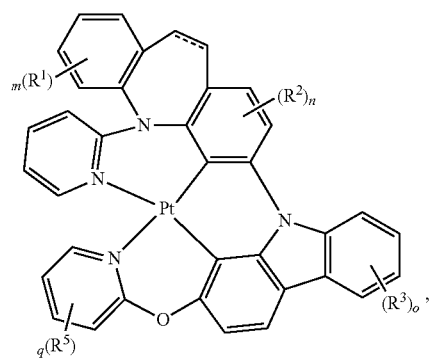
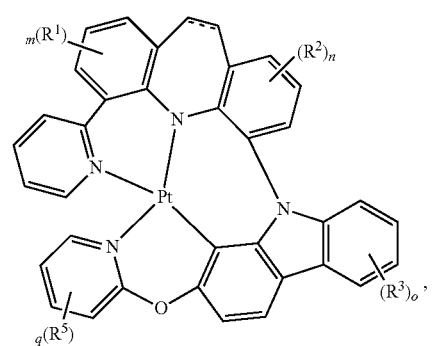
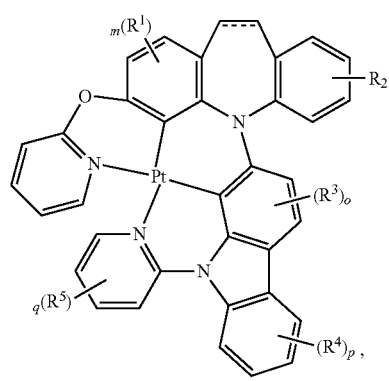
132
-continued
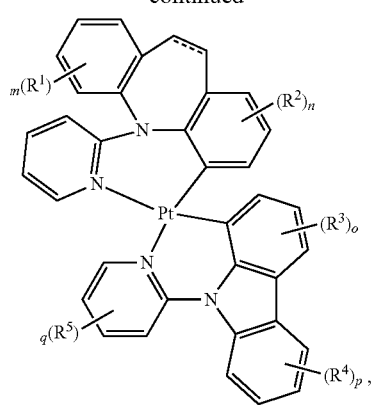
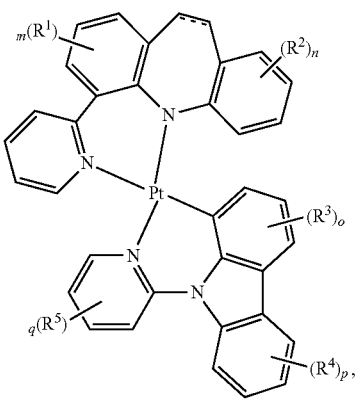
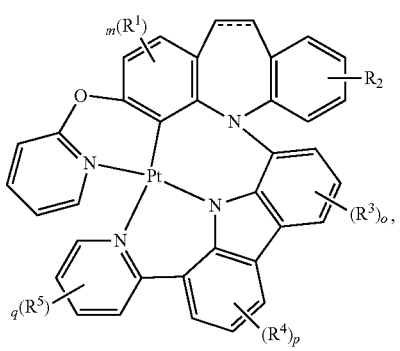
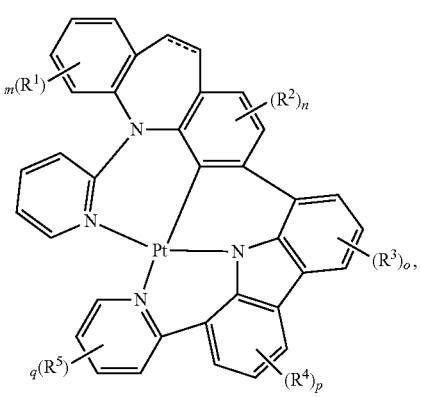

133
-continued
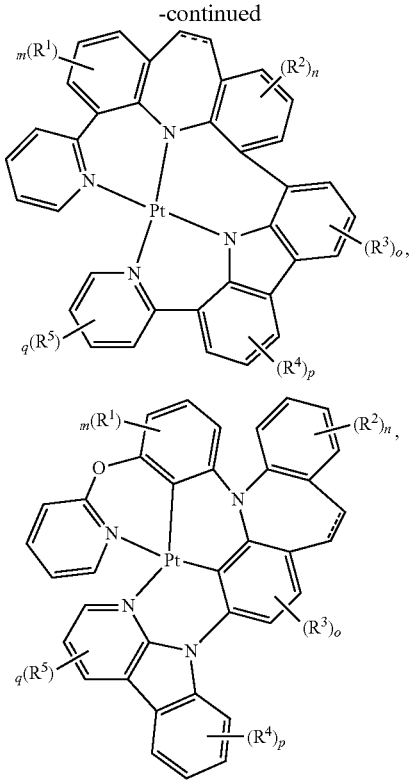
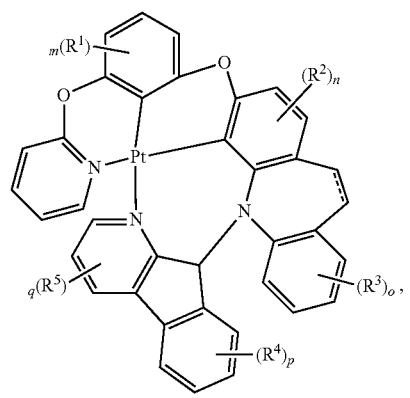
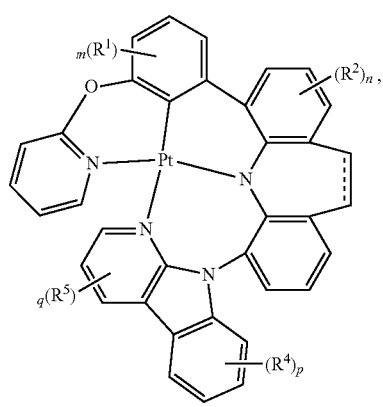
134
-continued
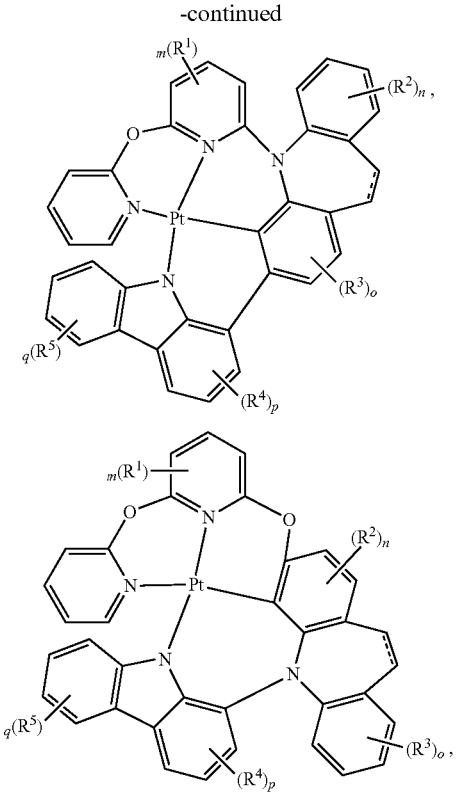
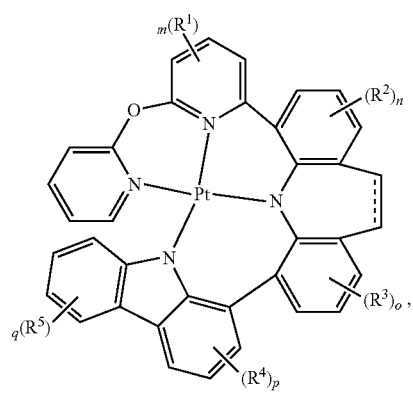
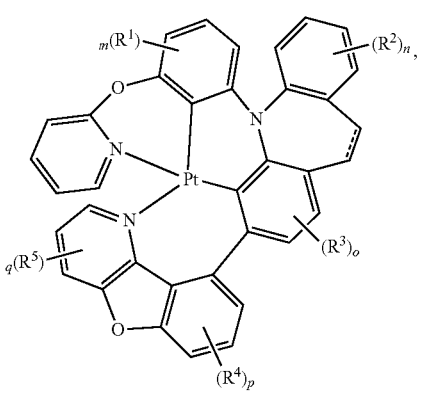

135
-continued
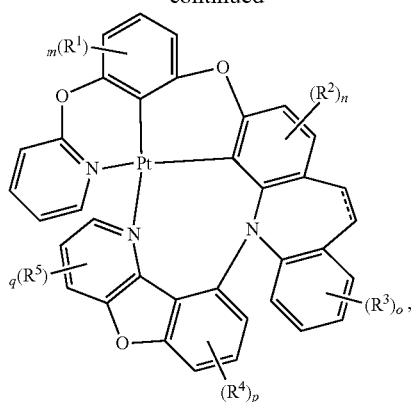
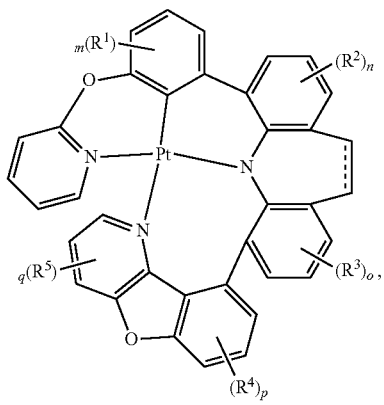
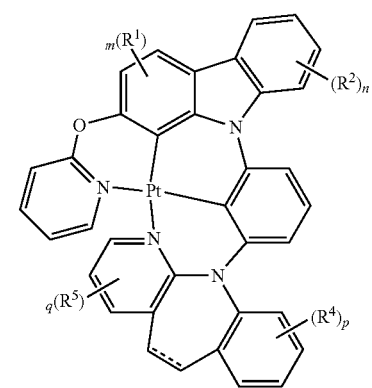
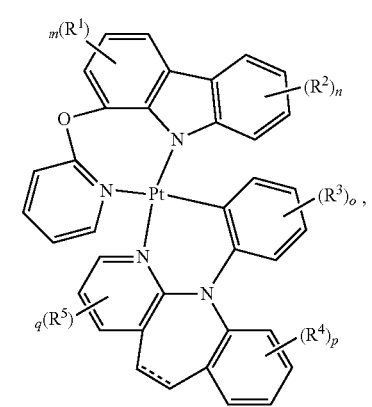
136
-continued
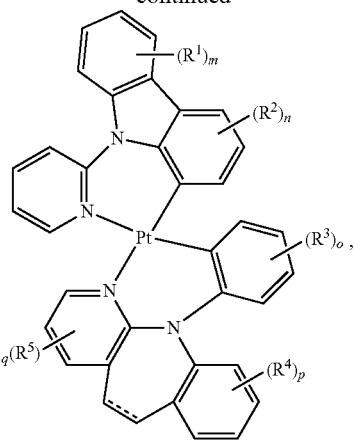
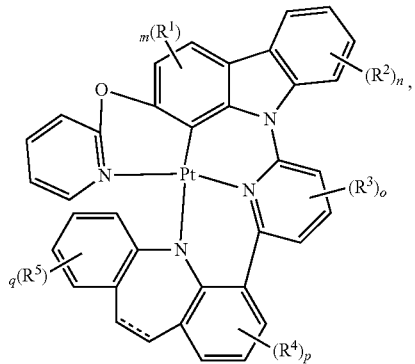
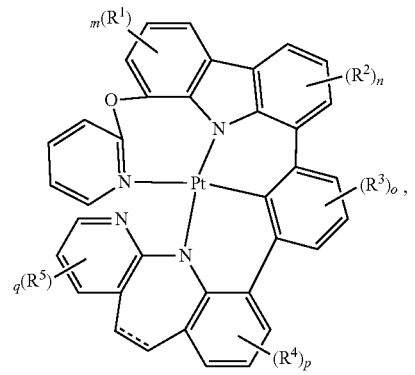
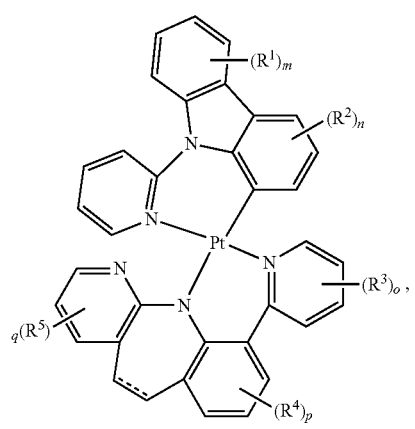

137
-continued
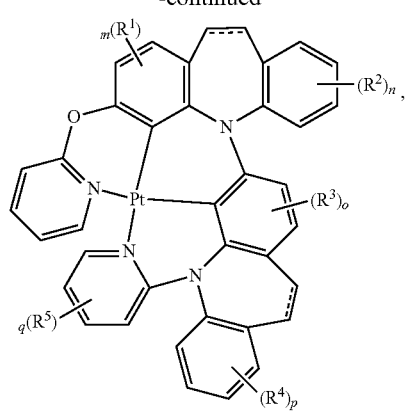
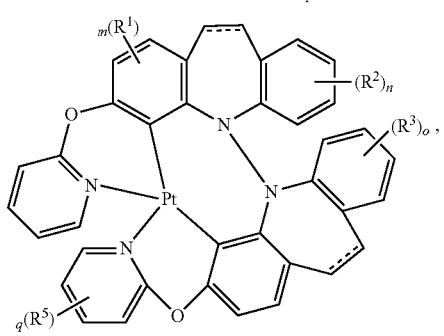
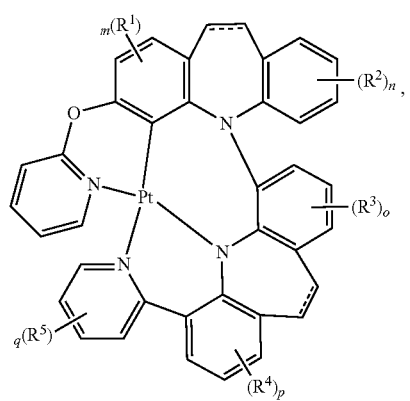
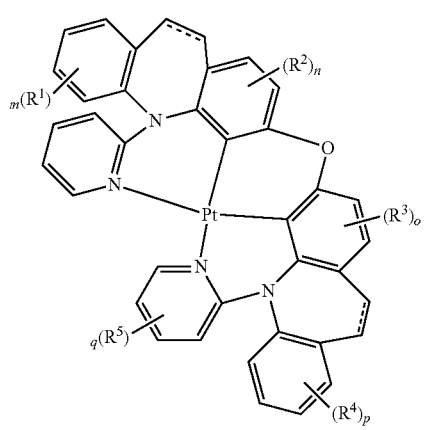
138
-continued
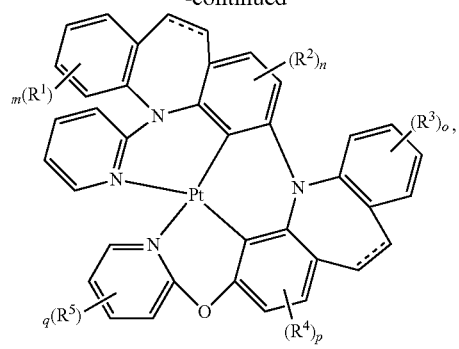
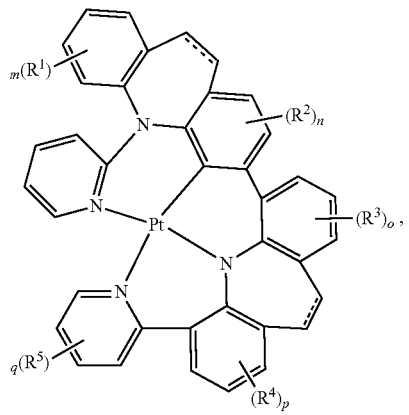
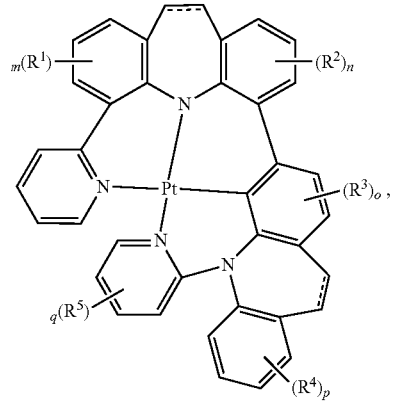
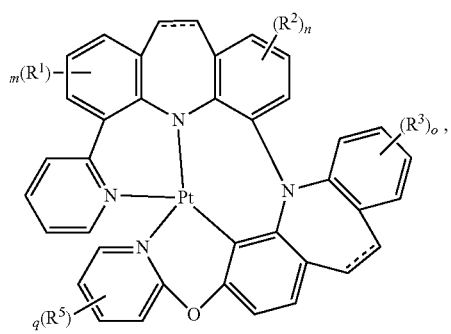

-continued
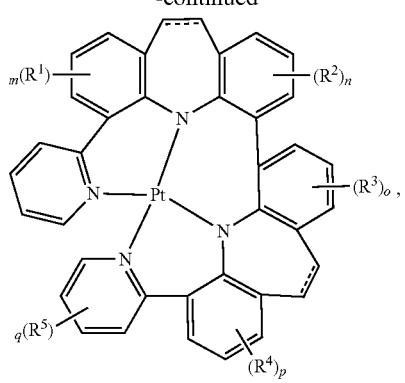
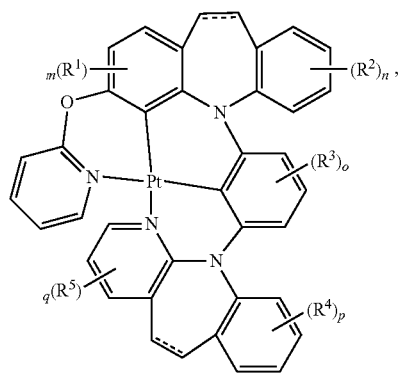
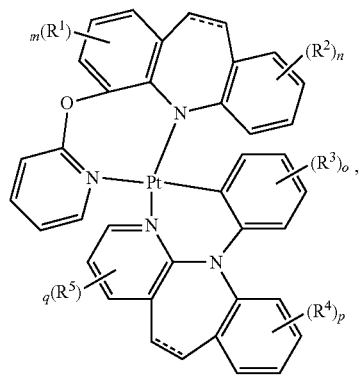
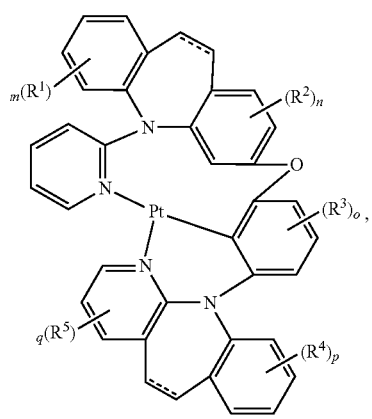
-continued
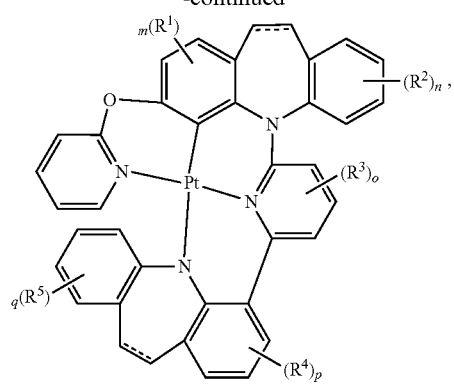
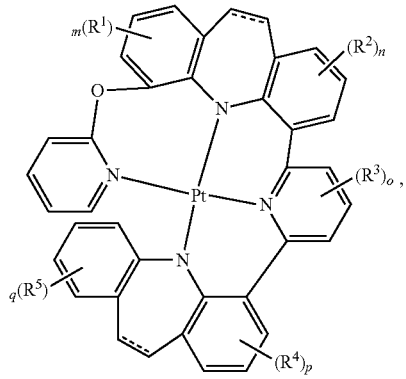
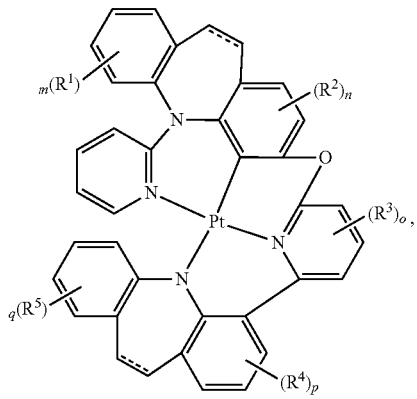
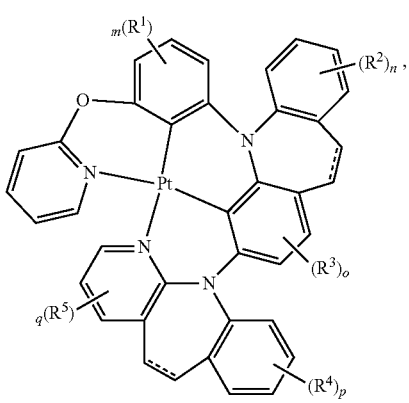

141
-continued
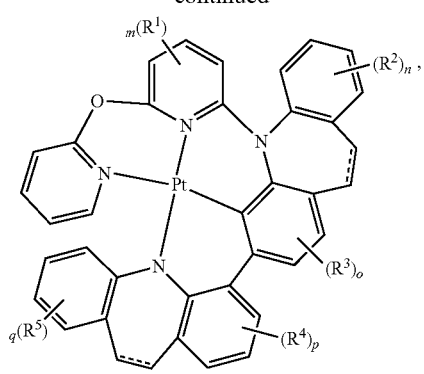
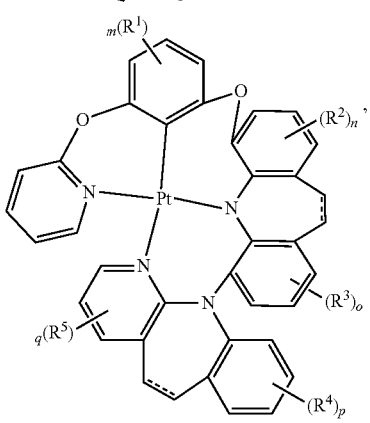
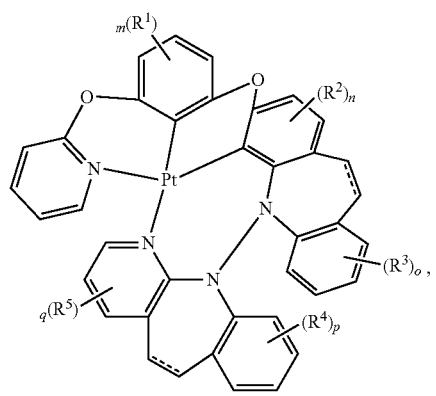
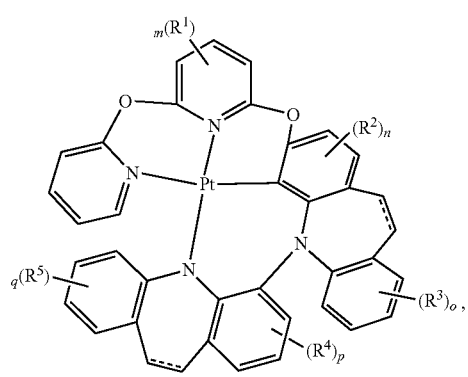
142
-continued
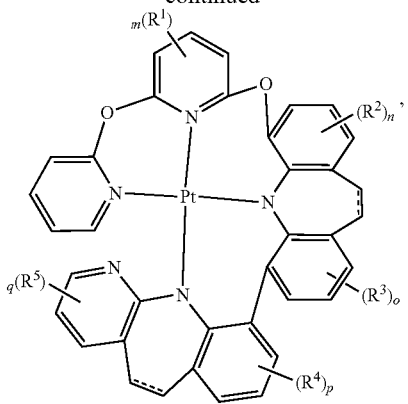
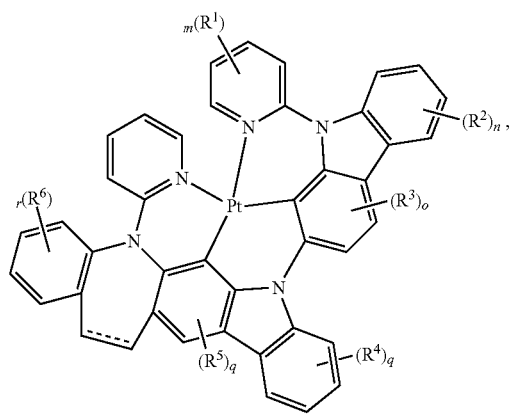
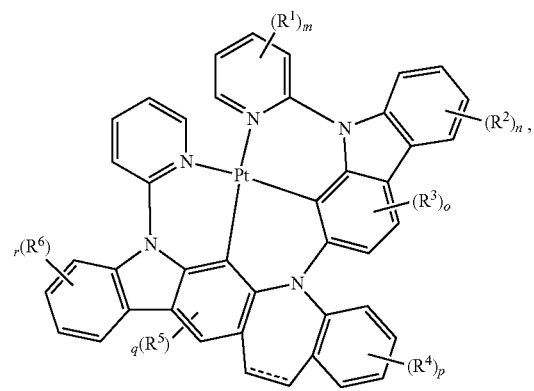
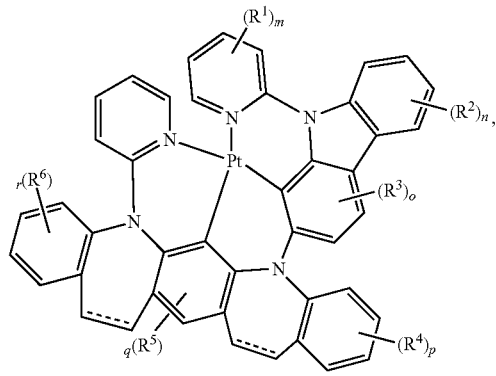

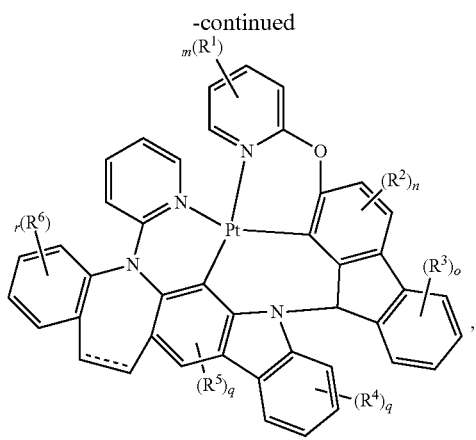
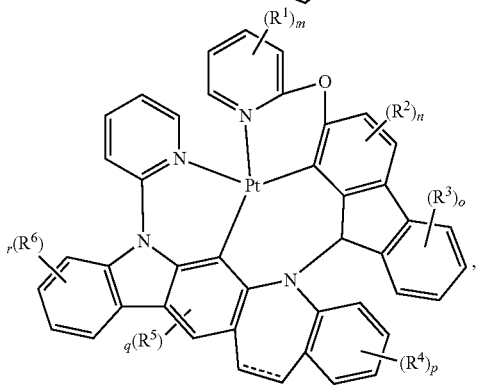
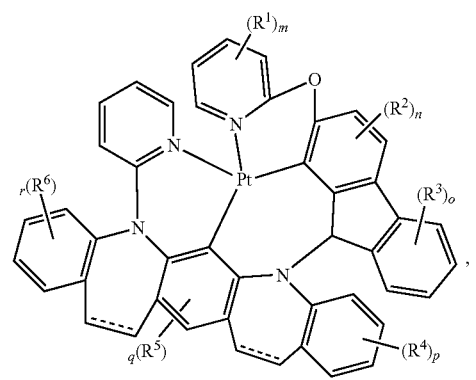
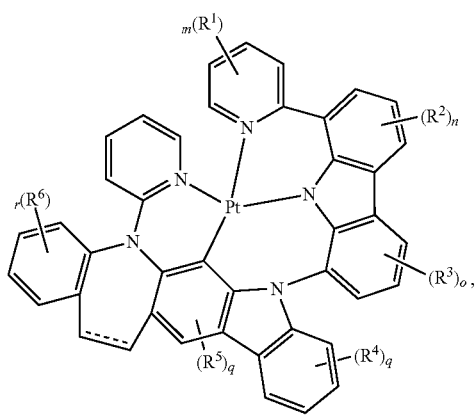
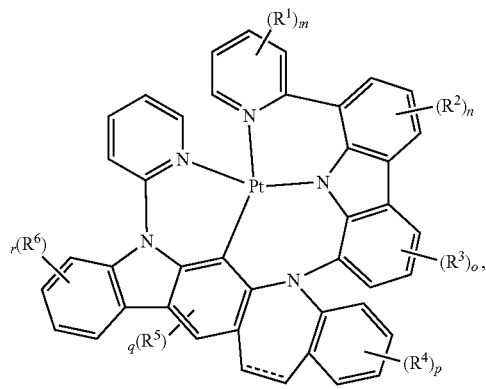
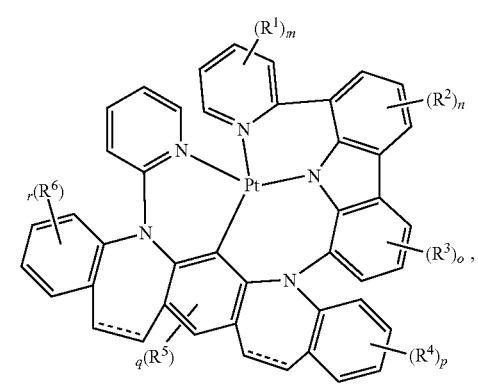
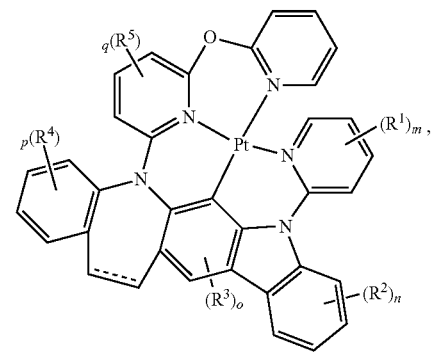
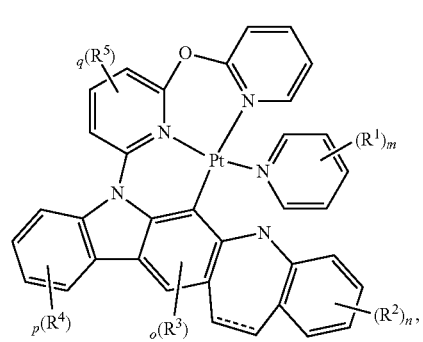

-continued
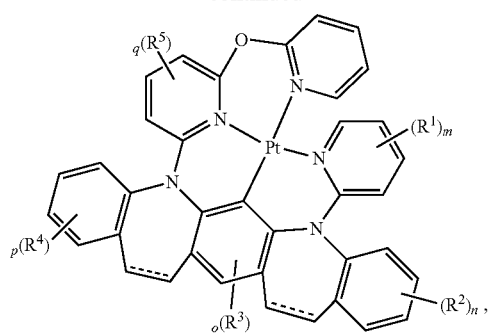
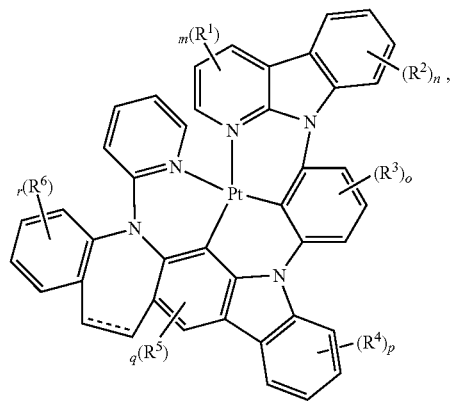
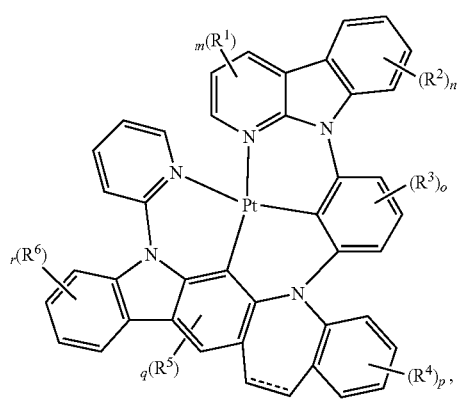
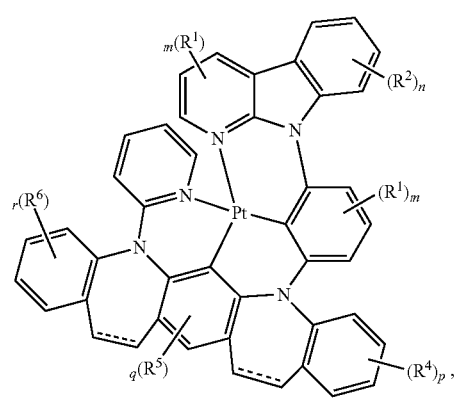
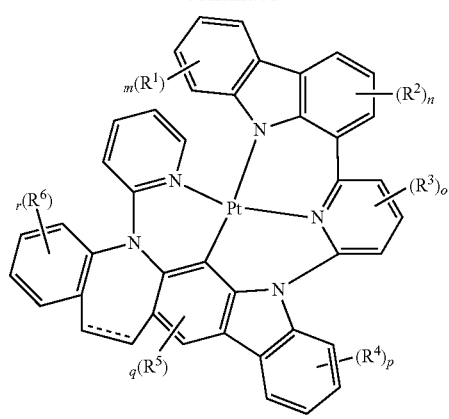
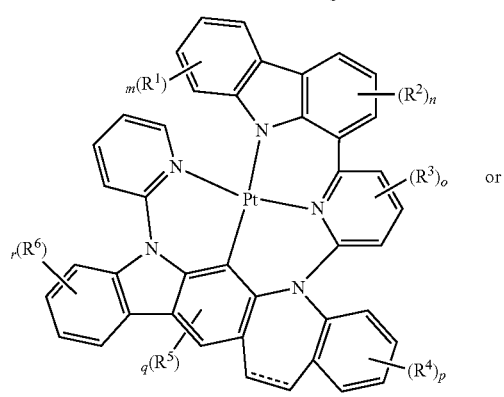
or
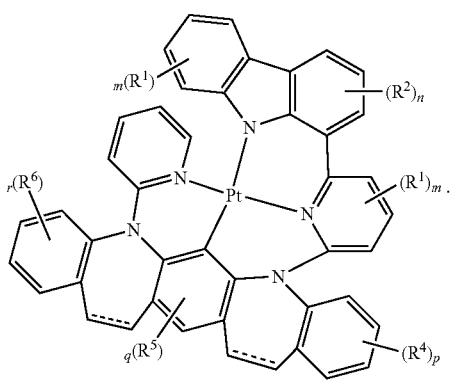
In one aspect, the compound has the structure:
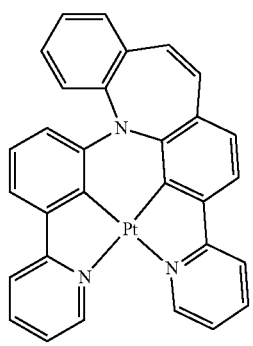
PtN″3PPy such as, for example

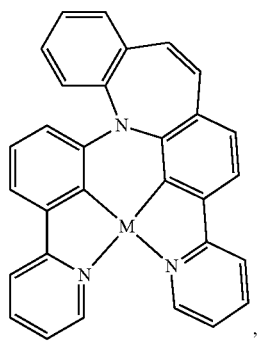
,

It should be noted that each of multiple recitations or illustrations of a particular structure, reference letter or numeral, etc., appearing in one or more structures of this disclosure can represent the same or different species, and that both aspects wherein they represent the same and wherein they represent different species are intended to be disclosed.

3. Methods

The disclosed compound can be made by one or more of the methods of synthesizing disclosed herein.

In one aspect, the disclosed compounds can be made by a synthesis comprising one or more of the following reactions or steps:

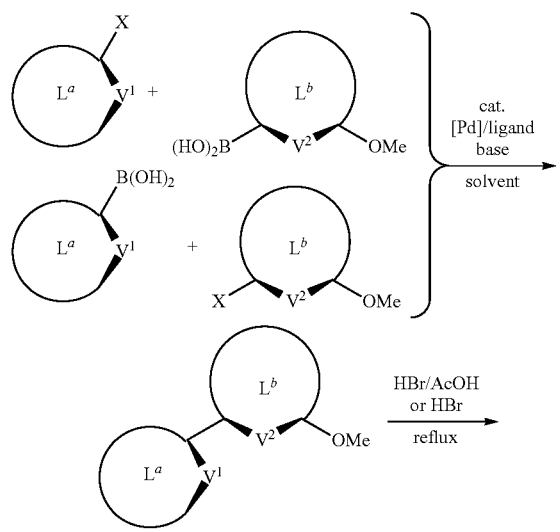

A

X = I, Br, Cl, OTf
$L^a = L^1$ or $L^4$
$L^b = L^2$ or $L^3$

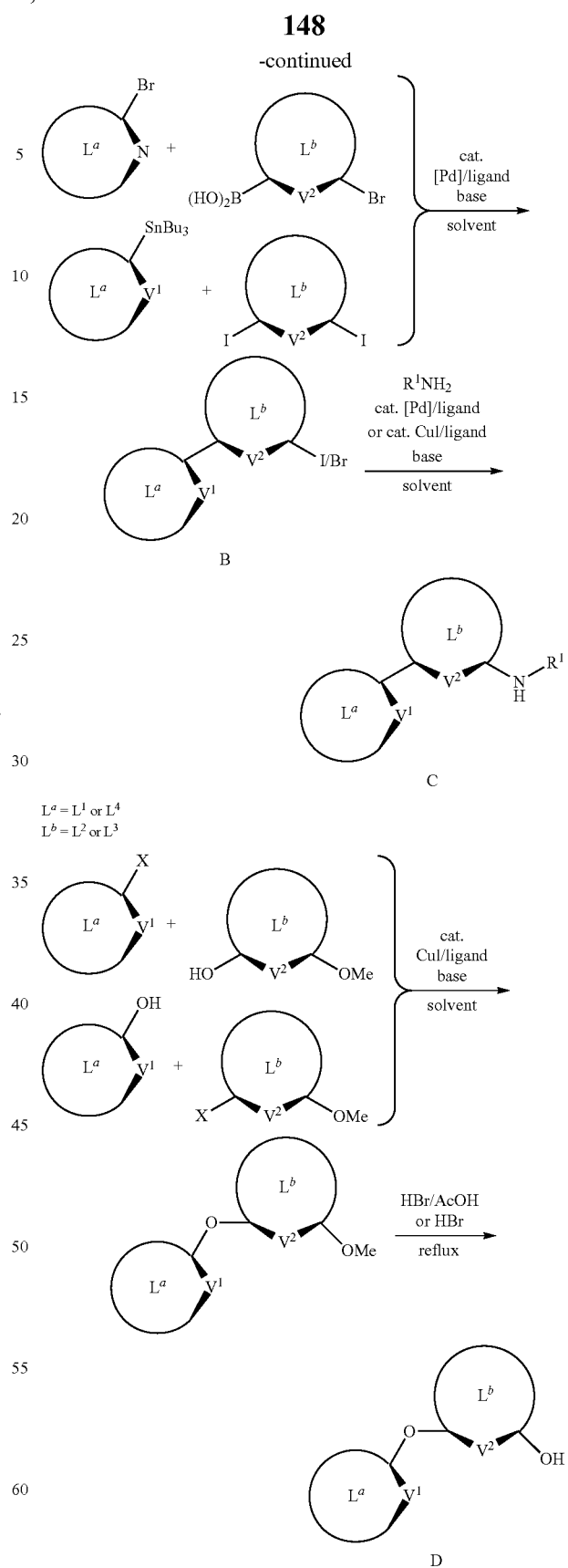

X = I, Br,
$L^a = L^1$ or $L^4$
$L^b = L^2$ or $L^3$

-continued
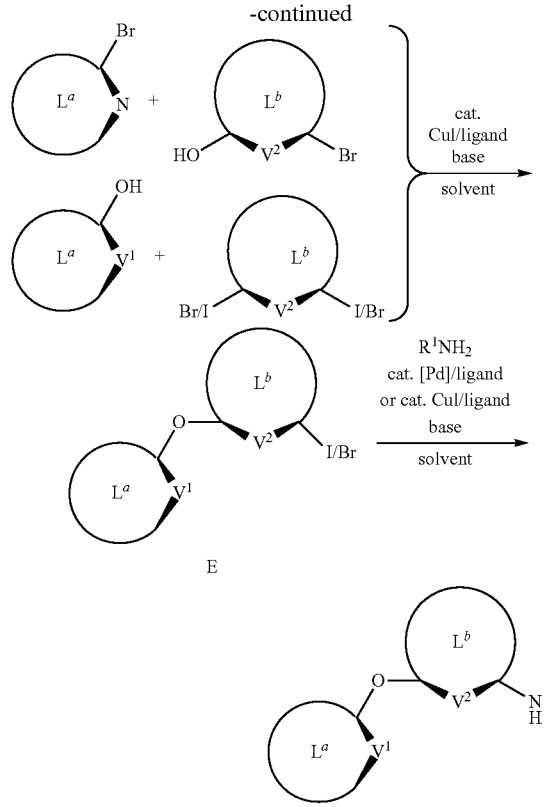
E
F
-continued
$L^a = L^1$ or $L^4$
$L^b = L^2$ or $L^3$
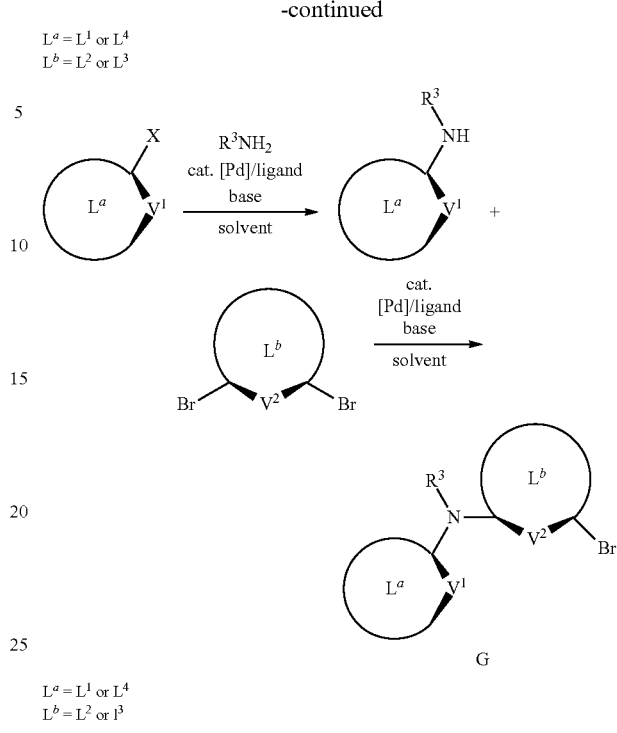
G
$L^a = L^1$ or $L^4$
$L^b = L^2$ or $L^3$
In another aspect, the disclosed compounds can be made by a synthesis comprising one or more of the following reactions or steps:

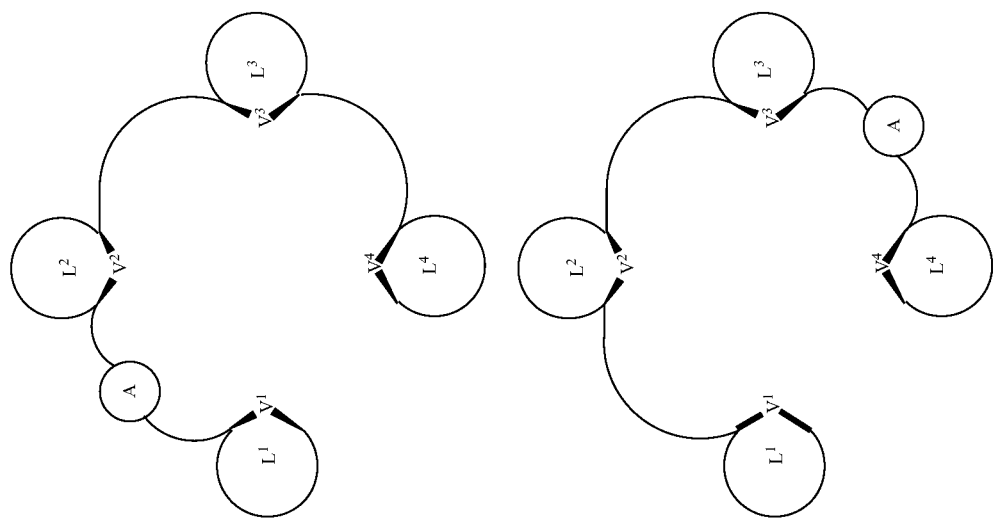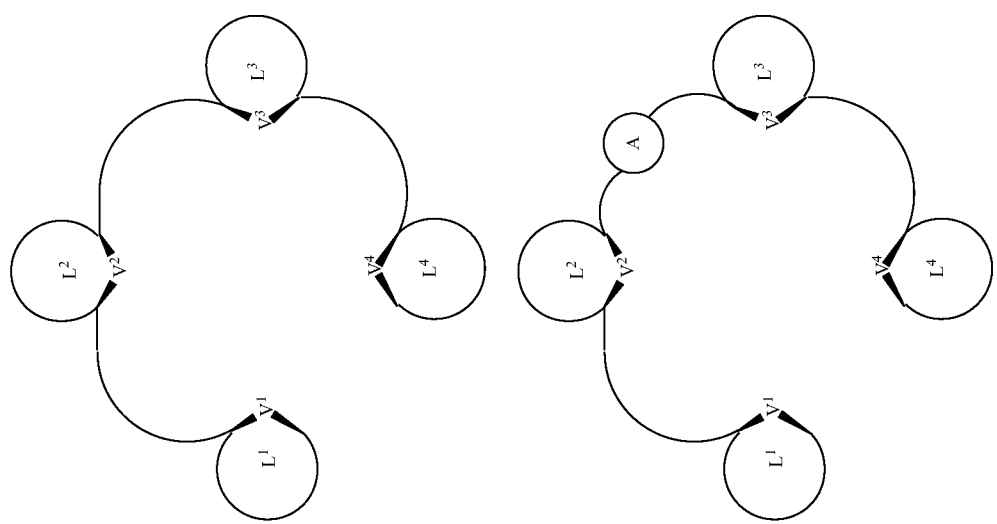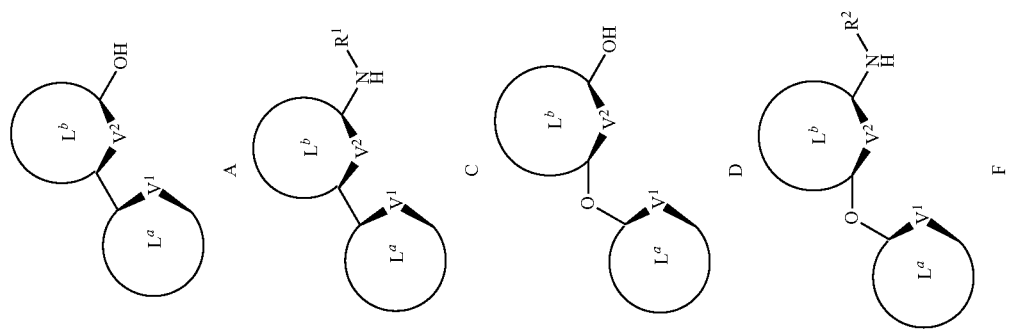

-continued
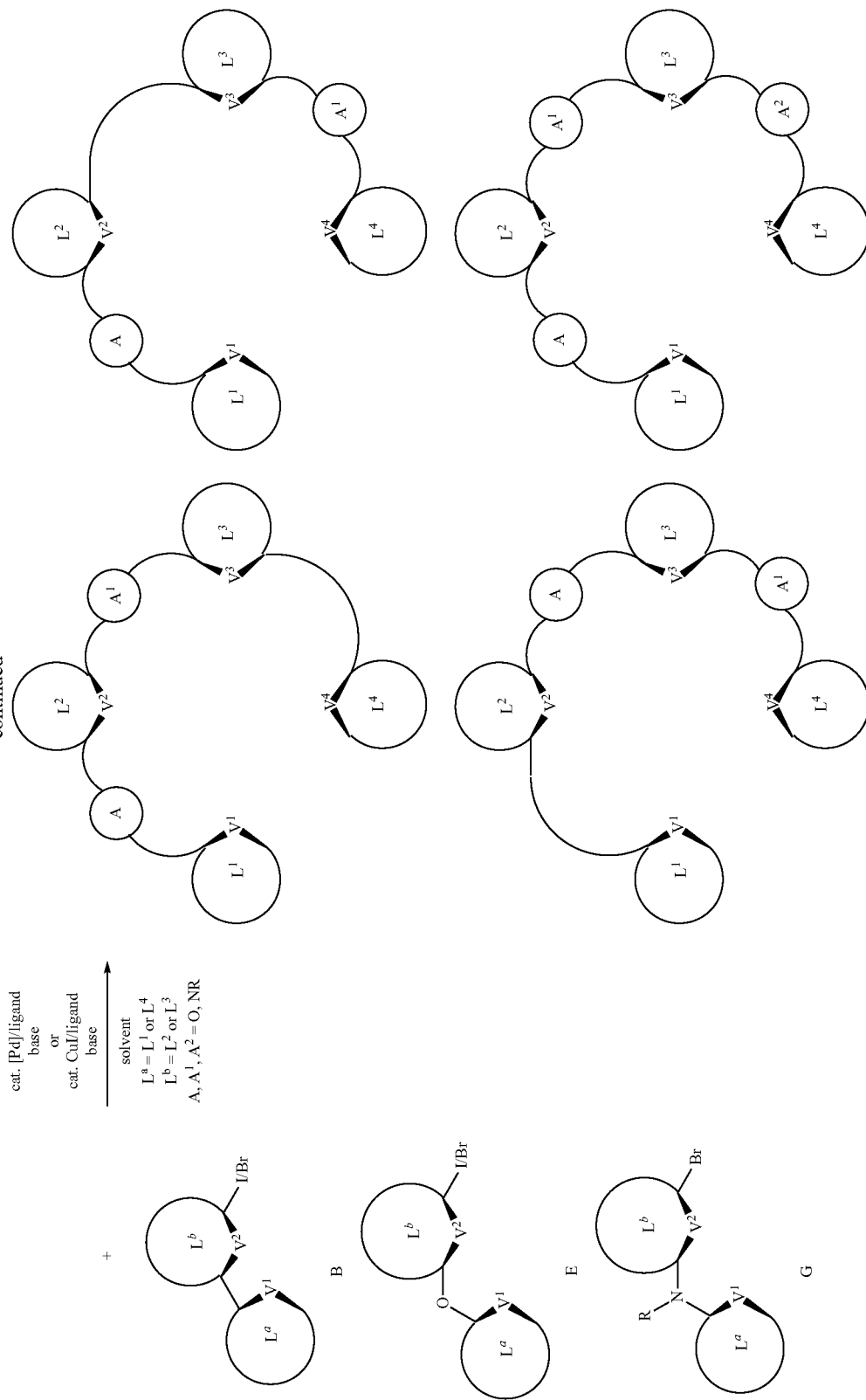

In another aspect, the disclosed compounds can be made by a synthesis comprising one or more of the following reactions or steps:
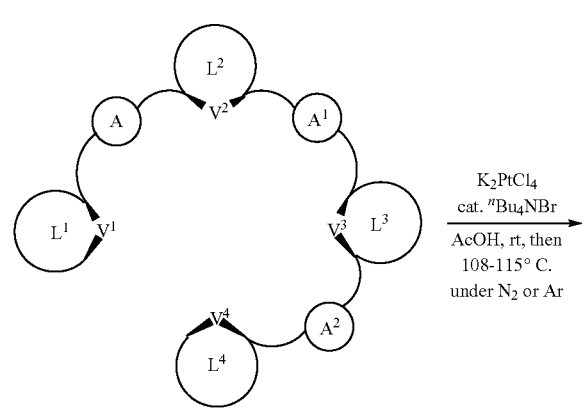
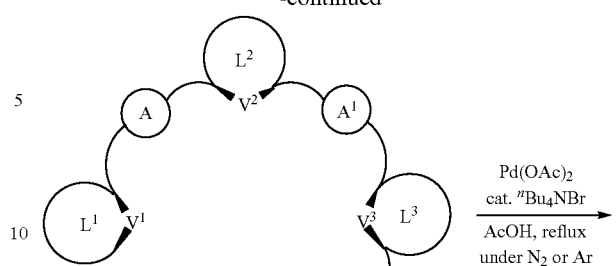
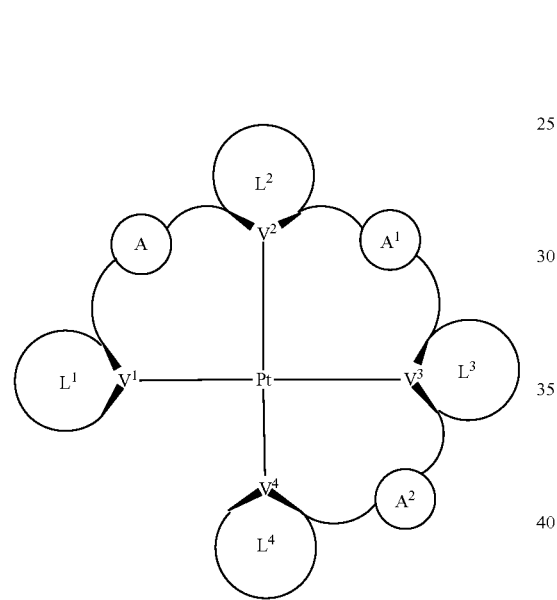
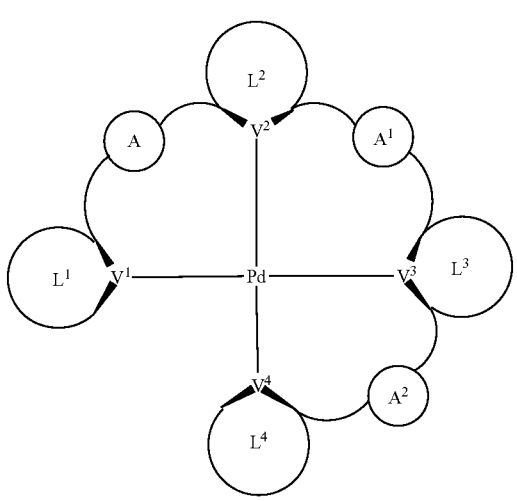
In yet another aspect, some of the disclosed compounds can be made by a synthesis comprising one or more of the following reactions or steps:
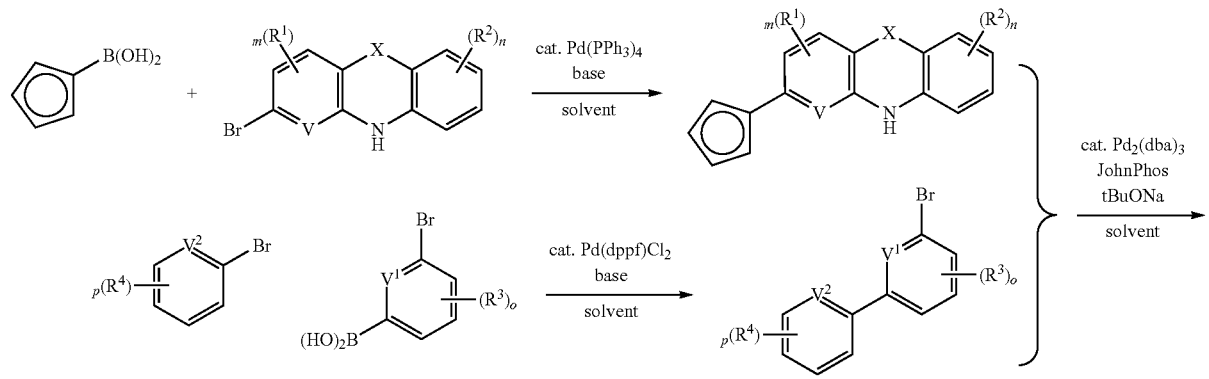

-continued
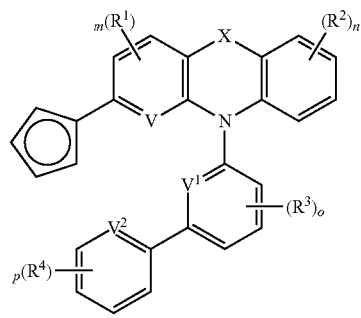
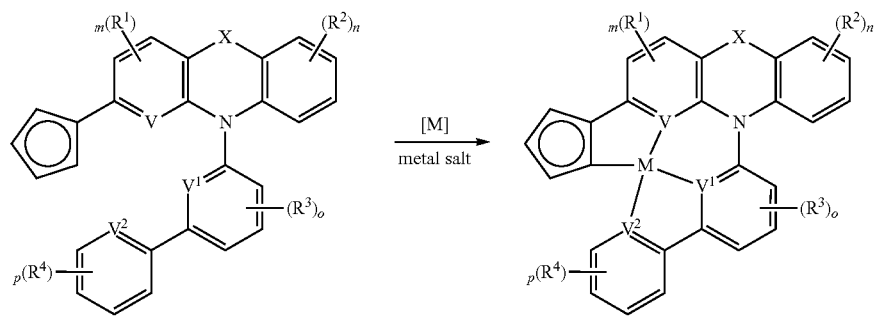
30
For example, a platinum compound can be made by a reaction comprising one or more of the following reactions or steps:
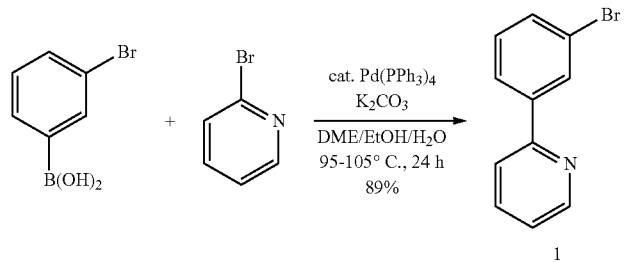
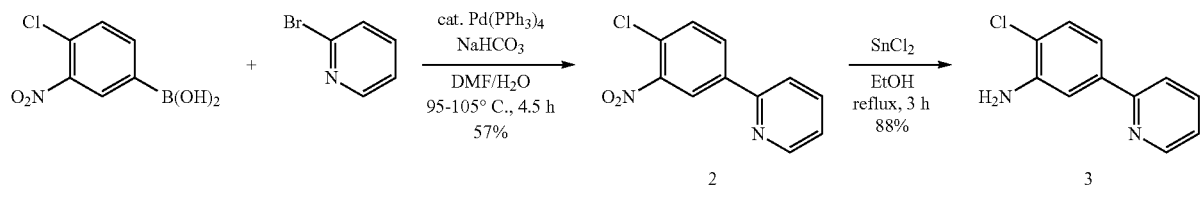
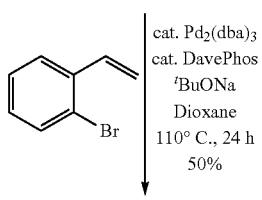

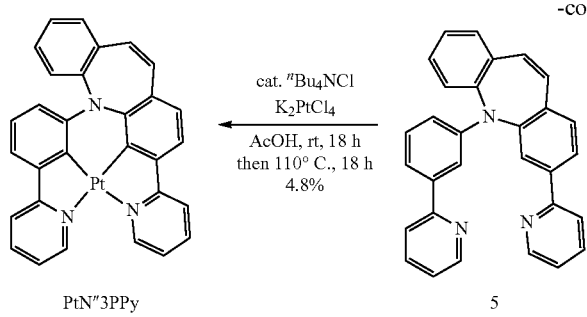
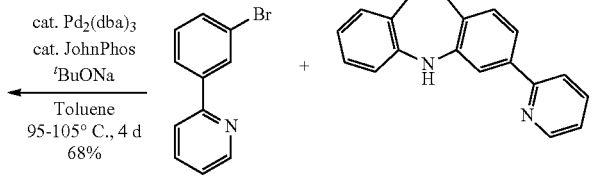

4. Devices

As briefly described above, the present invention is directed to metal compounds. In one aspect, the compounds disclosed herein can be used as host materials for OLED applications, such as full color displays.

The disclosed compounds can be useful in a wide variety of applications, such as, for example, lighting devices. In a particular aspect, one or more of the compounds can be host materials for an organic light emitting display device.

The compounds are useful in a variety of applications. As light emitting materials, the compounds can be useful in organic light emitting diodes (OLED)s, luminescent devices and displays, and other light emitting devices. The device can be a phosphorescent OLED device. The device can also be a fluorescent OLED device.

In one aspect, the device is a photovoltaic device. In another aspect, the device is a luminescent display device. In yet another aspect, the device is a light emitting device.

The energy profile of the compounds can be tuned by varying the structure of the ligand surrounding the metal center. For example, compounds having a ligand with electron withdrawing substituents will generally exhibit different properties, than compounds having a ligand with electron donating substituents. Generally, a chemical structural change affects the electronic structure of the compound, which thereby affects the electrical transport and transfer functions of the material. Thus, the compounds of the present invention can be tailored or tuned to a specific application that desires an energy or transport characteristic.

In another aspect, the disclosed compounds can provide improved efficiency and/or operational lifetimes in lighting devices, such as, for example, organic light emitting devices, as compared to conventional materials.

In other various aspects, the disclosed compounds can be useful as, for example, host materials for organic light emitting diodes, lighting applications, and combinations thereof.

In one embodiment, the compounds can be used in an OLED. FIG. 1 shows a cross-sectional view of an OLED 100, which includes substrate 102 with an anode 104, which is typically a transparent material, such as indium tin oxide, a layer of hole-transporting material(s) (HTL) 106, a layer of light processing material 108, such as an emissive material (EML) including an emitter and a host, a layer of electron-transporting material(s) (ETL) 110, and a metal cathode layer 112.

In one aspect, a light emitting device, such as, for example, an OLED, can comprise one or more layers. In various aspects, any of the one or more layers can comprise indium tin oxide (ITO), poly(3,4-ethylenedioxythiophene) (PEDOT), polystyrene sulfonate (PSS), N,N'-di-1-naphthyl-N,N'-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

In this embodiment, the layer of light processing material 108 can comprise one or more of the disclosed compounds optionally together with a host material. The host material can be any suitable host material known in the art. The emission color of an OLED is determined by the emission energy (optical energy gap) of the light processing material 108, which as discussed above can be tuned by tuning the electronic structure of the emitting compounds and/or the host material. Both the hole-transporting material in the HTL layer 106 and the electron-transporting material(s) in the ETL layer 110 can comprise any suitable hole-transporter known in the art. A selection of which is well within the purview of those skilled in the art.

It will be apparent that the compounds of the present invention can exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

The compounds of the invention can be made using a variety of methods, including, but not limited to those recited in the examples provided herein. In other aspects, one of skill in the art, in possession of this disclosure, could readily determine an appropriate method for the preparation of an iridium complex as recited herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Hereinafter, the preparation method of the compounds for the displays and lighting applications will be illustrated. However, the following embodiments are only exemplary and do not limit the scope of the present invention. Temperatures, catalysts, concentrations, reactant compositions, and other process conditions can vary, and one of skill in the art, in possession of this disclosure, could readily select appropriate reactants and conditions for a desired complex.
1. Prophetic Synthetic Routes
A general proposed synthetic route for the compounds disclosed herein includes:
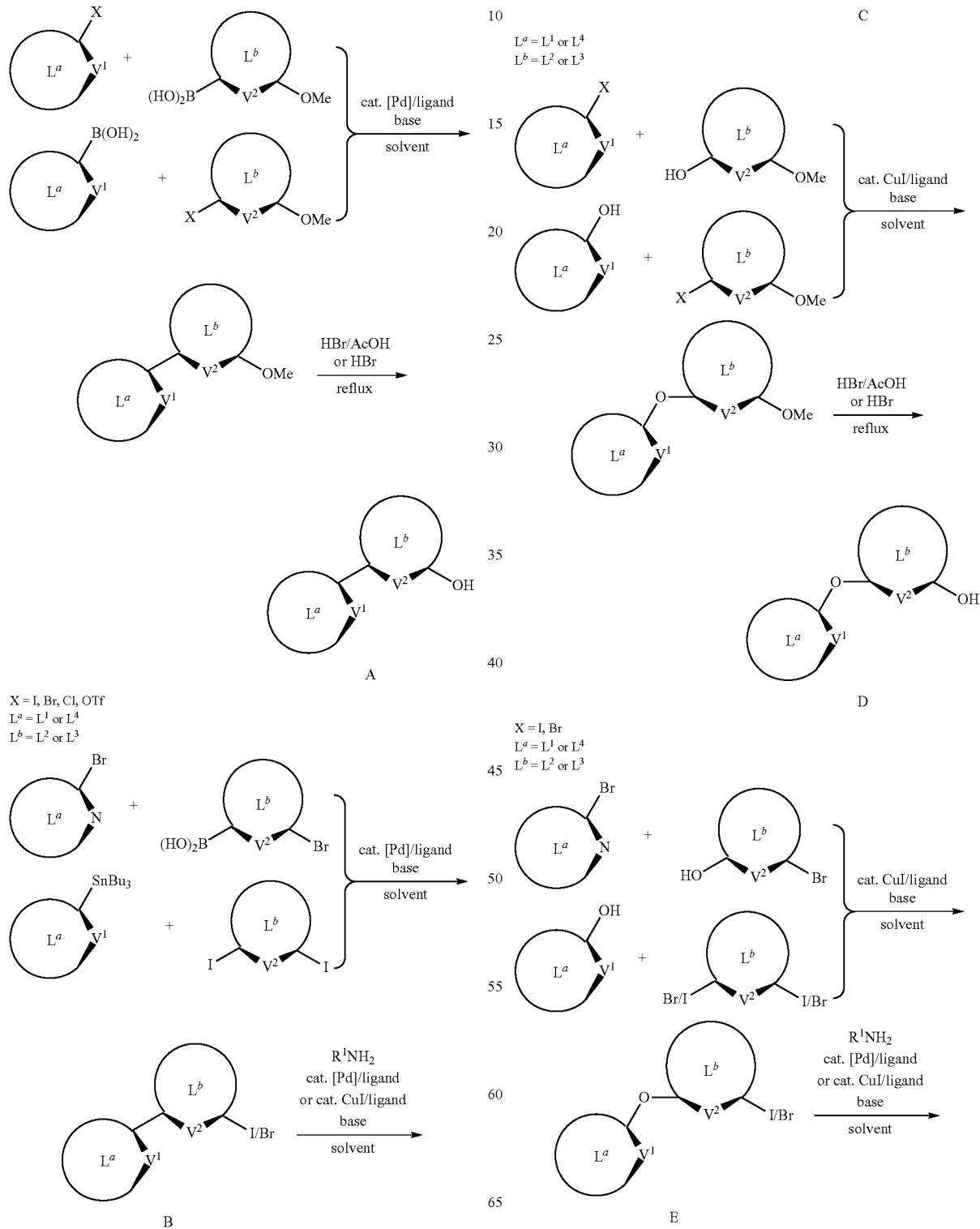

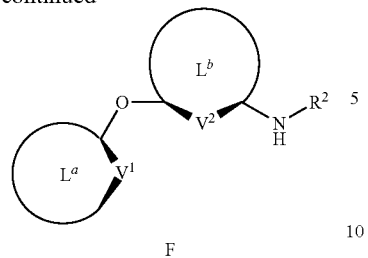
F
$L^a = L^1$ or $L^4$
$L^b = L^2$ or $L^3$
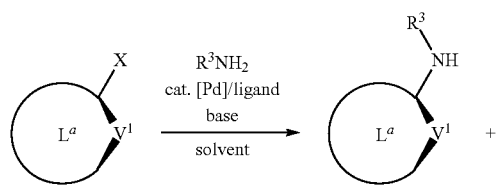
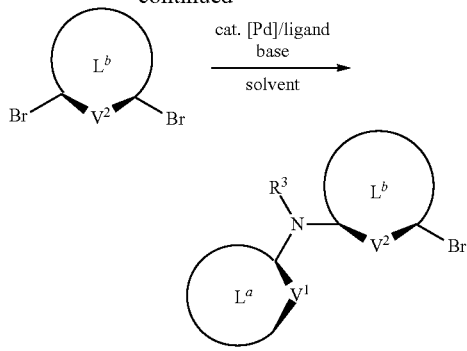
G
$L^a = L^1$ or $L^4$
$L^b = L^2$ or $L^3$
A proposed synthesis for the disclosed compounds herein also includes:

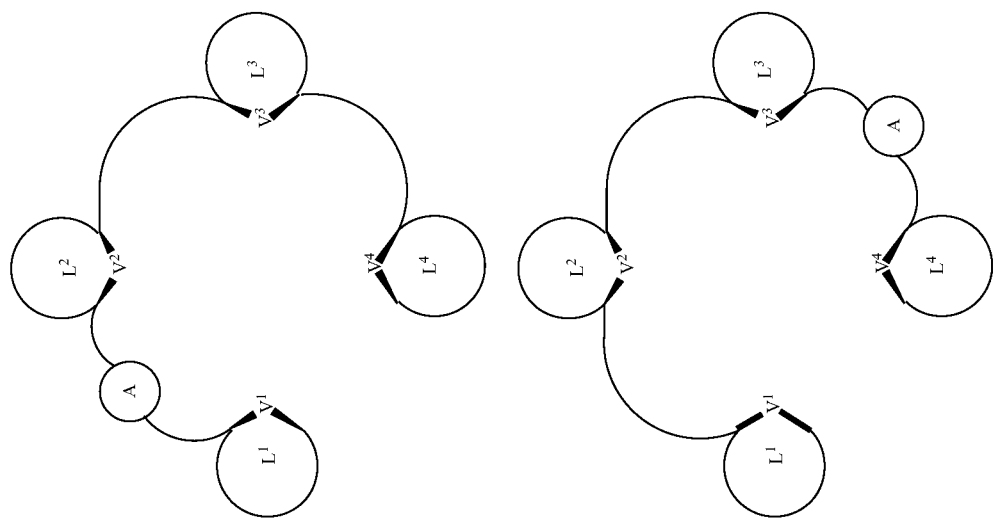
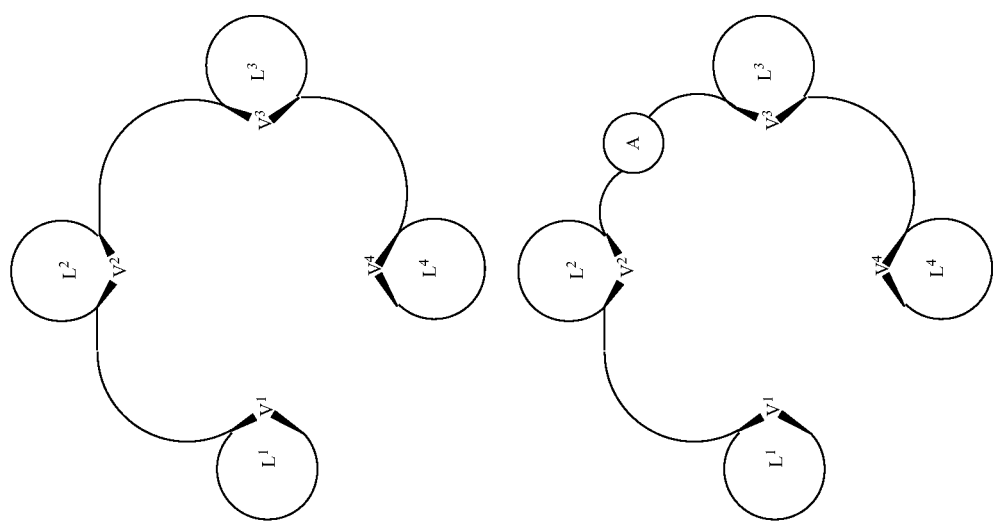
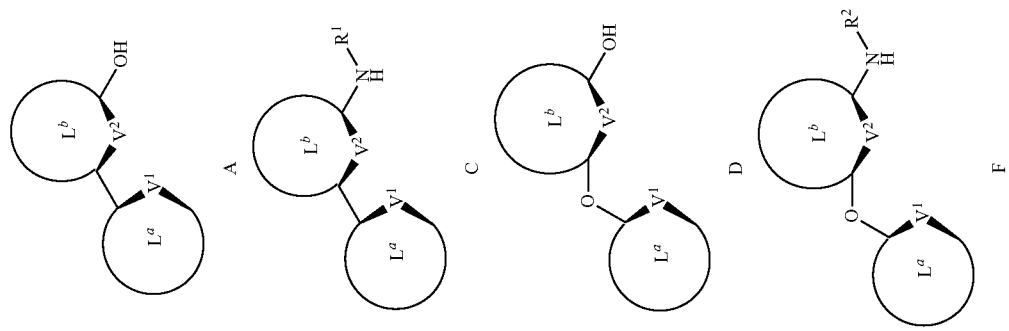

-continued
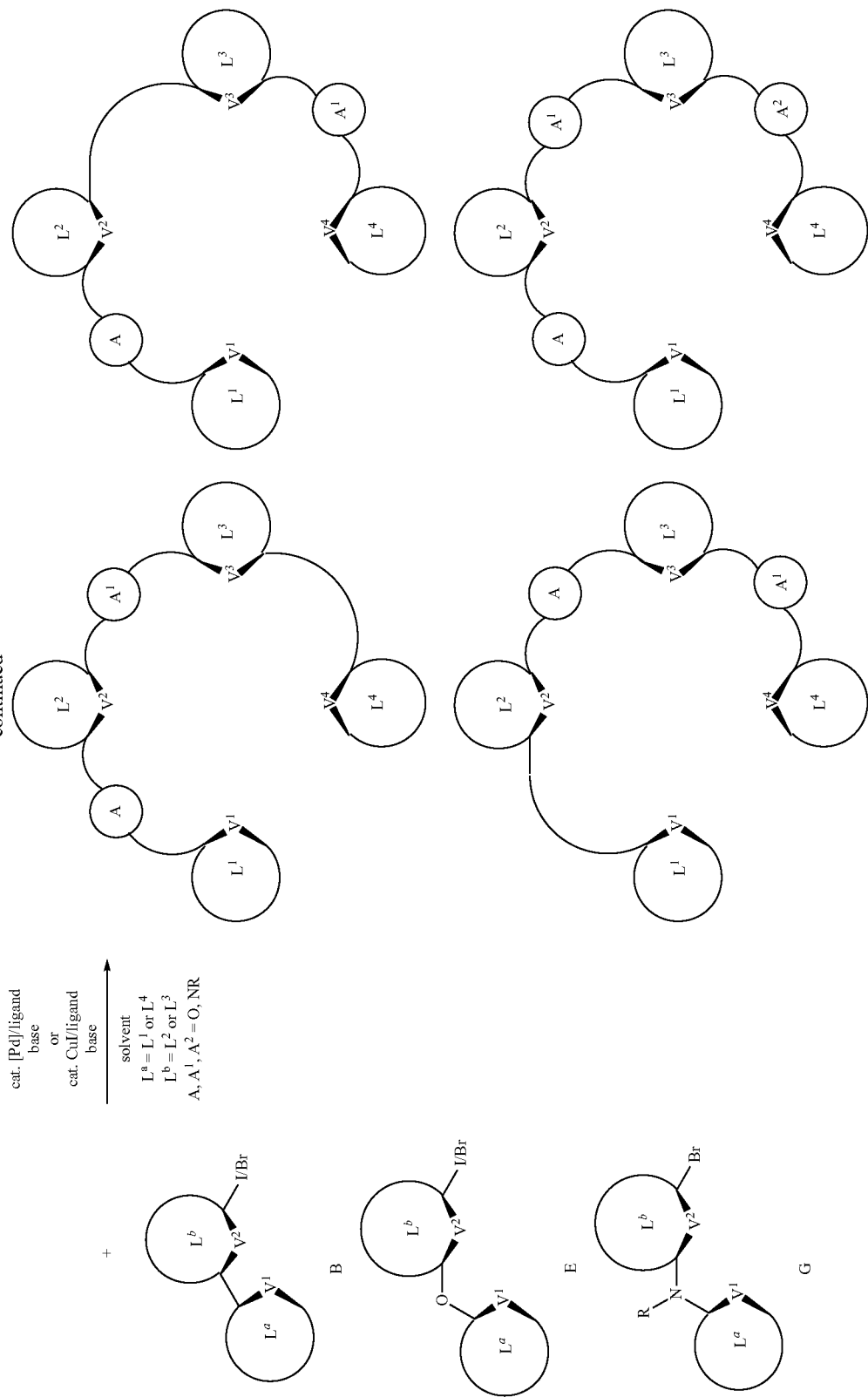

A proposed synthesis for some of the metal compounds, such as platinum or palladium compounds, disclosed herein is:
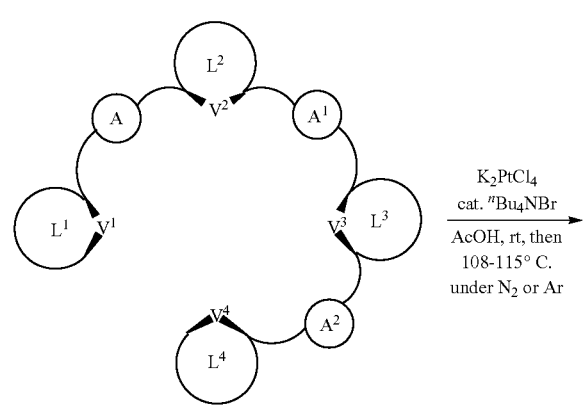
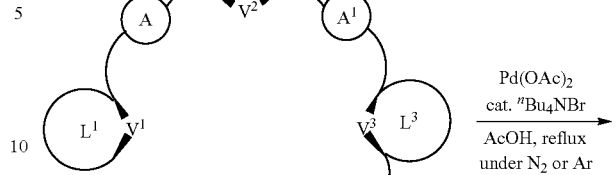
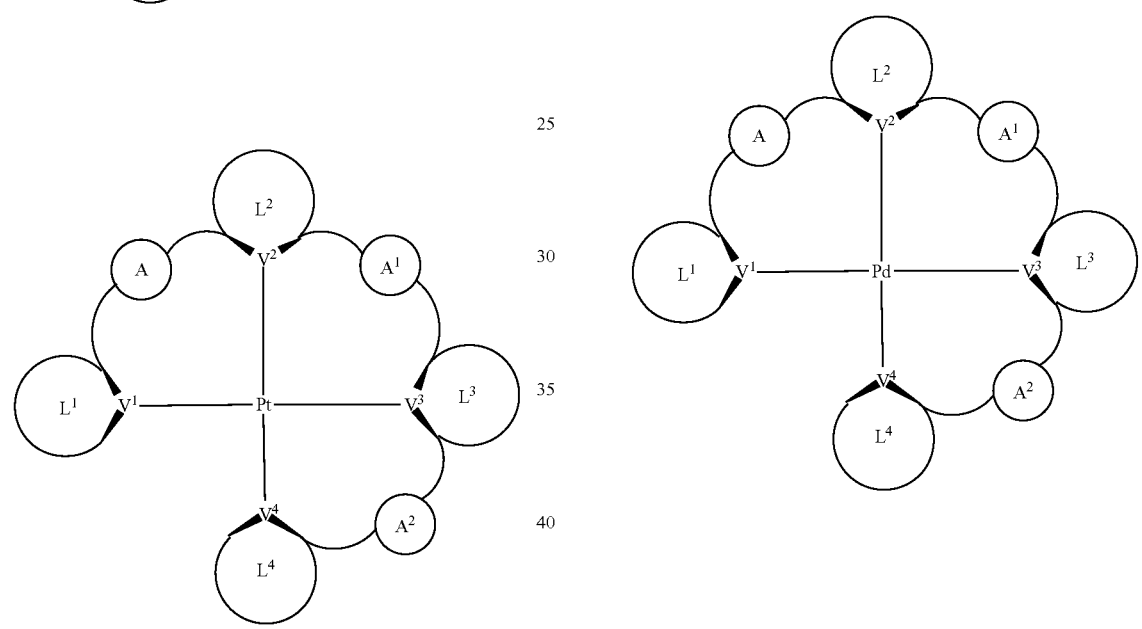
A proposed synthesis for a metal compound is:
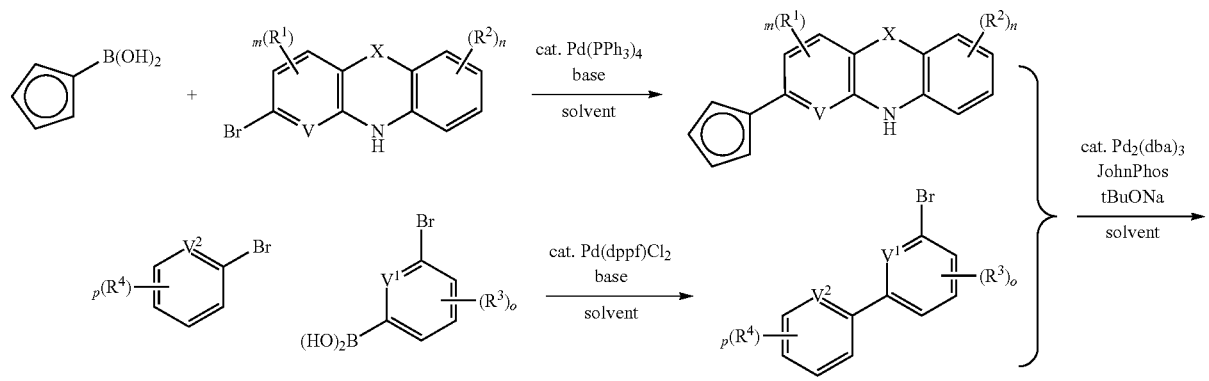

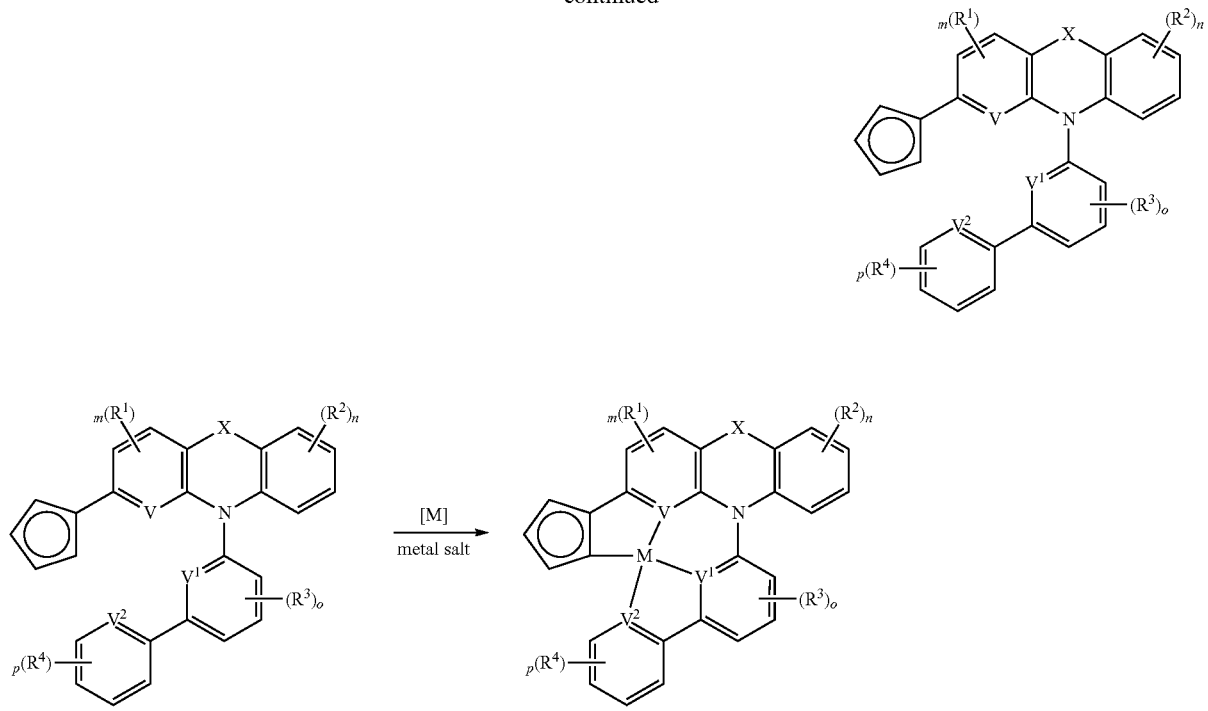
2. Synthesis of PtN3″PPy
Platinum complex PtN3″PPy was prepared according to the following scheme:
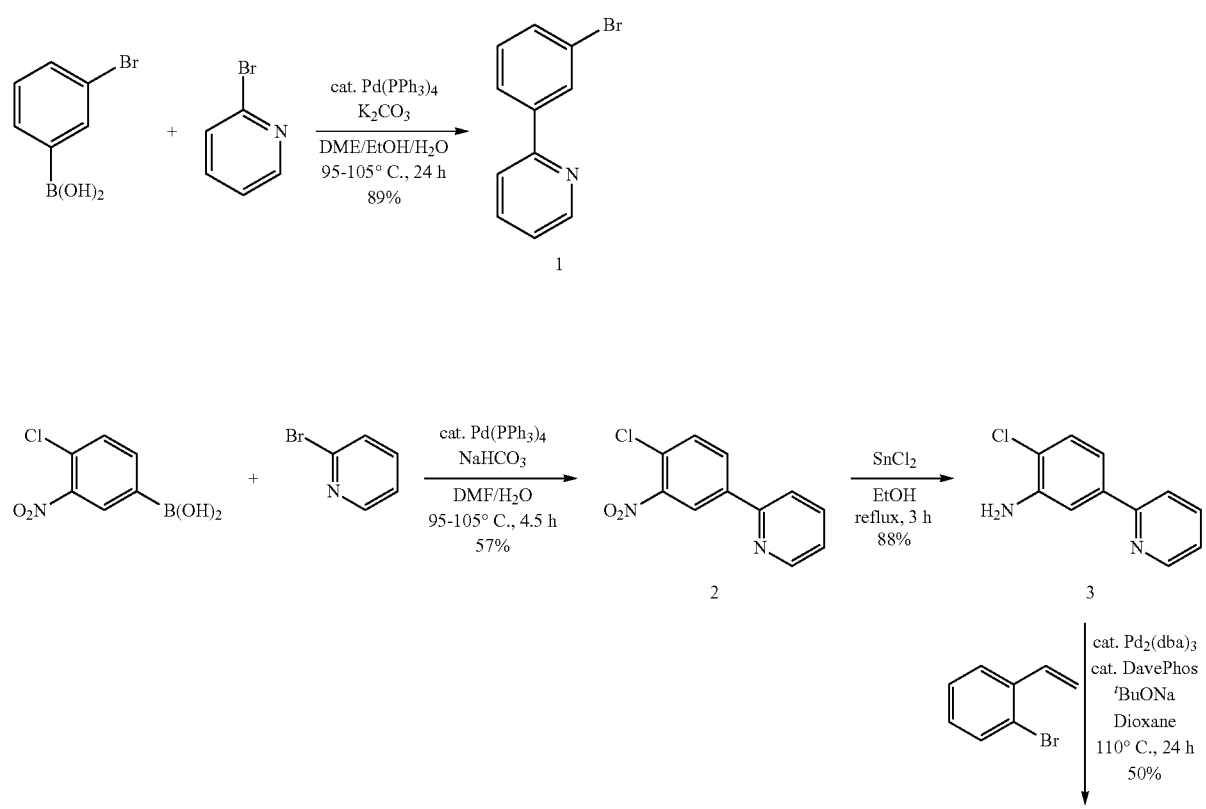

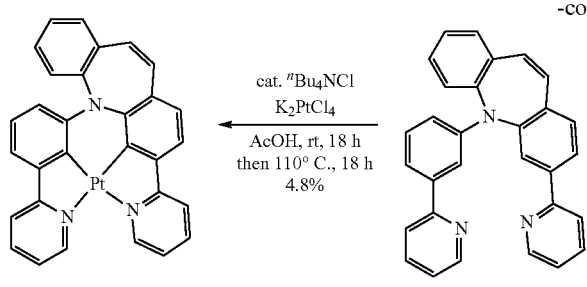
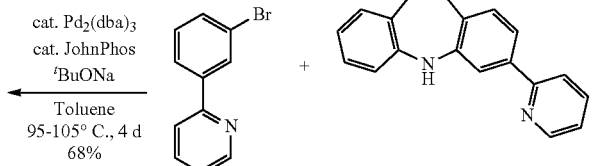

Synthesis of 2-(3-bromophenyl)pyridine 1: To a three-necked flask equipped with a magnetic stir bar and a condenser, added 3-bromophenylboronic acid (8033 mg, 40 mmol) and $K_2CO_3$ (12.16 g, 88 mmol). The flask was sealed and then evacuated and backfilled with nitrogen. Repeated the evacuation and backfill procedure four additional times. After that solvents DME (100 mL), EtOH (32 mL) and $H_2O$ (44 mL) were added independently by syringe. The mixture was bubbled with nitrogen through a needle for 30 minutes. Then 2-bromopyridine (3.89 mL, 40 mmol) and $Pd(PPh_3)_4$ (924 mg, 0.8 mmol) were added under the atmosphere of nitrogen. The mixture was heated to reflux (about 95-105° C.) in an oil bath. The reaction was monitored by TLC and about 24 hours later the reaction was completed. Then cooled down to ambient temperature and water was added until the salt dissolved completely. Then the organic layer was separated and the aqueous layer was extracted with ethyl acetate for twice. The combined organic layer was dried over sodium sulfate. Then filtered and washed with ethyl acetate. The filtrate was concentrated under reduced pressure using a rotary evaporator and the residue was purified through column chromatography on silica gel using hexane and ethyl acetate (20:1) as eluent to afford the desired product 2-(3-bromophenyl)pyridine 1 as a colorless liquid 8.33 g in 89% yield. $^1$H NMR ($CDCl_3$, $Me_4Si$, 400 MHz): δ 7.25-7.28 (m, 1H), 7.34 (td, J=8.0, 1.2 Hz, 1H), 7.53-7.56 (m, 1H), 7.71 (dd, J=8.0, 0.8 Hz, 1H), 7.75-7.80 (m, 1H), 7.90-7.93 (m, 1H), 8.18-8.19 (m, 1H), 8.70-8.81 (m, 1H). $^1$H NMR (DMSO-$d_6$, 400 MHz): δ 7.39-7.42 (m, 1H), 7.47 (t, J=8.0 Hz, 1H), 7.65 (dt, J=8.4, 0.8 Hz, 1H), 7.91 (tt, J=7.2, 0.8 Hz, 1H), 8.02-8.04 (m, 1H), 8.09-8.12 (m, 1H), 8.29-8.30 (m, 1H), 8.68-8.70 (m, 1H).

Synthesis of 2-(4-chloro-3-nitrophenyl)pyridine 2: To a three-necked flask equipped with a magnetic stir bar and a condenser, added 4-chloro-3-nitrophenylboronic acid (3968 mg, 19.7 mmol) and $NaHCO_3$ (3310 mg, 39.4 mmol). The flask was sealed and then evacuated and backfilled with nitrogen. Repeated the evacuation and backfill procedure four additional times. After that solvents DMF (40 mL) and $H_2O$ (20 mL) were added independently by syringe. The mixture was bubbled with nitrogen through a needle for 30 minutes. Then 2-bromopyridine (3.11 mL, 21.7 mmol) and $Pd(PPh_3)_4$ (1138 mg, 0.99 mmol) were added under the atmosphere of nitrogen. The mixture was heated to reflux (about 95-105° C.) in an oil bath. The reaction was monitored by TLC and after about 4.5 hours the reaction was completed. Then cooled down to ambient temperature and water was added. Then the mixture was filtered and washed with ethyl acetate. The organic layer of the filtrate was separated and the aqueous layer was extracted with ethyl acetate for twice. The combined organic layer was dried over sodium sulfate. Then filtered and washed with ethyl acetate. The filtrate was concentrated under reduced pressure using a rotary evaporator and the residue was purified through column chromatography on silica gel using hexane and ethyl acetate (20:1-15:1-10:1-5:1) as eluent to afford the desired product 2-(4-chloro-3-nitrophenyl)pyridine 2 as a grey solid 2.65 g in 57% yield. $^1$H NMR (DMSO-$d_6$, 400 MHz): δ 7.47-7.50 (m, 1H), 7.92 (d, J=8.4 Hz, 1H), 7.99 (td, J=7.6, 0.8 Hz, 1H), 8.16 (d, J=8.0 Hz, 1H), 8.44 (dd, J=8.0, 0.8 Hz, 1H), 8.74-8.75 (m, 1H), 8.77 (d, J=2.0 Hz, 1H).

Synthesis of 2-chloro-5-(pyridin-2-yl)benzenamine 3: To a single-necked flask equipped with a magnetic stir bar, added 2-(4-chloro-3-nitrophenyl)pyridine 2 (2.65 g, 11.29 mmol) and $SnCl_2$ (21.41 g, 112.90 mmol). Then a condenser was equipped and the system was evacuated and backfilled with nitrogen. Repeated the evacuation and backfill procedure twice additional times. After that solvent EtOH (150 mL) was added under the atmosphere of nitrogen. The mixture was heated to 60-70° C. in an oil bath. The reaction was monitored by TLC and after about 3 hours the reaction was completed. Then cooled down to ambient temperature and quenched with water. Then the pH of the mixture was adjusted to 9-10 using 1 N NaOH aqueous solution. Filtered and washed with ethyl acetate. The organic layer of the filtrate was separated and the aqueous layer was extracted with ethyl acetate for three times. The combined organic layer was dried over sodium sulfate. Then filtered and washed with ethyl acetate. The filtrate was concentrated under reduced pressure using a rotary evaporator and the residue was purified through column chromatography on silica gel using hexane and ethyl acetate (5:1-3:1-2:1) as eluent to afford the desired product 2-chloro-5-(pyridin-2-yl)benzenamine 3 as a colorless liquid 2.03 g in 88% yield. $^1$H NMR (DMSO-$d_6$, 400 MHz): δ 5.48 (bs, 2H), 7.23 (dd, J=8.0, 2.0 Hz, 1H), 7.29 (d, J=8.0 Hz, 1H), 7.33-7.36 (m, 1H), 7.60 (d, J=2.0 Hz, 1H), 7.82-7.89 (m, 2H), 8.63-8.64 (m, 1H).

Synthesis of 3-(pyridin-2-yl)-5H-dibenzo[b,f]azepine 4: To an oven dried pressure vessel equipped with a magnetic stir bar, added $Pd_2(dba)_3$ (268 mg, 0.29 mmol), DavePhos (346 mg, 0.88 mmol) and $^tBuONa$ (2817 mg, 29.31 mmol). The vessel was evacuated and backfilled with nitrogen. Repeated the evacuation and backfill procedure four additional times. Then a degassed solution of 2-chloro-5-(pyridin-2-yl)benzenamine 3 (2000 mg, 9.77 mmol) and 2-bromostyrene (1.52 mL, 11.72 mmol) in dioxane (20 mL) was added under the atmosphere of nitrogen. The sealed vessel was then placed in a preheated oil bath at a temperature of 110° C. The reaction was stirred and monitored by TLC and after about 24 hours the reaction was completed. Cooled down to ambient temperature and quenched with water. Then diluted with ethyl acetate and stirred for 10 minutes, filtered and washed with ethyl acetate. The organic layer of the filtrate was separated and the aqueous layer was extracted with ethyl acetate for three times. The combined organic layer was dried over sodium sulfate. Then filtered and washed with ethyl acetate. The filtrate was concentrated under reduced pressure using a rotary evaporator and the residue was purified through column chromatography on silica gel using hexane and ethyl acetate (5:1-3:1) as eluent to afford the desired product 3-(pyridin-2-yl)-5H-dibenzo[b,f]azepine 4 as a brown-yellow solid 1.33 g in 50% yield. $^1$H NMR (DMSO-d$_6$, 400 MHz): δ 6.10 (s, 2H), 6.65 (d, J=8.0 Hz, 1H), 6.69 (td, J=7.6, 1.2 Hz, 1H), 6.76 (dd, J=7.6, 1.6 Hz, 1H), 6.85 (d, J=8.0 Hz, 1H), 6.98 (td, J=8.0, 1.6 Hz, 1H), 7.13 (s, 1H), 7.33-7.39 (m, 2H), 7.47 (d, J=1.6 Hz, 1H), 7.82-7.89 (m, 2H), 8.64 (dd, J=4.8, 0.8 Hz, 1H).

Synthesis of 3-(pyridin-2-yl)-5-(3-(pyridin-2-yl)phenyl)-5H-dibenzo[b,f]azepine 5: To an oven dried pressure vessel equipped with a magnetic stir bar, added 3-(pyridin-2-yl)-5H-dibenzo[b,f]azepine 4 (1.33 g, 4.92 mmol), Pd$_2$(dba)$_3$ (180 mg, 0.20 mmol), JohnPhos (118 mg, 0.39 mmol) and $^t$BuONa (756 mg, 7.87 mmol). The vessel was evacuated and backfilled with nitrogen. Repeated the evacuation and backfill procedure four additional times. Then a degassed solution of 2-(3-bromophenyl)pyridine 1 (1728 mg, 7.38 mmol) in toluene (20 mL) was added under the atmosphere of nitrogen. The sealed vessel was then placed in a preheated oil bath at a temperature of 95-105° C. The reaction was stirred and monitored by TLC and after about 4 days the reaction was completed. Cooled down to ambient temperature. The solvent was removed under reduced pressure using a rotary evaporator and the residue was purified through column chromatography on silica gel using hexane and ethyl acetate (5:1-3:1) as eluent to afford the desired ligand 3-(pyridin-2-yl)-5-(3-(pyridin-2-yl)phenyl)-5H-dibenzo[b,f]azepine 5 as a brown solid 1.42 g in 68% yield. $^1$H NMR (DMSO-d$_6$, 400 MHz): δ 6.25 (dd, J=8.0, 2.4 Hz, 1H), 6.97-6.98 (m, 1H), 7.01 (s, 2H), 7.11 (t, J=8.0 Hz, 1H), 7.23-7.27 (m, 1H), 7.29 (d, J=7.6 Hz, 1H), 7.38-7.42 (m, 1H), 7.47-7.51 (m, 1H), 7.61 (s, 1H), 7.63 (s, 1H), 7.65 (dd, J=7.2, 1.6 Hz, 1H), 7.68 (dd, J=7.6, 1.6 Hz, 1H), 7.71 (d, J=8.4 Hz, 1H), 7.78 (td, J=7.6, 2.0 Hz, 1H), 7.92 (td, J=8.0, 1.6 Hz, 1H), 8.11 (d, J=8.0 Hz, 1H), 8.20 (dd, J=8.0, 2.0 Hz, 1H), 8.33 (d, J=2.0 Hz, 1H), 8.51 (dd, J=4.8, 0.8 Hz, 1H), 8.71 (dd, J=4.8, 0.8 Hz, 1H).

Synthesis of platinum complex PtN"3PPy: To an oven dried pressure vessel equipped with a magnetic stir bar, added ligand 3-(pyridin-2-yl)-5-(3-(pyridin-2-yl)phenyl)-5H-dibenzo[b,f]azepine 5 (84.7 mg, 0.20 mmol), K$_2$PtCl$_4$ (87.2 mg, 0.21 mmol) and $^n$Bu$_4$NCl (5.5 mg, 0.02 mmol). The vessel was taken into a glove box. Then solvent acetic acid (12 mL) was added. The mixture was bubbled with nitrogen for 30 minutes. Then the vessel was sealed and taken out of the glove box and stirred at ambient temperature for 18 hours. After that the mixture was heated in an oil bath at a temperature of 110° C. for another 18 hours. Cooled down to ambient temperature and water (about 24 mL) was added. The precipitate was collected through filter and washed with water for three times. The precipitate was dried in air and purified through column chromatography on silica gel using dichloromethane as eluent to obtain a crude product which was further purified by recrystallization in dichloromethane and ether at refrigerator to get the desired platinum complex PtN"3PPy as a brown-yellow solid 5.9 mg in 4.8% yield. $^1$H NMR (DMSO-d$_6$, 400 MHz): δ 6.43 (d, J=8.0 Hz, 1H), 6.75 (d, J=8.4 Hz, 1H), 6.92 (d, J=7.2 Hz, 1H), 6.98-7.07 (m, 5H), 7.19 (dd, J=7.4, 1.6 Hz, 1H), 7.58-7.63 (m, 3H), 7.67 (d, J=8.0 Hz, 1H), 8.11 (d, J=7.2 Hz, 1H), 8.15 (d, J=7.6 Hz, 1H), 8.21 (d, J=8.0 Hz, 1H), 8.11 (d, J=8.0 Hz, 1H), 8.25 (d, J=7.6 Hz, 1H), 9.15 (d, J=5.2 Hz, 1H), 8.17 (d, J=5.2 Hz, 1H); HRMS (MALDI/DHB) for C$_{30}$H$_{20}$N$_3$Pt [M+H]$^+$: calcd 617.13, found 617.33.

3. Synthesis of PtN"3N

Platinum complex PtN"3N can be prepared according to the following scheme:

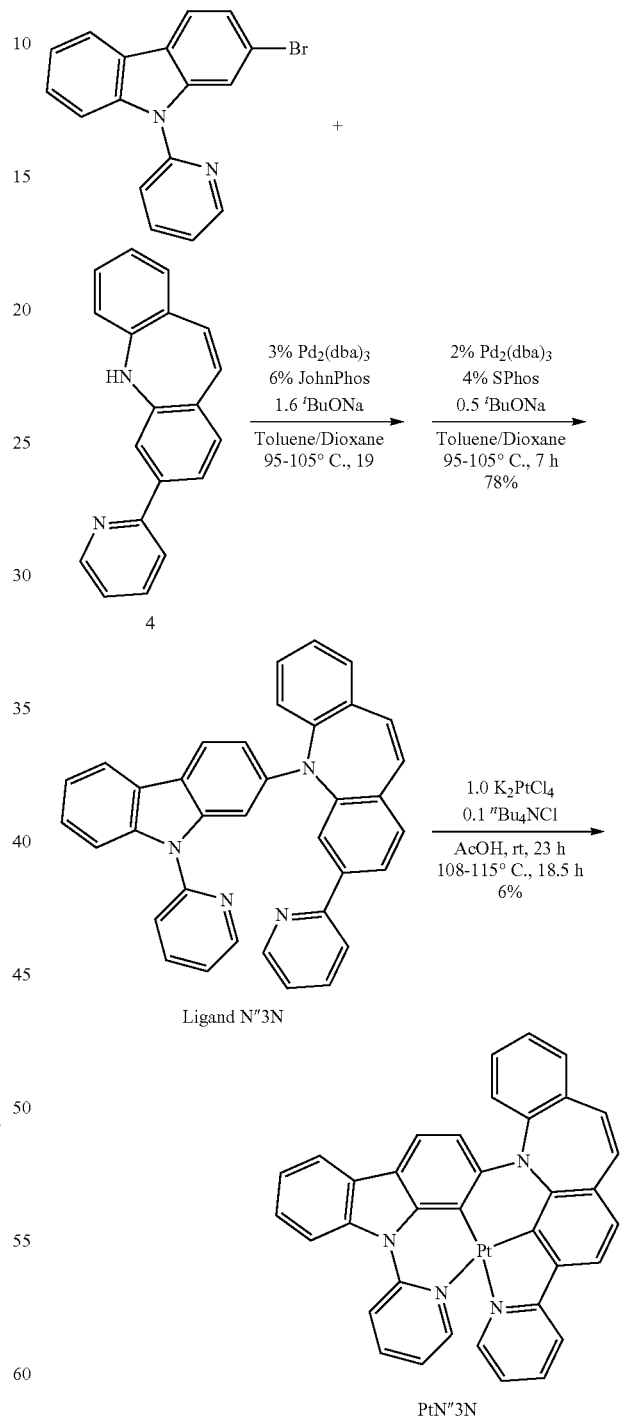

Synthesis of 3-(pyridin-2-yl)-5-(9-(pyridin-2-yl)-9H-carbazol-2-yl)-5H-dibenzo[b,f]azepine Ligand N"3N: To a dry Schlenk tube equipped with a magnetic stir bar, added of 3-(pyridin-2-yl)-5H-dibenzo[b,f]azepine 4 (92 mg, 0.34 mmol, 1.0 eq), 2-bromo-9-(pyridin-2-yl)-9H-carbazole (132 mg, 0.41 mmol, 1.2 eq), Pd$_2$(dba)$_3$ (9 mg, 0.010 mmol, 0.03 eq), JohnPhos (6 mg, 0.020 mmol, 0.06 eq) and $^t$BuONa (52 mg, 0.54 mmol, 1.6 eq). The tube was evacuated and back-filled with nitrogen and this evacuation/back-fill procedure was repeated for another twice. Then dry solvents toluene (4 mL) and dioxane (3 mL) were added under the atmosphere of nitrogen, the tube was then sealed quickly. And then the mixture was stirred in an oil bath at a temperature of 95-105° C. The reaction was monitored by TLC. 19 hours later, much of the starting material 4 was not consumed. So more Pd$_2$(dba)$_3$ (6 mg, 0.0067 mmol, 0.02 eq), and SPhos (5.6 mg, 0.0134 mmol, 0.04 eq), $^t$BuONa (16 mg, 0.21 mmol, 0.5 eq) were added. The mixture was stirred in an oil bath at a temperature of 95-105° C. for another 7 hours, cooled down to ambient temperature. The mixture was concentrated and the residue was purified through column chromatography on silica gel using hexane/ethyl acetate (20:1-10:1-5:1-3:1)) as eluent to obtain the desired product Ligand N"3N as a brown solid 135 mg in 78% yield. $^1$H NMR (DMSO-d$_6$, 400 MHz): δ 6.26 (dd, J=8.4, 2.4 Hz, 1H), 6.73 (d, J=1.6 Hz, 1H), 6.98 (s, 2H), 7.21 (t, J=7.6 Hz, 1H), 7.26-7.31 (m, 2H), 7.41-7.52 (m, 3H), 7.60-7.70 (m, 5H), 7.79-7.83 (m, 2H), 7.93-7.97 (m, 2H), 8.11 (d, J=7.2 Hz, 1H), 8.18 (dd, J=7.6, 2.4 Hz, 1H), 8.36 (d, J=1.6 Hz, 1H), 8.40 (dd, J=4.8, 2.0 Hz, 1H), 8.72-8.73 (m, 1H).

Synthesis of 3-(pyridin-2-yl)-5-(9-(pyridin-2-yl)-9H-carbazol-2-yl)-5H-dibenzo[b,f]azepine platinum complex PtN"3N: To a dry pressure tube equipped with a magnetic stir bar, added 3-(pyridin-2-yl)-5-(9-(pyridin-2-yl)-9H-carbazol-2-yl)-5H-dibenzo[b,f]azepine Ligand N3"N (51 mg, 0.1 mmol, 1.0 eq), K$_2$PtCl$_4$ (42 mg, 0.1 mmol, 1.0 eq) and $^n$Bu$_4$NCl (2.8 mg, 0.01 mmol, 0.1 eq). Then the tube was taken into a glove box. Solvent acetic acid (6 mL) was added. The mixture was bubbled with nitrogen for 30 minutes and then the tube was sealed. The tube was taken out of the glove box and the mixture was stirred in an oil bath at a temperature of 108-115° C. for 18.5 hours. Then the mixture was cooled down to ambient temperature and water (12 mL) was added slowly. The precipitate was filtered off and washed with water for three times. Then the solid was dried in air under reduced pressure. The collected solid was purified through column chromatography on silica gel using dichloromethane/hexane (1:1) as eluent to obtain the desired product PtN"3N 4.5 mg in 6% yield.

What is claimed is:

1. A compound having a formula selected from:

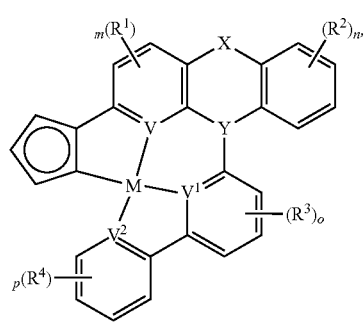

-continued

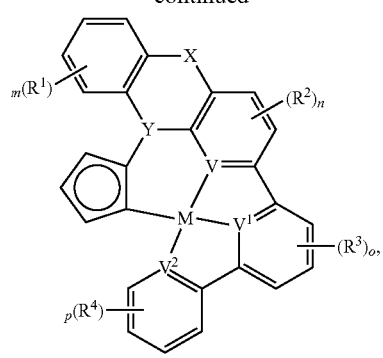

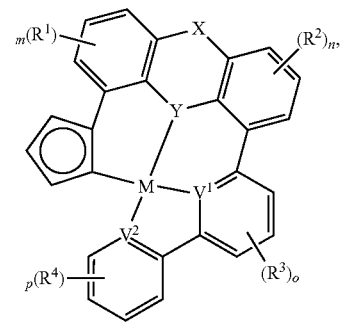

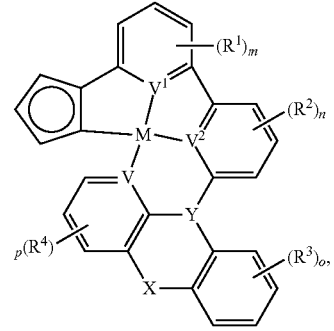

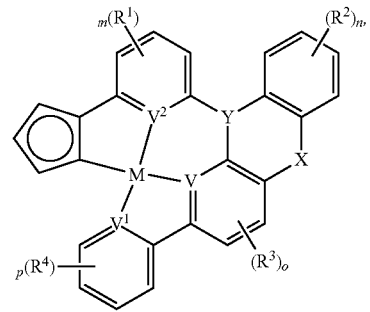

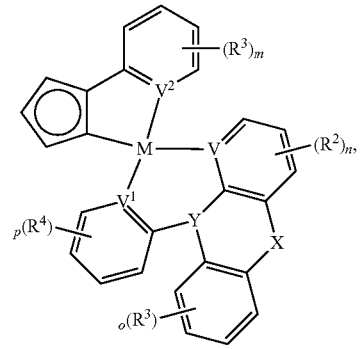

-continued
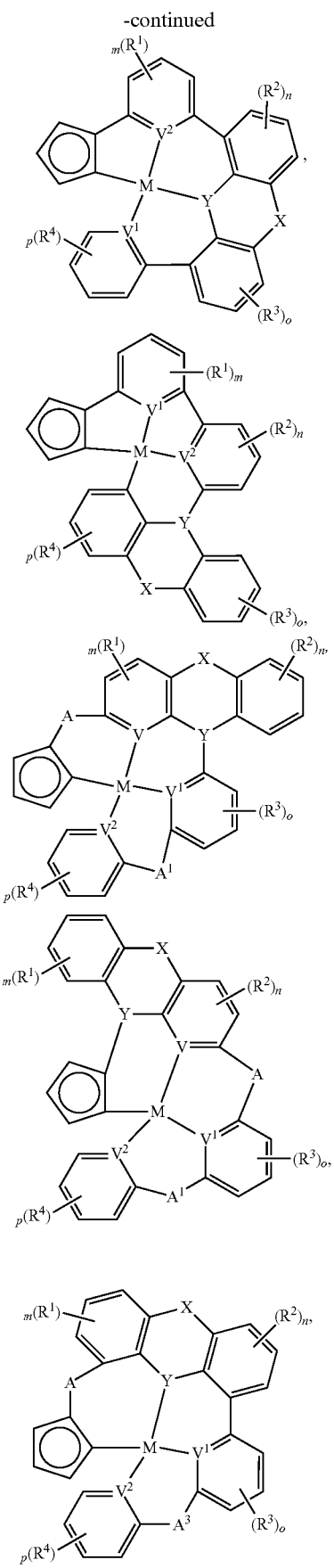
-continued
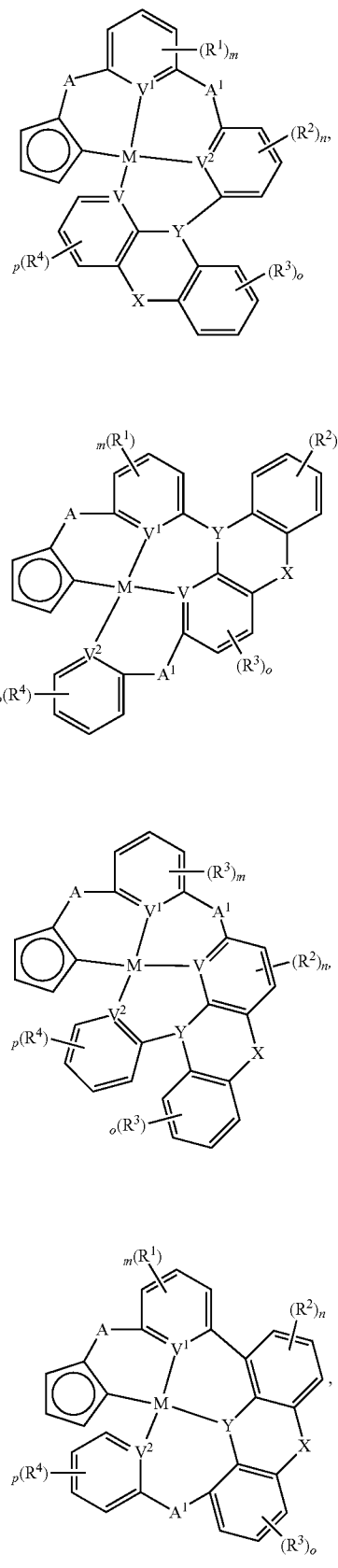

-continued
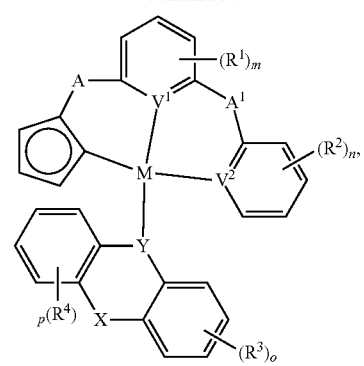
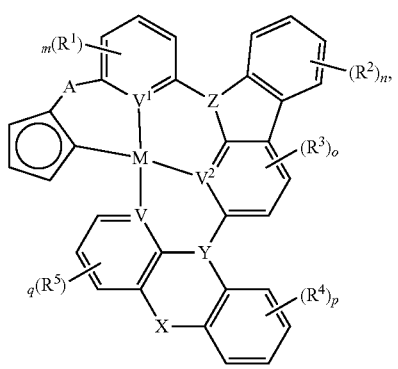
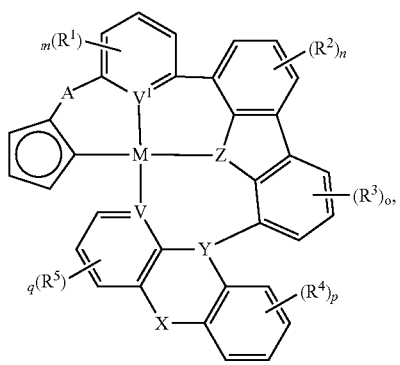
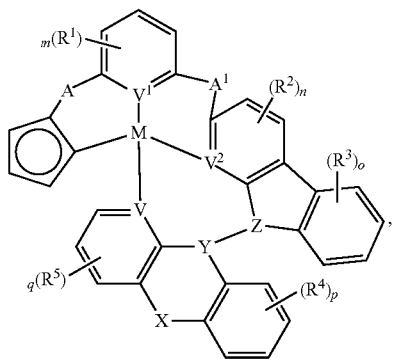
-continued
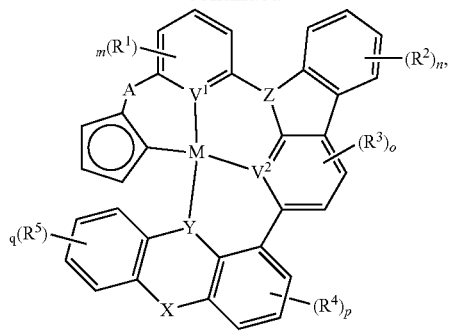
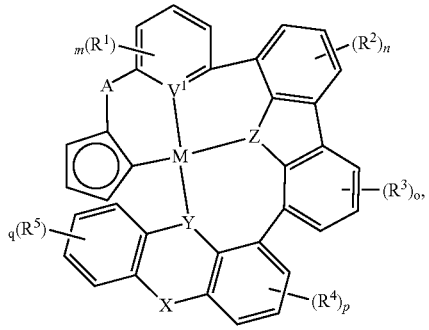
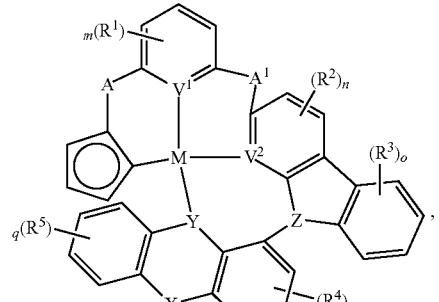
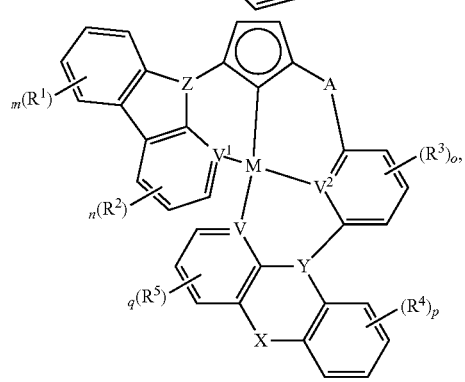
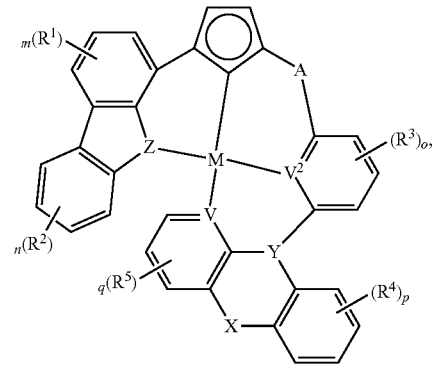

-continued
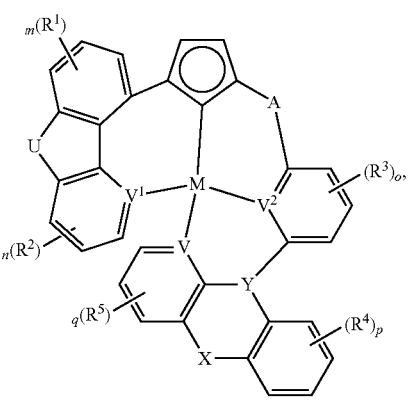
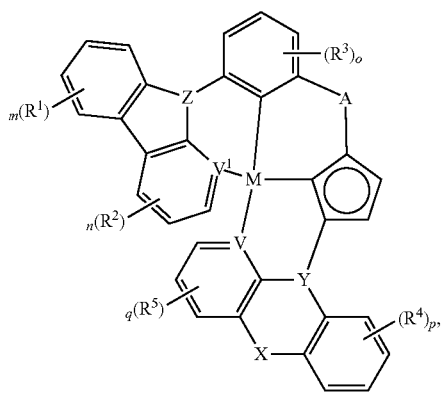
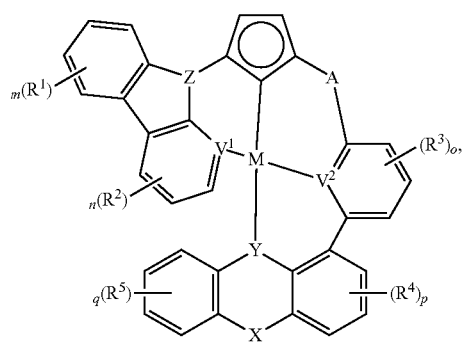
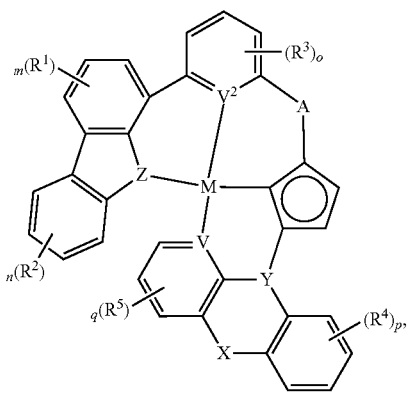
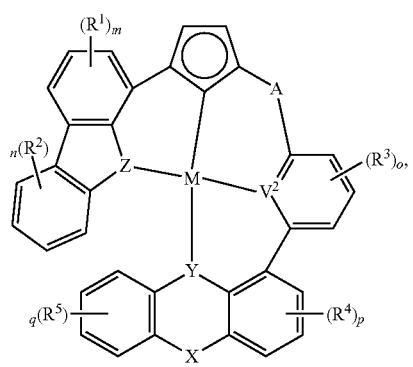
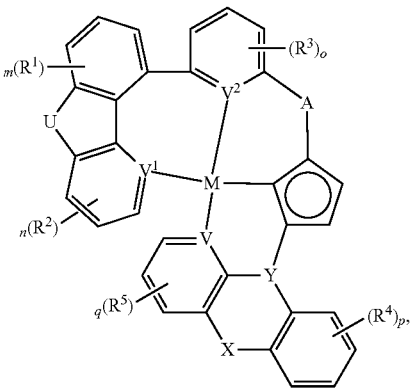
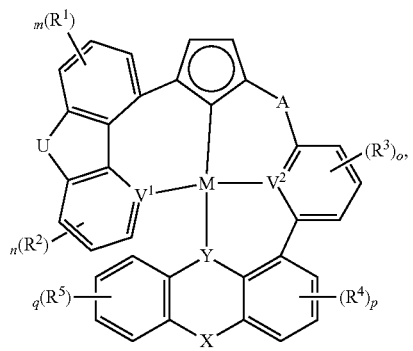
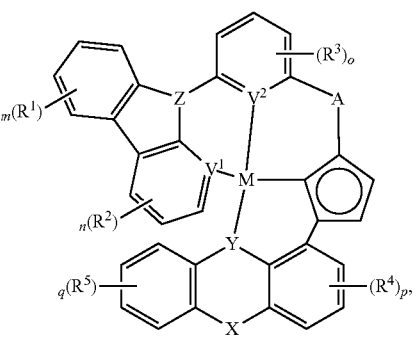

-continued
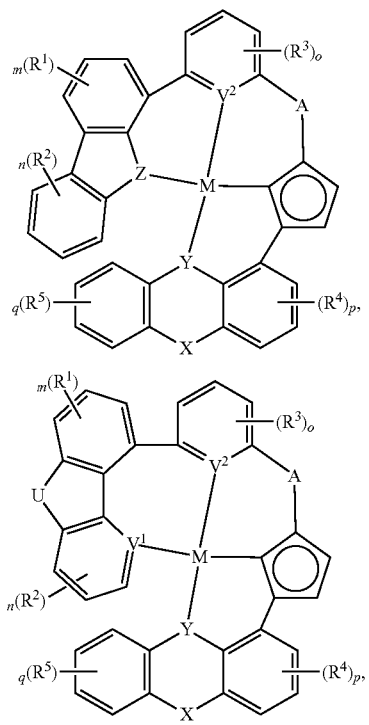
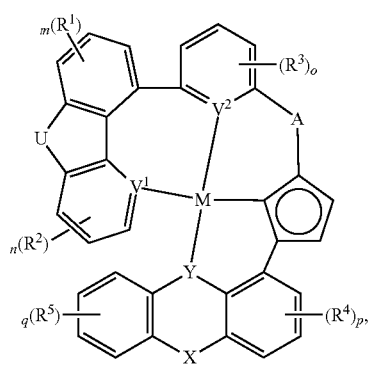
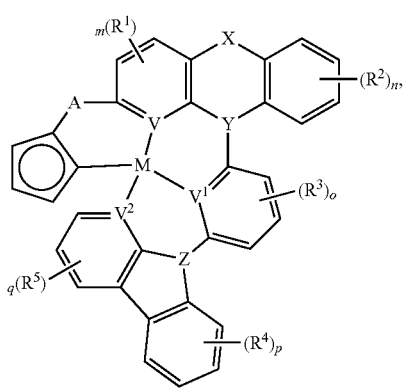
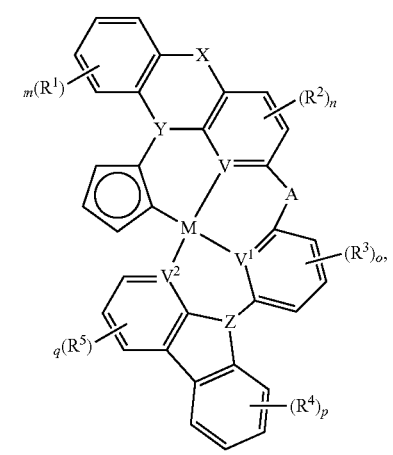
-continued
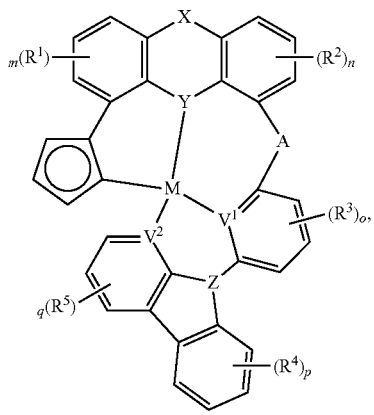
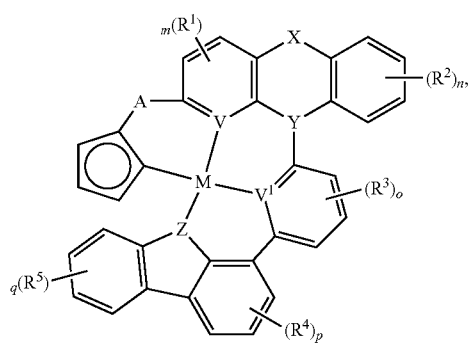
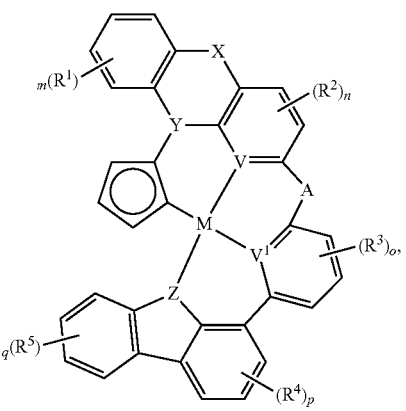
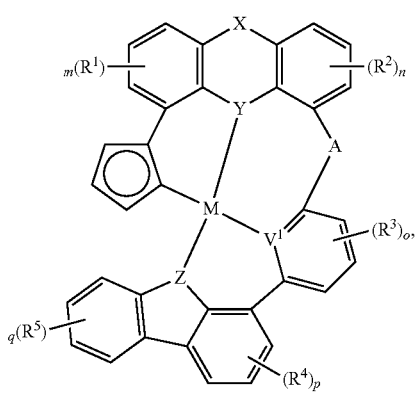

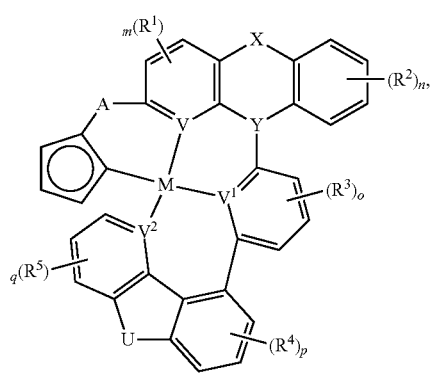
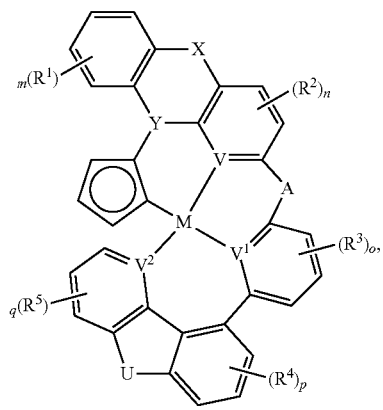
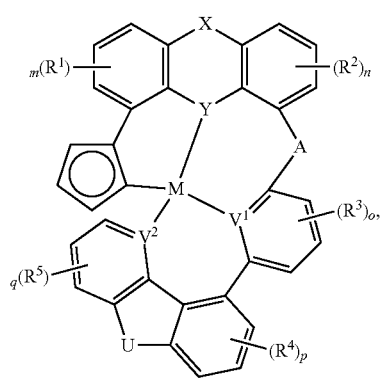
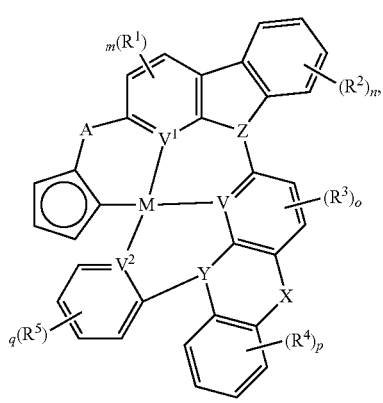
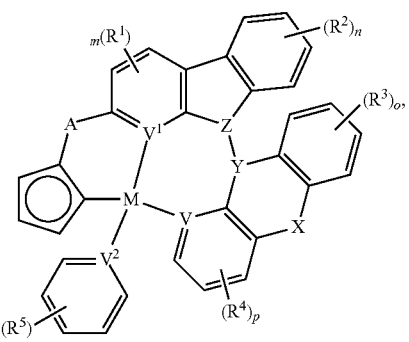
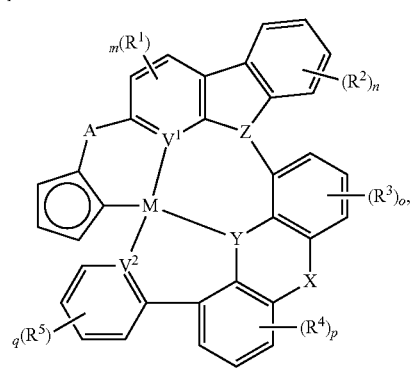
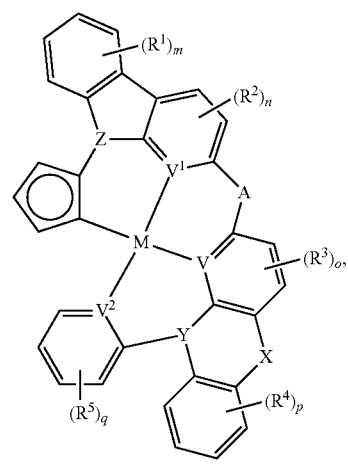
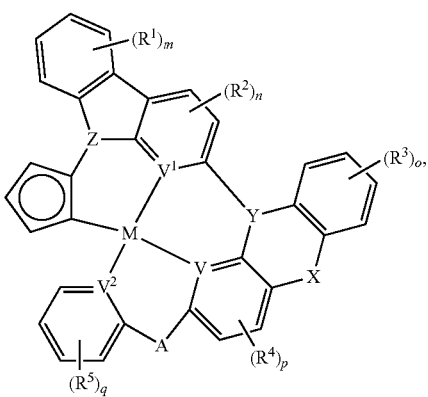

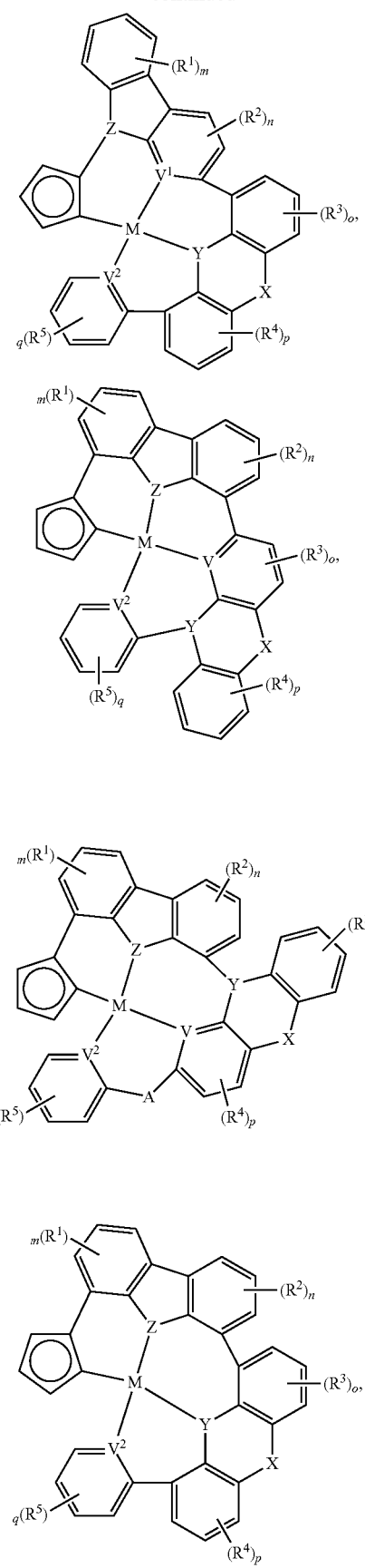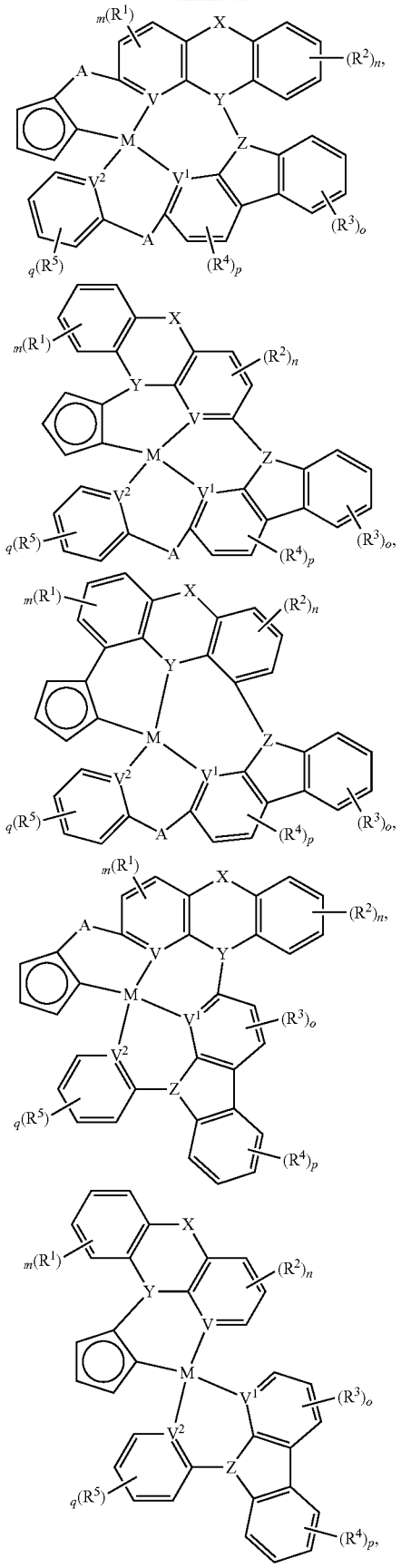

-continued
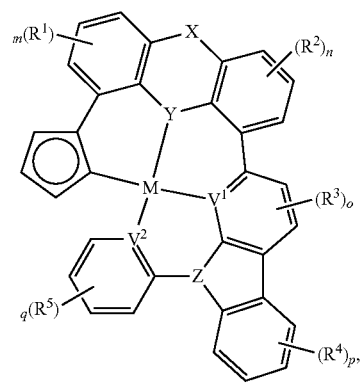
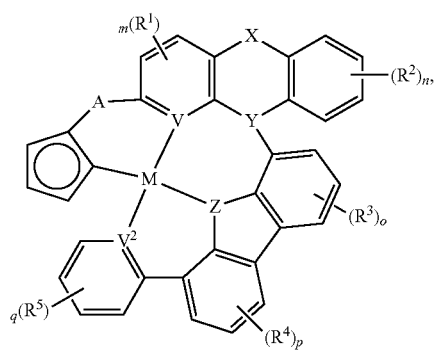
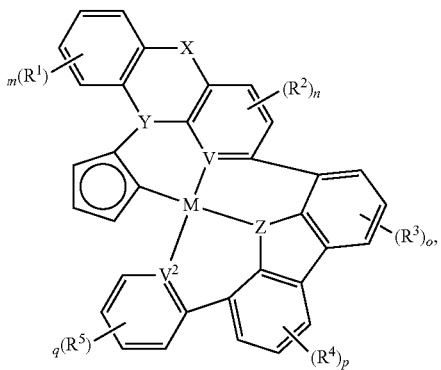
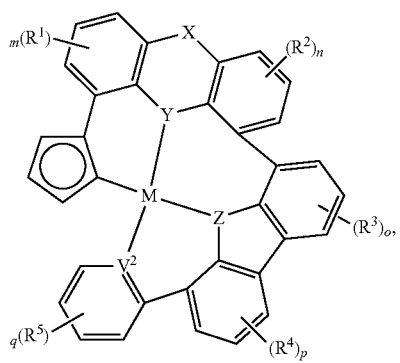
-continued
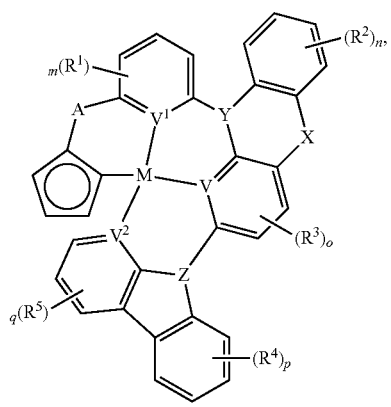
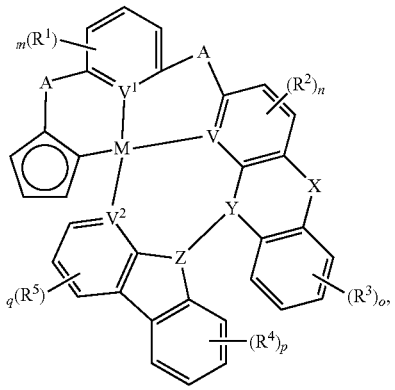
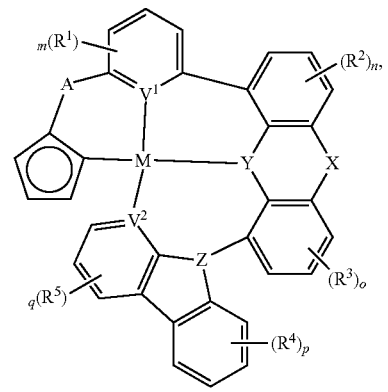
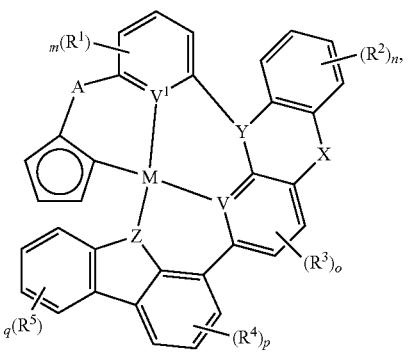

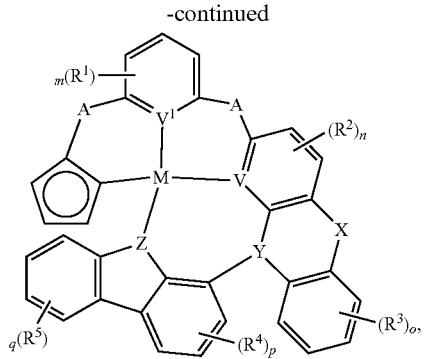
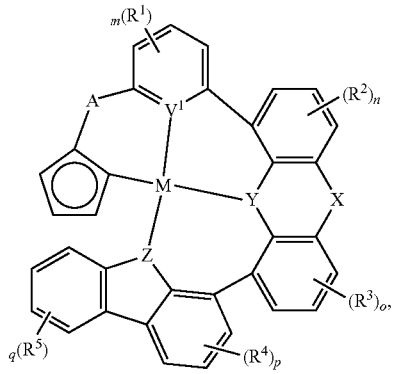
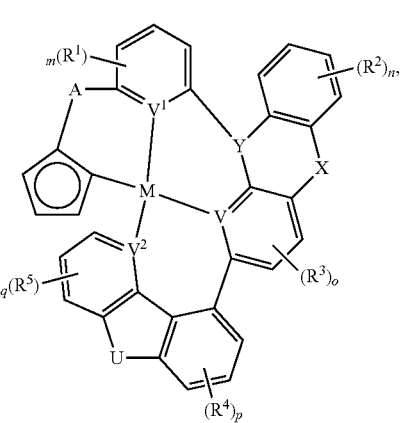
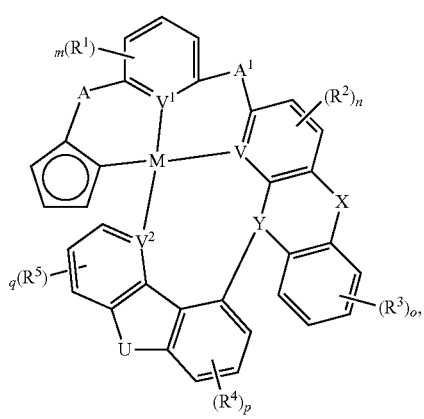
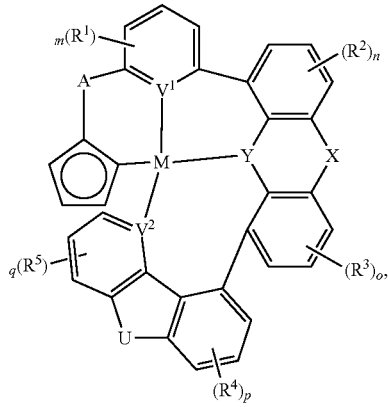
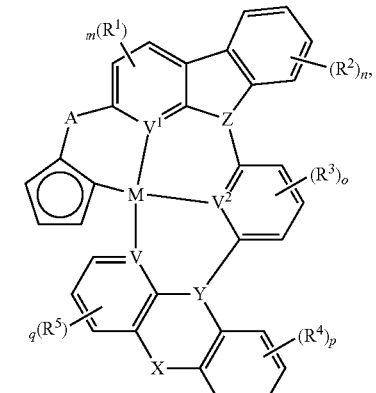
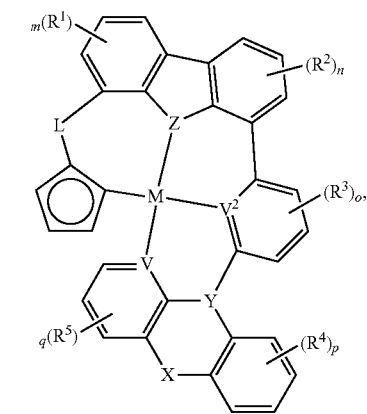
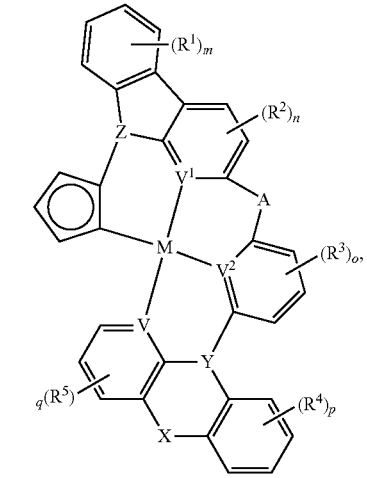

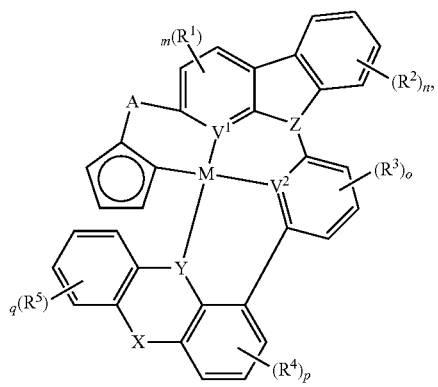
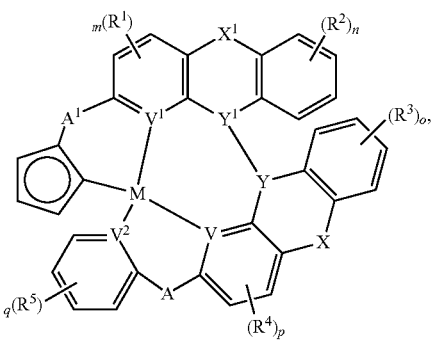
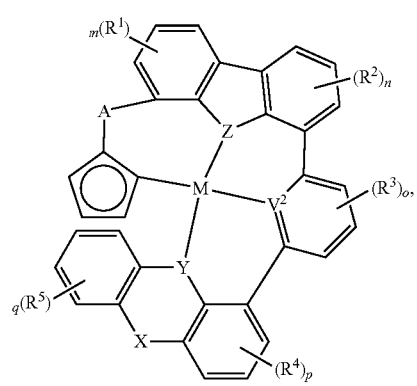
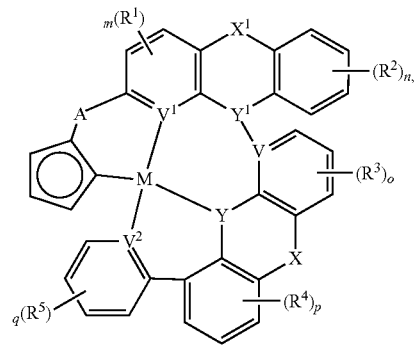
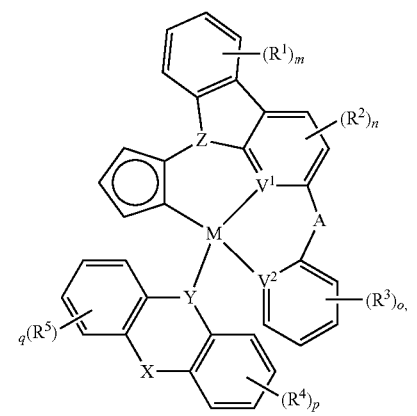
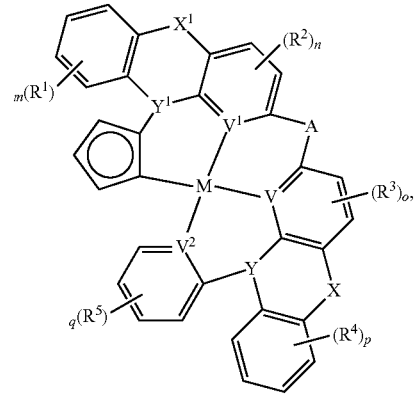
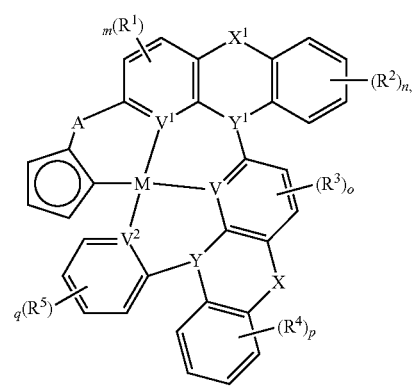

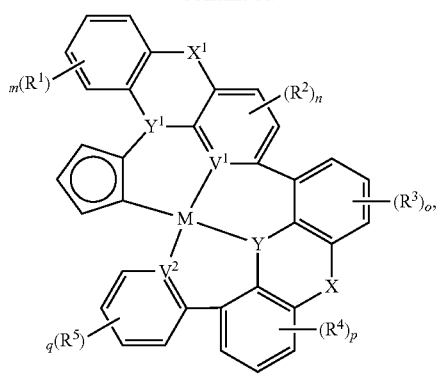
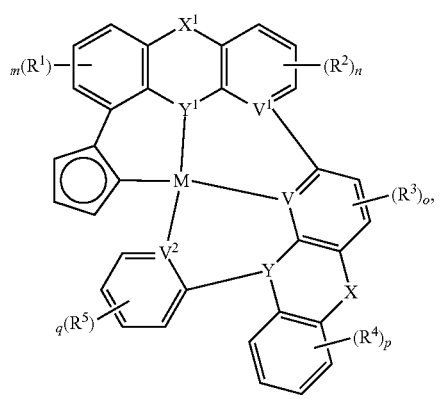
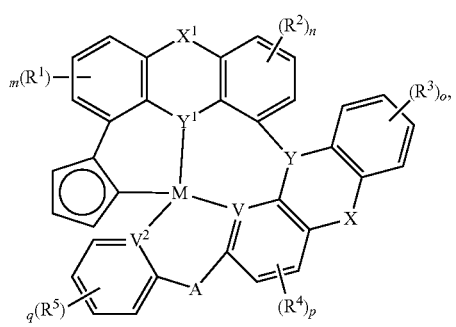
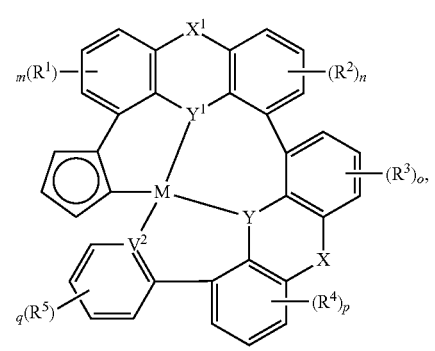
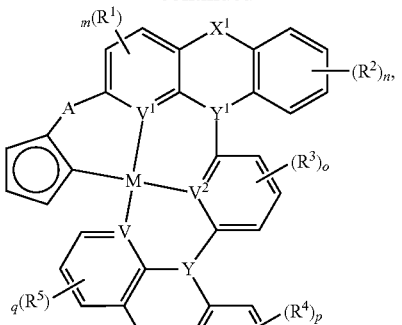
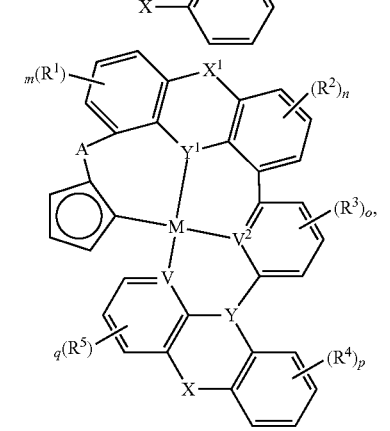
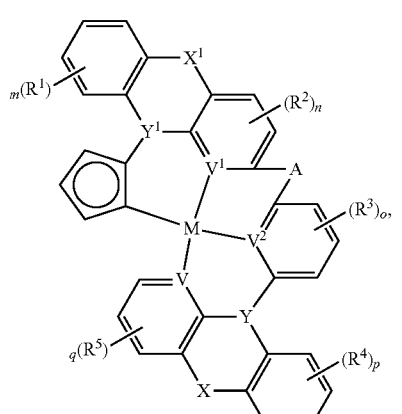
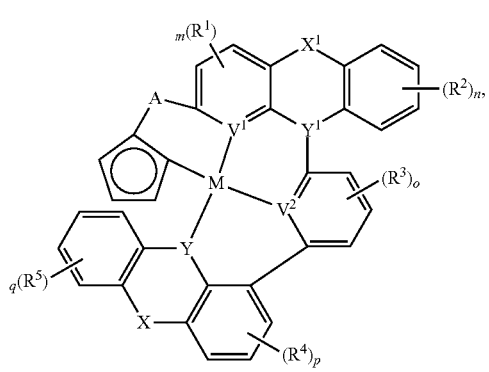

199
-continued
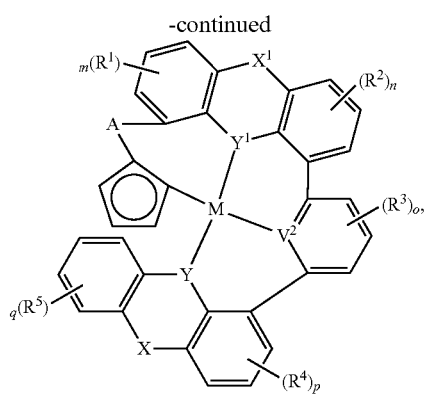
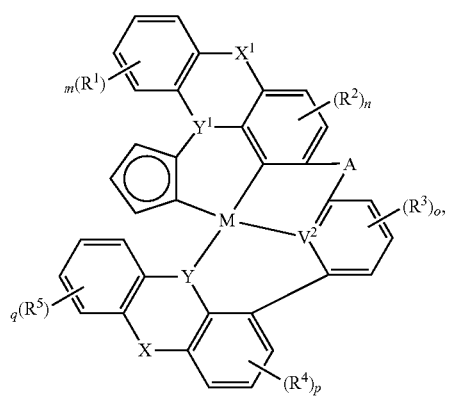
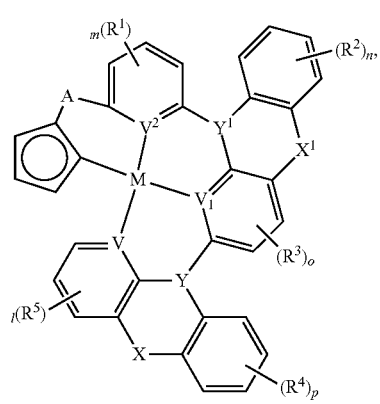
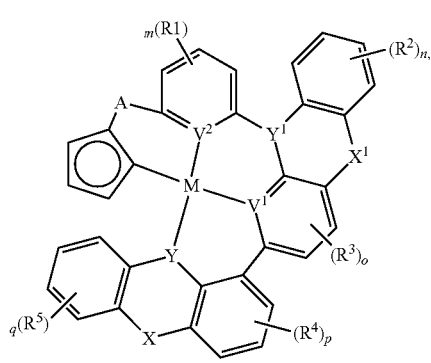
200
-continued
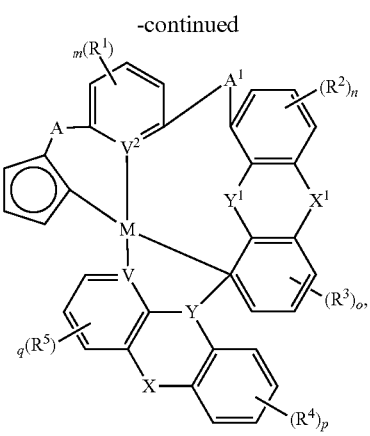
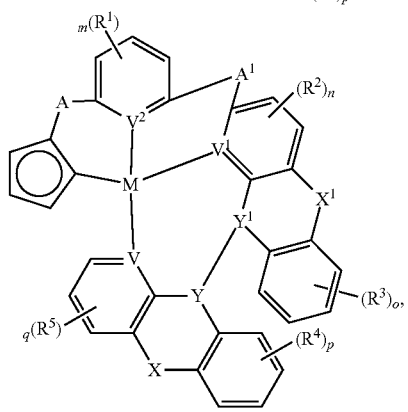
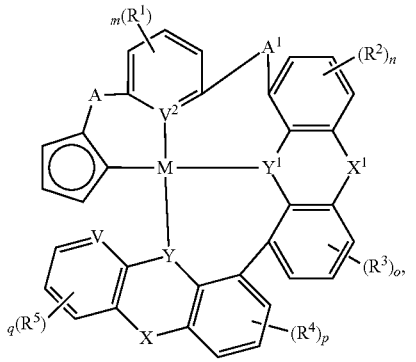

201
-continued
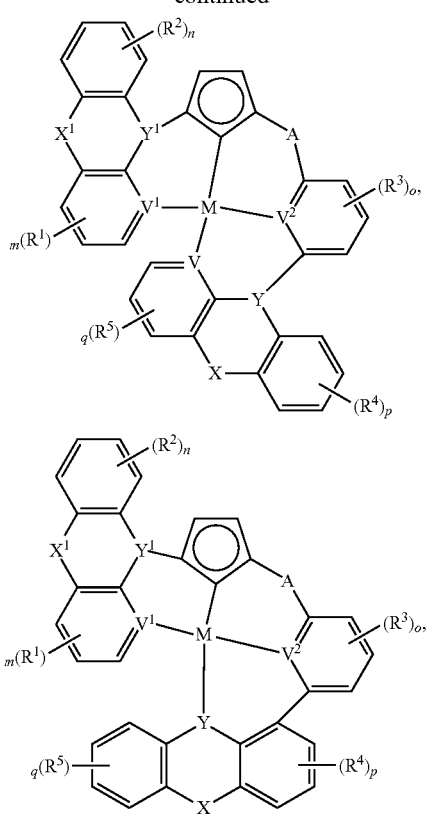
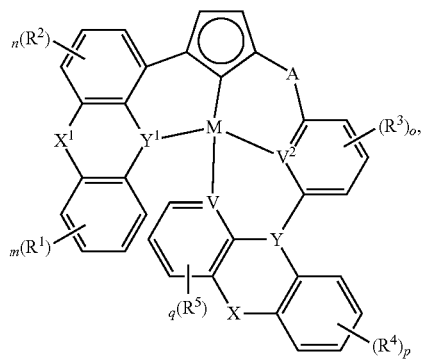
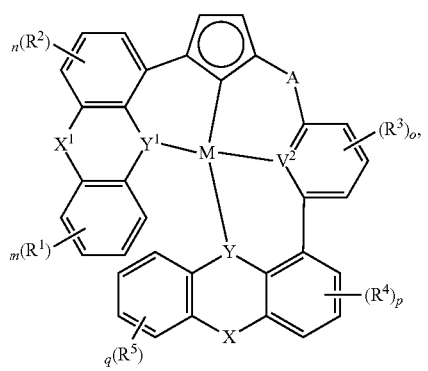
202
-continued
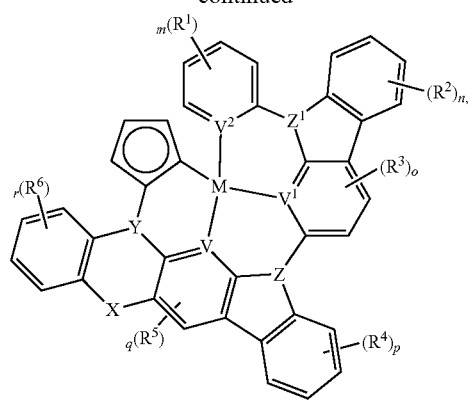
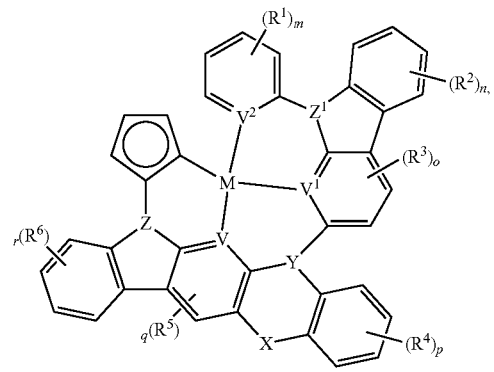
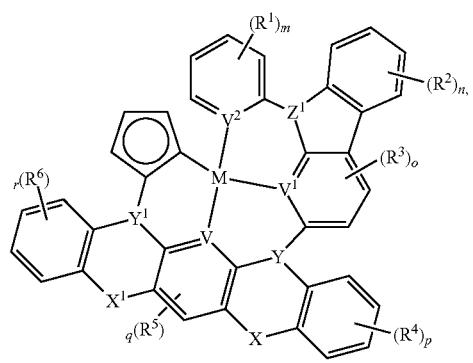
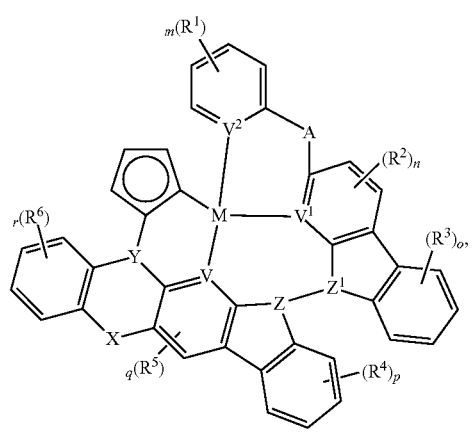

-continued
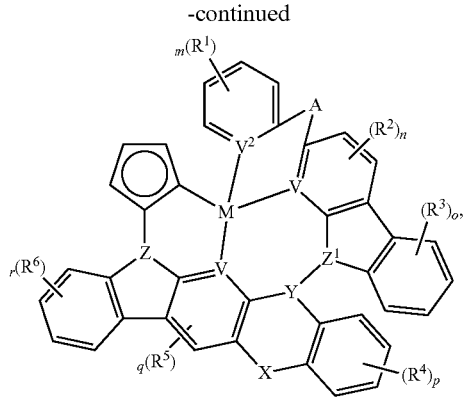
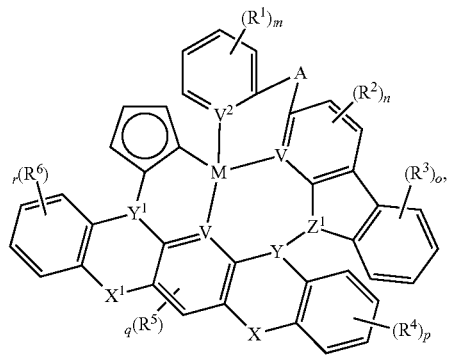
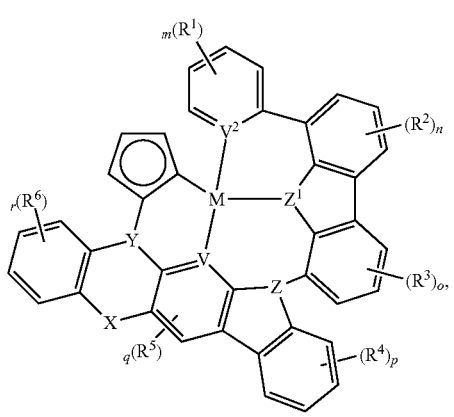
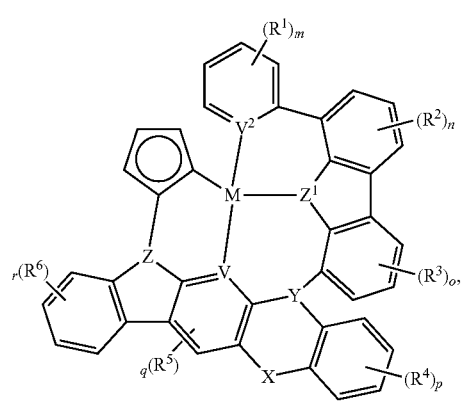
-continued
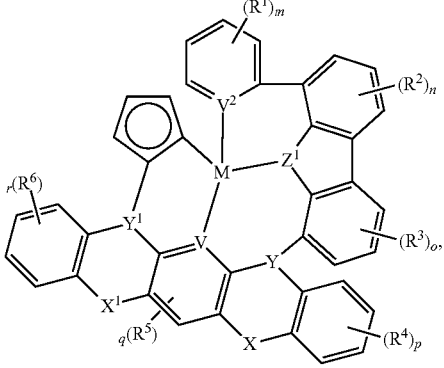
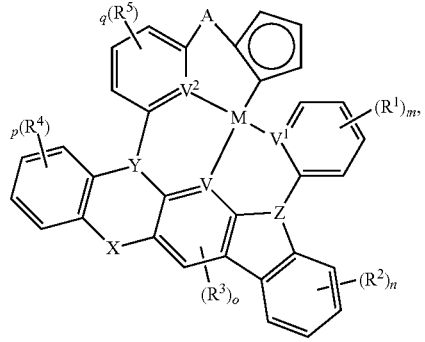
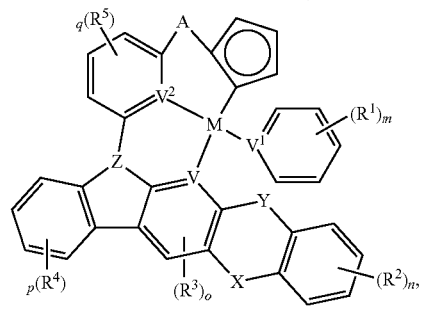
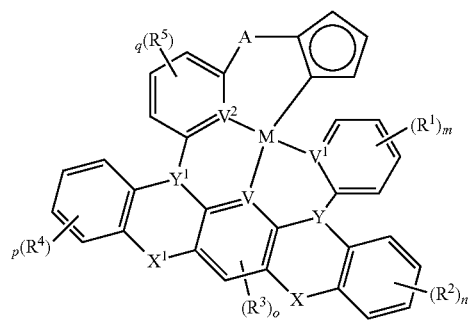
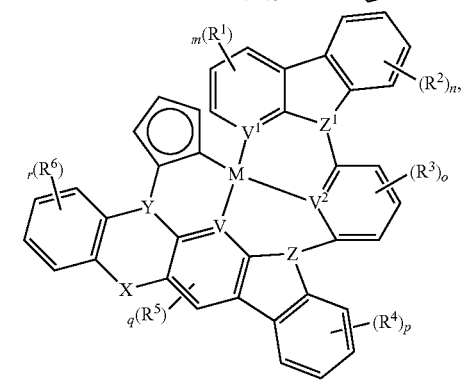

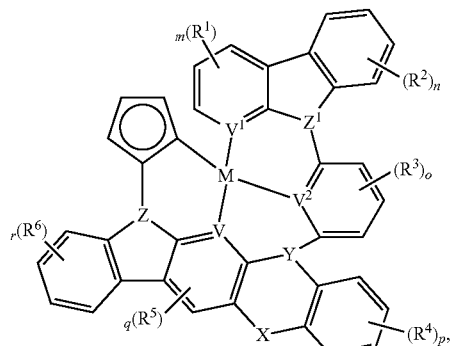
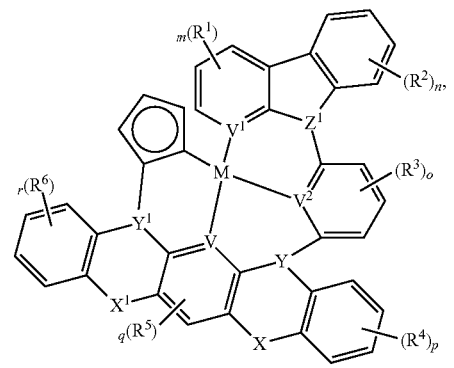
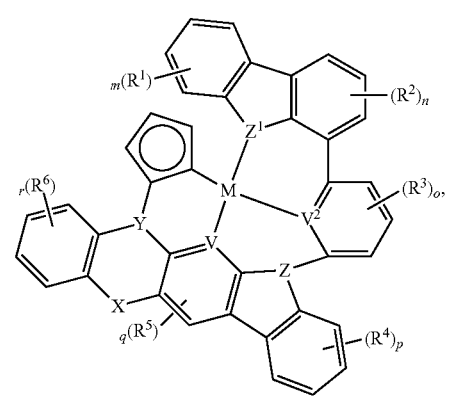
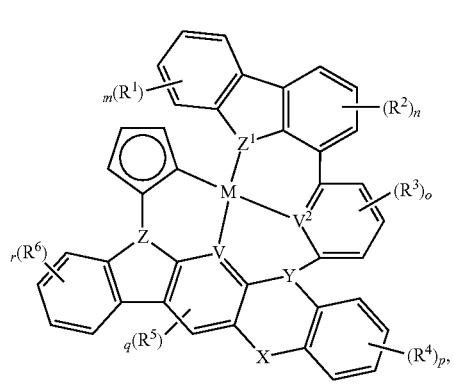
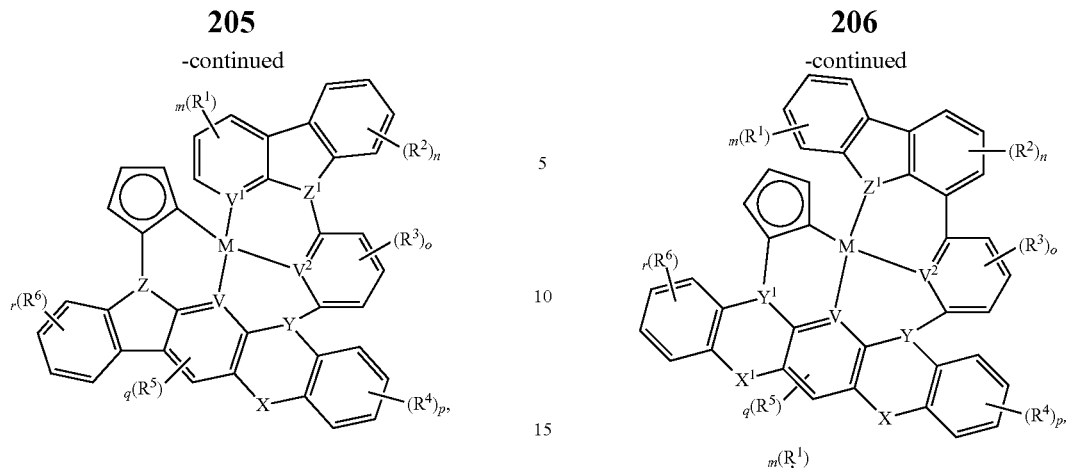
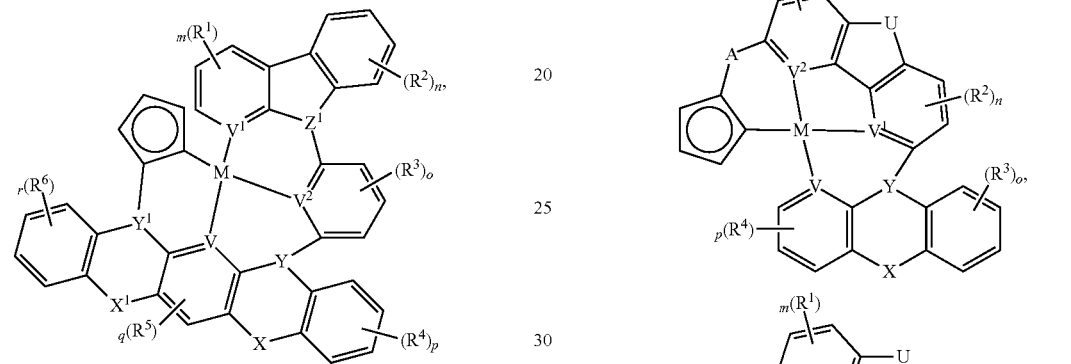
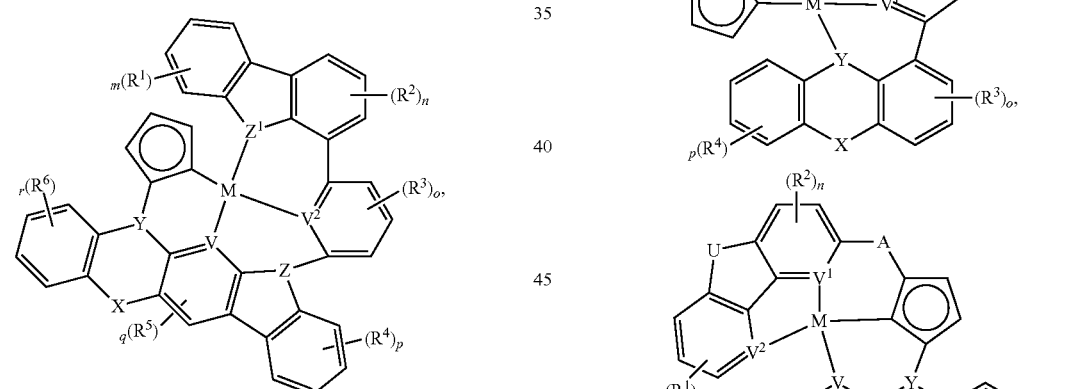
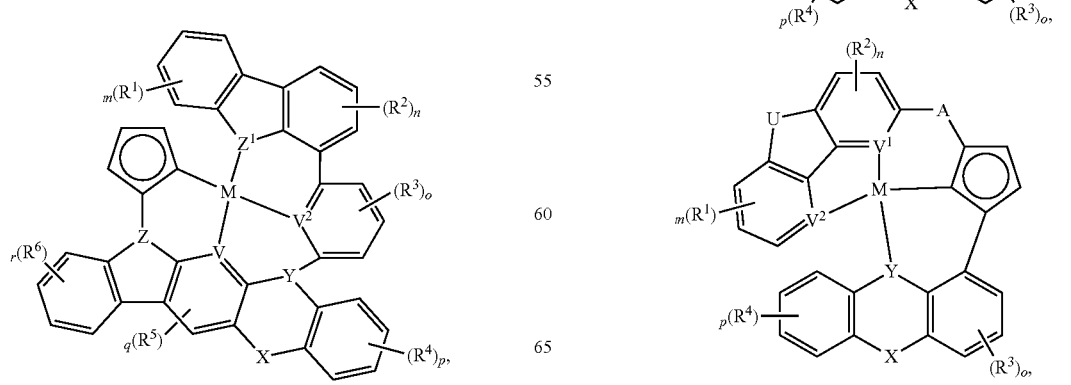

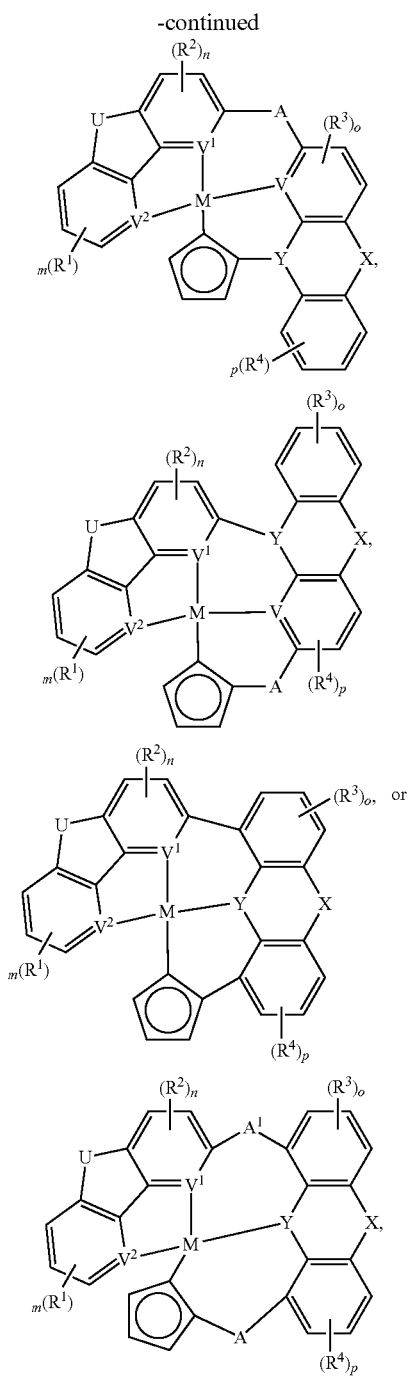
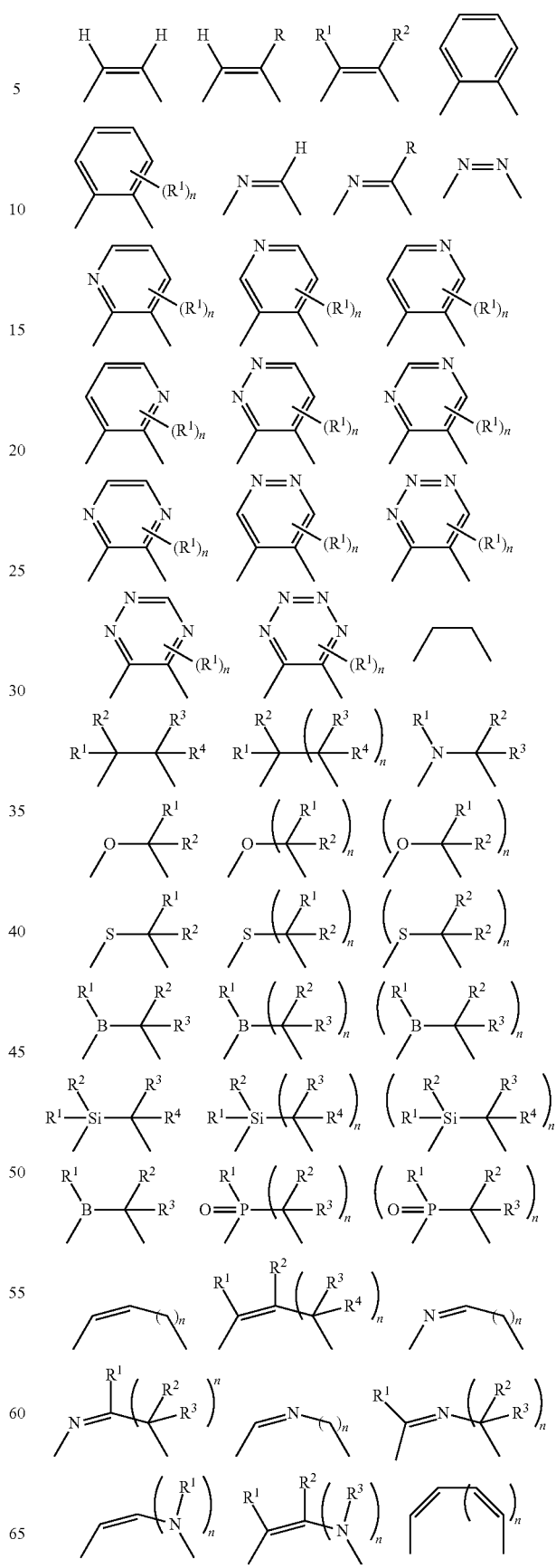

wherein each of A or A¹ independently is O, S, S=O, SO₂, Se, NR³, PR³, RP=O, CR¹R², C=O, SiR¹R², GeR¹R², BH, P(O)H, PH, NH, CR¹H, CH₂, SiH₂, SiHR¹, BH, or BR³, wherein M is Pt, Pd, Au, Ir, Rh, Ru, Fe, Co, Ni, Cu, Zn, Ag, Hg, Cd, or Zr, wherein each of m and n independently is an integer from 0 to 4, wherein each X, independently is V¹, V², V³, V⁴, O, S=O, SO₂, Se, NR³, PR³, R¹P=O, CR¹R², C=O, SiR¹R², GeR¹R², BH, P(O)H, PH, NH, CR¹H, CH₂, SiH₂, SiHR¹, BH, or BR³, or any one of

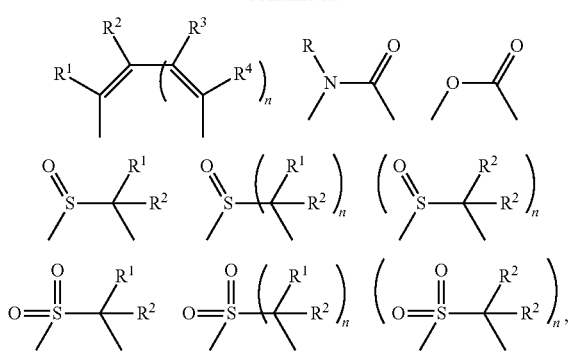

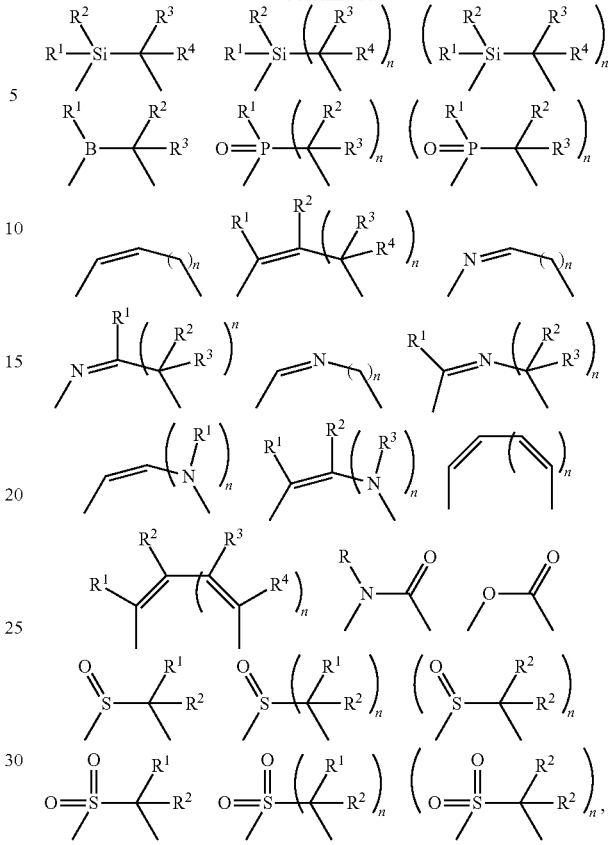

wherein each of U, V, X¹, Y, Y¹, Z, and Z¹ independently is $V^1$, $V^2$, $V^3$, $V^4$, O, S, S=O, $SO_2$, Se, $NR^3$, $PR^3$, $R^1P$=O, $CR^1R^2$, C=O, $SiR^1R^2$, $GeR^1R^2$, BH, P(O)H, PH, NH, $CR^1H$, $CH_2$, $SiH_2$, $SiHR^1$, BH, or $BR^3$, or any one of

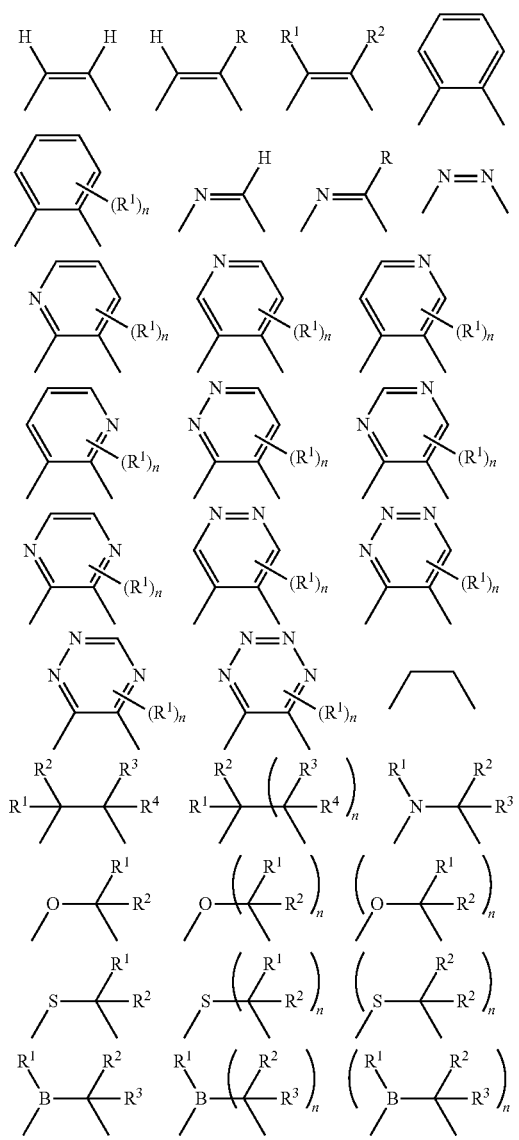

wherein at least one of U, V, X, X¹, Y¹, Y¹, Z, or Z¹ is $V^1$, $V^2$, $V^3$, or $V^4$, wherein each of m and n independently is an integer from 0 to 4, wherein each of $V^1$, $V^2$, $V^3$, and $V^4$ independently is coordinated to M, and wherein each of $V^1$, $V^2$, $V^3$, and $V^4$ independently is N, C, CH, P, B, SiH, or Si, wherein each of R, $R^1$, $R^2$, $R^3$, $R^4$, $R^5$, and $R^6$ independently is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted silyl, or polymerizable, or any conjugate or combination thereof, wherein each of $V^1$, $V^2$, $V^3$ and $V^4$ independently optionally is substituted for any one of $V^1$, $V^2$, $V^3$ and $V^4$, wherein each of o, p, q, and r independently is an integer of 0 to 4.

2. The compound of claim 1, wherein at least one of $V^1$, $V^2$, $V^3$, and $V^4$ is N.

3. The compound of claim 1, wherein the compound comprises at least one phenyl and at least one pyridine.

4. The compound of claim 1, wherein M is Pt or Pd.

5. The compound of claim 1, wherein M is Pt.

6. A photovoltaic device comprising one or more compounds of claim 1.

7. A luminescent display device comprising one or more compounds of claim 1.

8. A light emitting device comprising one or more compounds of claim 1.

9. The compound of claim 1, wherein each of U, V, X, X¹, Y, Z, and Z¹ independently is N, NH, C, CH, or

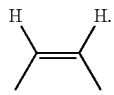

10. A device comprising one or more compounds of claim 1.

11. The device of claim 10, wherein the device is a full color display.

12. The device of claim 10, wherein the device is an organic light emitting diode.

13. The device of claim 12, wherein the organic light emitting diode is a phosphorescent OLED device.

14. The device of claim 12, wherein the organic light emitting diode is a fluorescent OLED device.

15. A compound, wherein the compound has one of the following structures:

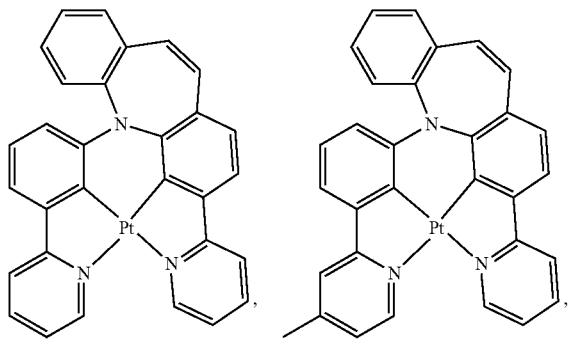

-continued

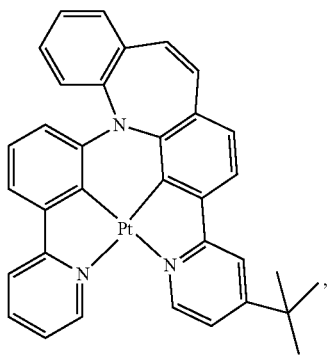

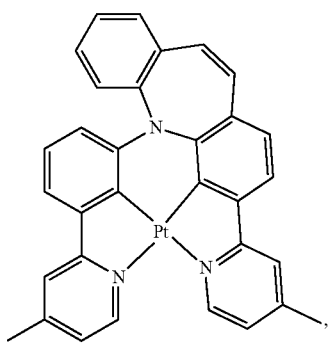

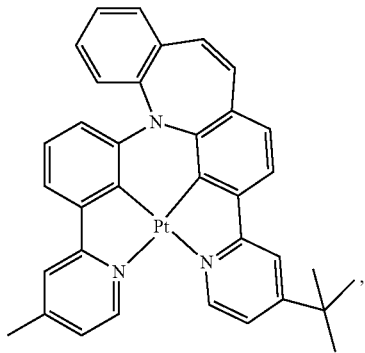

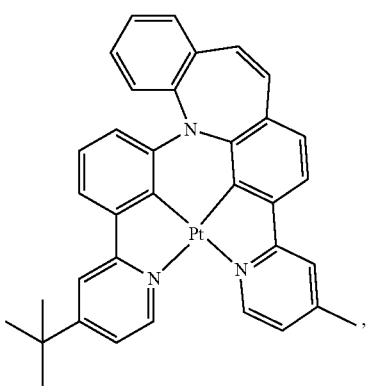

213
-continued
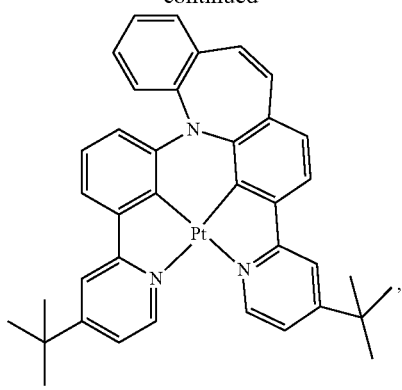
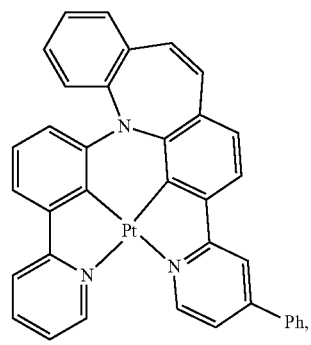
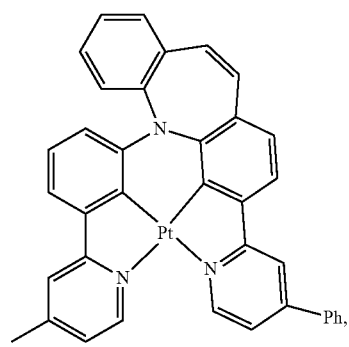
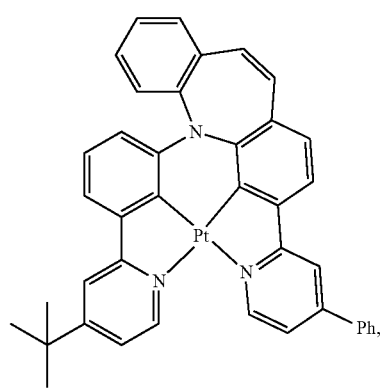
214
-continued
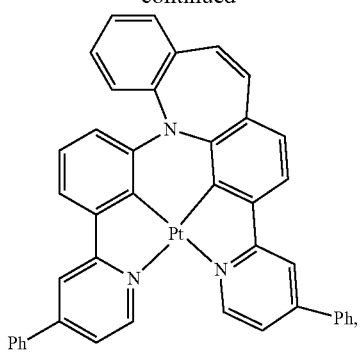
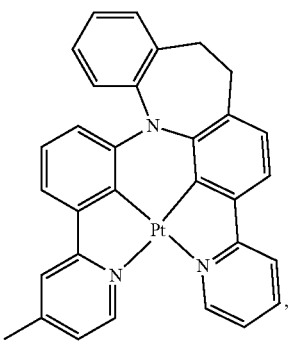
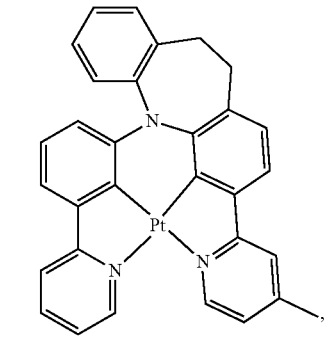
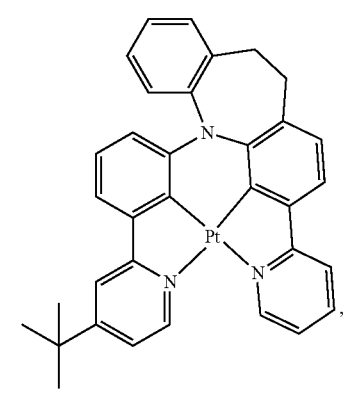

215
-continued
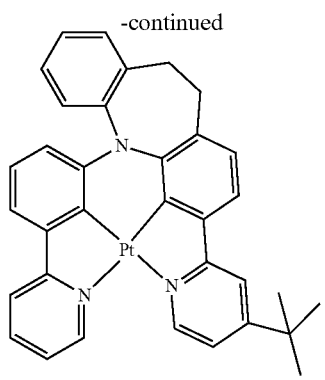
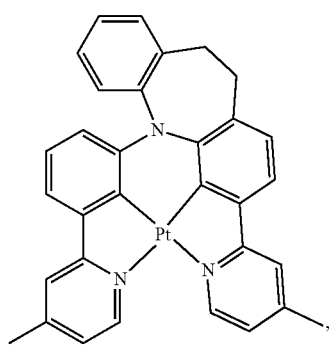
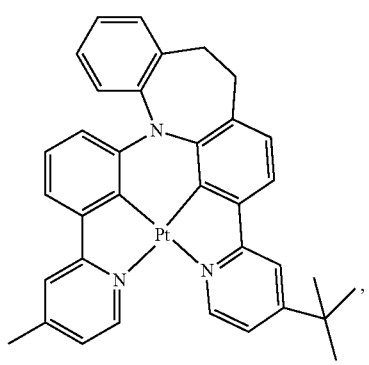
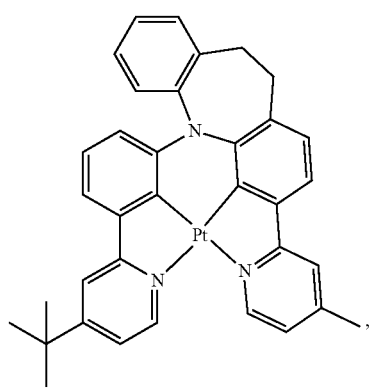
216
-continued
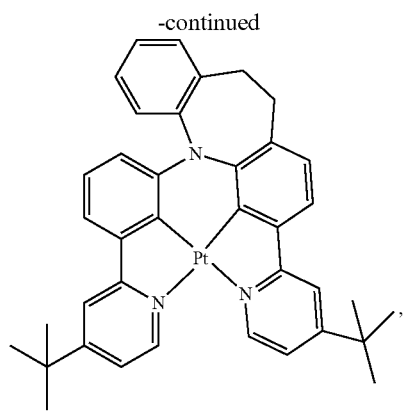
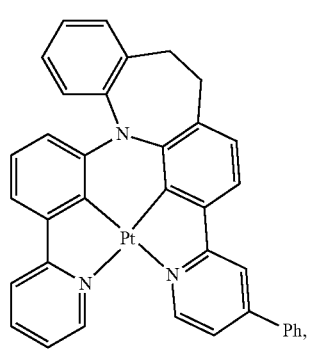
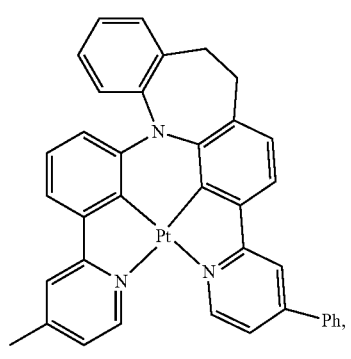
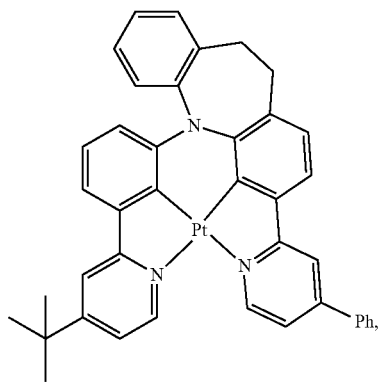

217
-continued
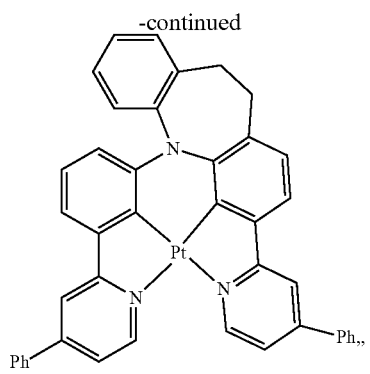
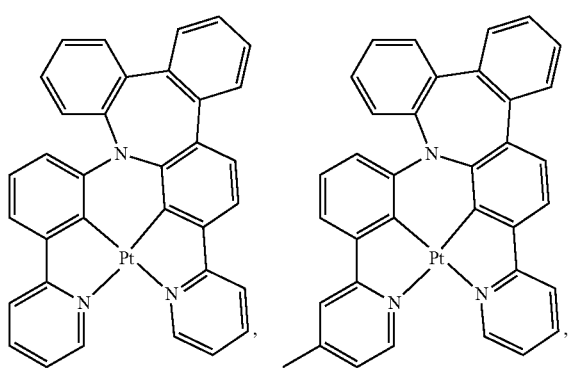
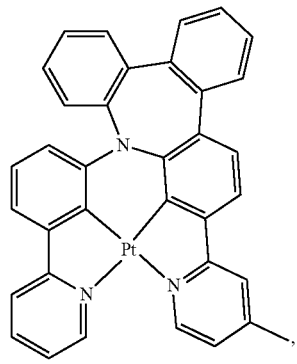
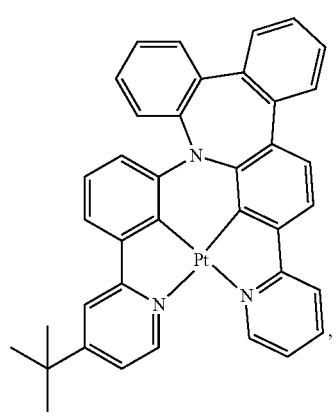
218
-continued
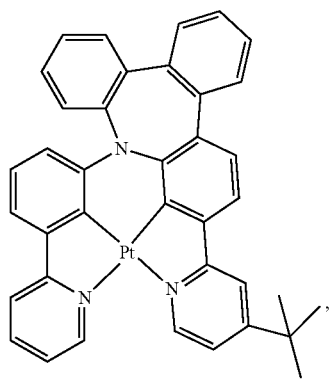
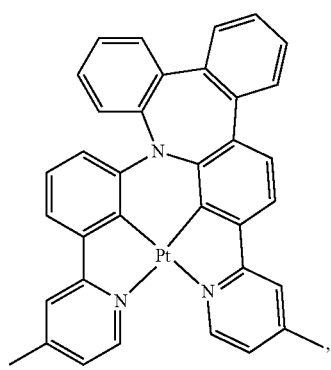
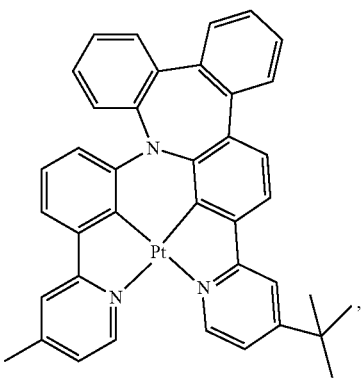
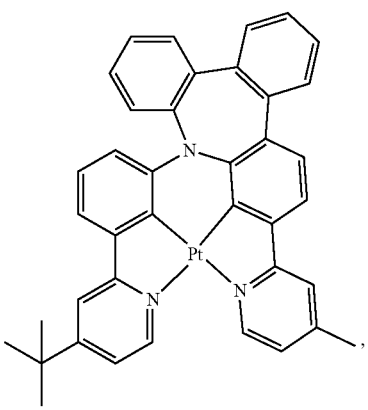

219
-continued
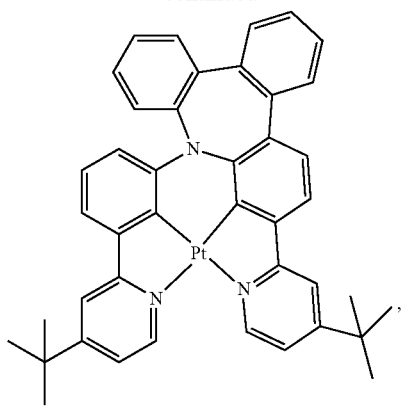
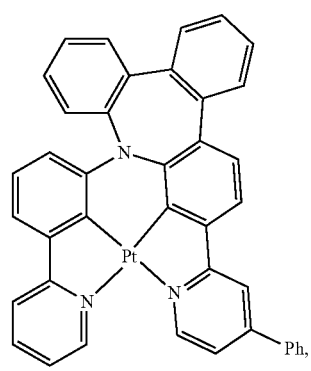
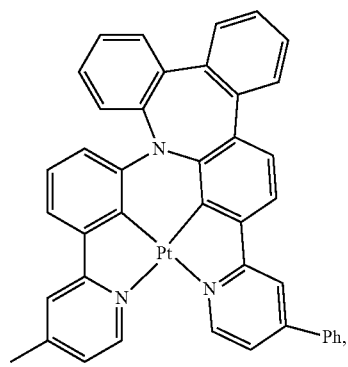
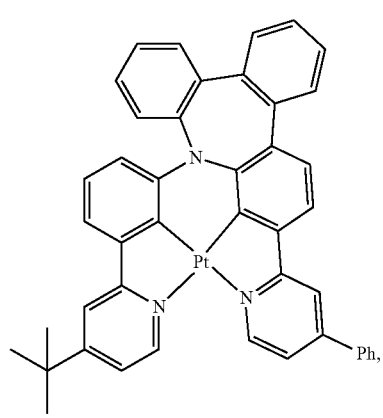
220
-continued
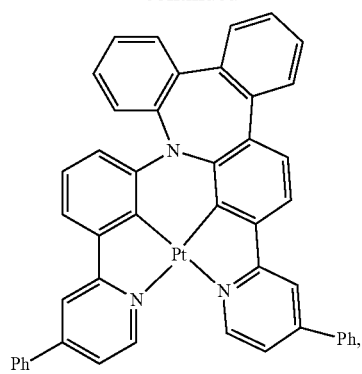
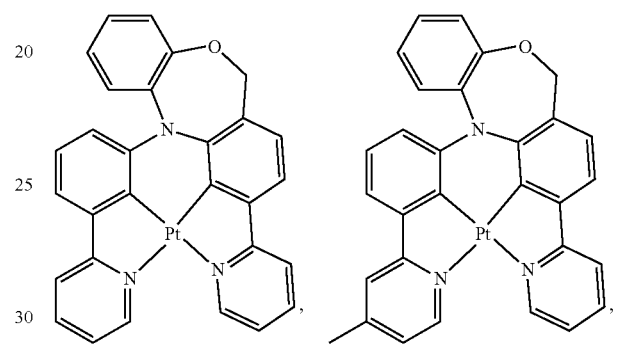
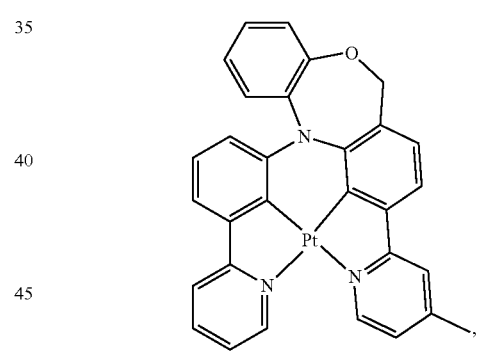
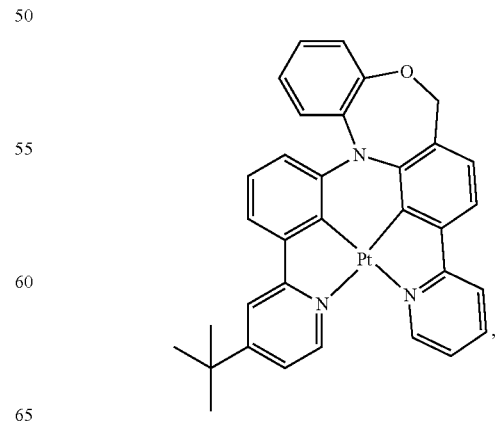

221
-continued
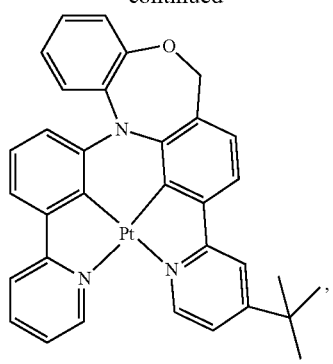
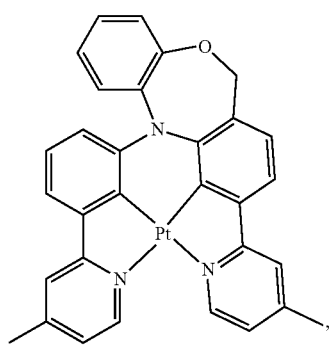
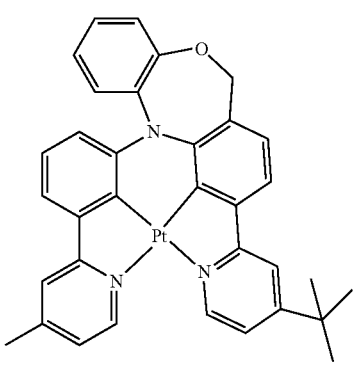
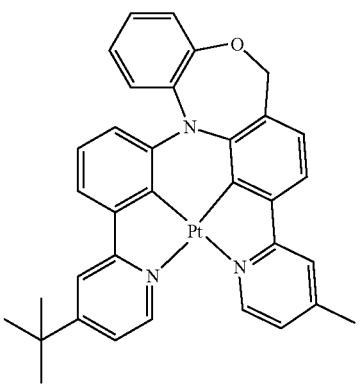
222
-continued
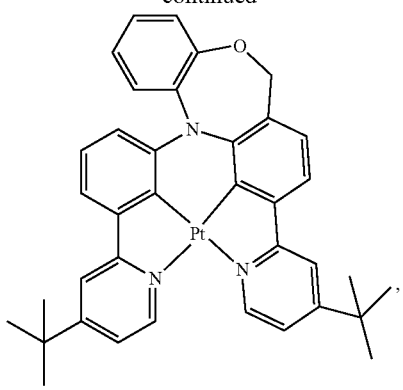
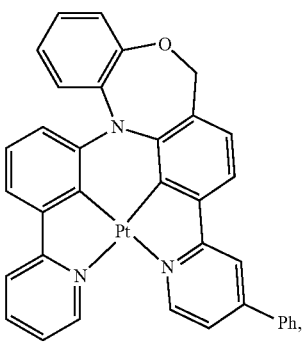
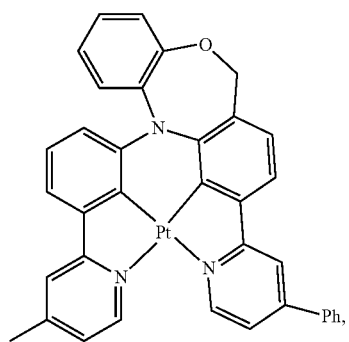
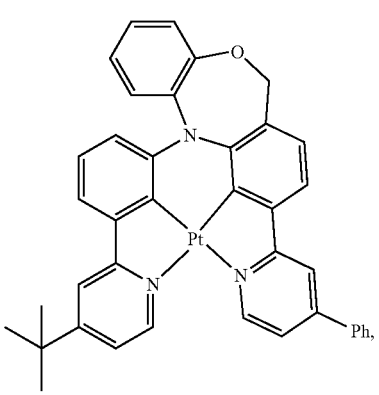

223
-continued
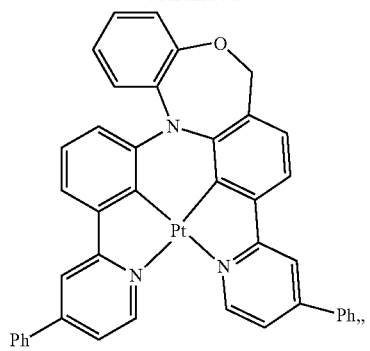
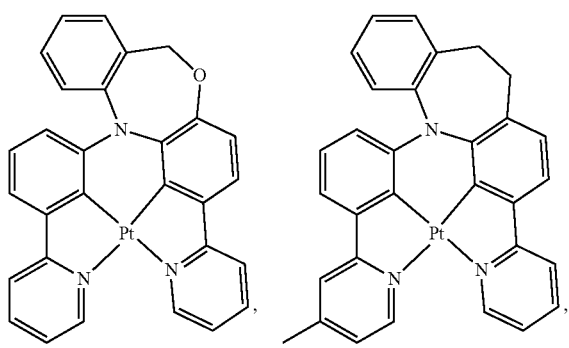
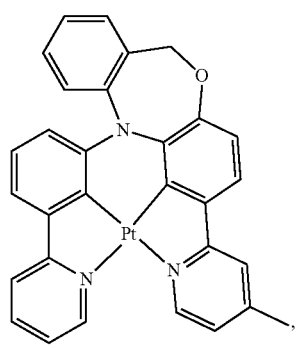
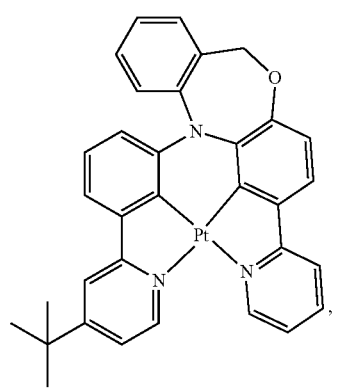
224
-continued
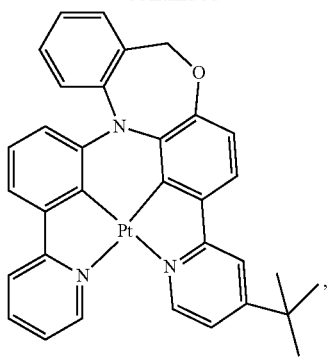
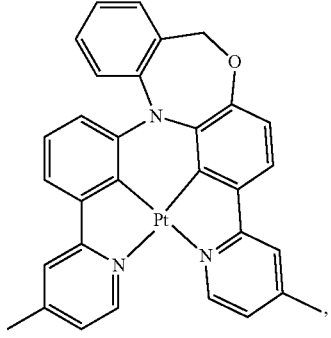
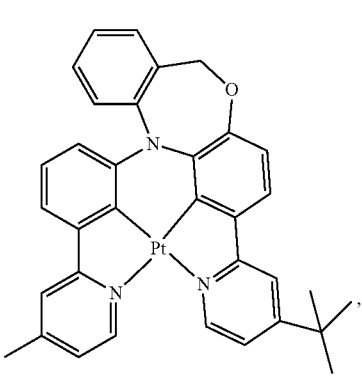
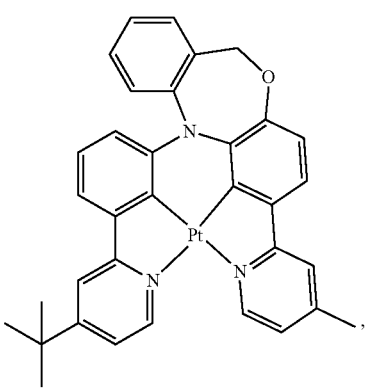

225
-continued
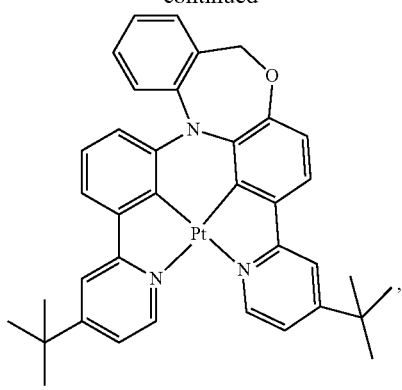
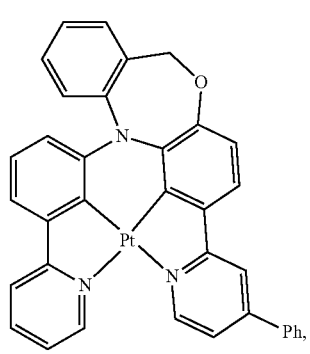
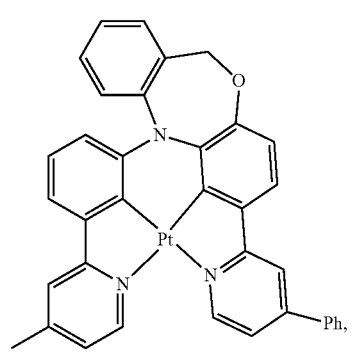
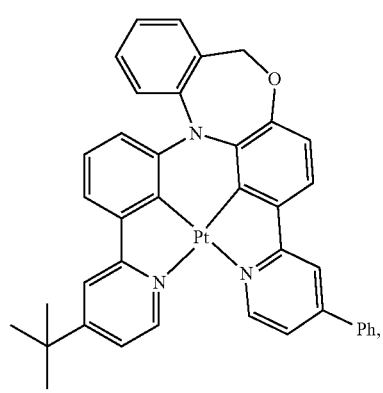
226
-continued
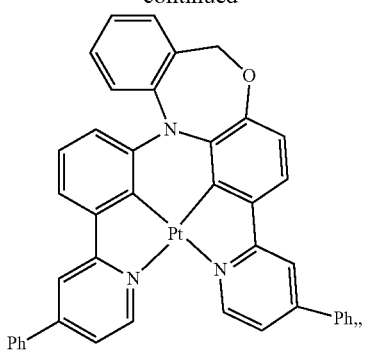
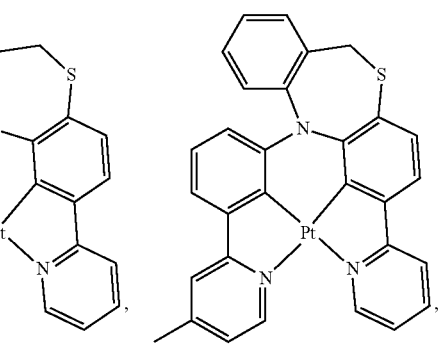
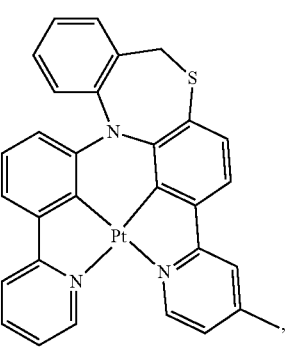
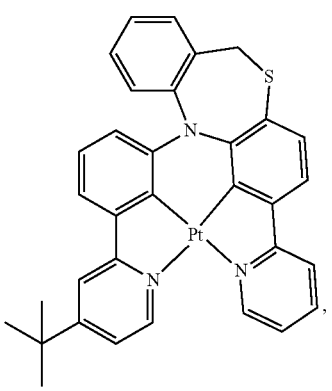

227
-continued
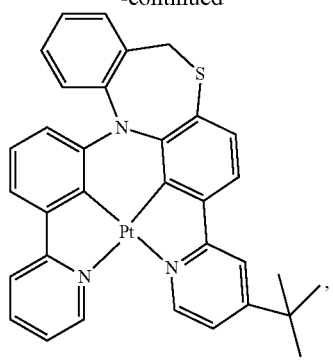
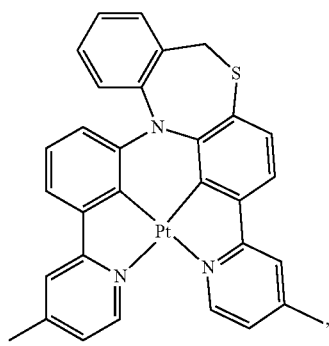
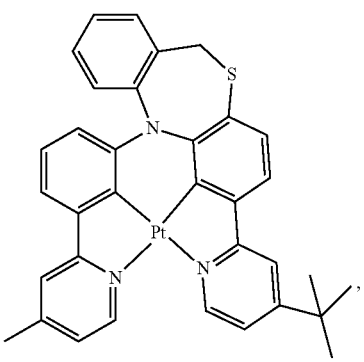
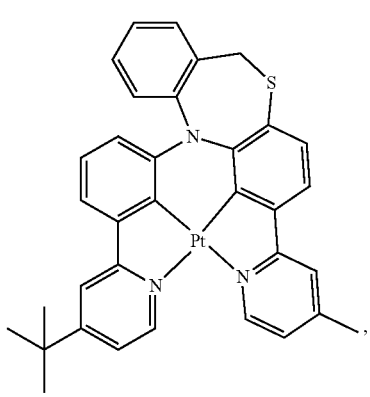
228
-continued
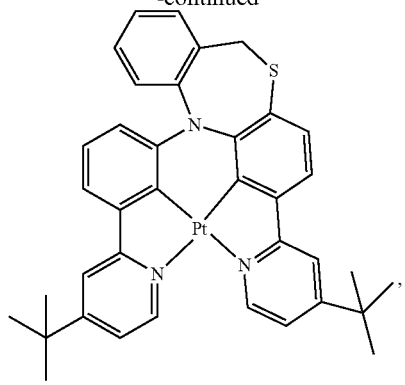
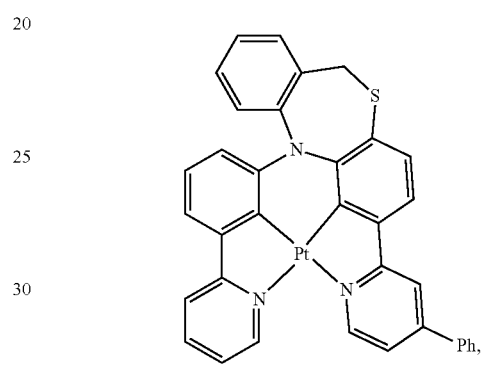
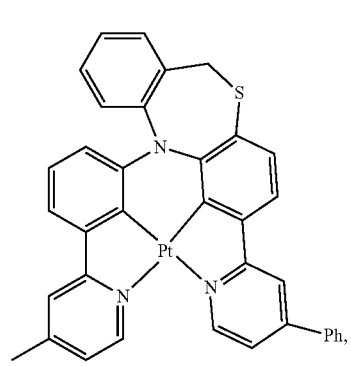
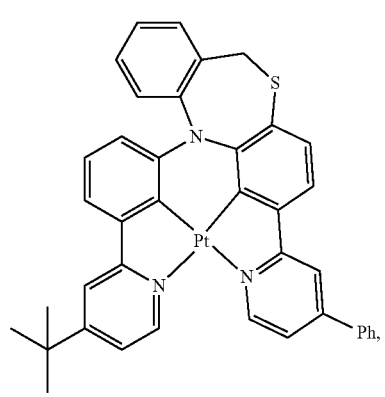

229
-continued
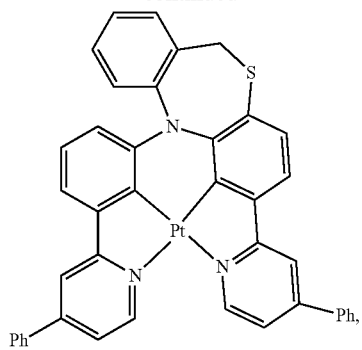
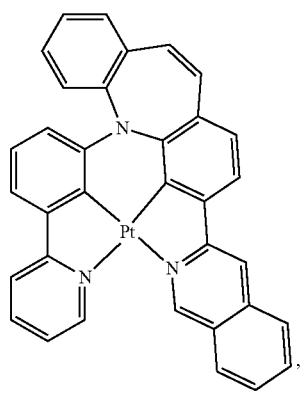
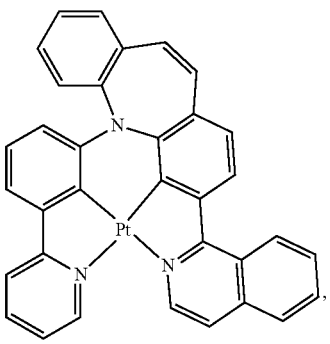
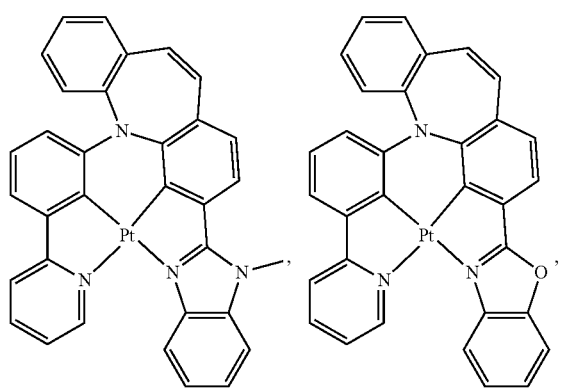
230
-continued
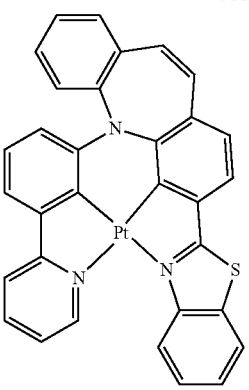
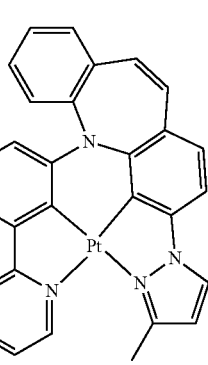 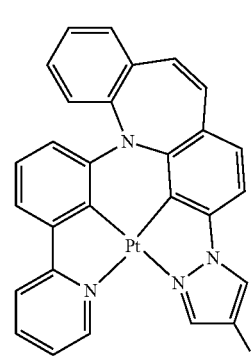
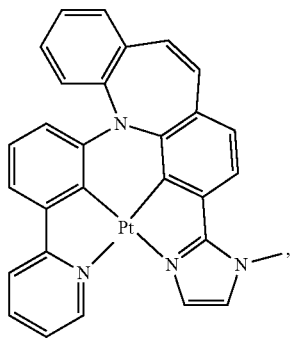
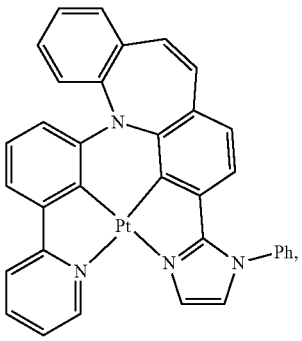 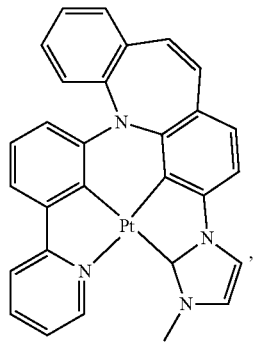

231
-continued
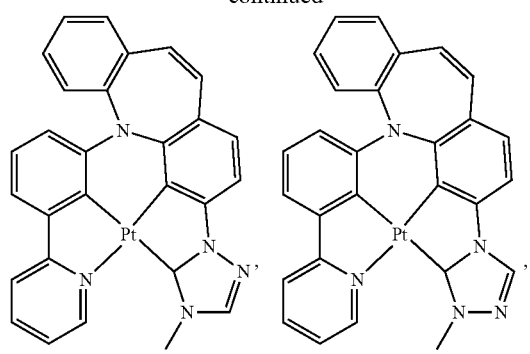
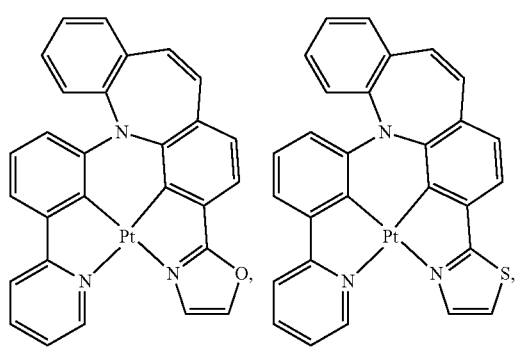
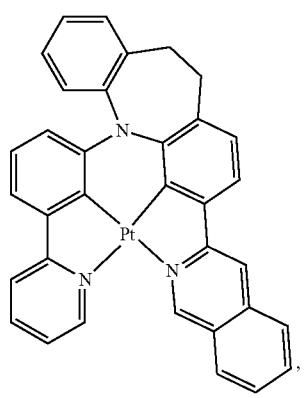
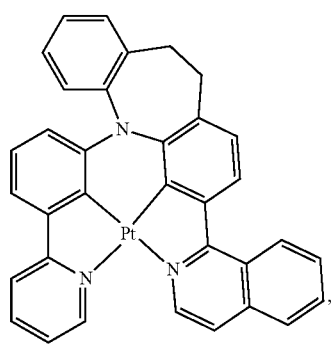
232
-continued
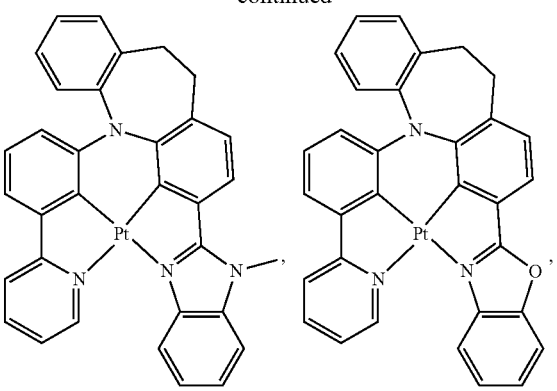
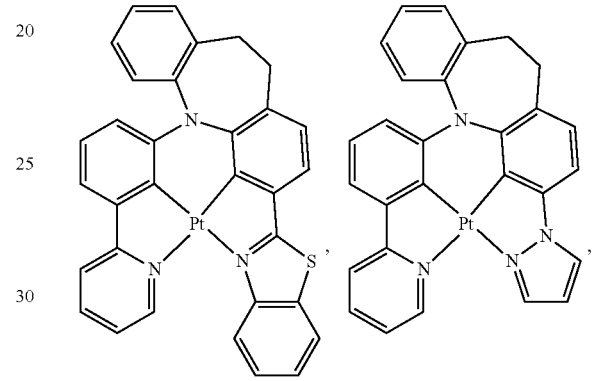
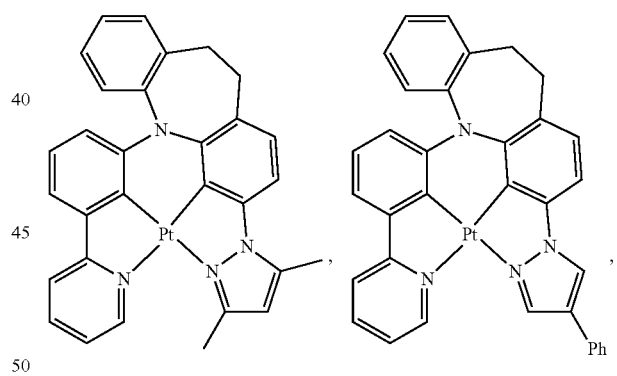
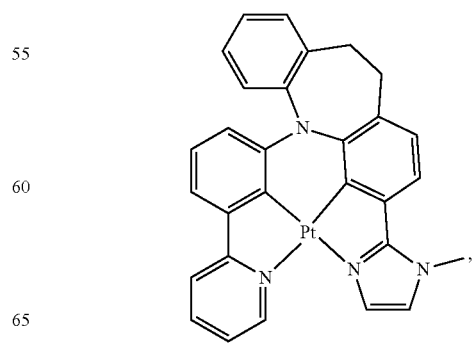

233
-continued
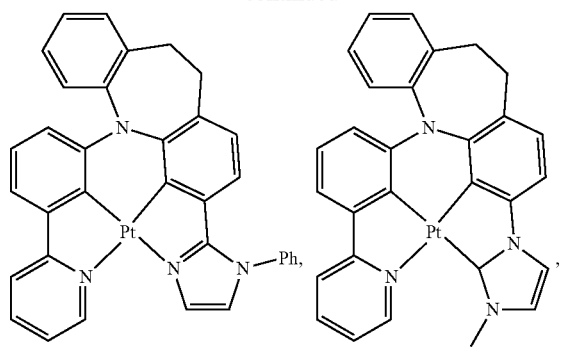
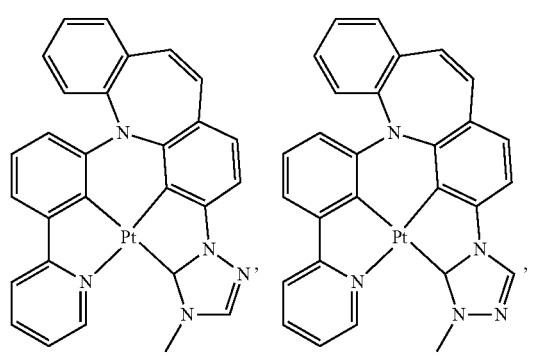
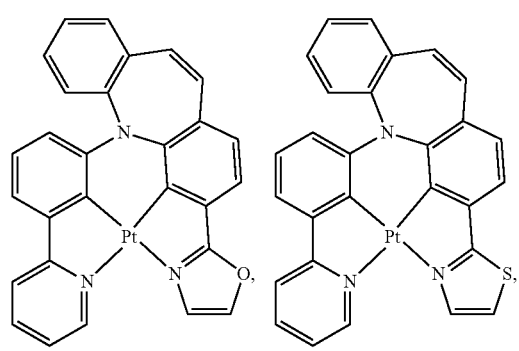
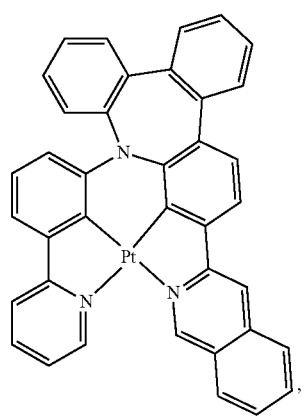
234
-continued
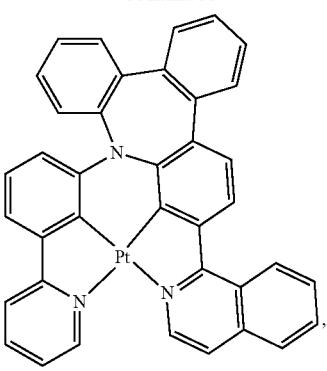
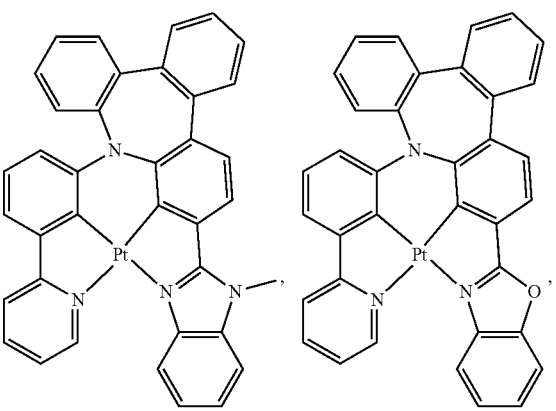
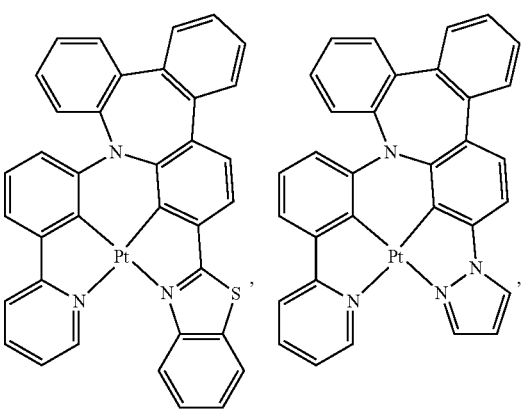
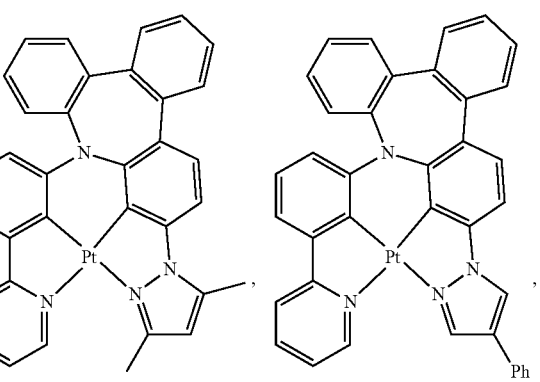

235
-continued
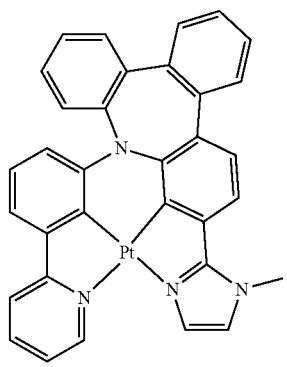
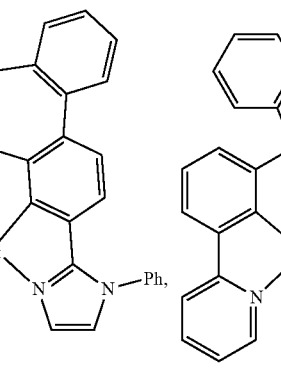 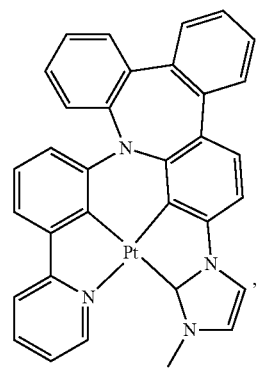
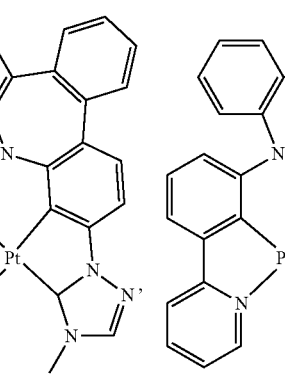 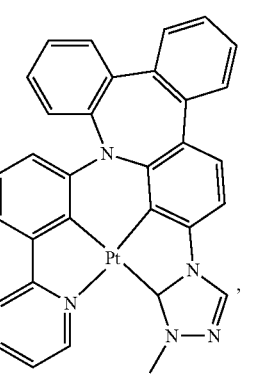
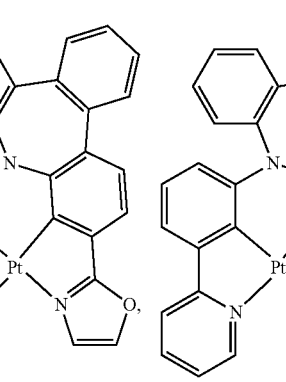 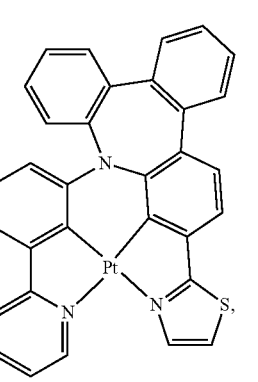
236
-continued
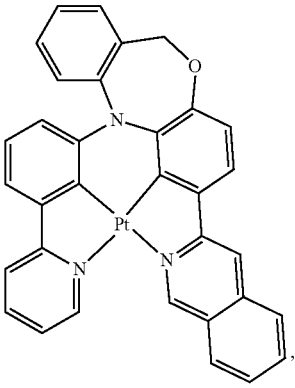
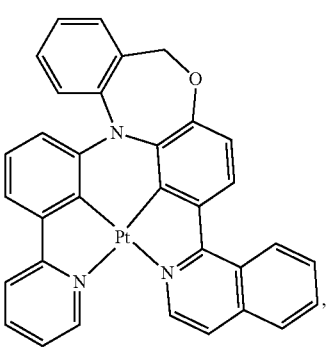
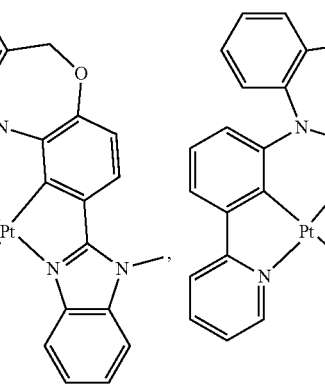 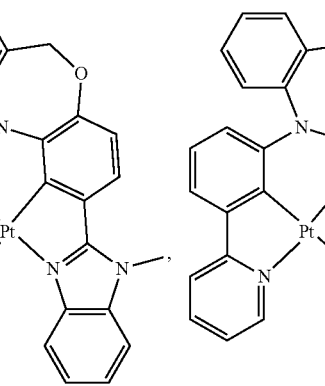
 

237
-continued
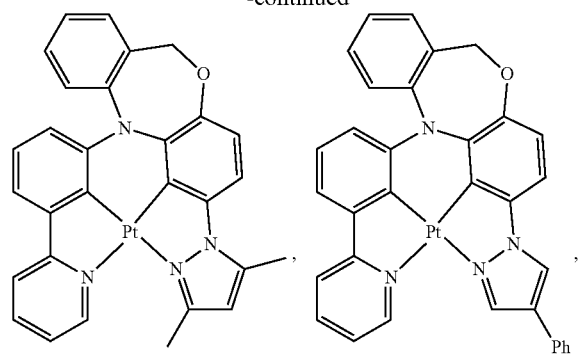
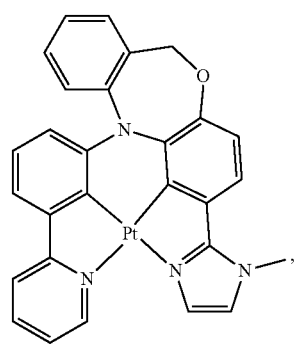
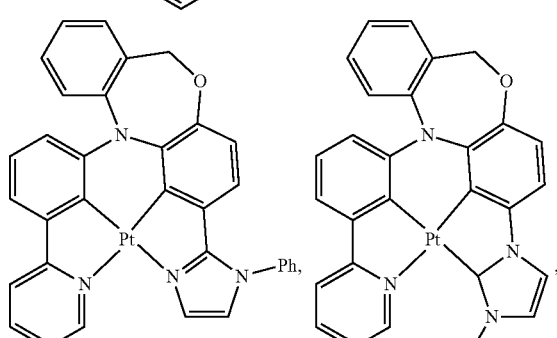
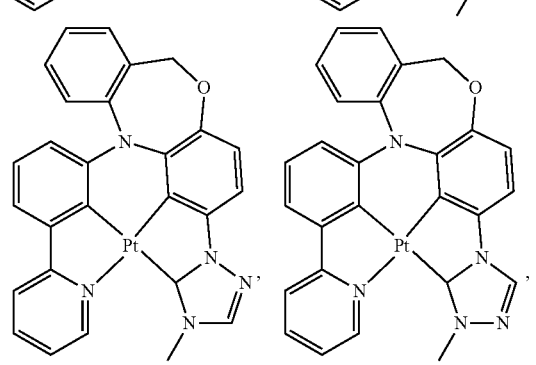
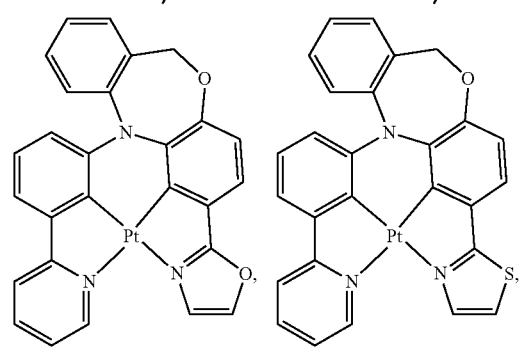
238
-continued
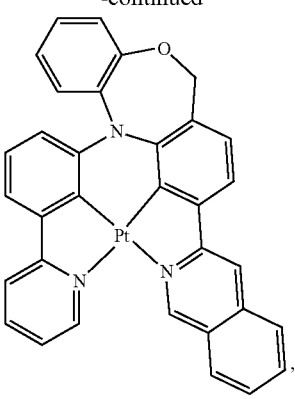
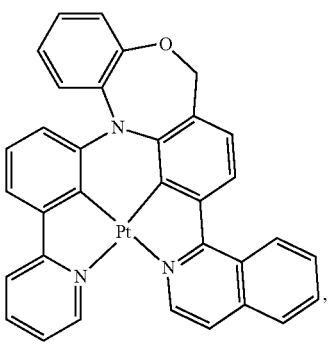
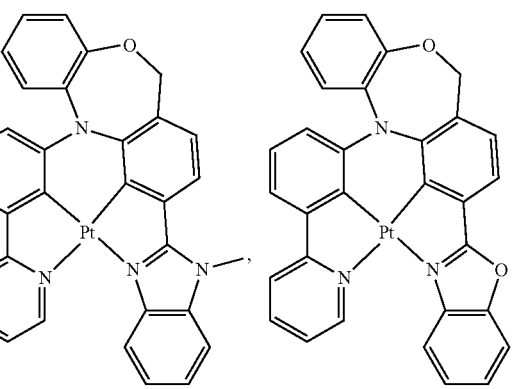
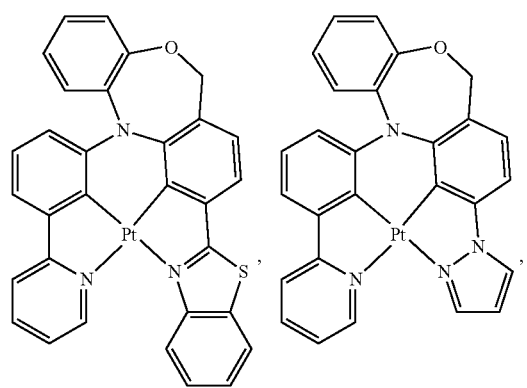

239
-continued
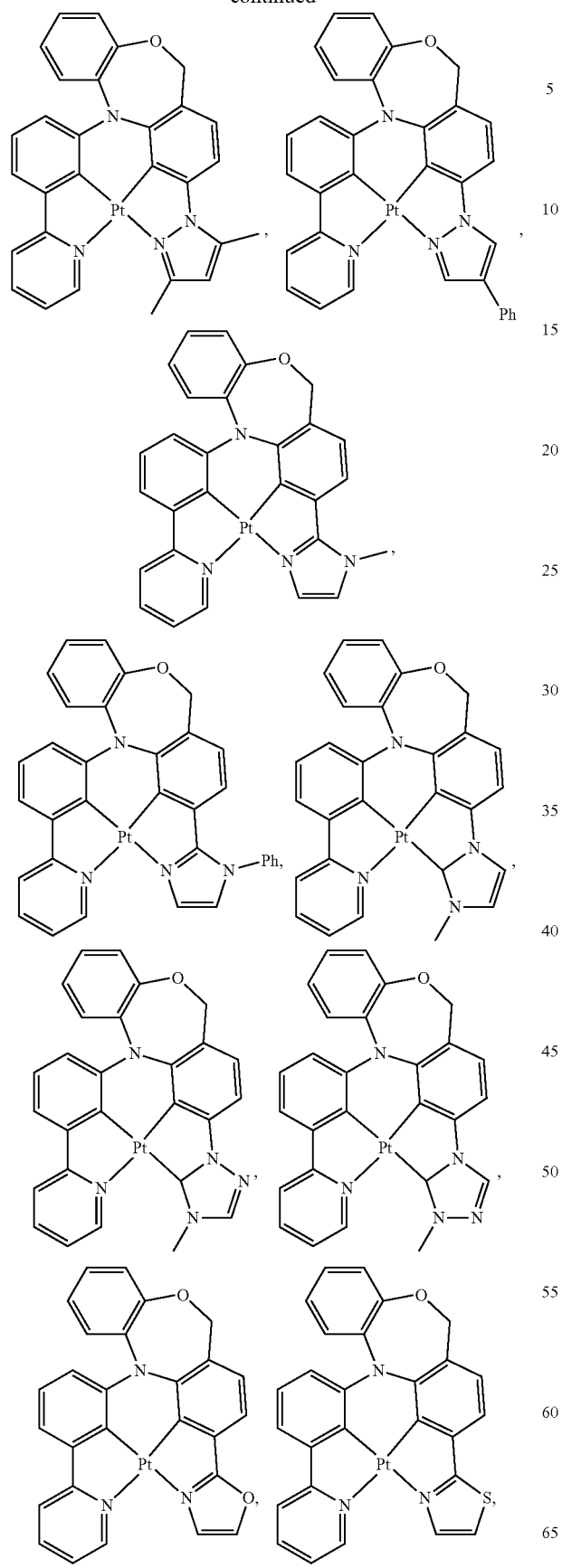
240
-continued
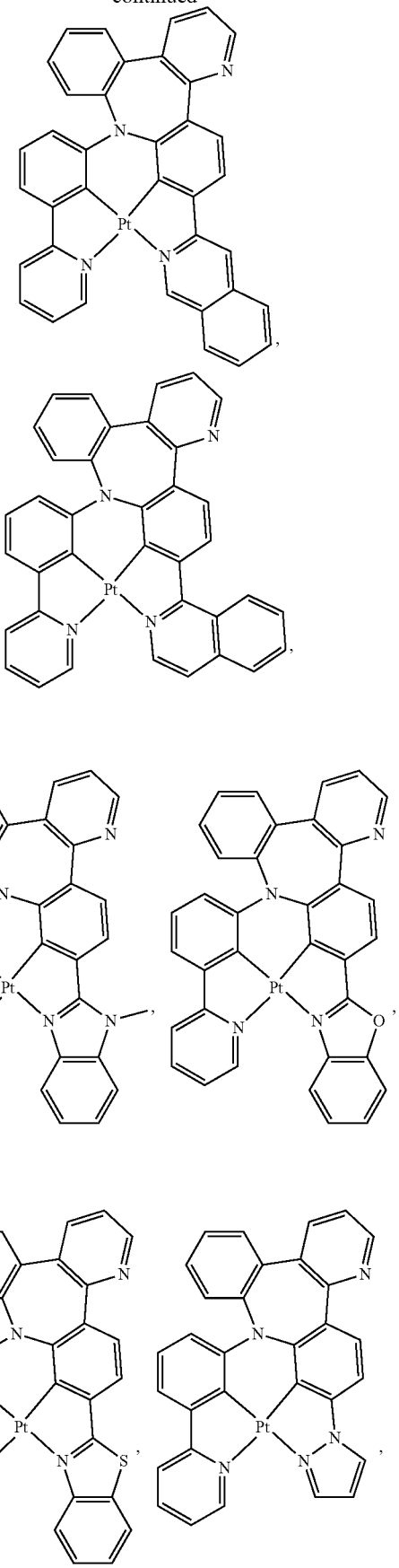

241
-continued
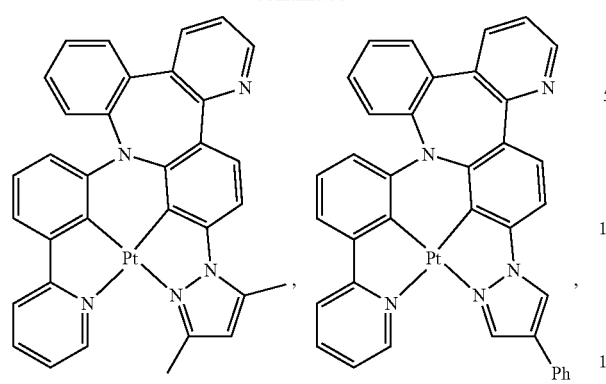
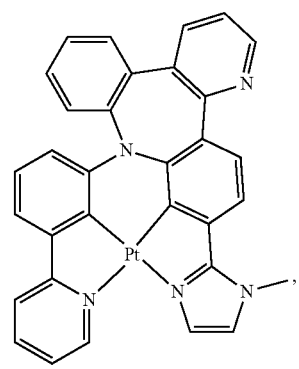
242
-continued
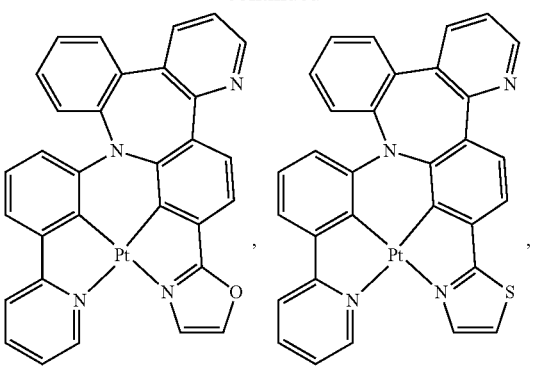
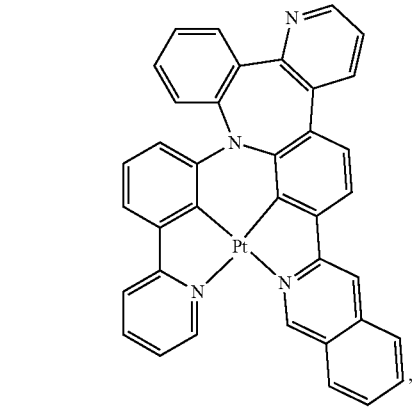
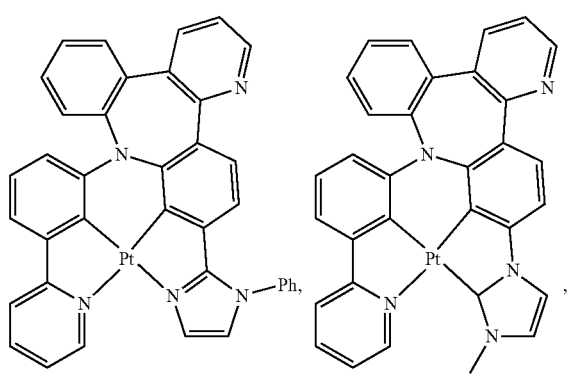
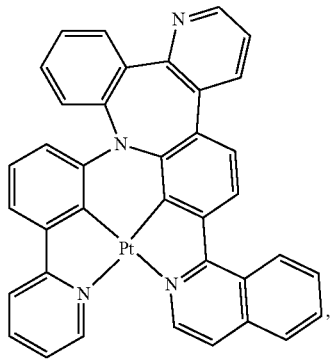
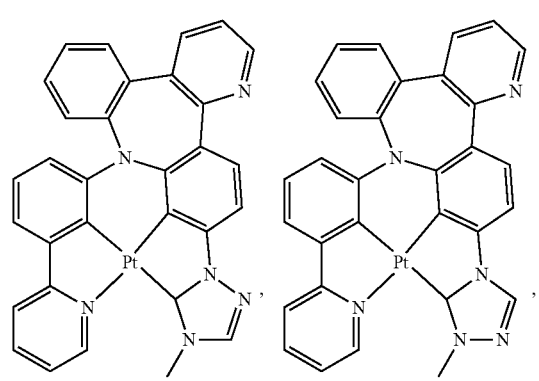
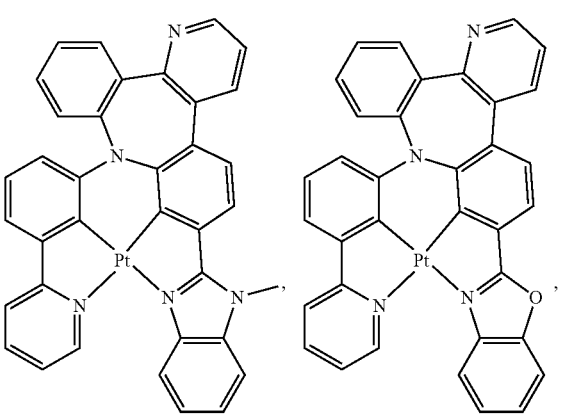

243
-continued
244
-continued
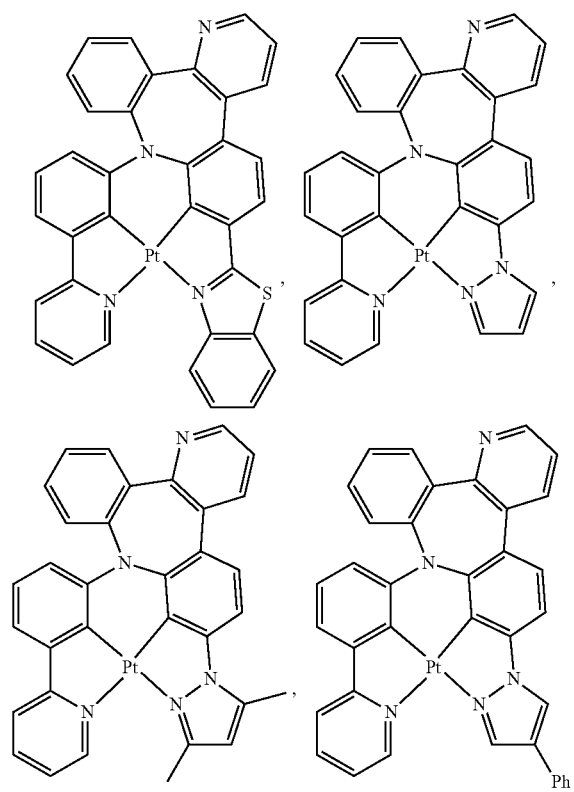
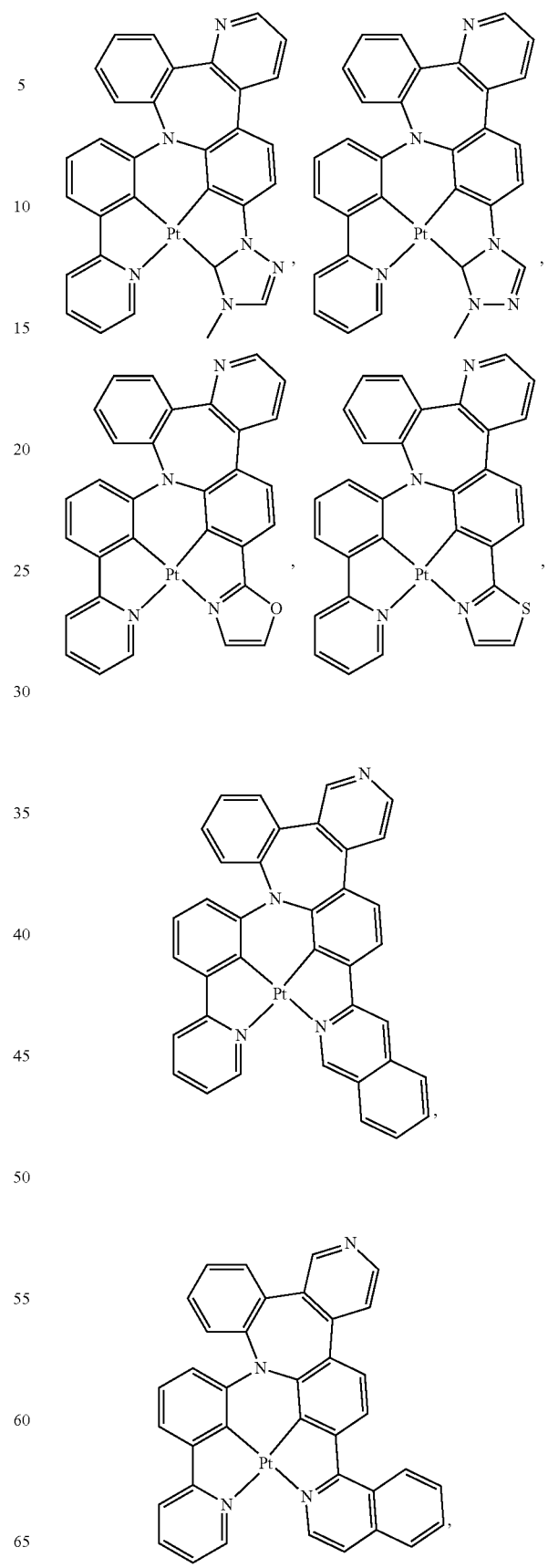

-continued
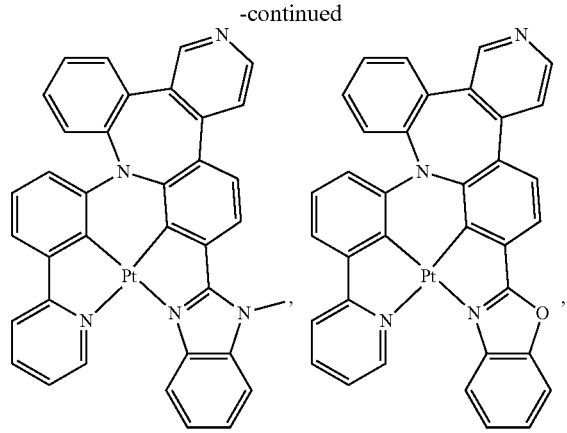
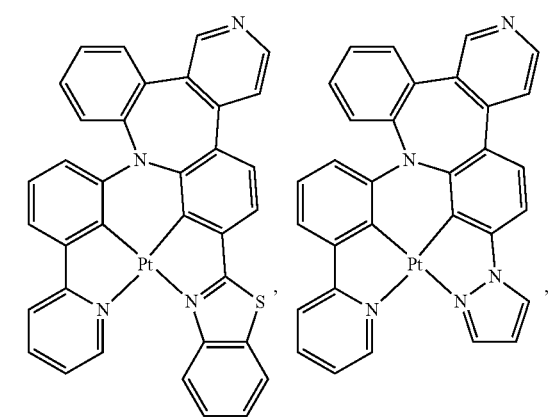
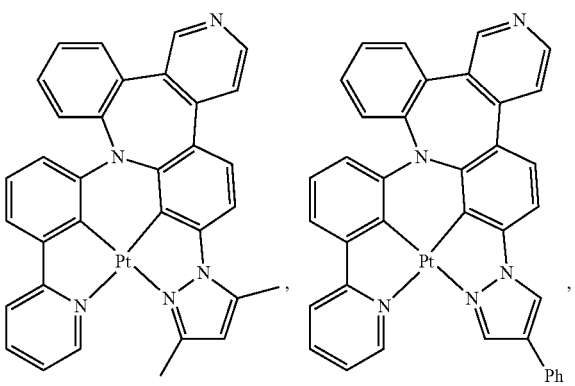
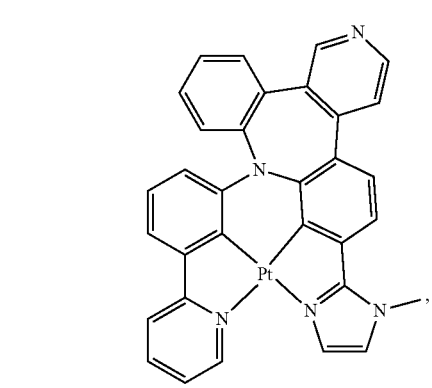
-continued
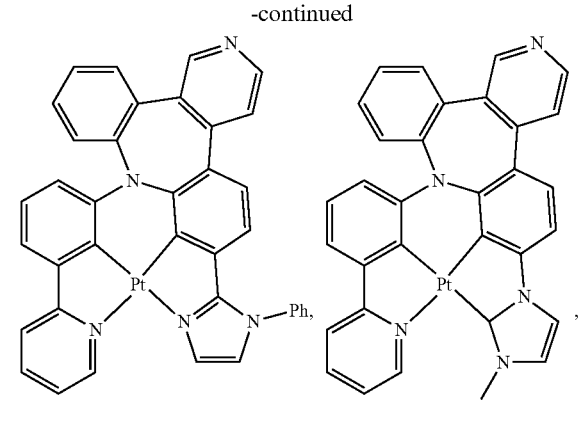
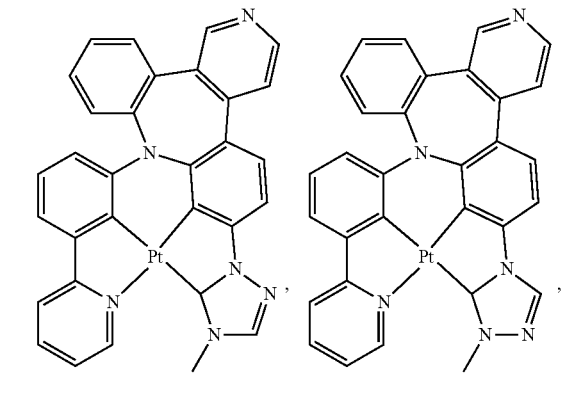
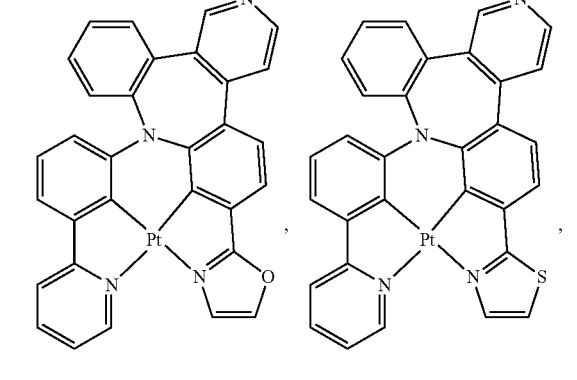
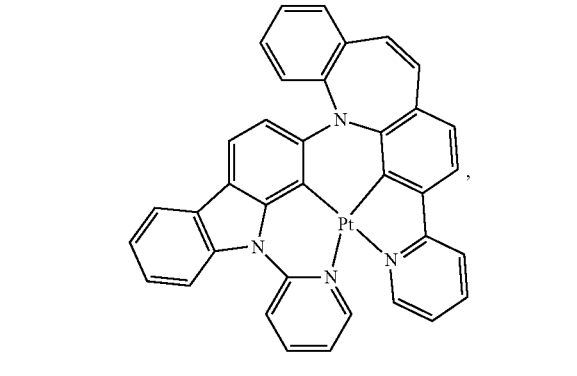

247
-continued
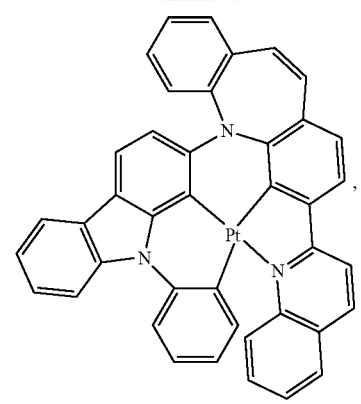
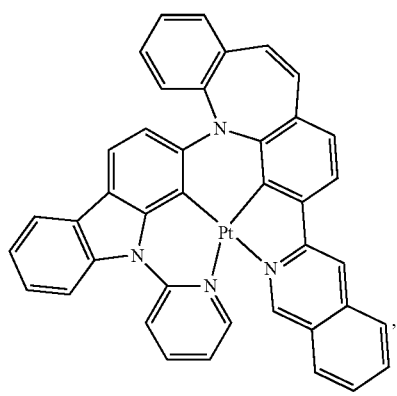
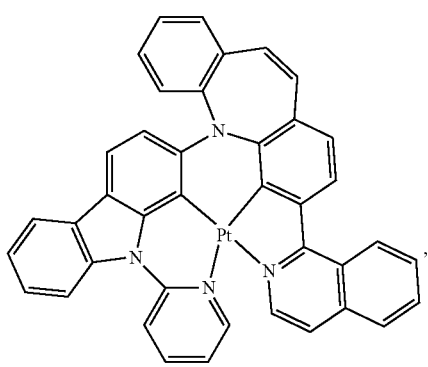
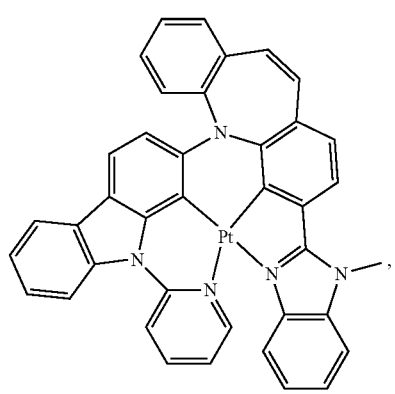
248
-continued
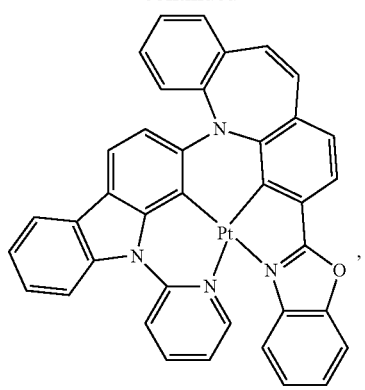
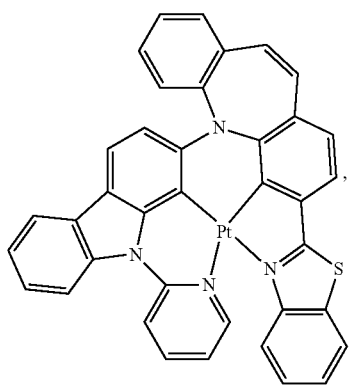
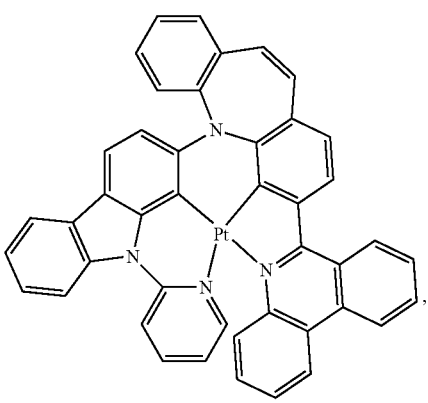
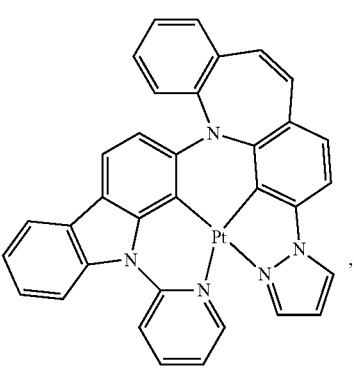

249
-continued
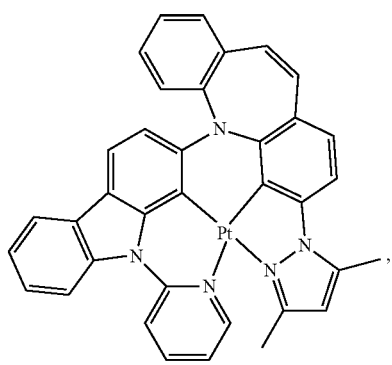
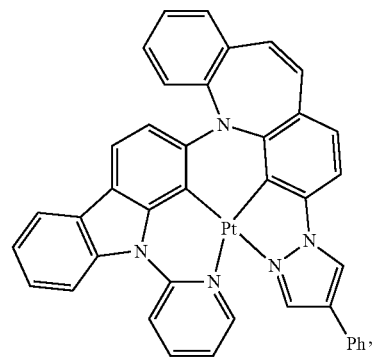
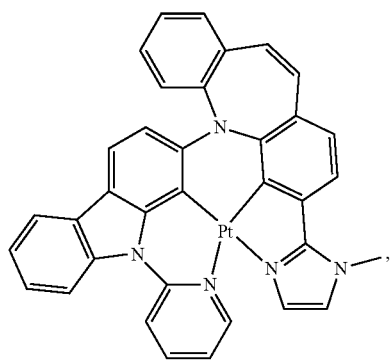
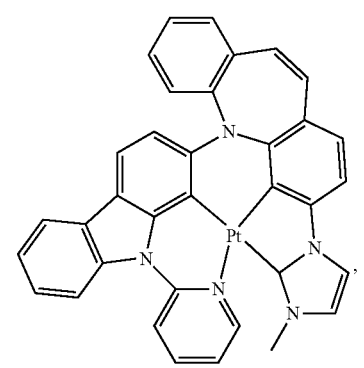
250
-continued
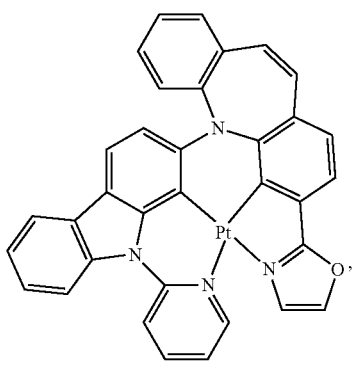
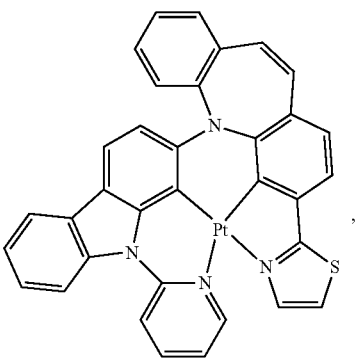
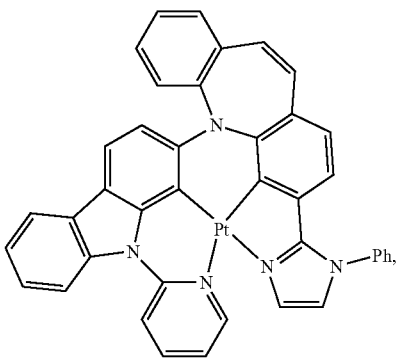
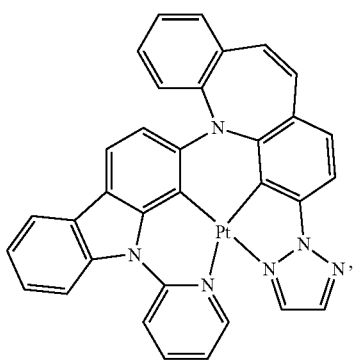

251
-continued
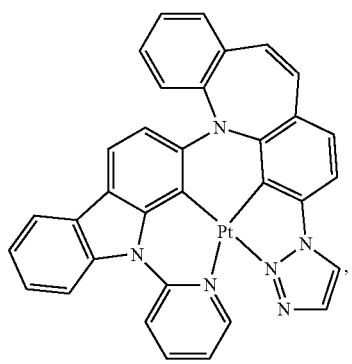
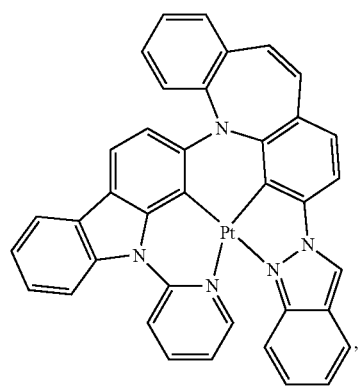
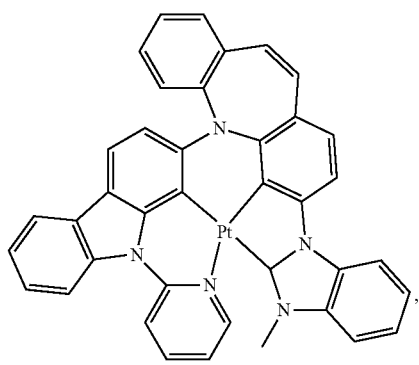
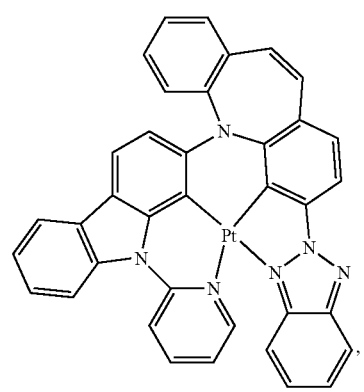
252
-continued
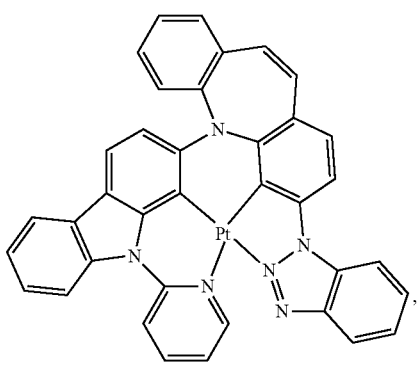
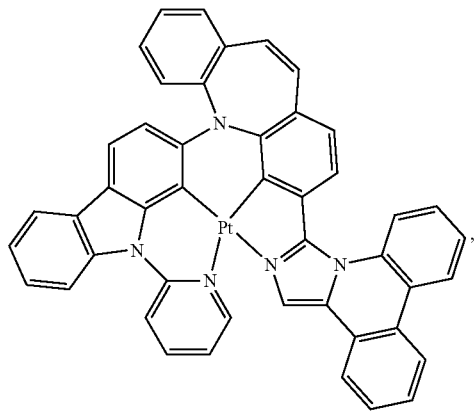
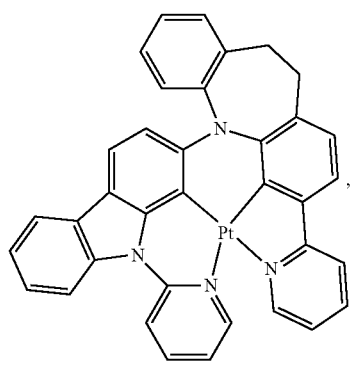
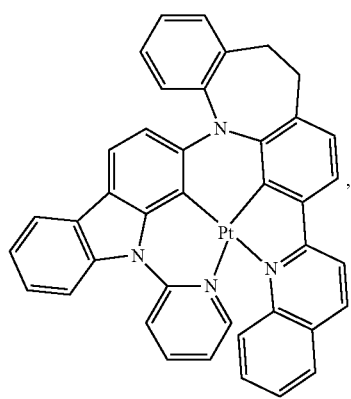

253
-continued
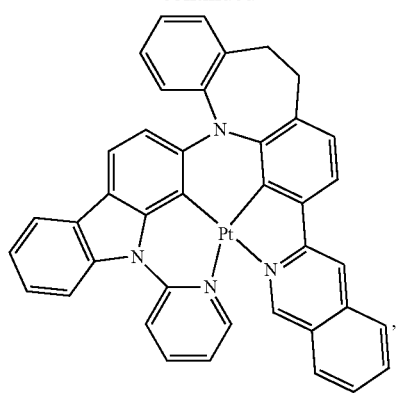
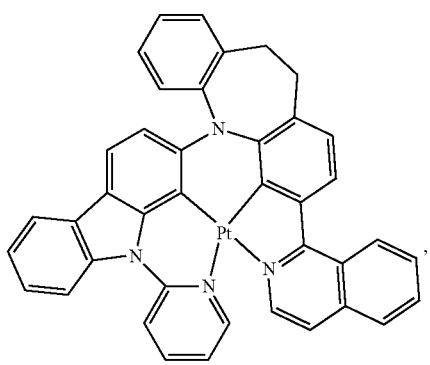
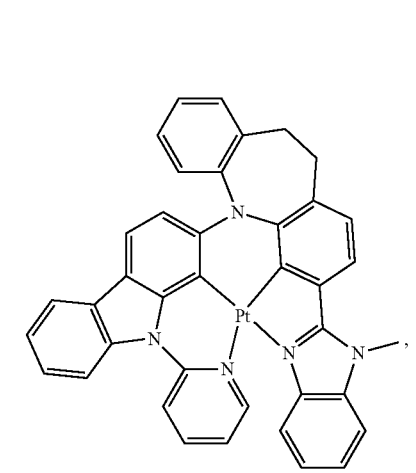
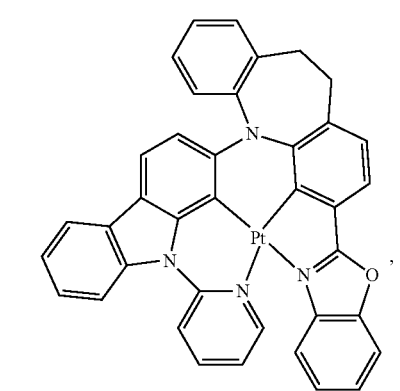
254
-continued
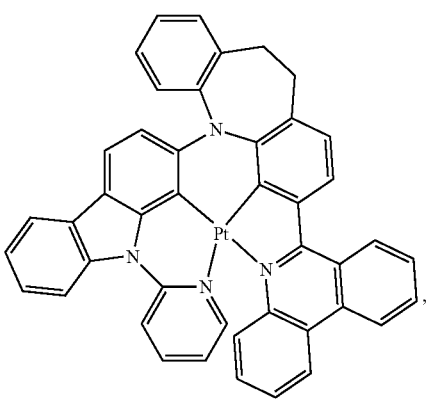
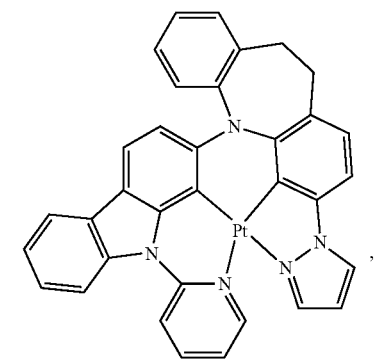
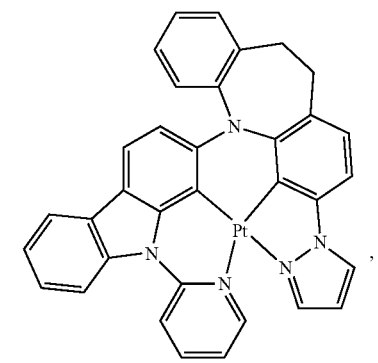
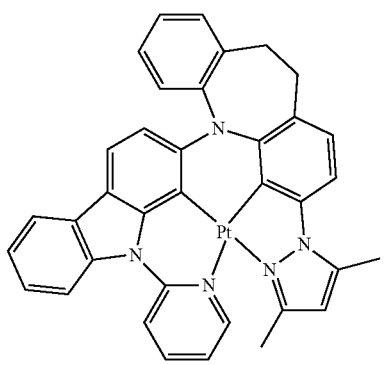

255
-continued
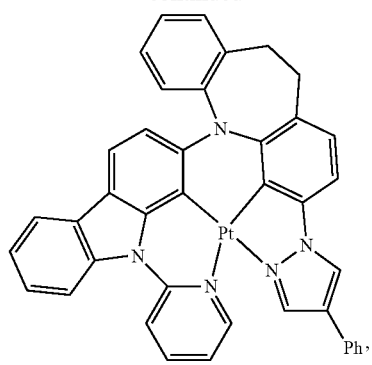
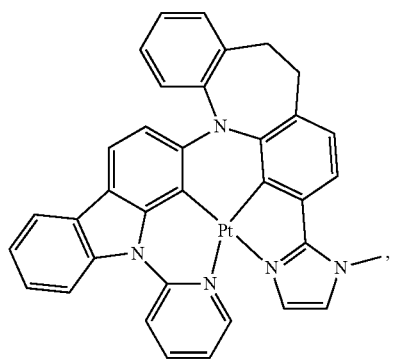
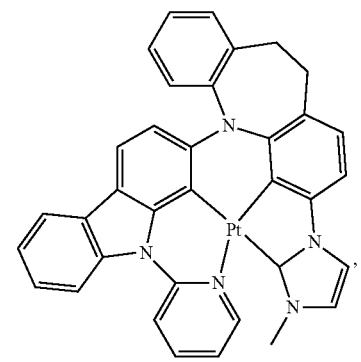
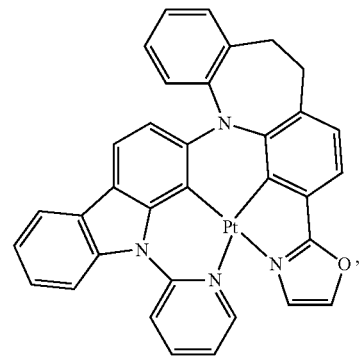
256
-continued
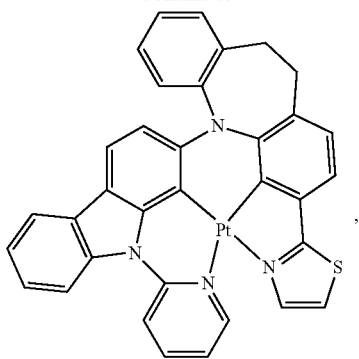
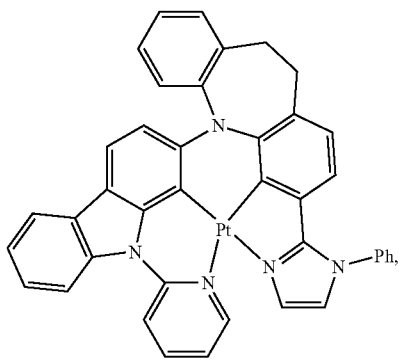
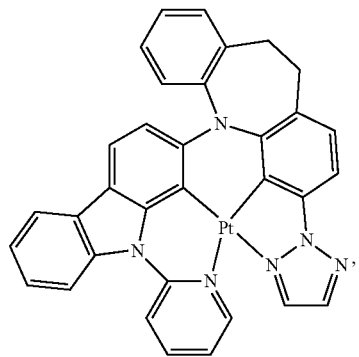
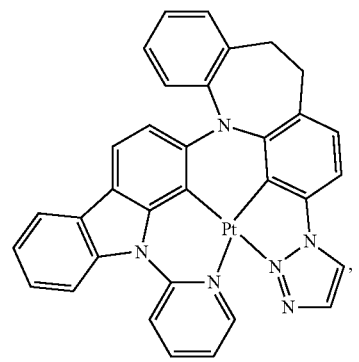

-continued
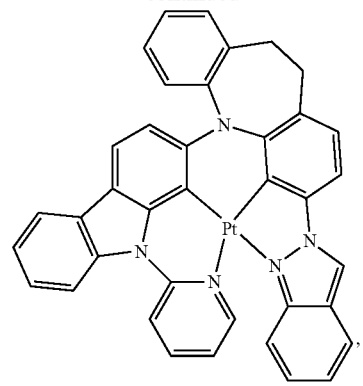
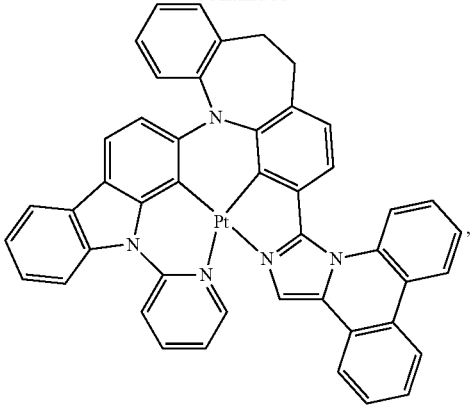
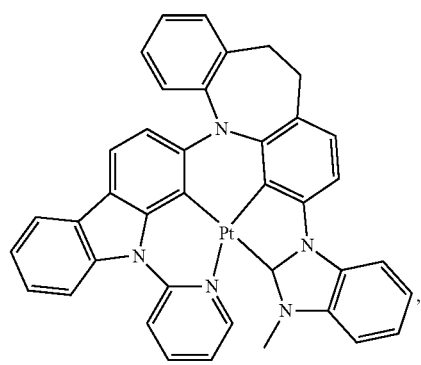
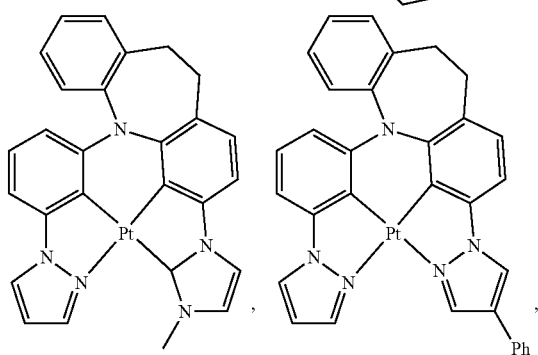
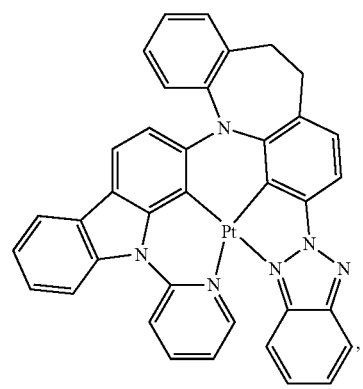
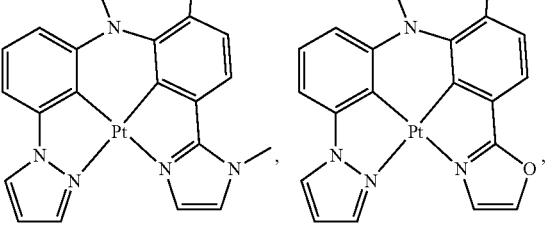
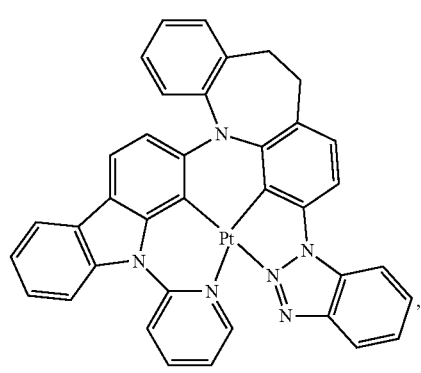
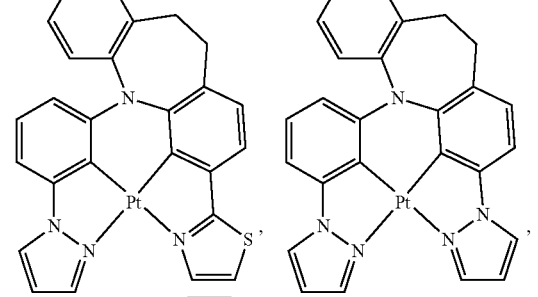

259
-continued
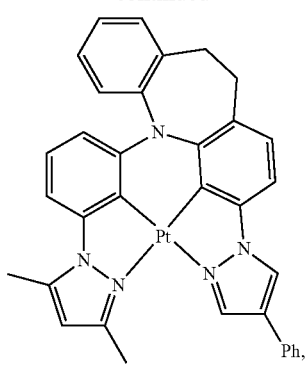
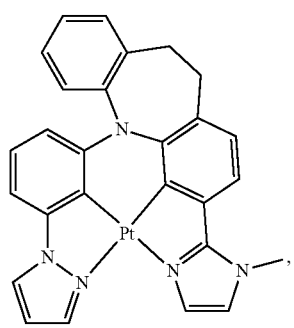
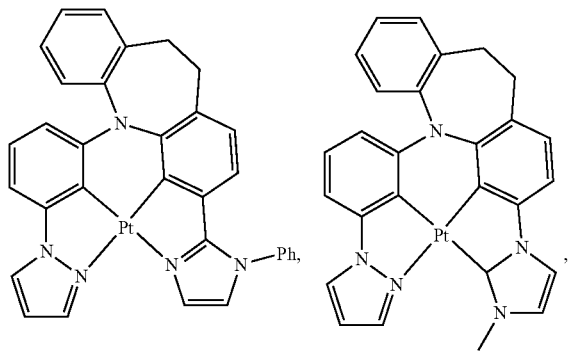
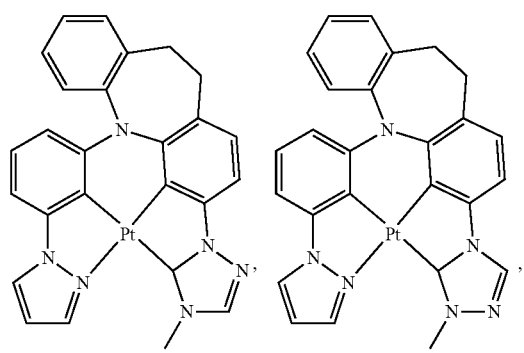
260
-continued
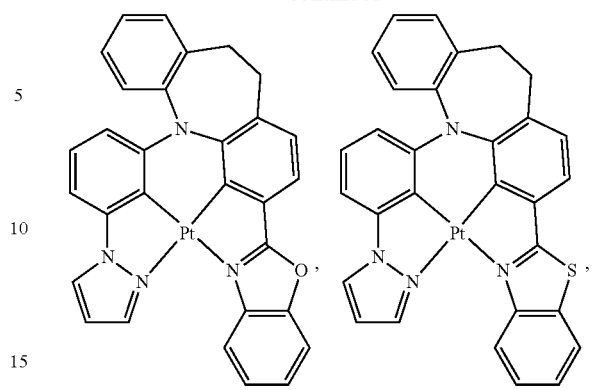
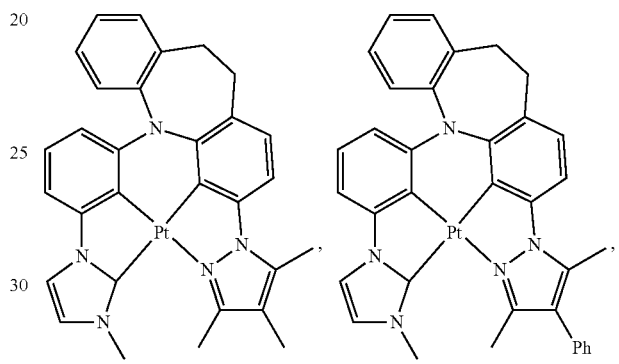
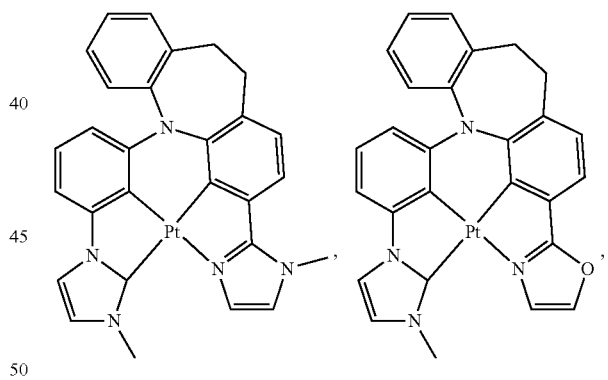
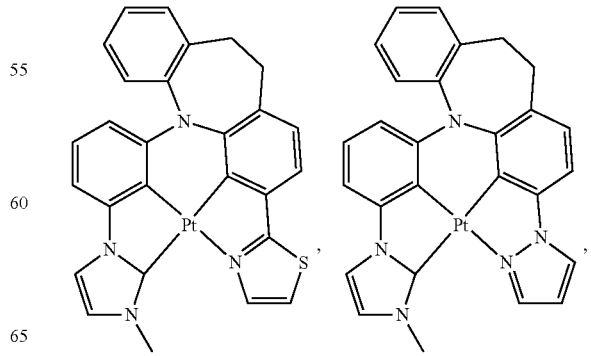

261
-continued
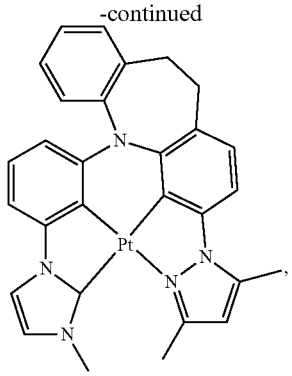
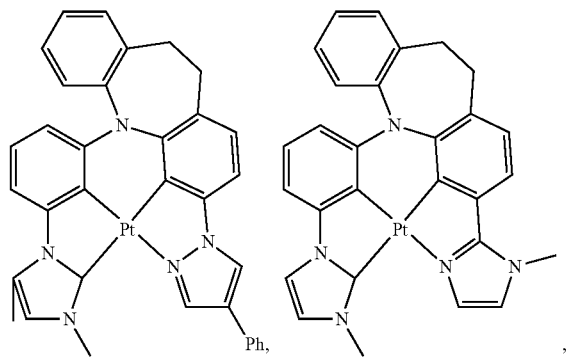
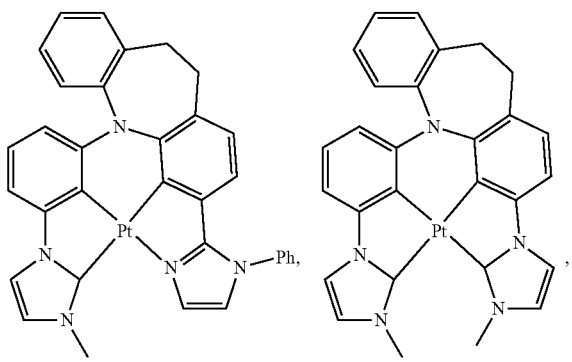
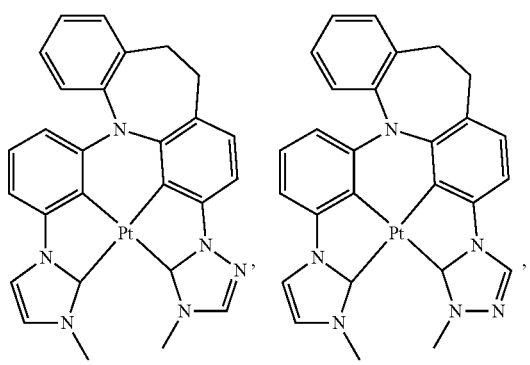
262
-continued
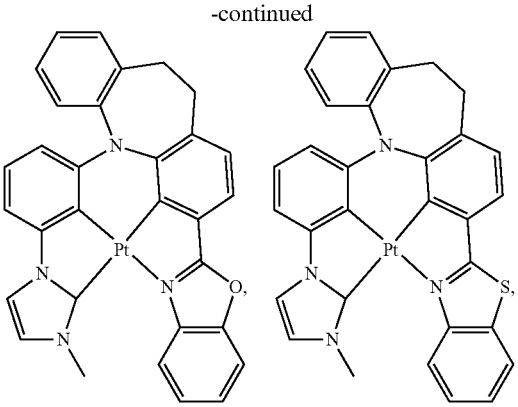
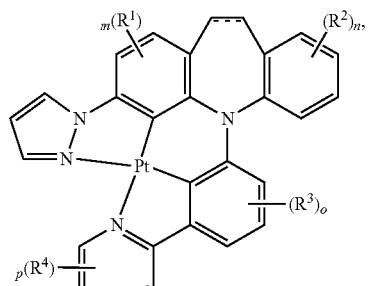
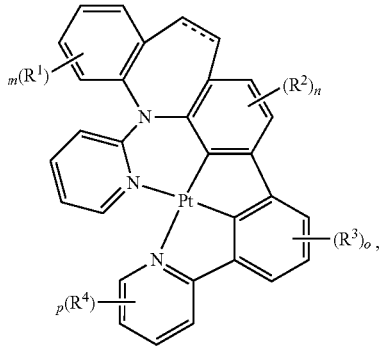
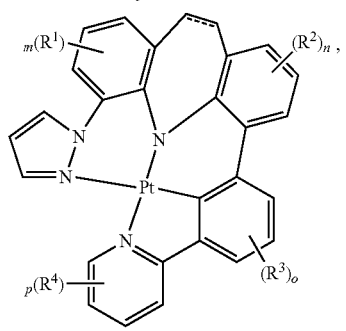
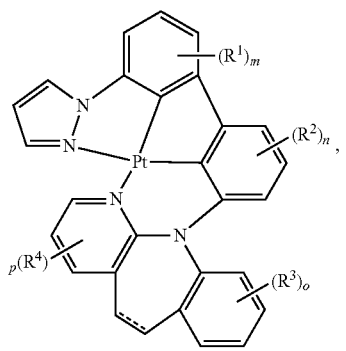

263
-continued
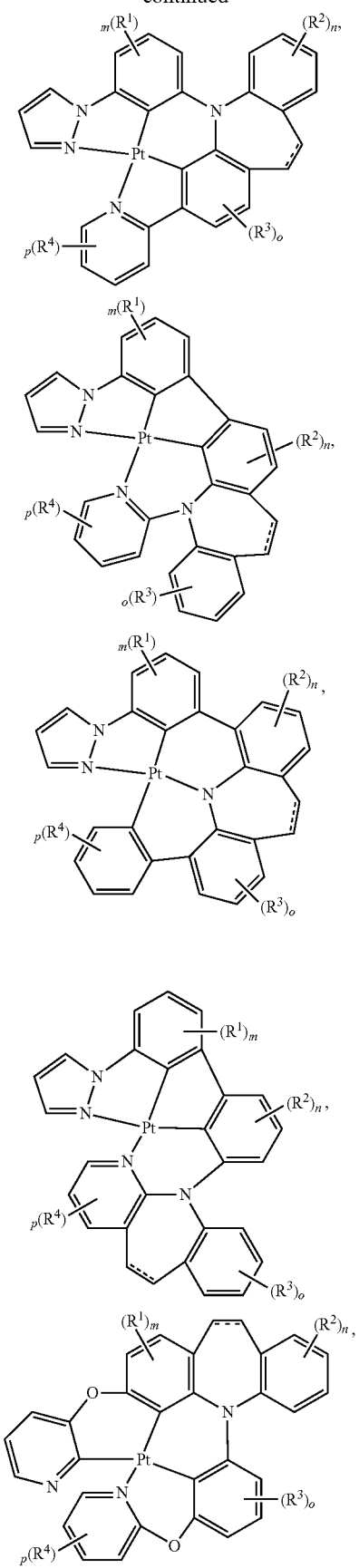
264
-continued
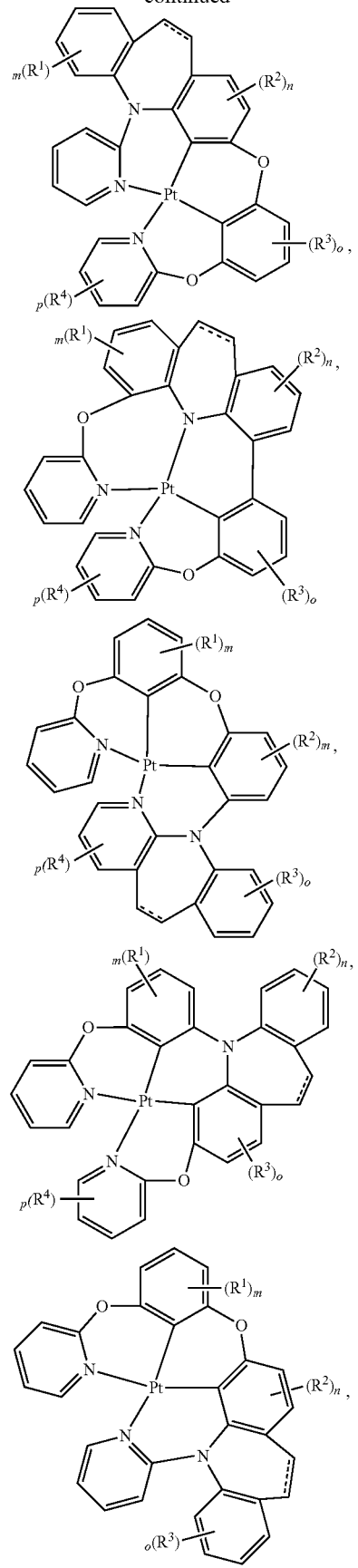

-continued
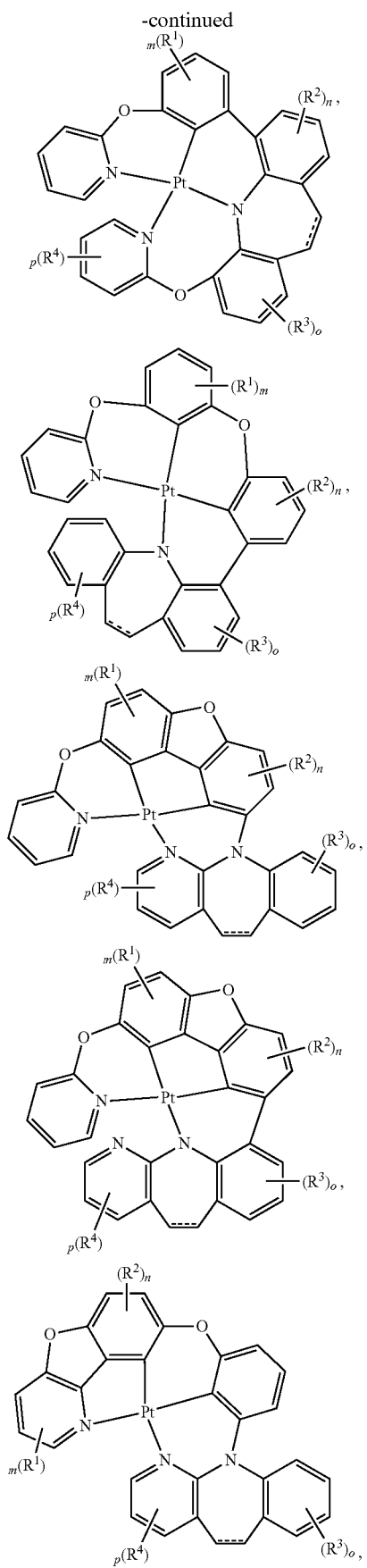
-continued
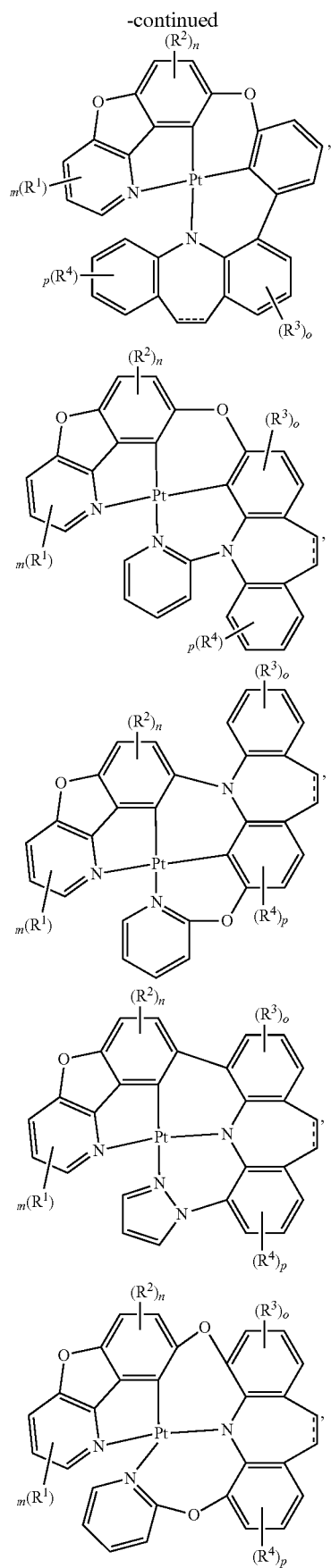

267
-continued
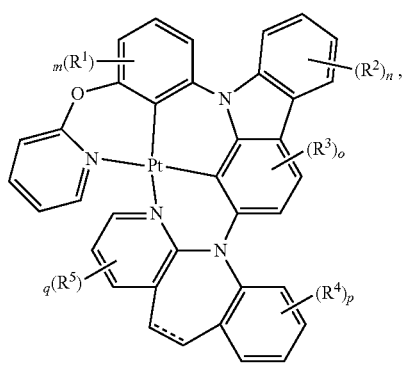
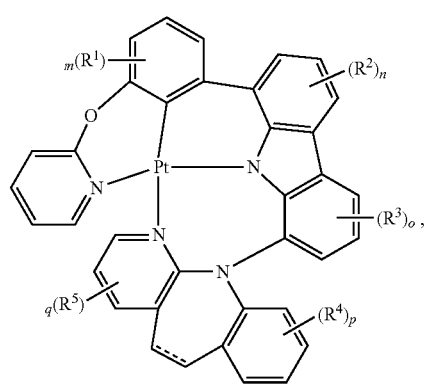
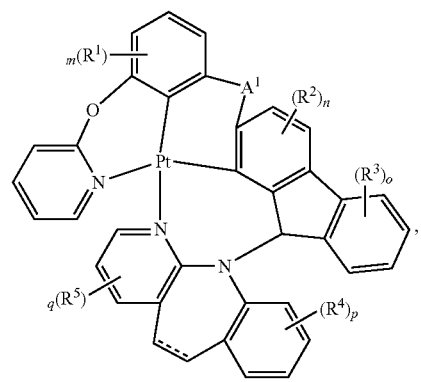
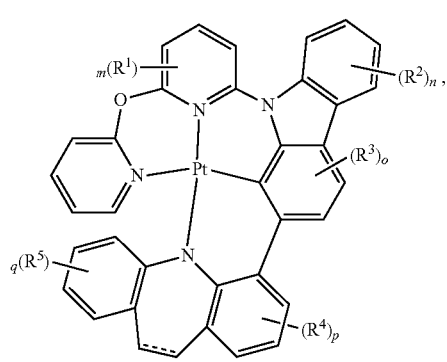
268
-continued
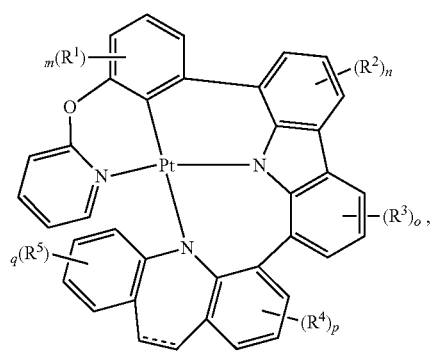
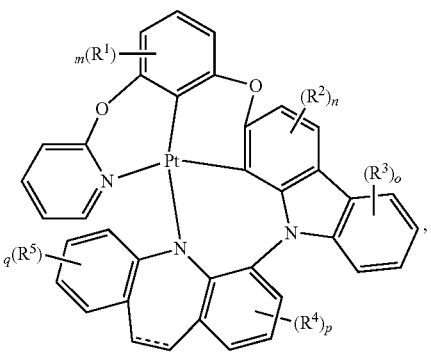
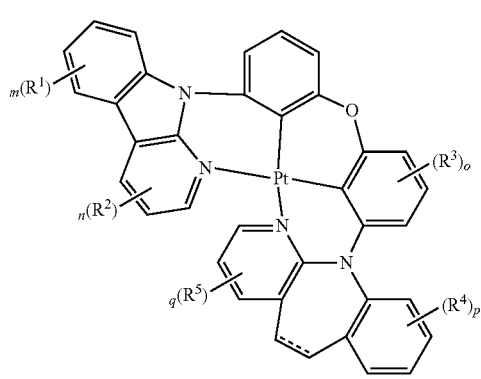
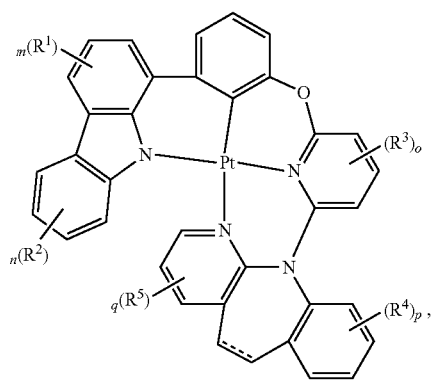

269
-continued
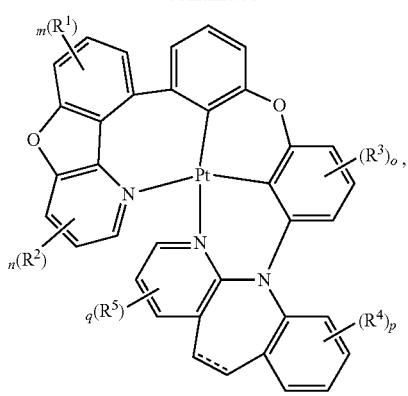
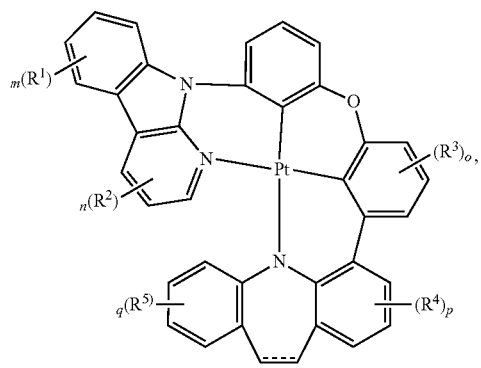
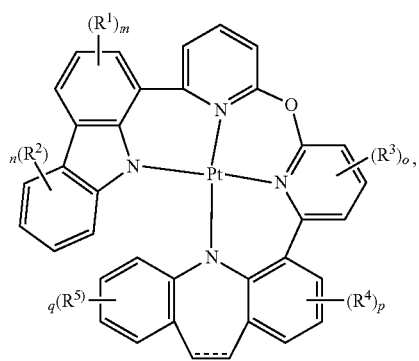
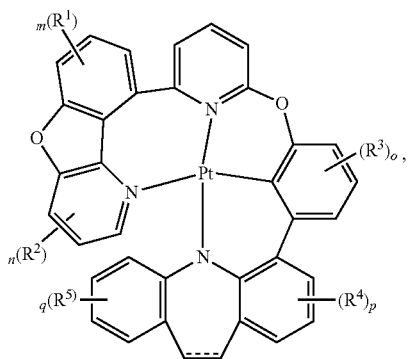
270
-continued
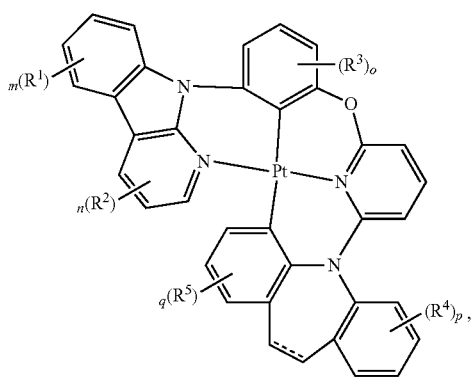
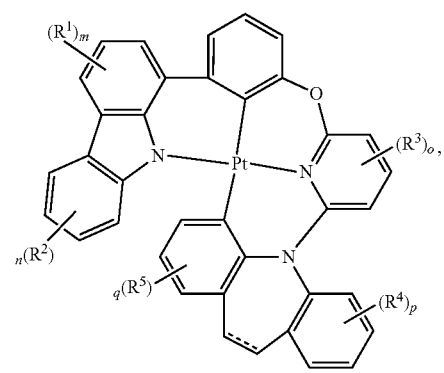
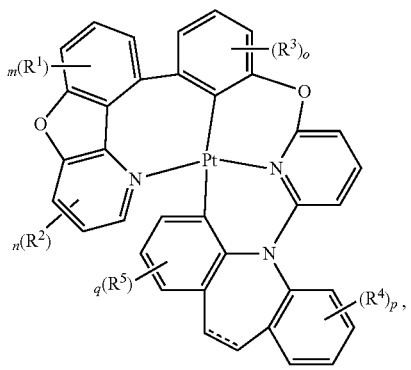
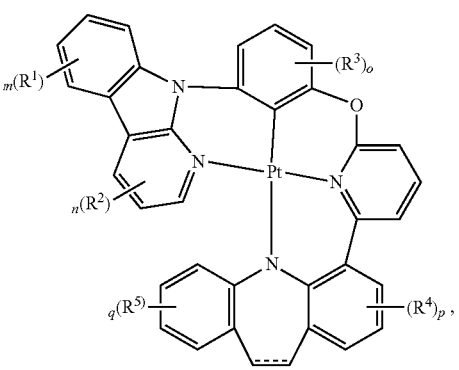

271
-continued
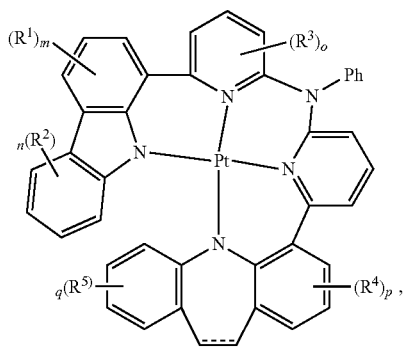
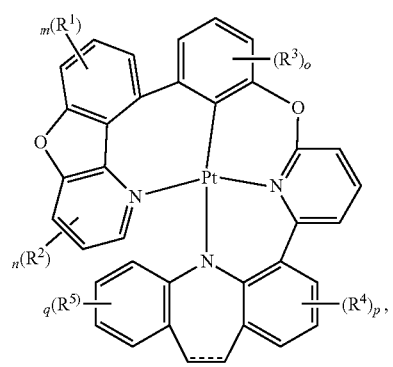
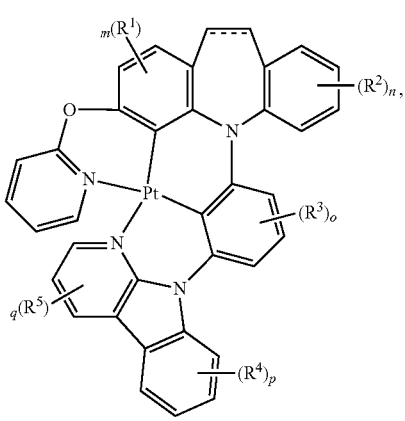
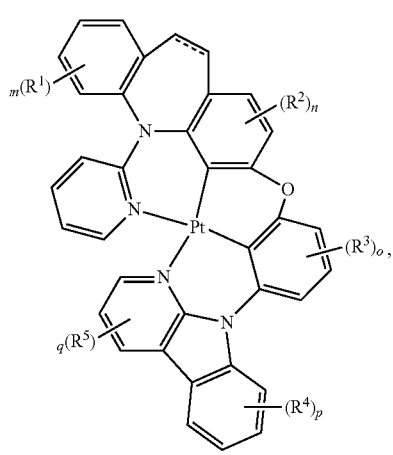
272
-continued
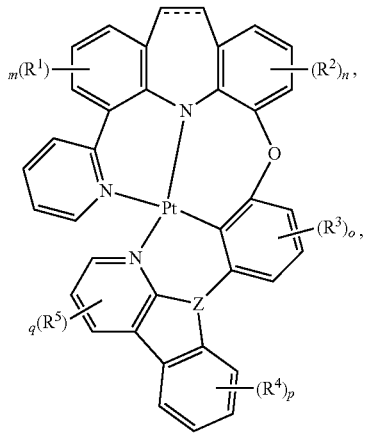
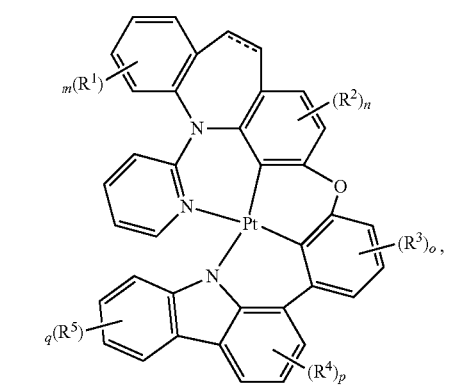
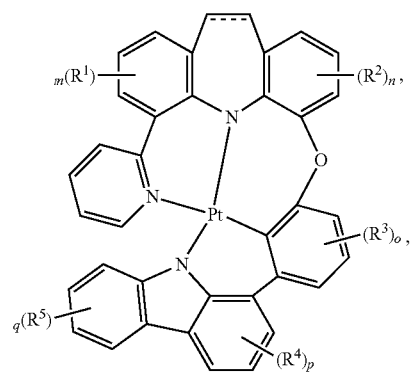

-continued
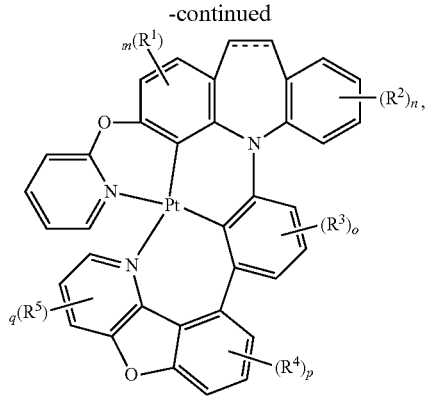
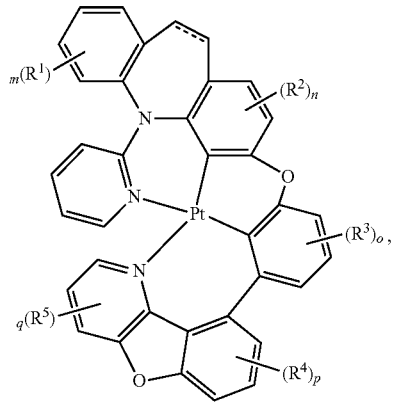
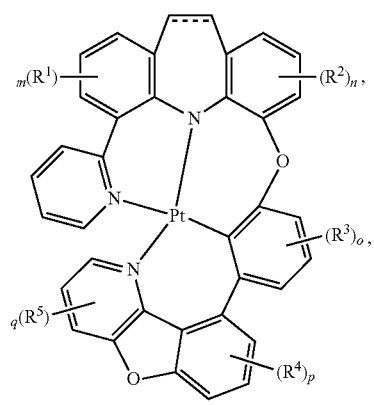
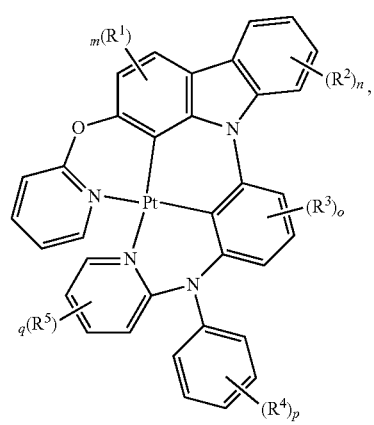
-continued
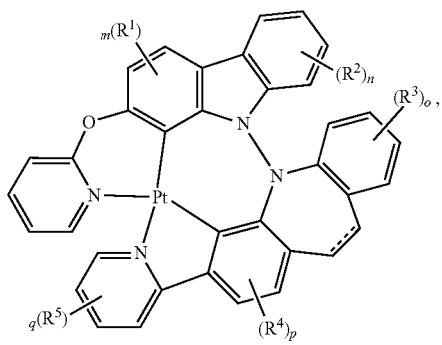
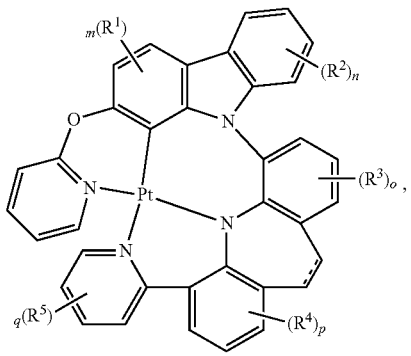
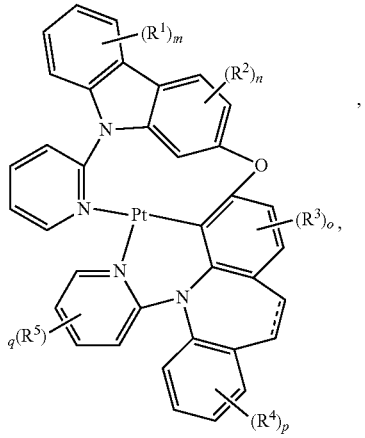
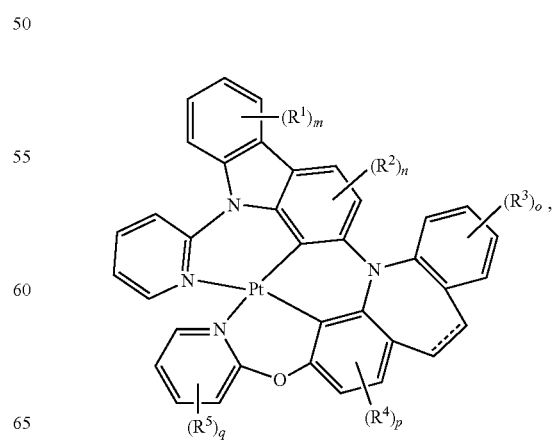

275
-continued
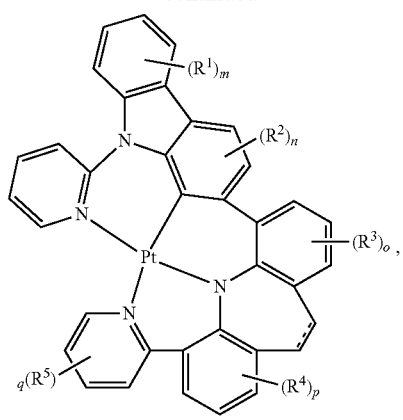
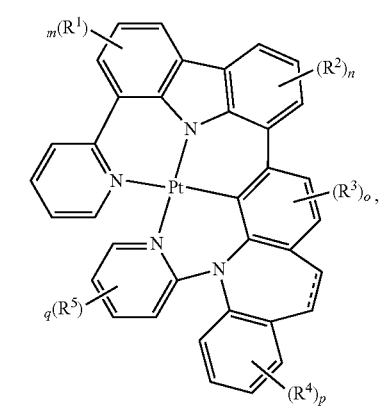
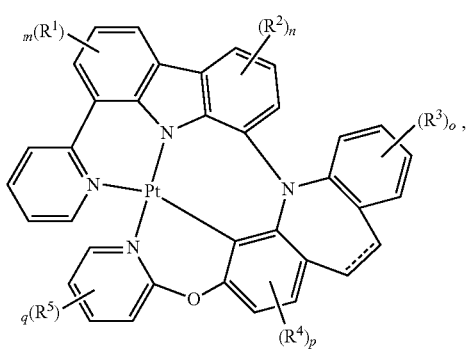
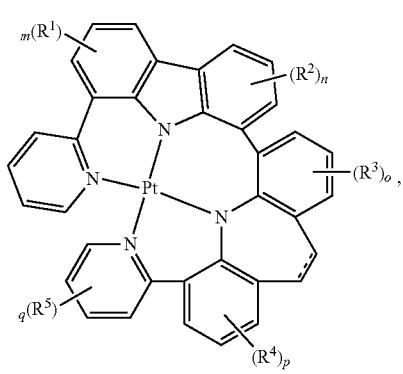
276
-continued
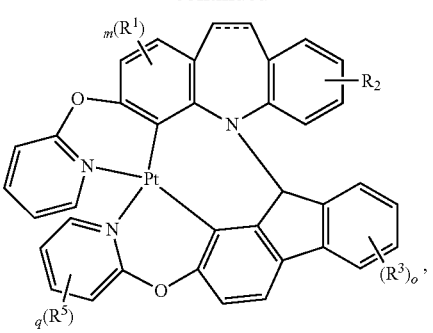
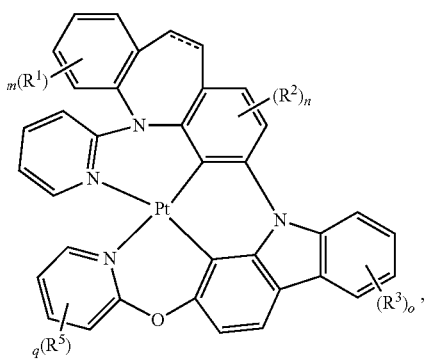
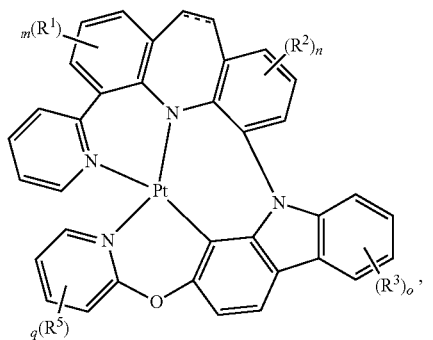
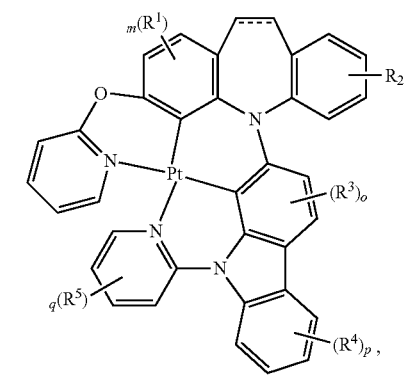

277
-continued
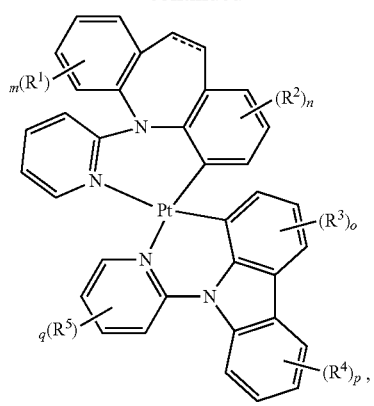
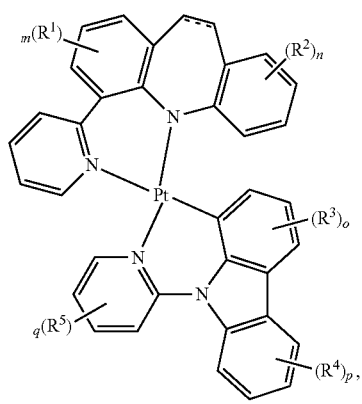
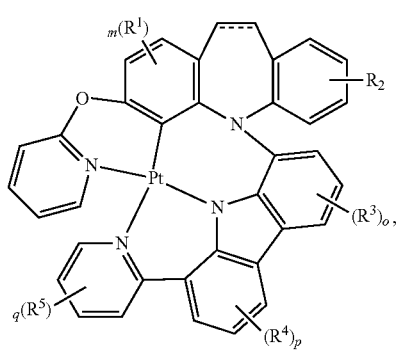
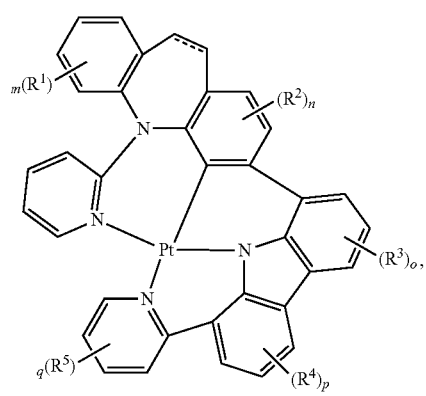
278
-continued
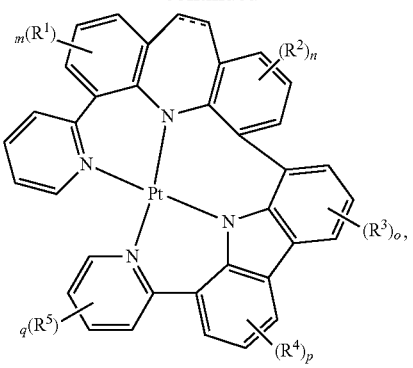
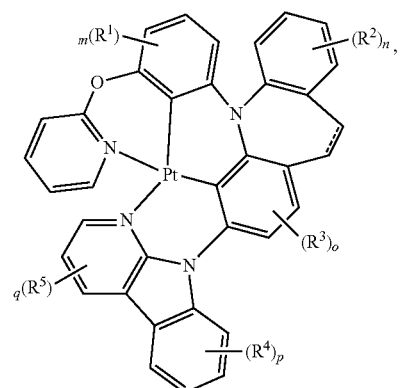
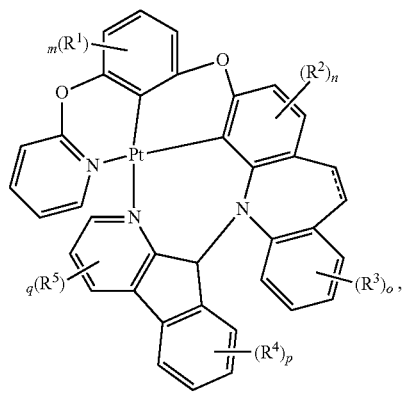
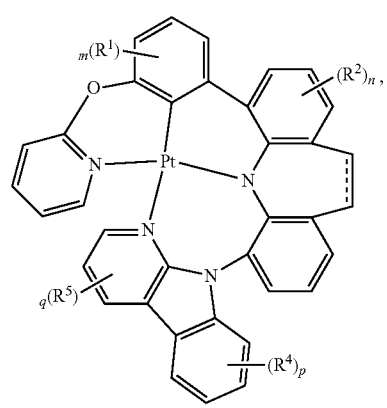

279
-continued
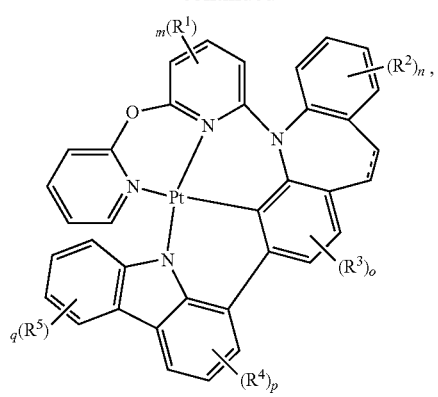
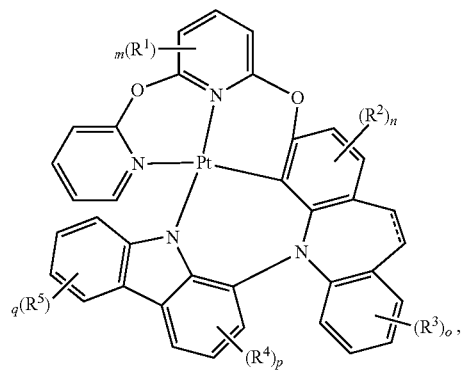
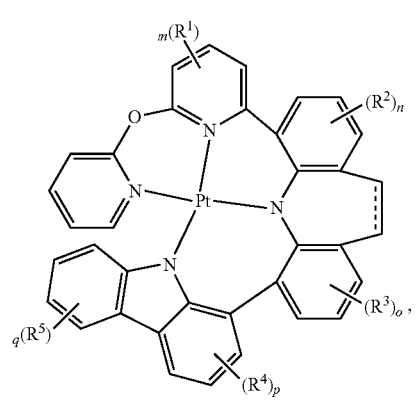
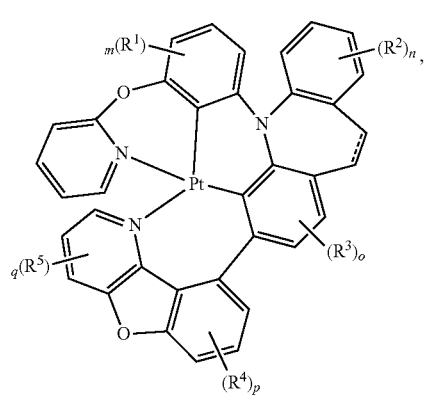
280
-continued
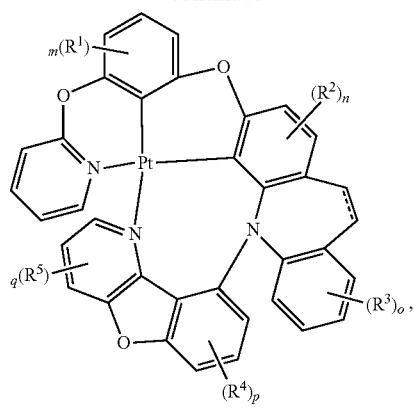
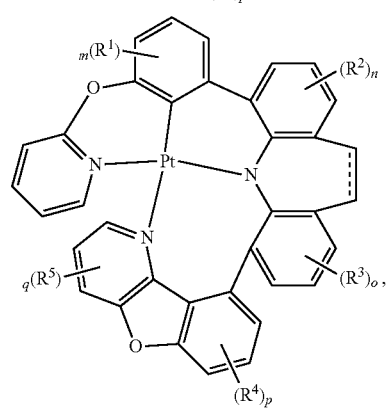
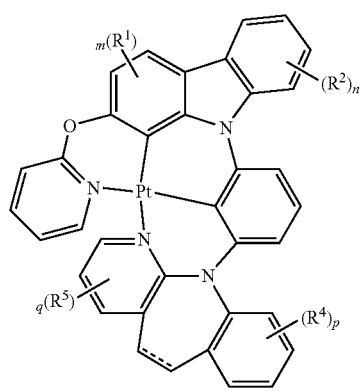
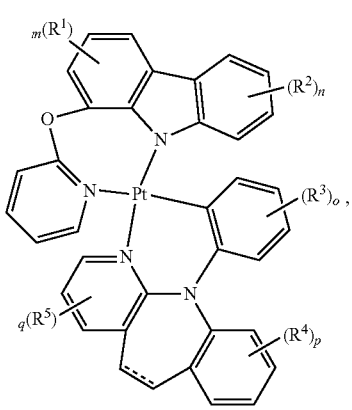

281
-continued
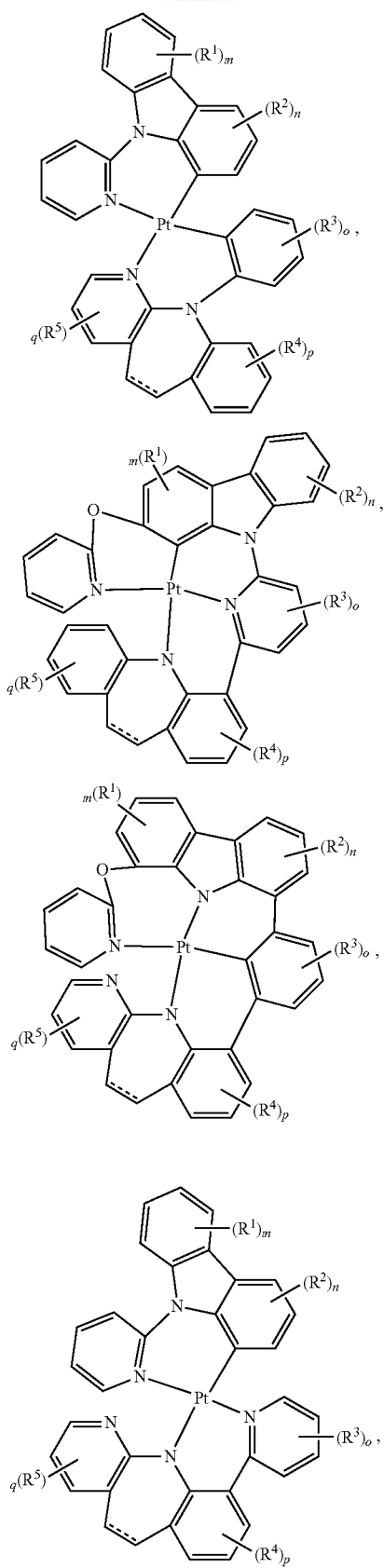
282
-continued
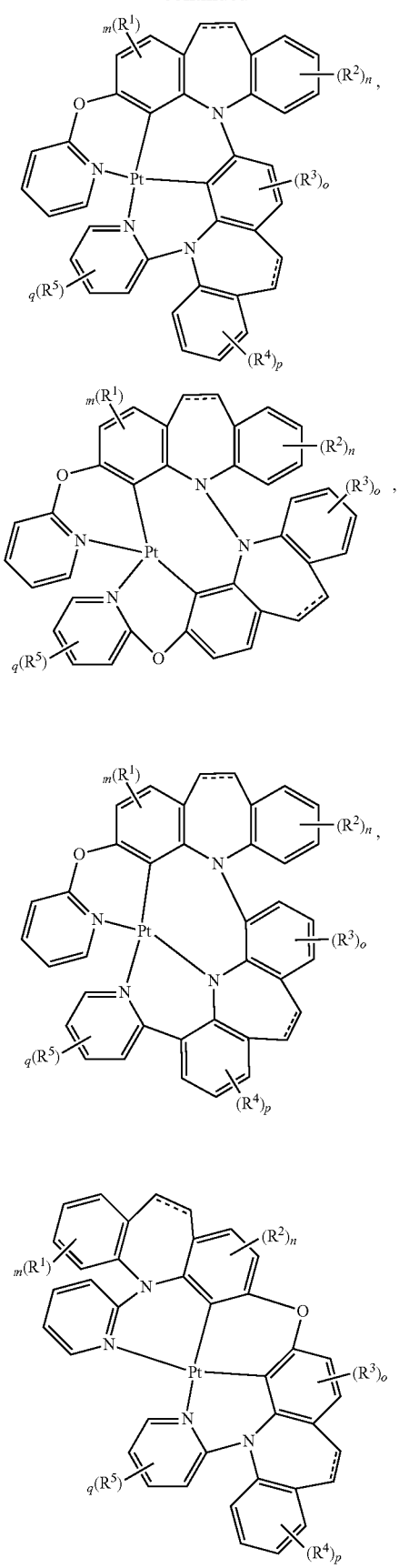

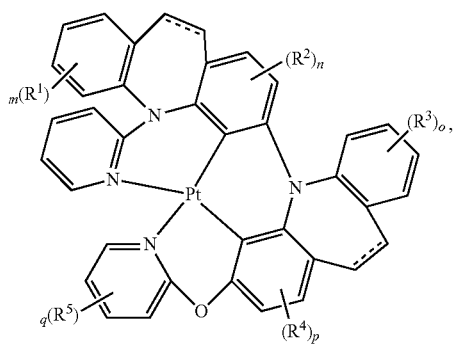
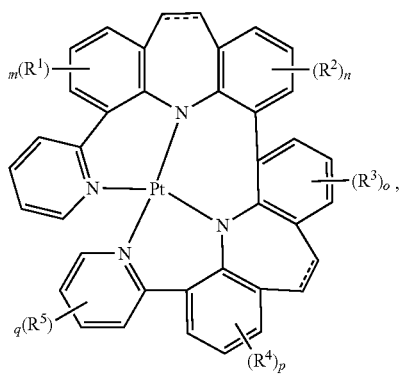
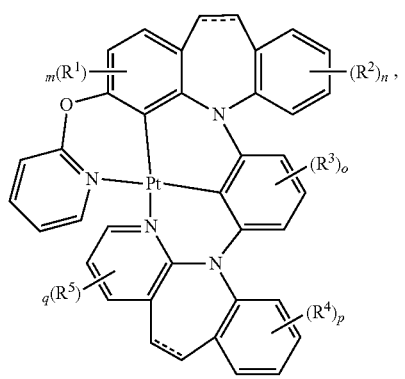
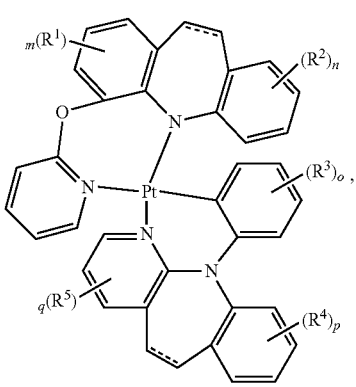
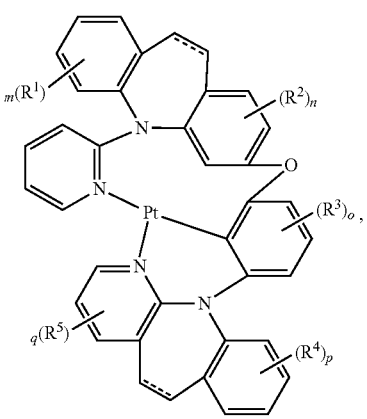

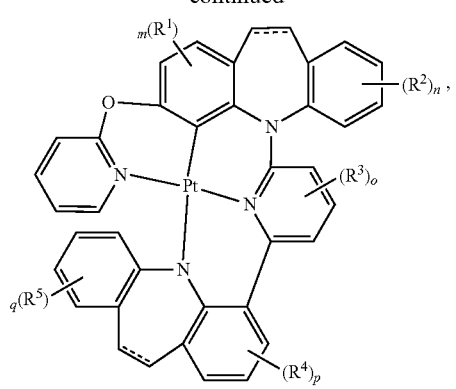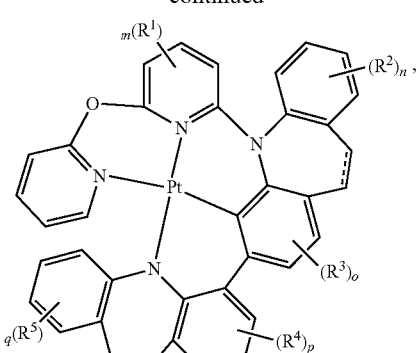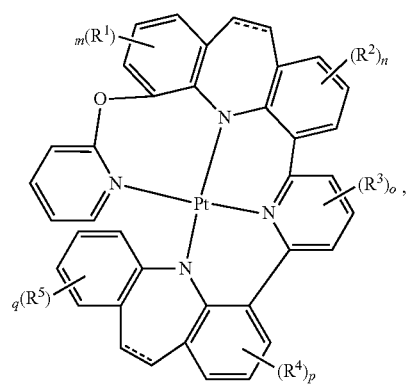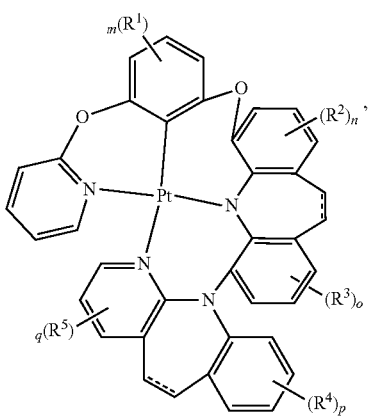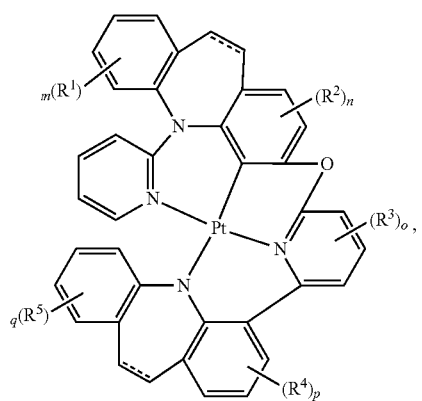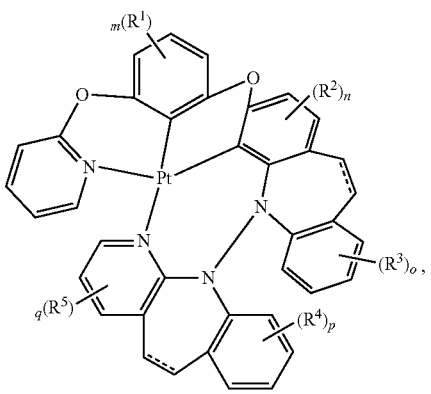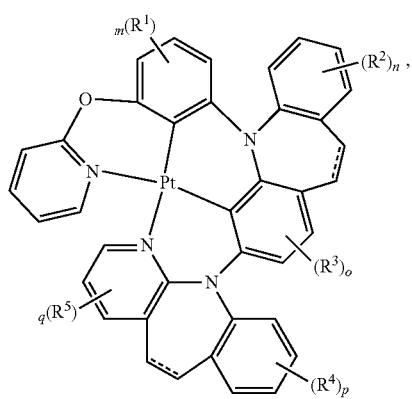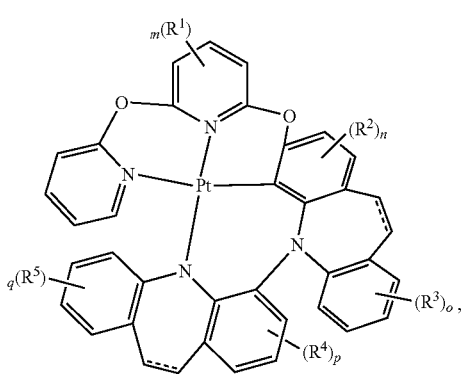

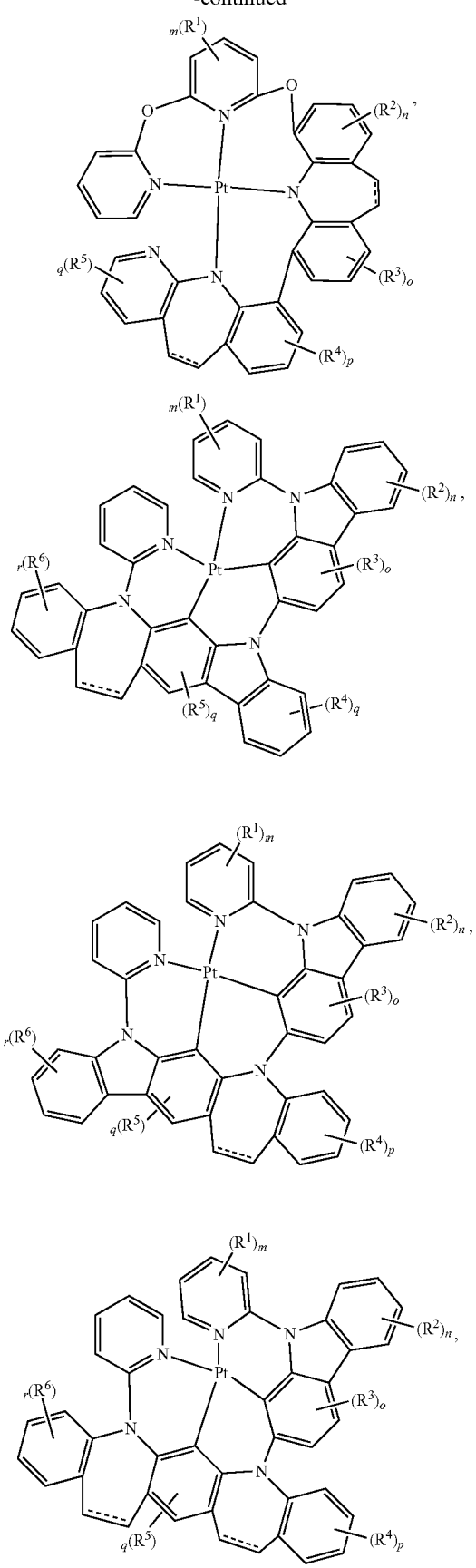
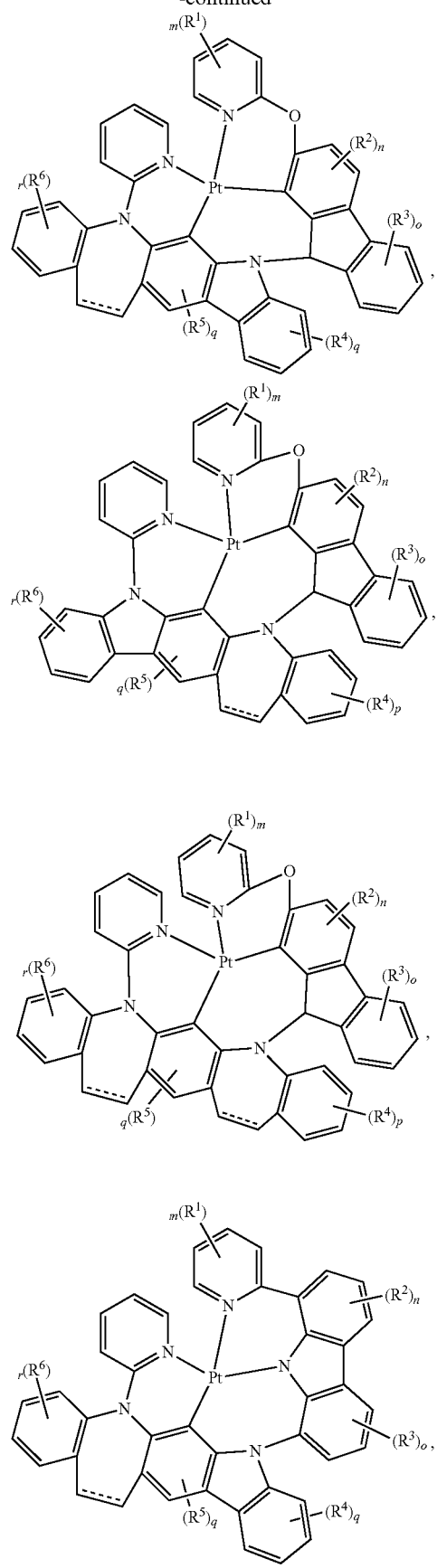

-continued
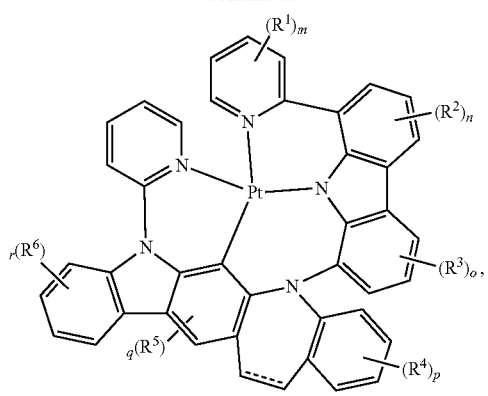
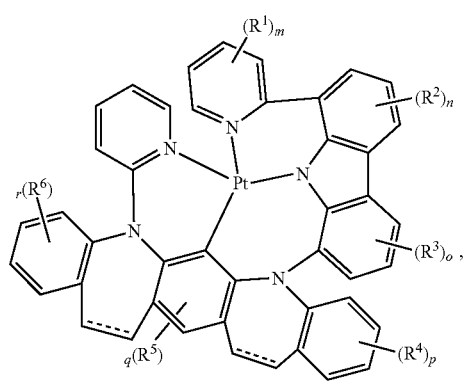
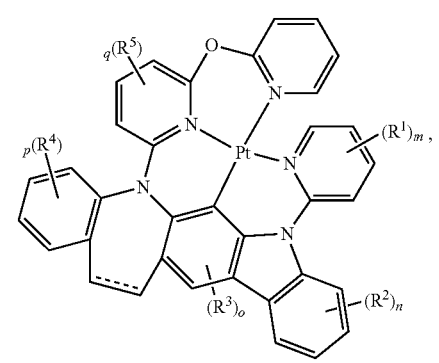
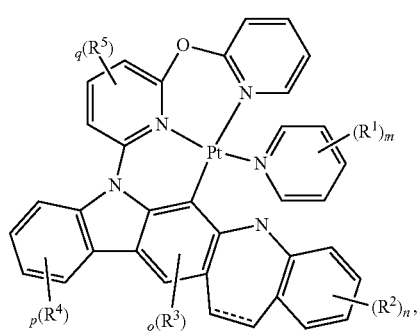
-continued
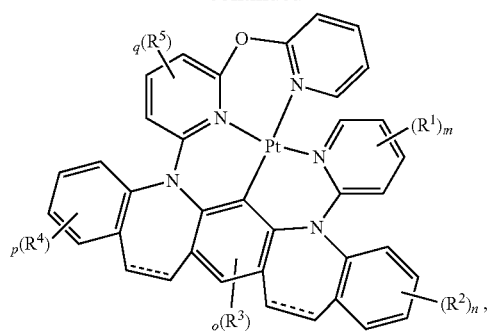
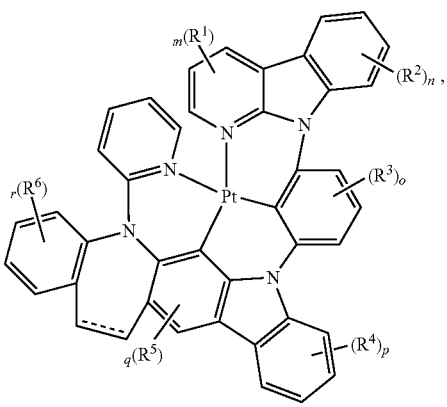
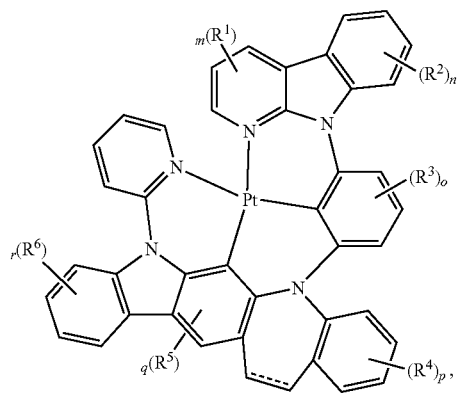
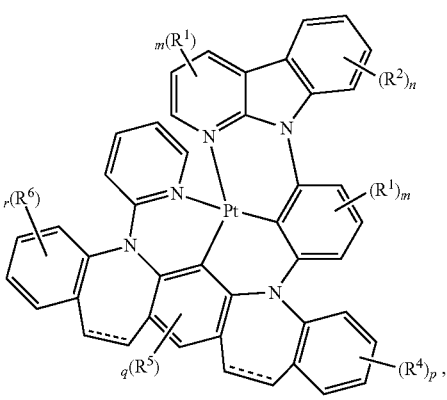

-continued

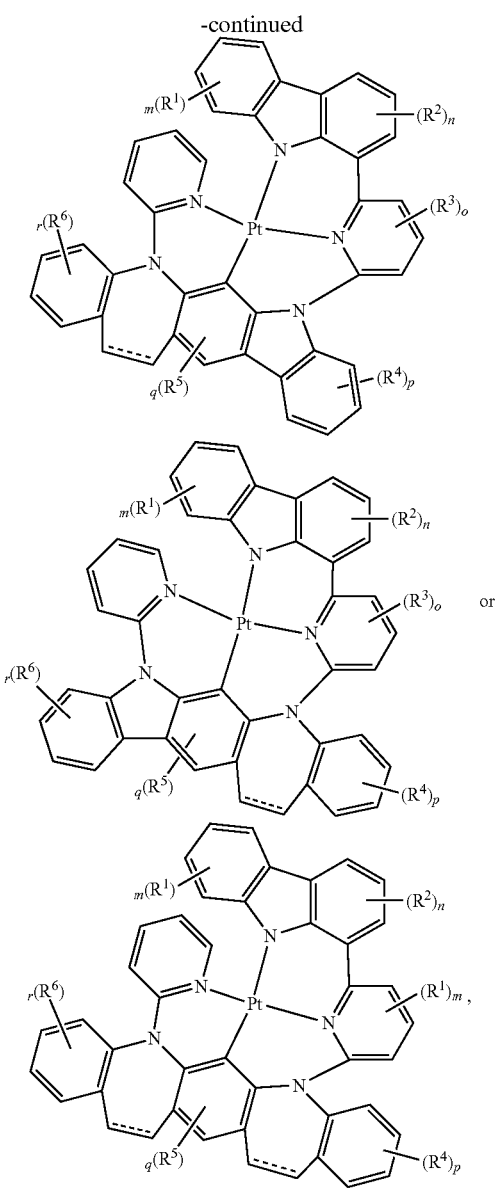

wherein each of R¹, R², R³, R⁴, R⁵, and R⁶ independently is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted silyl, or polymerizable, or any conjugate or combination thereof, and each of o, p, q, and r independently is an integer of 0 to 4.

16. A compound, wherein the compound has the structure:

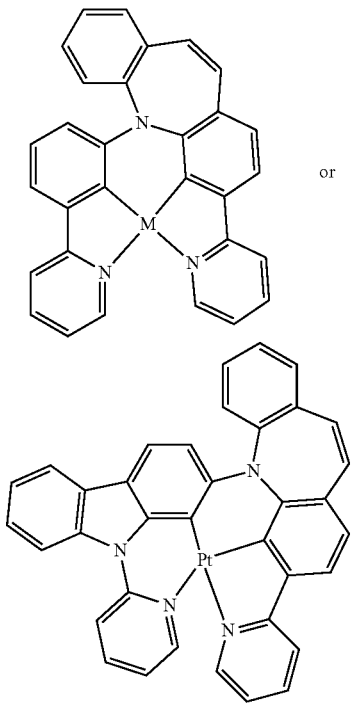

* * * * *

UNITED STATES PATENT AND TRADEMARK OFFICE
CERTIFICATE OF CORRECTION

PATENT NO.        : 9,882,150 B2
APPLICATION NO.   : 14/430454
DATED             : January 30, 2018
INVENTOR(S)       : Jian Li and Guijie Li It is certified that error appears in the above-identified patent and that said Letters Patent is hereby corrected as shown below:

In the Claims

In Claim 1, Column 210, Line 35 (Approx.) delete "U" and insert -- U, --, therefor.

In Claim 1, Column 210, Line 35 (Approx.) delete "$Y^1$, $Y^1$," and insert -- Y, $Y^1$, --, therefor.

In Claim 9, Column 211, Line 4 (Approx.) delete "Y," and insert -- Y, $Y^1$, --, therefor.

In Claim 15, Column 217, Line 1-13 (Approx.)

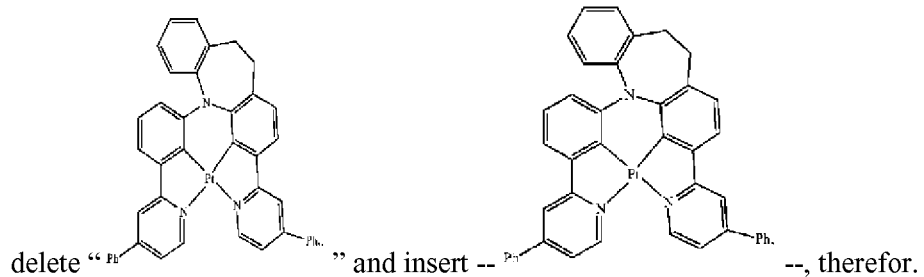

delete " " and insert -- --, therefor.

In Claim 15, Column 223, Line 1-13 (Approx.)

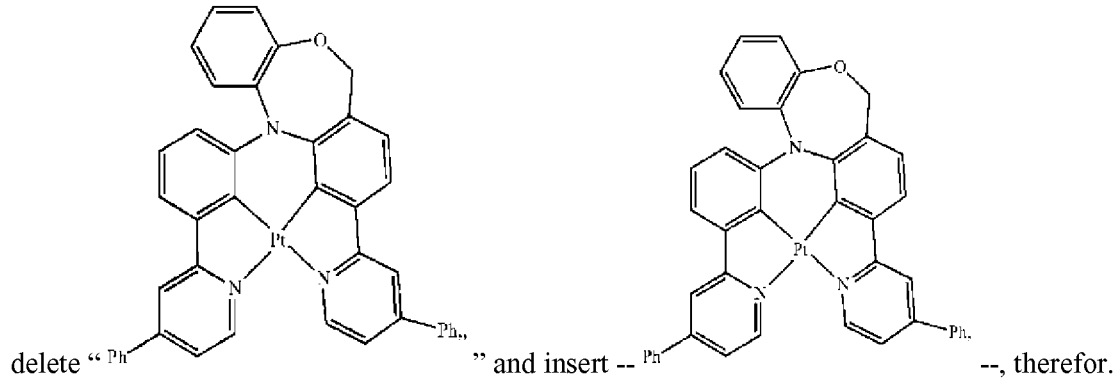

delete " " and insert -- --, therefor.

Signed and Sealed this
Twenty-fourth Day of April, 2018

Andrei Iancu
*Director of the United States Patent and Trademark Office*

CERTIFICATE OF CORRECTION (continued)
U.S. Pat. No. 9,882,150 B2

In Claim 15, Column 226, Line 1-13 (Approx.)

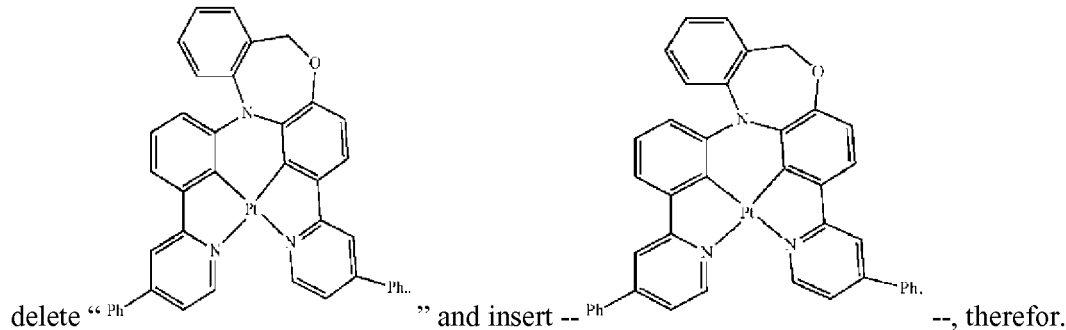

delete " " and insert -- --, therefor.

In Claim 15, Column 233, Line 17-30 (Approx.)

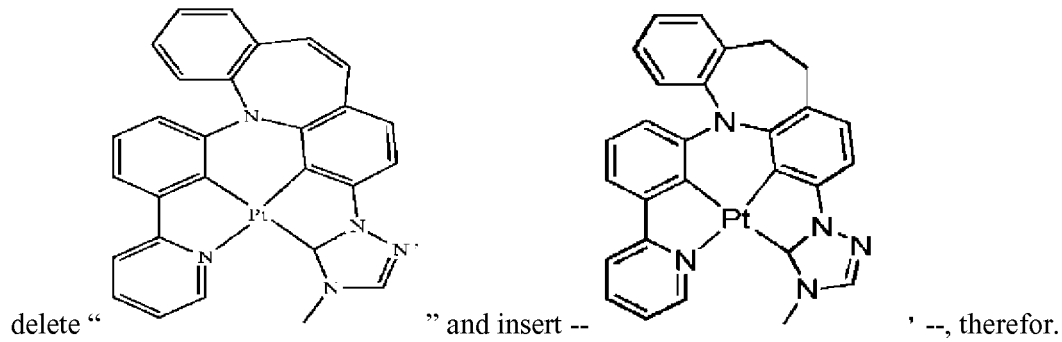

delete " " and insert -- --, therefor.

In Claim 15, Column 233, Line 17-30 (Approx.)

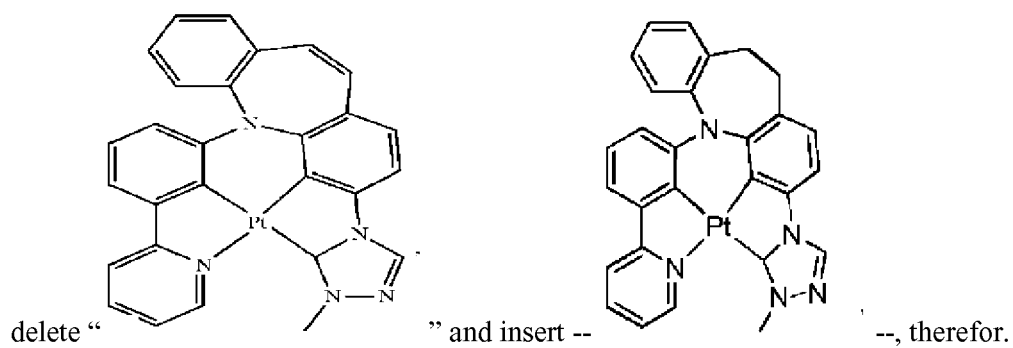

delete " " and insert -- --, therefor.

In Claim 15, Column 233, Line 35-46 (Approx.)

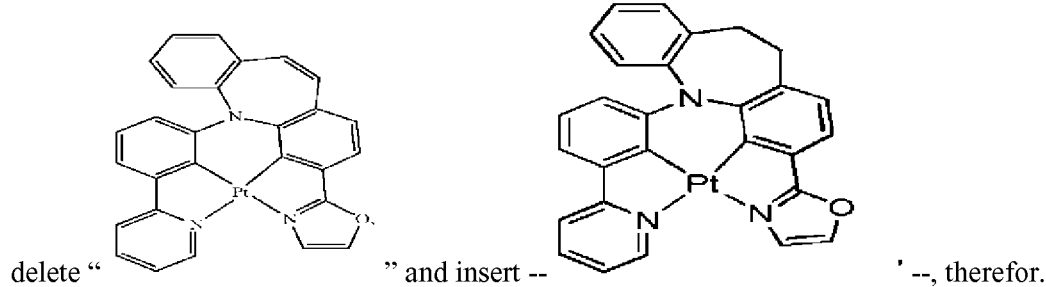

delete " " and insert -- --, therefor.

In Claim 15, Column 233, Line 35-46 (Approx.)
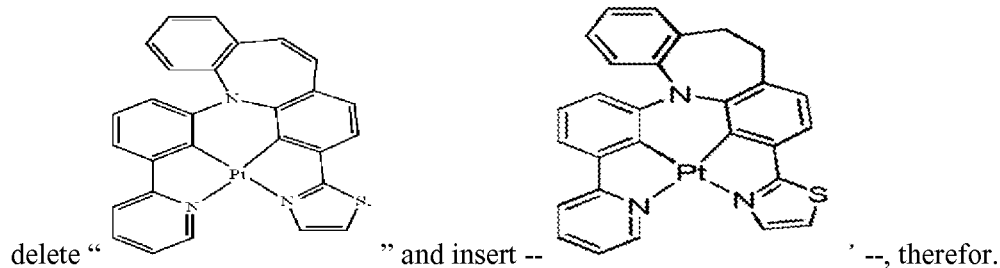
delete " " and insert -- ' --, therefor.
In Claim 15, Column 247, Line 1-16 (Approx.)
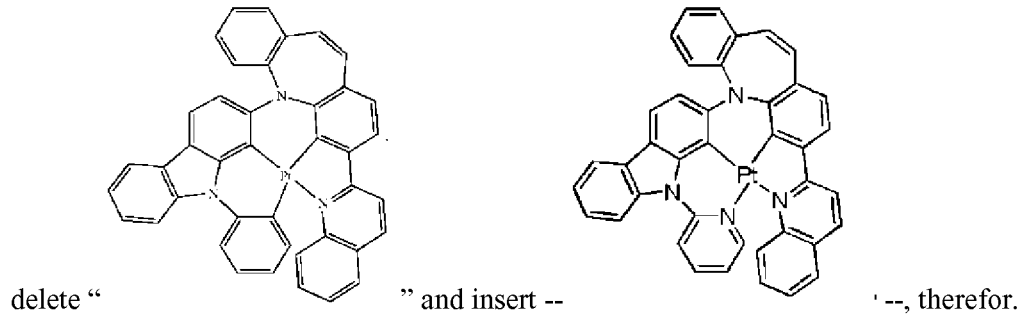
delete " " and insert -- ' --, therefor.
In Claim 15, Column 263, Line 1-14 (Approx.)
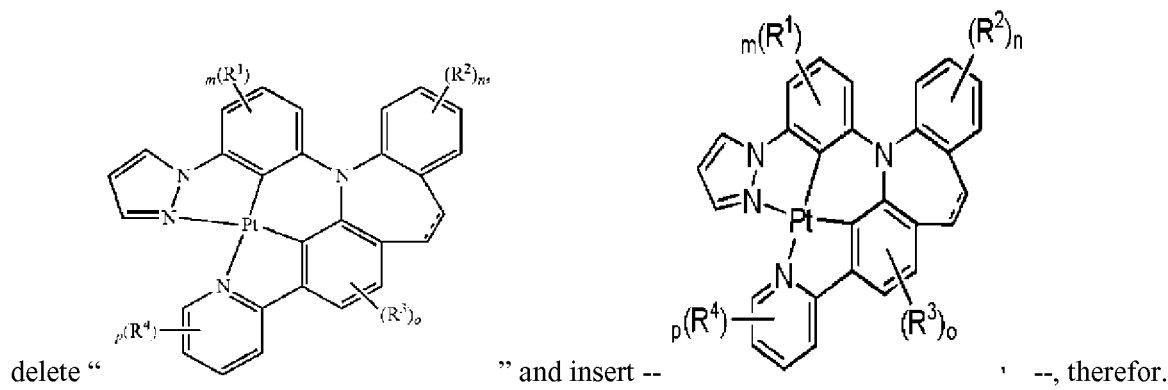
delete " " and insert -- ' --, therefor.
In Claim 15, Column 263, Line 15-27 (Approx.)
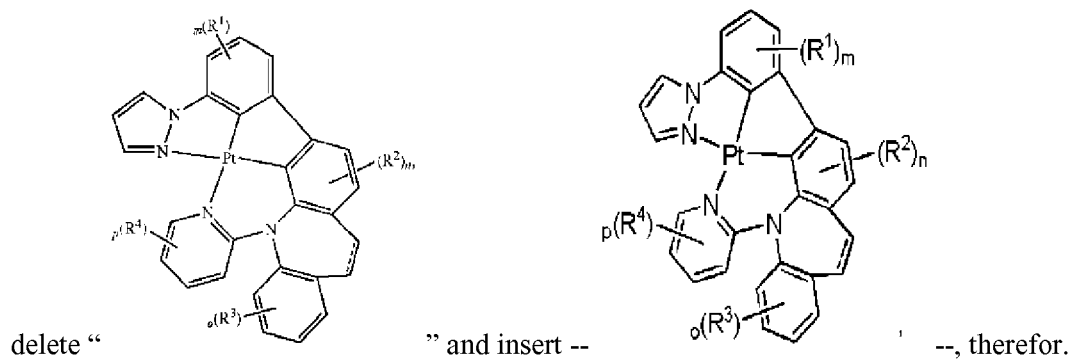
delete " " and insert -- ' --, therefor.

CERTIFICATE OF CORRECTION (continued)
U.S. Pat. No. 9,882,150 B2

In Claim 15, Column 263, Line 43-55 (Approx.)

delete " 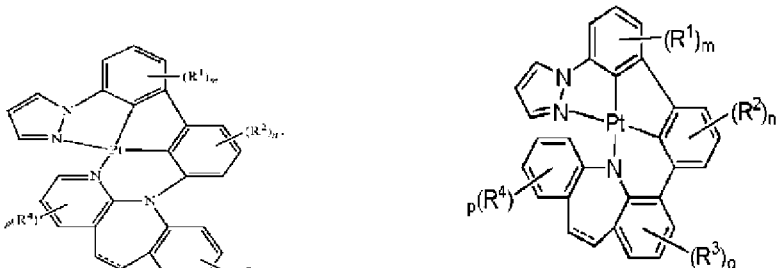 " and insert -- -- , therefor.

In Claim 15, Column 263, Line 56-66 (Approx.)

delete " 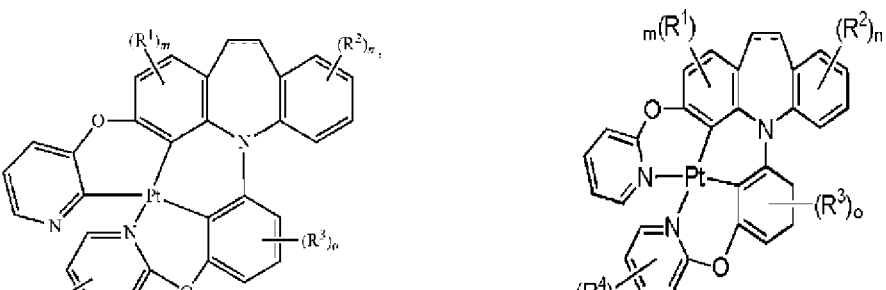 " and insert -- -- , therefor.

In Claim 15, Column 264, Line 54-66 (Approx.)

delete " 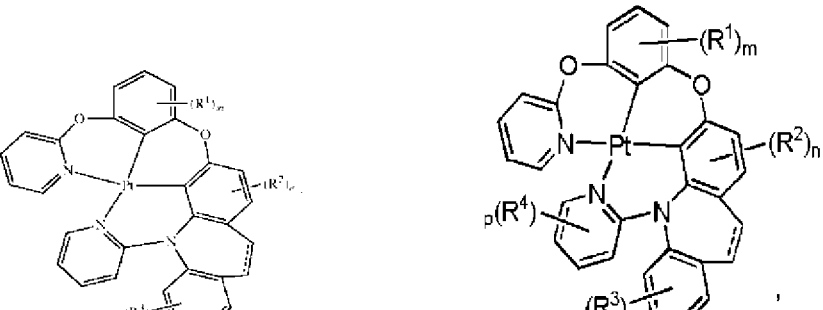 " and insert -- -- , therefor.

In Claim 15, Column 265, Line 41-52 (Approx.)

delete " 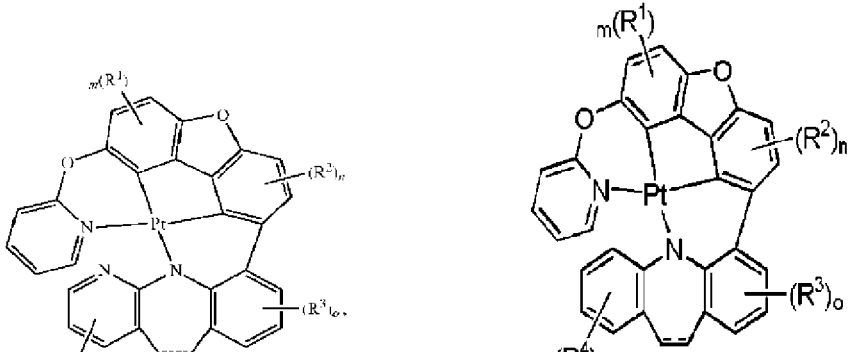 " and insert -- -- , therefor.

CERTIFICATE OF CORRECTION (continued)
U.S. Pat. No. 9,882,150 B2

In Claim 15, Column 265, Line 54-66 (Approx.)

delete " 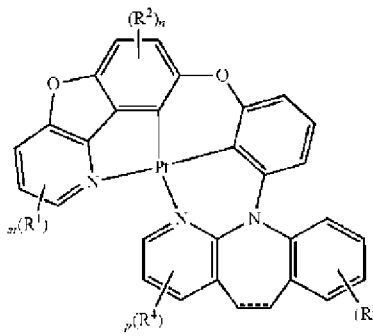 " and insert -- 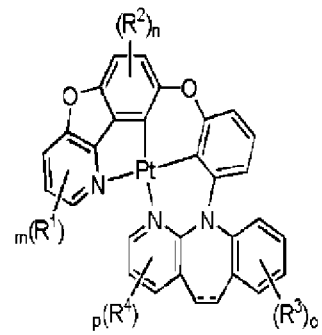 --, therefor.

In Claim 15, Column 266, Line 42-54 (Approx.)

delete " 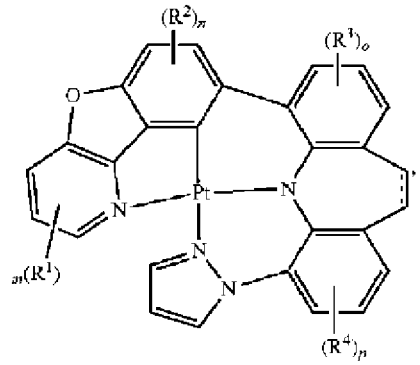 " and insert -- 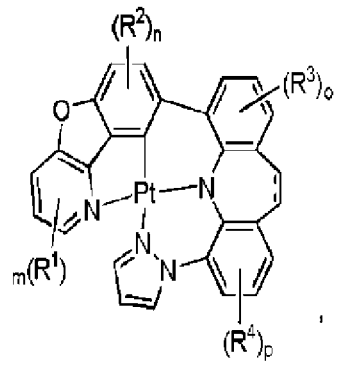 --, therefor.

In Claim 15, Column 268, Line 35-49 (Approx.)

delete " 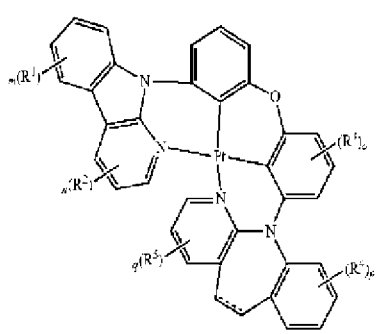 " and insert -- 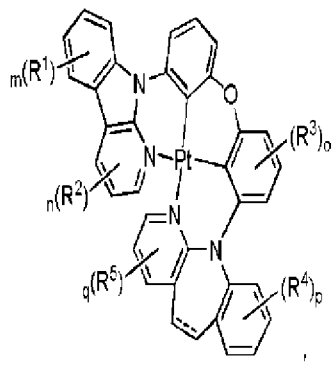 --, therefor.

In Claim 15, Column 270, Line 1-16 (Approx.)
delete " 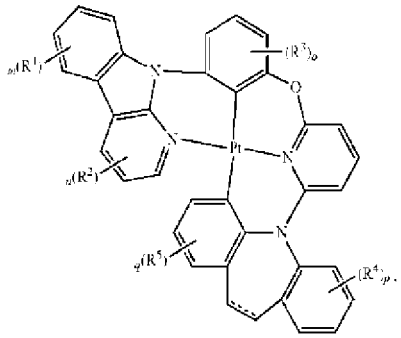 " and insert -- 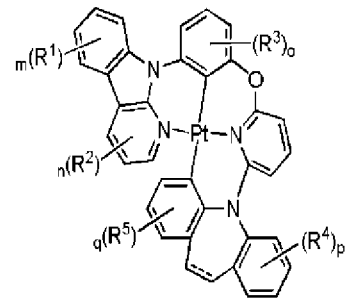 --, therefor.
In Claim 15, Column 270, Line 19-33 (Approx.)
delete " 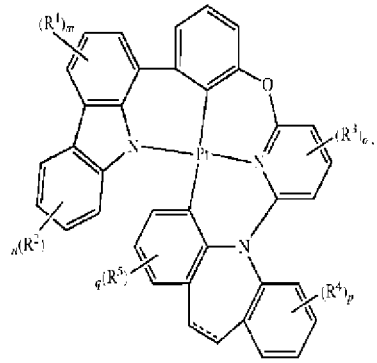 " and insert -- 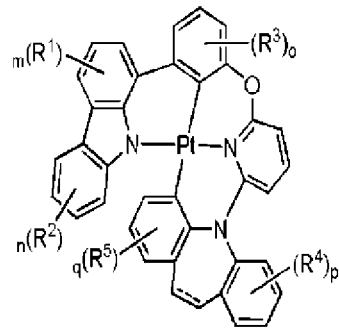 --, therefor.
In Claim 15, Column 270, Line 52-66 (Approx.)
delete " 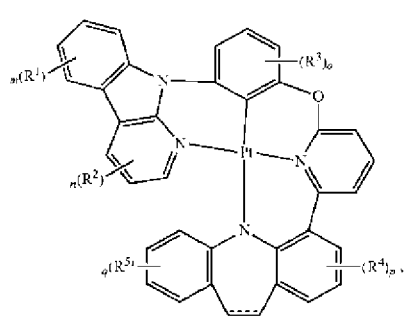 " and insert -- 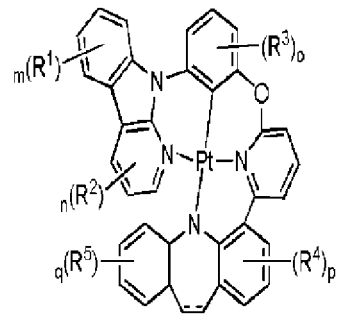 --, therefor.

CERTIFICATE OF CORRECTION (continued)
U.S. Pat. No. 9,882,150 B2

In Claim 15, Column 271, Line 1-15 (Approx.)

delete " 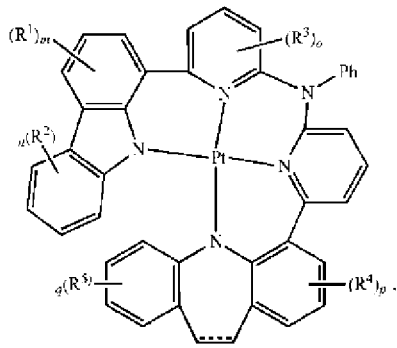 " and insert -- 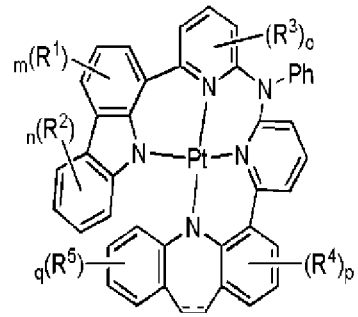 ' --, therefor.

In Claim 15, Column 271, Line 16-29 (Approx.)

delete " 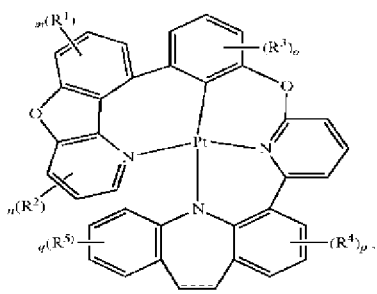 " and insert -- 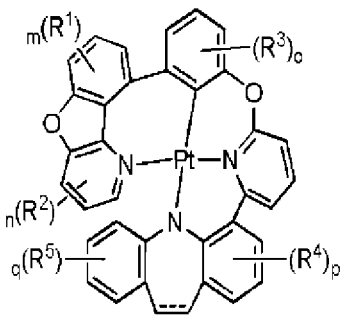 ' --, therefor.

In Claim 15, Column 272, Line 1-17 (Approx.)

delete " 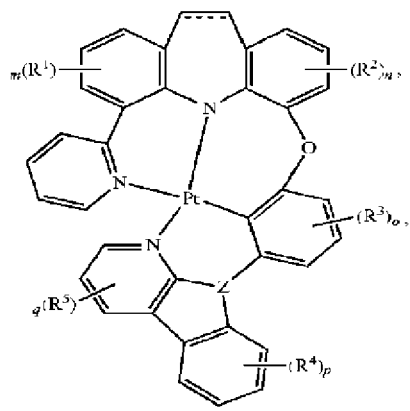 " and insert -- 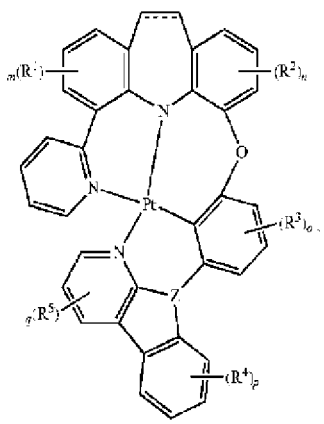 --, therefor.

In Claim 15, Column 272, Line 19-32 (Approx.)
delete " 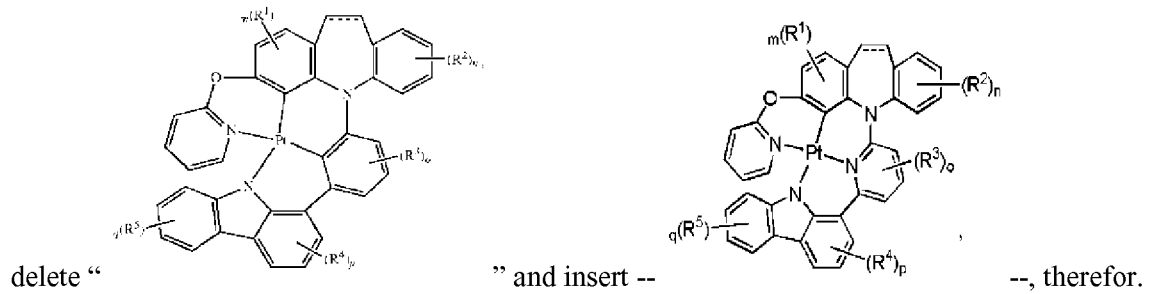 " and insert -- --, therefor.
In Claim 15, Column 272, Line 36-40 (Approx.)
delete " 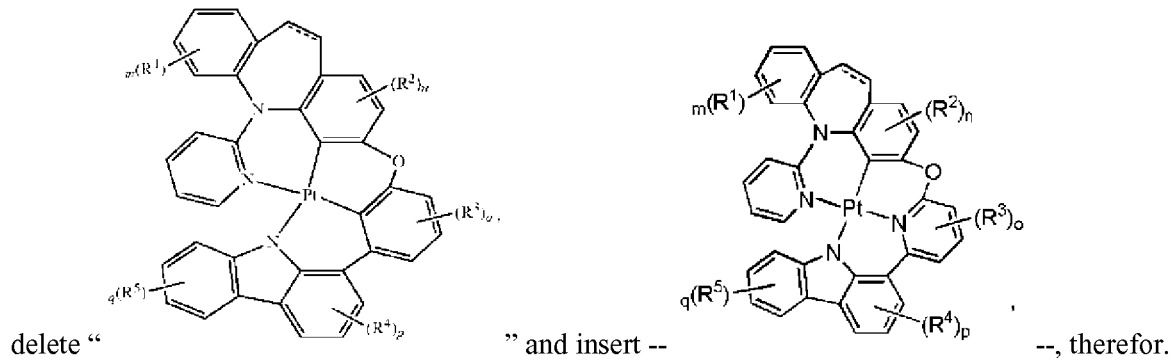 " and insert -- --, therefor.
In Claim 15, Column 272, Line 53-66 (Approx.)
delete " 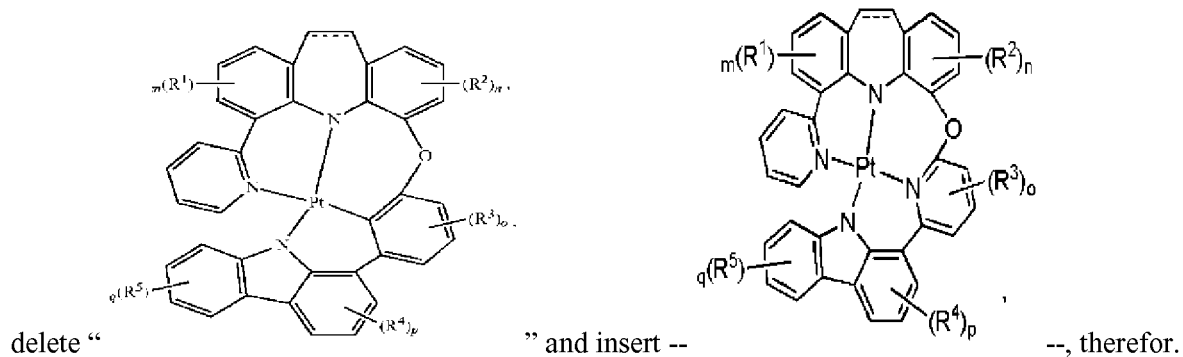 " and insert -- --, therefor.

In Claim 15, Column 273, Line 51-66 (Approx.)
delete " 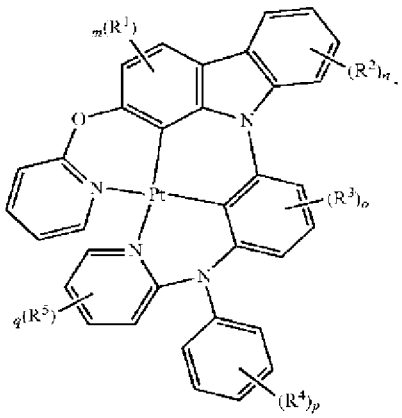 " and insert -- 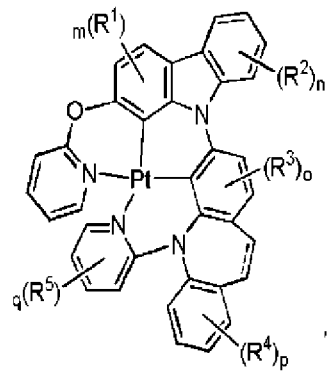 --, therefor.
In Claim 15, Column 274, Line 1-14 (Approx.)
delete " 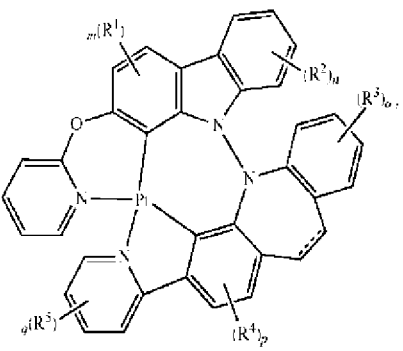 " and insert -- 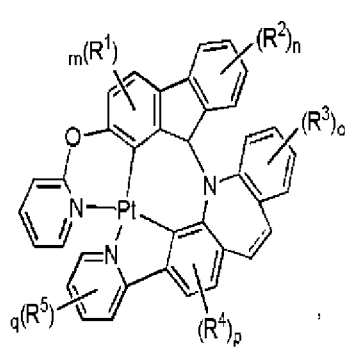 --, therefor.
In Claim 15, Column 274, Line 16-27 (Approx.)
delete " 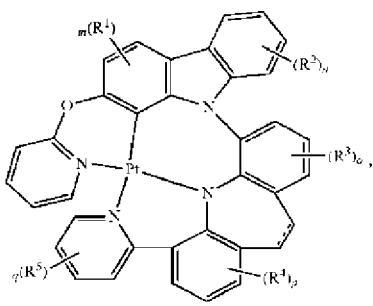 " and insert -- 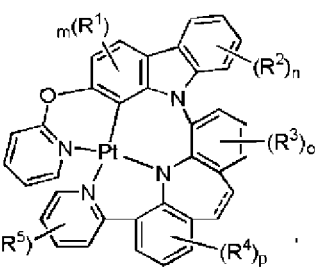 --, therefor.

CERTIFICATE OF CORRECTION (continued)
U.S. Pat. No. 9,882,150 B2

In Claim 15, Column 274, Line 32-47 (Approx.)

delete " 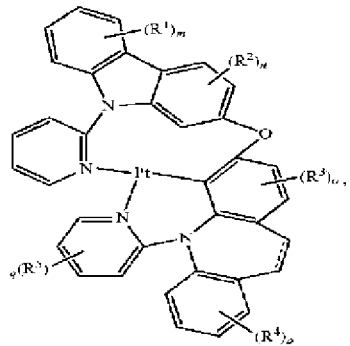 " and insert -- 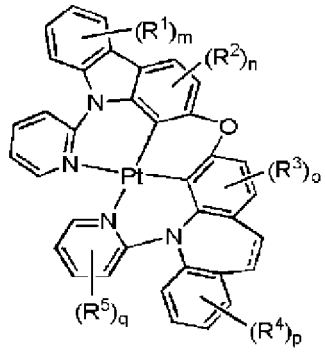 --, therefor.

In Claim 15, Column 275, Line 20-36 (Approx.)

delete " 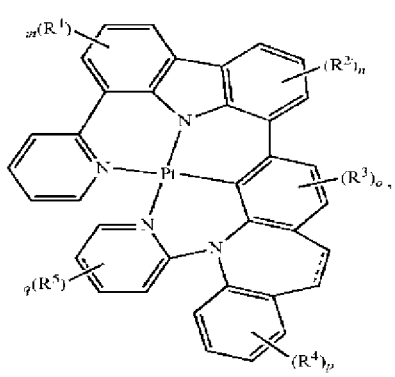 " and insert -- 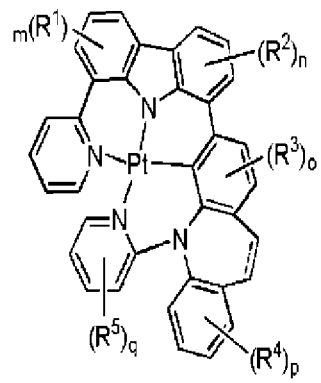 --, therefor.

In Claim 15, Column 276, Line 1-14 (Approx.)

delete " 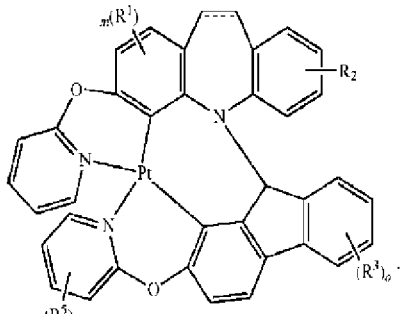 " and insert -- 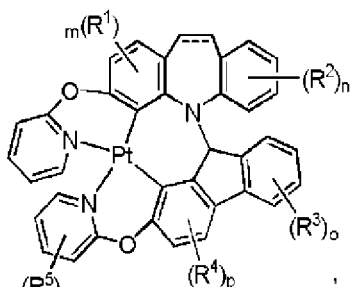 --, therefor.

CERTIFICATE OF CORRECTION (continued)
U.S. Pat. No. 9,882,150 B2

In Claim 15, Column 276, Line 19-31 (Approx.)

delete " 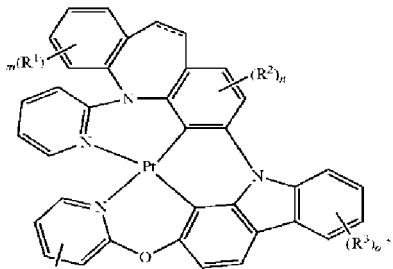 " and insert -- 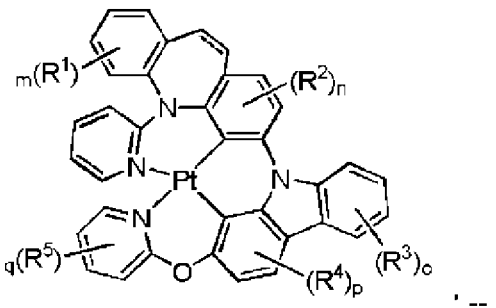 --,
therefor.

In Claim 15, Column 276, Line 35-47 (Approx.)

delete " 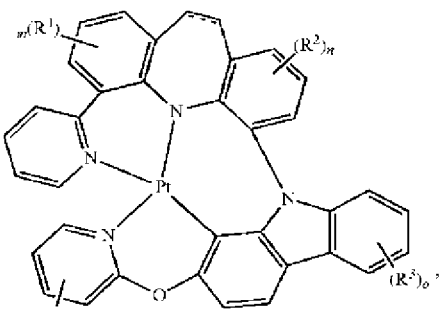 " and insert -- 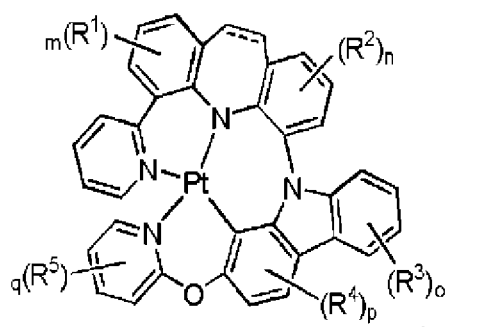 --,
therefor.

In Claim 15, Column 276, Line 51-65 (Approx.)

delete " 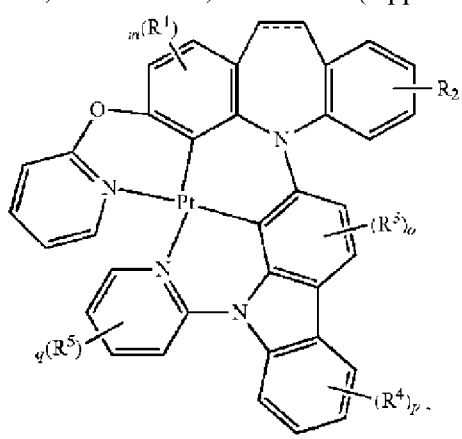 " and insert -- 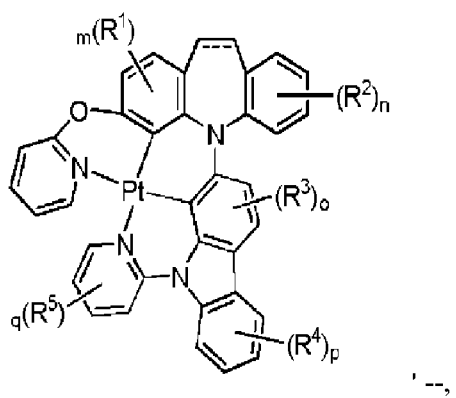 --,
therefor.

In Claim 15, Column 277, Line 35-47 (Approx.)
delete " 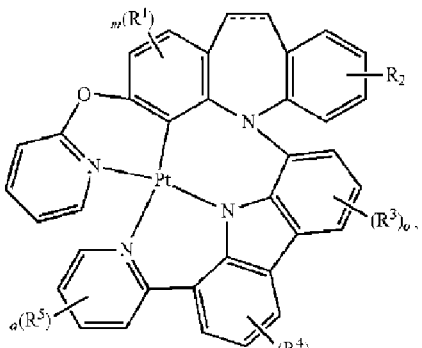 " and insert -- 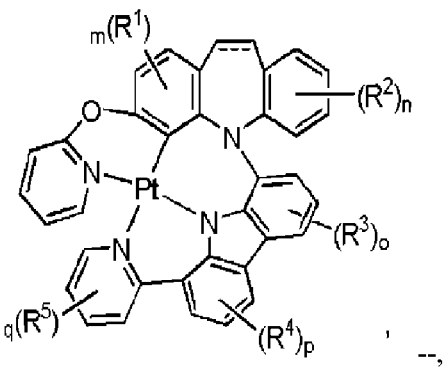 --,
therefor.
In Claim 15, Column 278, Line 51-65 (Approx.)
delete " 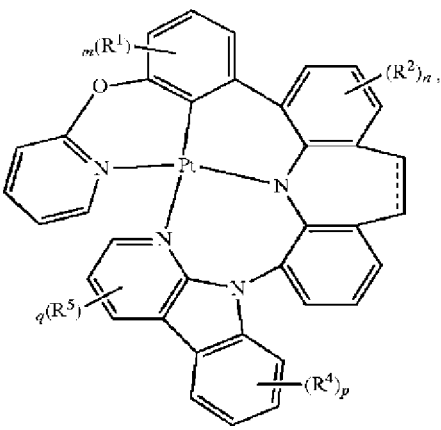 " and insert -- 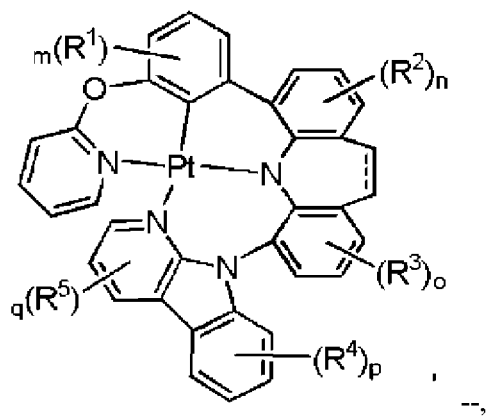 --,
therefor.
In Claim 15, Column 280, Line 34-48 (Approx.)
delete " 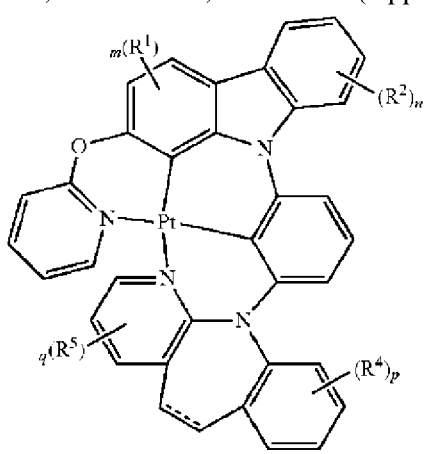 " and insert -- 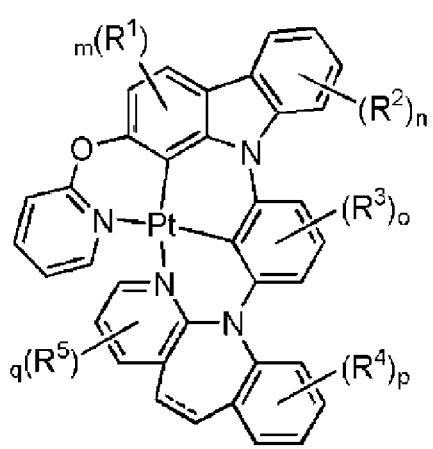 --,
therefor.

CERTIFICATE OF CORRECTION (continued)
U.S. Pat. No. 9,882,150 B2

In Claim 15, Column 280, Line 52-66 (Approx.)

delete " 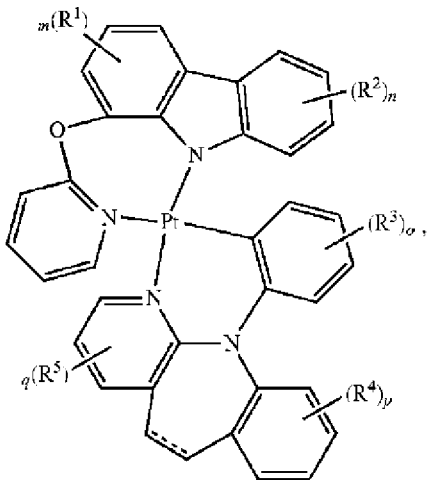 " and insert -- 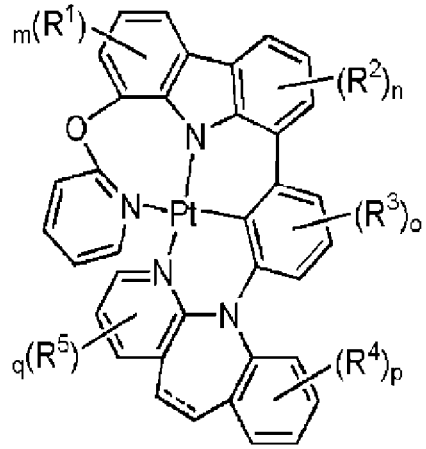 --,
therefor.

In Claim 15, Column 281, Line 34-46 (Approx.)

delete " 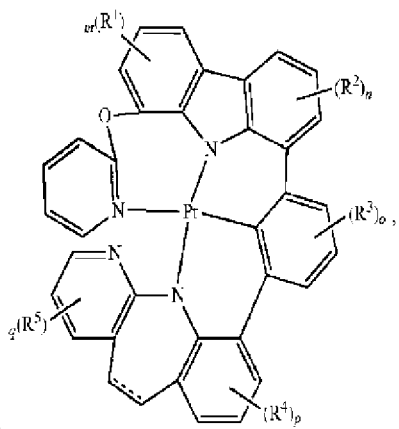 " and insert -- 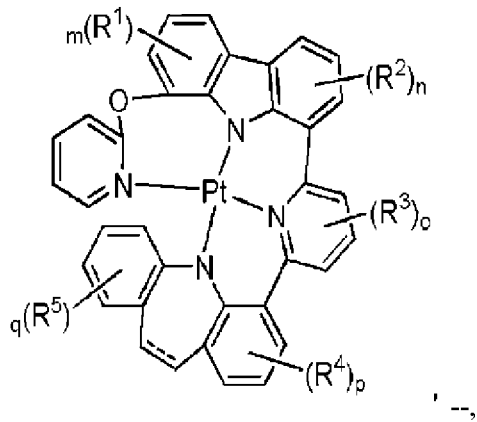 --,
therefor.

In Claim 15, Column 281, Line 50-65 (Approx.)

delete " 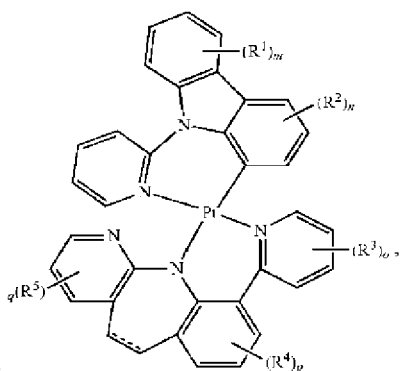 " and insert -- 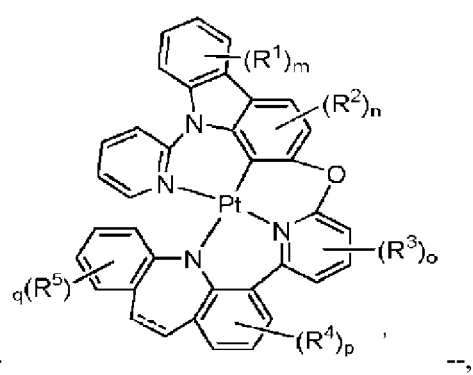 --,
therefor.

CERTIFICATE OF CORRECTION (continued)
U.S. Pat. No. 9,882,150 B2

In Claim 15, Column 282, Line 18-30 (Approx.)

delete " 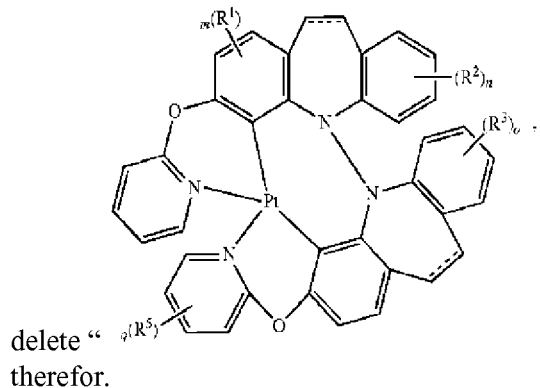 " and insert -- 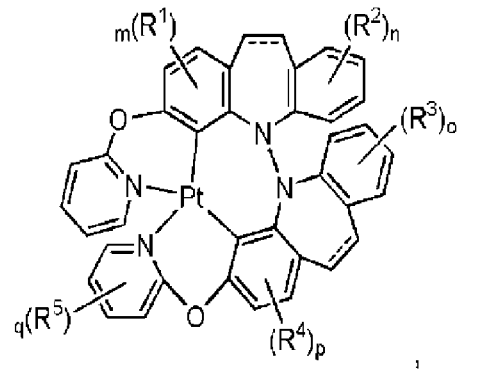 --, therefor.

In Claim 15, Column 282, Line 34-47 (Approx.)

delete " 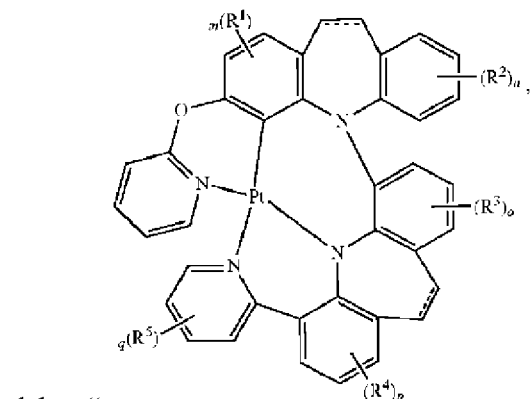 " and insert -- 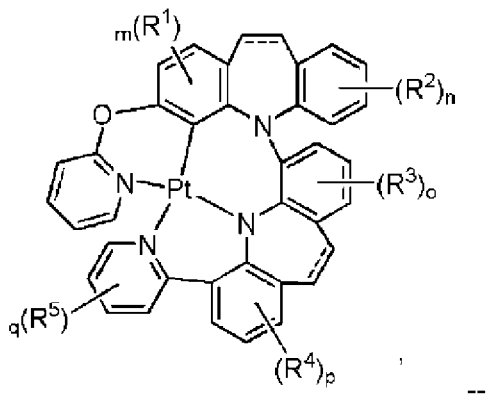 --, therefor.

In Claim 15, Column 283, Line 18-32 (Approx.)

delete " 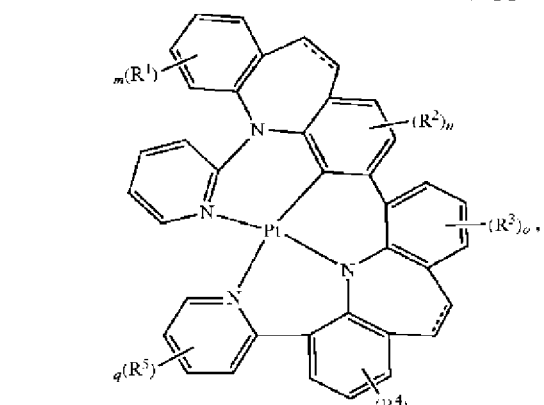 " and insert -- 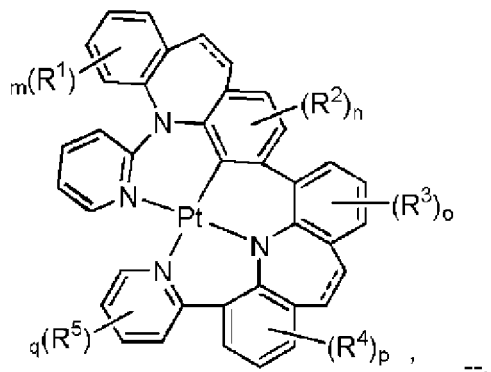 --, therefor.

In Claim 15, Column 283, Line 54-65 (Approx.)
delete " 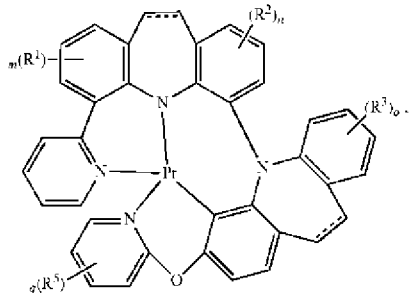 " and insert -- 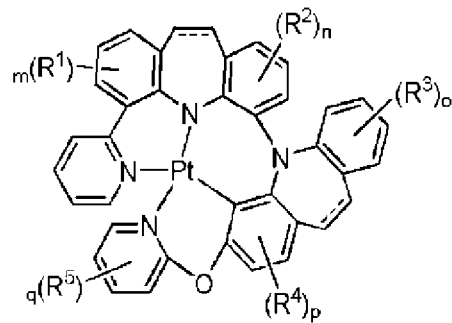 --, therefor.
In Claim 15, Column 284, Line 1-15 (Approx.)
delete " 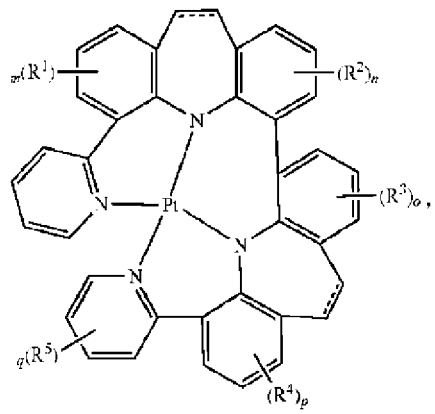 " and insert -- 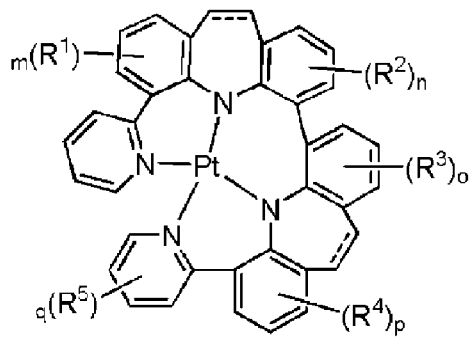 --, therefor.
In Claim 15, Column 284, Line 16-30 (Approx.)
delete " 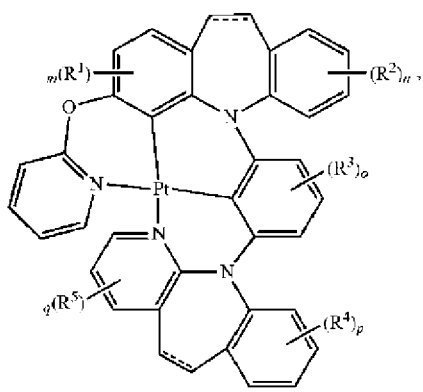 " and insert -- 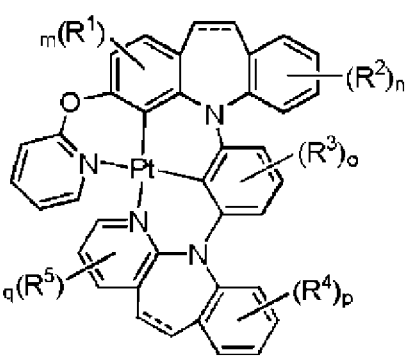 --, therefor.

CERTIFICATE OF CORRECTION (continued)
U.S. Pat. No. 9,882,150 B2

In Claim 15, Column 285, Line 1-15 (Approx.)

delete " 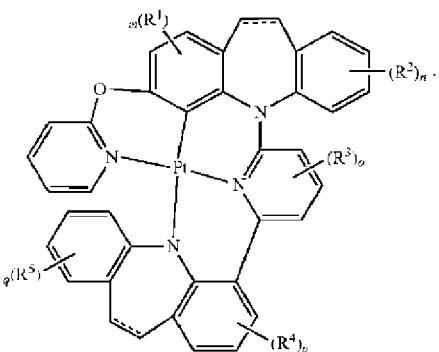 " and insert -- 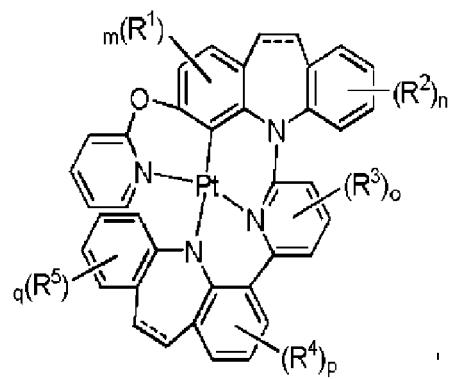 --,
therefor.

In Claim 15, Column 285, Line 17-30 (Approx.)

delete " 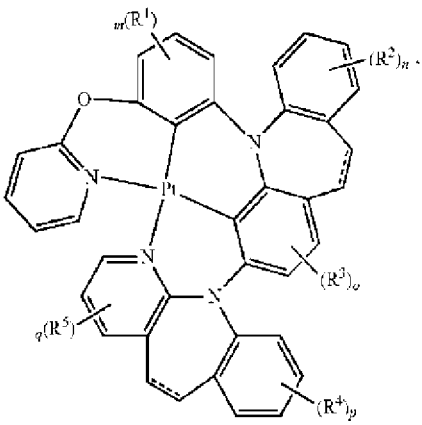 " and insert -- 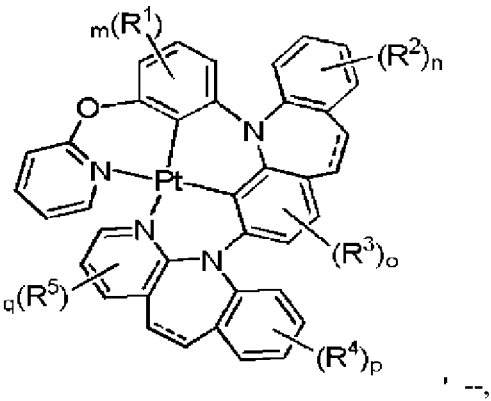 --,
therefor.

In Claim 15, Column 286, Line 1-16 (Approx.)

delete " 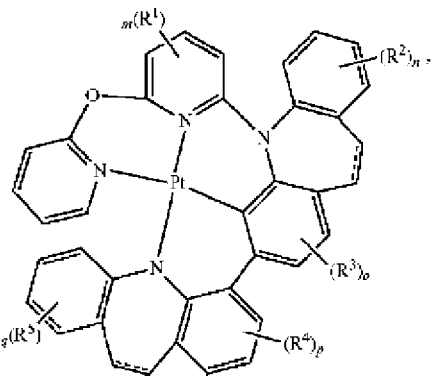 " and insert -- 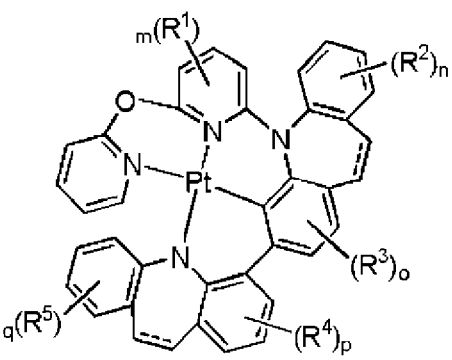 --,
therefor.

CERTIFICATE OF CORRECTION (continued)
U.S. Pat. No. 9,882,150 B2

In Claim 15, Column 286, Line 17-31 (Approx.)

delete " 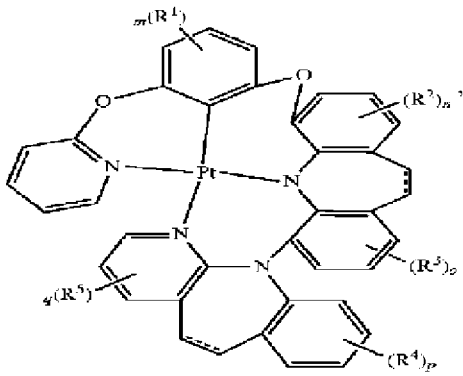 " and insert -- 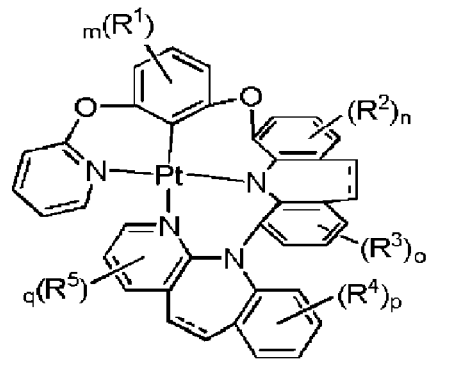 --, therefor.

In Claim 15, Column 287, Line 1-17 (Approx.)

delete " 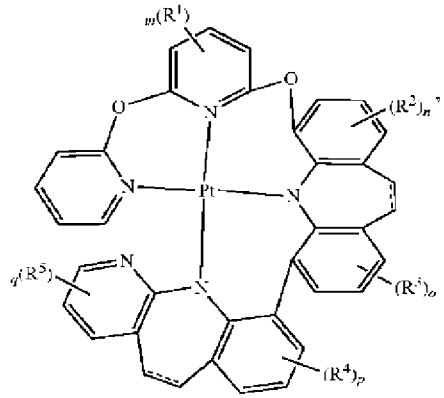 " and insert -- 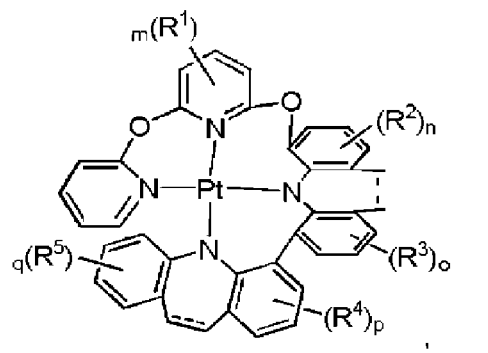 --, therefor.

In Claim 15, Column 287, Line 18 (Approx.)
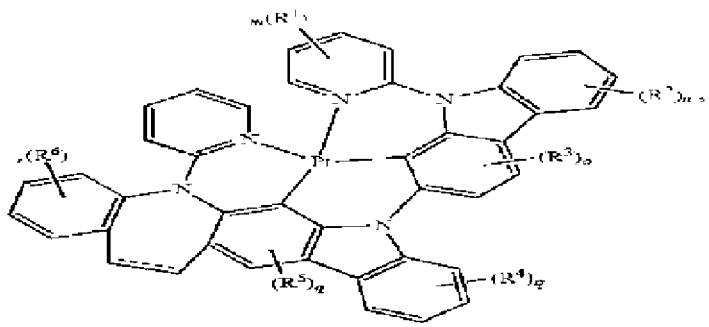
before " "
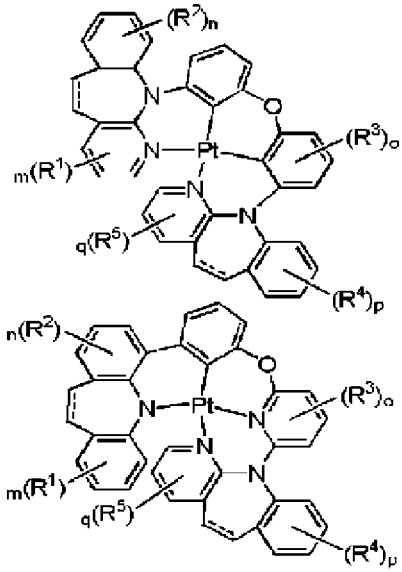 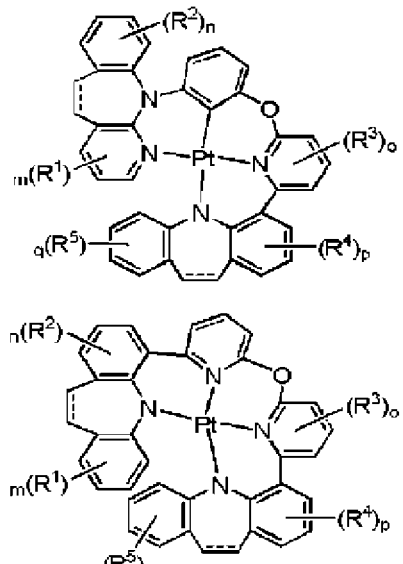
insert --
therefor.
In Claim 15, Column 289, Line 37-51 (Approx.)
delete " 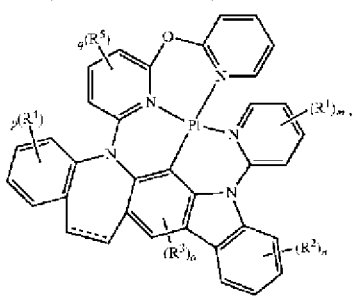 " and insert -- 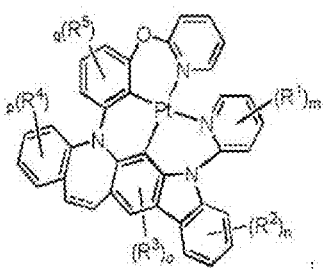 --, therefor.

CERTIFICATE OF CORRECTION (continued)
U.S. Pat. No. 9,882,150 B2

In Claim 15, Column 290, Line 51-66 (Approx.)

delete " 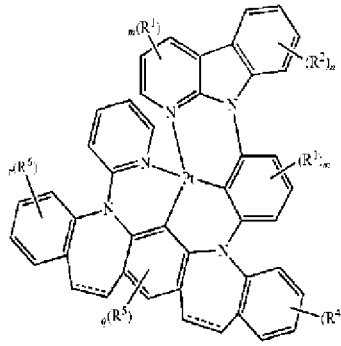 " and insert -- 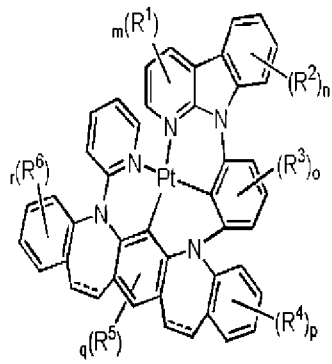 --, therefor.

In Claim 15, Column 291, Line 31-45 (Approx.)

delete " 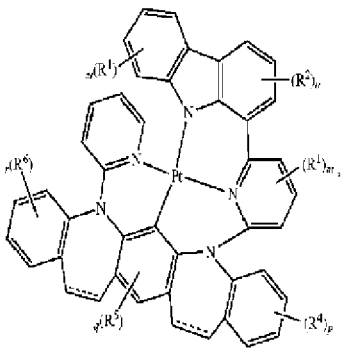 " and insert -- 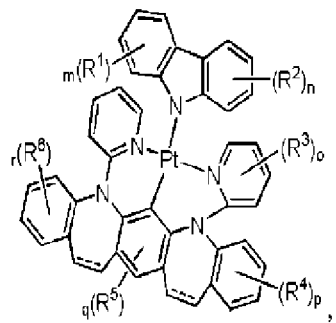 --, therefor.